US012421206B2

(12) United States Patent
Scherrer et al.

(10) Patent No.: US 12,421,206 B2
(45) Date of Patent: Sep. 23, 2025

(54) ARYL-N-ARYL DERIVATIVES FOR TREATING A RNA VIRUS INFECTION

(71) Applicants: ABIVAX, Paris (FR); CENTRE NATIONAL DE LA RECHERCHE SCIENTIFIQUE, Paris (FR); UNIVERSITE DE MONTPELLIER, Montpellier (FR); INSTITUT CURIE, Paris (FR)

(72) Inventors: Didier Scherrer, Castelnau-le-Lez (FR); Jamal Tazi, Clapiers (FR); Florence Mahuteau-Betzer, Saint Remy-les-Chevreuse (FR); Romain Najman, L'Hay-les-Roses (FR); Julien Santo, Grabels (FR); Cécile Apolit, Grabels (FR)

(73) Assignees: ABIVAX, Paris (FR); CENTRE NATIONAL DE LA RECHERCHE SCIENTIFIQUE, Paris (FR); UNIVERSITE DE MONTPELLIER, Montpellier (FR); INSTITUT CURIE, Paris (FR)

( * ) Notice: Subject to any disclaimer, the term of this patent is extended or adjusted under 35 U.S.C. 154(b) by 849 days.

(21) Appl. No.: 17/259,451

(22) PCT Filed: Jul. 9, 2019

(86) PCT No.: PCT/EP2019/068465
§ 371 (c)(1),
(2) Date: Jan. 11, 2021

(87) PCT Pub. No.: WO2020/011816
PCT Pub. Date: Jan. 16, 2020

(65) Prior Publication Data
US 2021/0122732 A1 Apr. 29, 2021

(30) Foreign Application Priority Data
Jul. 9, 2018 (EP) .................................... 18305911

(51) Int. Cl.
*C07D 401/12* (2006.01)
*A61P 31/12* (2006.01)
(Continued)

(52) U.S. Cl.
CPC ............ *C07D 401/12* (2013.01); *A61P 31/12* (2018.01); *C07C 233/65* (2013.01);
(Continued)

(58) Field of Classification Search
CPC .............................. A61P 31/12; C07D 401/12
See application file for complete search history.

(56) References Cited

U.S. PATENT DOCUMENTS

2005/0154232 A1 7/2005 Lardy et al.
2007/0197625 A1 8/2007 Casara et al.
(Continued)

FOREIGN PATENT DOCUMENTS

CN 101142208 A 3/2008
JP 2011-026251 A 2/2011
(Continued)

OTHER PUBLICATIONS

Pd-Catalyzed Intermolecular Amidation of Aryl Halides: The Discovery that Xantphos Can Be Trans-Chelating in a Palladium Complex Yin et al. J. Am. Chem. Soc. 2002, 124, 6043-6048 (Year: 2002).*
(Continued)

*Primary Examiner* — Jeffrey S Lundgren
*Assistant Examiner* — Eric Tran
(74) *Attorney, Agent, or Firm* — Oliff PLC

(57) ABSTRACT

A compound of formula (Ie):

(Ie)

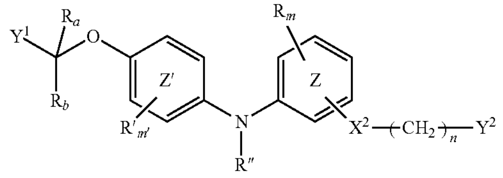

wherein $Y^1$ represents an aryl group, $X^2$ represents a —O— group, a —NH— group, a —S— group, a —CO—NH— group, a —NH—CO—NH— group, a —NH—CO— group, a —CH(OH)— group, a —CH(COOH)NH— group, a —CH($COOCH_3$)NH— group, a —C(OH)($CH_2OH$)—, a

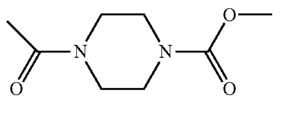

group, a divalent 5-membered heteroaromatic ring comprising 1, 2, 3 or heteroatoms, a —$SO_2$— group, or a —$SO_2$—NH— group, $Y^2$ represents a hydrogen atom, a hydroxyl group, a ($C_1$-$C_4$)alkoxy group, a —CHC$(OH)_2$, a $COOR_f$, wherein $R_f$ represents a hydrogen atom or a ($C_1$-$C_4$)alkyl group, a morpholinyl group, a dihydropyranyl group, a

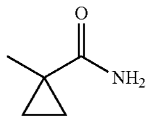

(Continued)

group, a

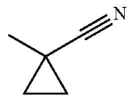

group, a —PO($OR_f$)($OR'_f$) group, wherein $R_f$ and $R'_f$ independently represents a hydrogen atom or a ($C_1$-$C_4$)alkyl group, an oxetanyl group, a —$Si(CH_3)_3$ group, a —NHCOO—($C_1$-$C_4$)alkyl group, or a —$CR^1R^2R^3$ group, or any of its pharmaceutically acceptable salt and pharmaceutical compositions containing them and to synthesis process for manufacturing them.

17 Claims, No Drawings

(51) Int. Cl.

| | |
|---|---|
| ***C07C 233/65*** | (2006.01) |
| ***C07C 237/40*** | (2006.01) |
| ***C07C 255/50*** | (2006.01) |
| ***C07C 311/16*** | (2006.01) |
| ***C07D 205/04*** | (2006.01) |
| ***C07D 213/38*** | (2006.01) |
| ***C07D 213/74*** | (2006.01) |
| ***C07D 213/75*** | (2006.01) |
| ***C07D 213/81*** | (2006.01) |
| ***C07D 239/16*** | (2006.01) |
| ***C07D 239/22*** | (2006.01) |
| ***C07D 239/42*** | (2006.01) |
| ***C07D 241/12*** | (2006.01) |
| ***C07D 403/12*** | (2006.01) |
| ***C07D 405/12*** | (2006.01) |
| ***C07D 413/12*** | (2006.01) |
| ***C07F 7/18*** | (2006.01) |

(52) U.S. Cl.

CPC .......... *C07C 237/40* (2013.01); *C07C 255/50* (2013.01); *C07C 311/16* (2013.01); *C07D 205/04* (2013.01); *C07D 213/38* (2013.01); *C07D 213/74* (2013.01); *C07D 213/75* (2013.01); *C07D 213/81* (2013.01); *C07D 239/16* (2013.01); *C07D 239/22* (2013.01); *C07D 239/42* (2013.01); *C07D 241/12* (2013.01); *C07D 403/12* (2013.01); *C07D 405/12* (2013.01); *C07D 413/12* (2013.01); *C07F 7/1804* (2013.01)

(56) References Cited

U.S. PATENT DOCUMENTS

| | | | | |
|---|---|---|---|---|
| 2007/0244120 A1* | 10/2007 | Dumas | C07D 285/135 514/369 |
| 2014/0187641 A1* | 7/2014 | Dalton | A61K 31/136 514/655 |
| 2014/0206690 A1* | 7/2014 | Scherrer | A61K 31/4545 544/131 |
| 2016/0031797 A1 | 2/2016 | Dalton et al. | |
| 2016/0143884 A1* | 5/2016 | Orlemans | A61K 31/404 514/406 |

FOREIGN PATENT DOCUMENTS

| | | | |
|---|---|---|---|
| NO | 2012/131656 | A2 | 10/2012 |
| RU | 2467007 | C2 | 11/2012 |
| RU | 2628800 | C2 | 8/2017 |
| WO | 2003/033467 | A1 | 4/2003 |
| WO | 2004/084901 | A1 | 10/2004 |
| WO | 2005/021544 | A2 | 3/2005 |
| WO | 2005/023255 | A2 | 3/2005 |
| WO | 2005/058869 | A1 | 6/2005 |
| WO | 2006/037117 | A1 | 4/2006 |
| WO | 2006/097534 | A1 | 9/2006 |
| WO | 2007/081517 | A2 | 7/2007 |
| WO | 2007/135106 | A1 | 11/2007 |
| WO | 2009/087238 | A2 | 7/2009 |
| WO | 2010/143168 | A2 | 12/2010 |
| WO | 2010/143169 | A2 | 12/2010 |
| WO | 2011/163355 | A1 | 12/2011 |
| WO | 2012/080953 | A1 | 6/2012 |
| WO | 2014/164667 | A1 | 10/2014 |
| WO | 2015/001518 | A1 | 1/2015 |
| WO | 2016/135053 | A1 | 9/2016 |
| WO | 2016/135055 | A1 | 9/2016 |
| WO | 2017/158201 | A1 | 9/2017 |

OTHER PUBLICATIONS

Apr. 11, 2023 Office Action issued in Chinese Patent Application No. 201980045913.6.

Berman Group IV viruses: Single-Stranded (+)Sense RNA; Chapter 42; pp. 237-246; 2012.

Berman Group V viruses: Single-Stranded (−)Sense RNA; Chapter 43; pp. 247-255; 2012.

Formulae of compounds having registry Nos. RN1875830-19-5, RN1216052-00-4, RN512834-81-0 and RN94631-91-1 found in "REGISTRY database" and "entered STN before Feb. 29, 2016".

Mar. 24, 2023 Office Action issued in Chinese Patent Application No. 201980045893.2.

Apr. 12, 2023 Notice of Allowance issued in U.S. Appl. No. 17/259,483.

Apr. 26, 2023 Corrected Notice of Allowance issued in U.S. Appl. No. 17/259,483.

Aug. 16, 2022 Office Action issued in Russian Patent Application No. 2020142702/04(079504).

Jul. 11, 2022 Office Action issued in Russian Patent Application No. 2020143617/04(081468).

Registry(STN)[online ], date-of-search Jul. 11, 2023: Sep. 9, 2016 RN: 1990473-92-1, Sep. 2, 2016 RN: 1985111-93-0, Sep. 2, 2016 RN: 1985111-90-7, Sep. 2, 2016RN: 1991597-00-2, May 13, 2016 RN: 1909835-58-0, May 9, 2016 RN:1906298-82-5.

R.I. Hernandez-Benitez et al, "Palladium-Catalyzed Synthesis of Diarylamines and 1- and 2-Oxy-genated Carbazoles: Total Syntheses of Natural Alkaloids Clauraila A, Clausenal, Clausine P, and 7-Methoxy-O-methylmukonal", Synthesis, Jul. 5, 2017, 49, A-O.

Suzuki et al., "Design, Synthesis, and Biological Activity of a Novel Series of Human Sirtuin-2-Selective Inhibitors", Journal of Medicinal Chemistry, 2012, 55(12), pp. 5760-5773.

Bianchi et al, "Compounds with antiulcer and antisecretory activity. I. 3-Aryl-benzimidazolin-2-ones and -thiones", Eur. J. Med. Chem. Chimica Therapeutica, Jul.-Aug. 1981-16, No. 4, pp. 321-326.

Jan. 3, 2023 Office Action Issued In U.S. Appl. No. 17/259,483.

Aug. 20, 2020 Search Report Issued in International Patent Application No. PCT/EP2020/070294.

U.S. Appl. No. 17/628,402, filed Jan. 19, 2022 in the name of Scherrer et al.

Oct. 7, 2019 Search Report Issued in International Patent Application No. PCT/EP2019/068465.

Schmidt et al.; "Transition metals in Organic Synthesis, Part 91: Palladium-catalyzed Approach to 2, 6-Dioxygenated Carbazole Alkaloids—First Total Synthesis of the Phytoalexin Carbalexin C"; Synlett; 2009; pp. 2,421-2,424.

Sep. 10, 2019 Search Report Issued in International Patent Application No. PCT/EP2019/068460.

Sep. 27, 2019 Search Report Issued in International Patent Application No. PCT/EP2019/068461.

Sep. 26, 2019 Search Report Issued in International Patent Application No. PCT/EP2019/068459.

(56) References Cited

OTHER PUBLICATIONS

U.S. Appl. No. 17/259,483, filed Jan. 11, 2021 in the name of Scherrer et al.
U.S. Appl. No. 17/259,364, filed Jan. 11, 2021 in the name of Scherrer et al.
U.S. Appl. No. 17/259,370, filed Jan. 11, 2021 in the name of Scherrer et al.
Feb. 28, 2024 Office Action issued in U.S. Appl. No. 17/259,370.
Dardonville et al., "Bisguanidine, bis(2- aminoimidazoline), and polyamine derivatives as potent and selective chemotherapeutic agents against Trypanosoma brucei rhodesiense. Synthesis and in vitro evaluation", J. Med. Chem. 2004, 47, 9, pp. 2296-2307.
STN database Compounds, 2016.
Dardonville et al., "Bisguanidine, Bis(2-aminoimidazoline) and Polyamine Derivatives as Potent and Selective Chemotherapeutic Agents against Trypanosoma brucei rhodesiense. Synthesis and in vitro evaluation", J. Med . Chem. 2004, 47, 2296-2307.
STN compounds having registry Nos. RN 1990430-84-6, entered Sep. 9, 2016; RN 1988220-74-1, entered Sep. 7, 2016; and RN 1923315-23-4, entered Jun. 2, 2016.
Registry (STN) Compounds (1)-(83), entered on or before Sep. 2016.
Rao et al., "Hypervalent iodine(III) catalyzed oxidative C-N bond formation in water: synthesis of benzimidazole-fused heterocycles," RSC Advances, 2014, vol. 4, No. 49, pp. 25600-25604.
Peng et al., "Synthesis and antitumor activity evaluation of anilinoquinoline derivatives by the effect on the expression of polo-like kinase," Medicinal Chemistry Research, 2013, vol. 23, No. 3, pp. 1437-1446.
Venkatesh et al., "Palladium-Catalyzed Intramolecular N-Arylation of Heteroarenes: A Novel and Efficient Route to Benzimdazol[1,2-a]quinolines," The Journal of Organic Chemistry, 2006, vol. 71, No. 3, pp. 1280-1283.
Database Registry [Online], CAS Registry No. 1110919-40-8, published Feb. 24, 2010.
Database Registry [Online], CAS Registry No. 924194-00-3, published Mar. 1, 2007.
Database Registry [Online], CAS Registry No. 600170-83-0, published Oct. 7, 2003.
Database Registry [Online], CAS Registry No. 1992203-70-9, published Sep. 13, 2006.
Database Registry [Online], CAS Registry No. 1992752-01-8, published Sep. 13, 2016.
Database Registry [Online], CAS Registry No. 2137046-09-2, published Oct. 30, 2017.
Database Registry [Online], CAS Registry No. 2109705-38-4, published Aug. 7, 2017.
Database Registry [Online], CAS Registry No. 2021522-02-9, published Oct. 31, 2016.
Database Registry [Online], CAS Registry No. 1882567-11-4, published Mar. 9, 2016.
Database Registry [Online], CAS Registry No. 1624283-58-4, published Sep. 22, 2014.
Database Registry [Online], CAS Registry No. 1382354-17-7, published Jul. 10, 2012.
Database Registry [Online], CAS Registry No. 1297213-68-3, published May 19, 2011.
Database Registry [Online], CAS Registry No. 97034-48-5, published Jul. 1, 1985.
Konstanze K. Julich-Gruner et al. "Synthesis of Carbalexin B, Clausine A, Clauszoline M, and 2,8-Dihydroxy-3- methylcarbazole," Chemistry-A European Journal, 2014, vol. 20, pp. 8493-8804.
Sep. 19, 2024 Notice of Allowance issued in U.S. Appl. No. 17/259,370.
Feb. 28, 2025 Office Action issued in U.S. Appl. No. 18/660,578.

* cited by examiner

ARYL-N-ARYL DERIVATIVES FOR TREATING A RNA VIRUS INFECTION

The present invention relates to compounds useful for preventing and/or treating a RNA virus infection, and most preferably a RNA virus infection caused by RNA viruses belonging to group IV or V of the Baltimore classification.

The present invention further relates to some new compounds, in particular useful for preventing and/or treating a RNA virus infection, and most preferably a RNA virus infection caused by a RNA virus belonging to group IV or V of the Baltimore classification.

It further relates to the pharmaceutical compositions containing said new compounds and to the chemical synthesis processes for obtaining them.

BACKGROUND

Viruses are one of the major causes of diseases around the world. Viruses are generally defined as small, non-living, infectious agents that replicate only within living cells, as they do not possess a completely autonomous replication mechanism. Although diverse in shape and size, they typically consist of a virus particle (known as a "virion"), made from a protein coat which comprises at least one nucleic acid molecule and optionally, depending on the type of virus, one or more proteins or nucleoproteins.

Because viruses do not possess a completely autonomous replication mechanism, they must necessarily rely on the machinery and metabolism of the infected cell or host, in order to replicate and produce multiple copies of themselves.

Even though their replication cycle varies greatly between species, it is generally recognized that the life cycle of viruses includes six basic steps: attachment, penetration, uncoating, replication, assembly and release.

Depending on the nature of the targeted virus, therapeutic molecules have been designed which may interfere with one or more of those mechanisms.

Among those, the replication step involves not only the multiplication of the viral genome, but also the synthesis of viral messenger RNA, of viral protein, and the modulation of the transcription or translation machinery of the host. However, it is also clear that the type of genome (single-stranded, double-stranded, RNA, DNA . . . ) characterizes dramatically this replication step. For instance, most DNA viruses assemble in the nucleus while most RNA viruses develop solely in the cytoplasm. Also, there is increasing evidence that single-stranded RNA viruses such as Influenza use the host RNA splicing and maturation machinery.

Accordingly, and considering the implications of a given type of genome in the replication step, the Baltimore classification of viruses was developed. This classification clusters viruses into families (or "groups") depending on their type of genome. The present virus classification, as in 2018, comprises seven different groups:

- Group I: double-stranded DNA viruses (dsDNA);
- Group II: single-stranded DNA viruses (ssDNA);
- Group III: double-stranded RNA viruses (dsRNA);
- Group IV: (+)strand or sense RNA viruses ((+)ssRNA);
- Group V: (−)strand or antisense RNA viruses ((−)ssRNA);
- Group VI: single-stranded RNA viruses having DNA intermediates (ssRNA-RT);
- Group VII: double-stranded DNA viruses having RNA intermediates (dsDNA-RT).

According to that classification, viruses belonging to the Group VI are not, stricto sensu, RNA viruses. For the same reasons, viruses belonging to the Group VII are not, stricto sensu, DNA viruses. One well-studied example of a virus family belonging to the Group VI is the family Retroviridae (retrovirus) which includes HIV. One well-studied example of a virus family belonging to the Group VII is the family Hepadnaviridae which includes the Hepatitis B virus (HBV).

As a representative of viruses pertaining to group IV one may cite the Picornaviruses (which is a family of viruses that includes well-known viruses like Hepatitis A virus, enteroviruses, rhinoviruses, poliovirus, and foot-and-mouth virus), SARS virus, Hepatitis C virus, yellow fever virus, and rubella virus. The Togaviridae family also pertains to the group IV and a known genus thereof is Alphavirus, encompassing the Chikungunya virus. Flaviridae is also a family pertaining to group IV, encompassing a famous virus transmitted by mosquitoes, i.e. the Dengue virus.

As a representative of viruses pertaining to group V one may cite the Filoviridae virus family encompassing the Ebola virus, the Paramyxoviridae family encompassing the Respiratory Syncytial virus (RSV), the Rhabdoviridae family, the Orthomyxoviridae family encompassing the Influenzavirus A, Influenzavirus B and Influenzavirus C.

Groups within the virus families particularly focused in the framework of the present invention are the ones encompassing RNA viruses, especially single-stranded RNA viruses, and more specifically RNA viruses belonging to group IV and group V of the Baltimore classification.

There are few cures for diseases caused by RNA virus infections, in particular single-stranded RNA viruses, and more specifically RNA virus infections from viruses belonging to group IV and V of the Baltimore classification. Treatment is focused on relieving the symptoms. Therefore, there is still a need to identify new antiviral drugs to treat RNA virus infections, such as RNA virus infection from group IV and V, in particular small chemical molecules.

Definitions

As used herein, the term "patient" refers to either an animal, such as a valuable animal for breeding, company or preservation purposes, or preferably a human or a human child, which is afflicted with, or has the potential to be afflicted with, one or more diseases and conditions described herein.

In particular, as used in the present application, the term "patient" refers to a mammal such as a rodent, cat, dog, primate or human, preferably said subject is a human and also extends to birds.

The identification of those patients who are in need of treatment of herein-described diseases and conditions is well within the ability and knowledge of one skilled in the art. A veterinarian or a physician skilled in the art can readily identify, by the use of clinical tests, physical examination, medical/family history or biological and diagnostic tests, those patients who are in need of such treatment.

In the context of the invention, the term "treating" or "treatment", as used herein, means reversing, alleviating, inhibiting the progress of, or preventing the disease resulting from RNA virus infection, and more particularly RNA virus infection from group IV or V, or one or more symptoms of such disease.

As used herein, an "effective amount" refers to an amount of a compound of the present invention which is effective in preventing, reducing, eliminating, treating or controlling the symptoms of the herein-described diseases and conditions, i.e. RNA virus infection, and more particularly RNA virus infection from group IV or V. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

The term "effective amount" includes "prophylaxis-effective amount" as well as "treatment-effective amount".

The term "preventing", as used herein, means reducing the risk of onset or slowing the occurrence of a given phenomenon, namely in the present invention, a disease resulting from a RNA virus infection, and more particularly a RNA virus infection from group IV or V.

As used herein, «preventing» also encompasses «reducing the likelihood of occurrence» or «reducing the likelihood of reoccurrence».

The term "prophylaxis-effective amount" refers to a concentration of compound of this invention that is effective in inhibiting, preventing, decreasing the likelihood of the disease by RNA viruses, and more particularly by a RNA virus from group IV or V of the Baltimore classification, or preventing the RNA virus infection and in particular a RNA virus infection from group IV or V or preventing the delayed onset of the disease by the RNA virus, and more particularly by a RNA virus from group IV or V, when administered before infection, i.e. before, during and/or slightly after the exposure period to the RNA virus, and in particular to the RNA virus from group IV or V.

Likewise, the term "treatment-effective amount" refers to a concentration of compound that is effective in treating the RNA virus infection, e.g. leads to a reduction in RNA viral infection, following examination when administered after infection has occurred.

As used herein, the term "pharmaceutically acceptable" refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

As used herein, a "viral infection or related condition" refers to an infection of condition related to a virus, more particularly said virus having a RNA genome, and especially a RNA virus belonging to group IV or V according to the Baltimore classification. Viruses may be further classified in distinct families, orders and genus.

For reference, the content of the "Baltimore classification" which is reported herein further references to the virus taxonomy as set forth in the database of the 2017 International Committee of Taxonomy of Viruses (ICTV) as released online on Mar. 12, 2018 at http://ictvonline.org/virusTaxonomy.asp. This taxonomy is incorporated herein in its entirety.

Alphaviruses may in particular be considered by the invention and pertain to the Group IV RNA viruses and the Togaviridae family, which can be defined as positive-sense single-stranded RNA viruses or (+)ssRNA viruses. Their order is "Unassigned" according to the Virus Taxonomy of 2017. The Togaviridae family includes the Alphavirus and Rubivirus genus.

Examples of Alphaviruses which are considered by the invention include: Barmah Forest virus, Chikungunya virus, Mayaro virus, O'nyong'nyong virus, Ross River virus, Semliki Forest virus, Una virus, Eastern equine encephalitis virus, Tonate virus, Venezuelan equine encephalitis virus and Wester equine encephalitis virus.

Most preferably, an Alphavirus infection or Alphavirus related condition, according to the invention, is a Chikungunya virus infection or Chikungunya virus-related condition.

More particularly, Chikungunya virus (CHIKV) is a RNA virus which pertains to the Alphavirus genus which in turn belongs to the Togaviridae family, i.e. Group IV from the Baltimore classification. Chikungunya is a mosquito-borne viral disease first described during an outbreak in southern Tanzania in 1952. CHIKV is an enveloped, positive sense, single-stranded RNA virus with a genome of approximately 12 kb nucleotides long. The genome of CHIKV is organized as follows: 5'-cap-nsP1-nsP2-nsP3-nsP4-(junction region)-C-E3-E2-6k-E1-poly(A)-3', in which the first four proteins (nsP1-4) are nonstructural proteins, and the structural proteins are the capsid (C) and the envelope proteins (E). There is no distinct serotypic difference among CHIKV isolated from Africa, Asia and the islands of the Indian Ocean. Phylogenetic analyses based on El gene sequences can group CHIKV into three genotypes (lineages): Asian, east/central/south African (ECSA), and West African. The Asian genotype differed from the ECSA and West African genotypes by nucleotide levels of ~5% and ~15%, respectively. The African genotypes (ECSA versus West African) were ~15% divergent. The amino acid identities across the three genotypes varied from 95.2 to 99.8%.

Chikungunya virus may cause outbreaks associated with severe morbidity.

Chikungunya is a viral disease transmitted to humans by infected mosquitoes.

Both *Ae. aegypti* and *Ae. albopictus* have been implicated in large outbreaks of Chikungunya. Whereas *Ae. aegypti* is confined within the tropics and sub-tropics, *Ae. albopictus* also occurs in temperate and even cold temperate regions. In recent decades, *Ae. albopictus* has spread from Asia to become established in areas of Africa, Europe and the Americas.

After infection with Chikungunya virus, there is an incubation period lasting 2-4 days on average, followed by disease symptoms. Among such symptoms, fever and severe joint pain may be cited. Other symptoms include muscle pain, headache, nausea, back pain, fatigue, myalgia and rash. Severe clinical manifestations of Chikungunya infection can also occur, for example, haemorrhagic fever, conjunctivitis, photophobia, hepatitis, stomatitis. Neurologic manifestations such as encephalitis, febrile seizures, meningeal syndrome and acute encephalopathy were also reported.

Joint pain is often debilitating and can vary in duration.

The proximity of mosquito breeding sites to human habitation is a significant risk factor for Chikungunya.

The distribution of Chikungunya virus mainly occurs in Africa, India and South Eastern Asia. In recent decades, mosquito vectors of Chikungunya have spread to Europe and the Americas. In 2007, disease transmission was reported for the first time in a localized outbreak in north-eastern Italy. Outbreaks have since been recorded in France and Croatia.

Dengue viruses which present various serotypes, may also be considered by the invention and pertain to the Group IV RNA viruses and the Flaviviridae family, which can be defined as a positive-sense single-stranded RNA or (+)ss RNA viruses. More particularly Dengue virus, is a (+)ssRNA virus belonging to group IV of the Baltimore classification. It is part of the Flavivirus genus, which belongs to the Flaviviridae family. Other viruses pertaining to the Flaviviridae family are hepatitis C virus and yellow fever virus.

Viruses of the Mononegavirales order are also particularly considered by the invention. The order Mononegavirales includes viruses belonging to Group V of the Baltimore classification. As of 2018, this order includes mainly the following virus families: Bornaviridae, Mymonaviridae, Filoviridae, Nyamiviridae, Paramyxoviridae, Pneumoviridae, Rhabdoviridae, and Sunviridae.

Human respiratory syncytial virus (HRSV) is a syncytial virus that causes respiratory tract infections. It is a major cause of lower respiratory tract infections and hospital visits during infancy and childhood. HRSV virus may in particular be considered by the invention and pertain to the Group V of RNA viruses. More particularly, RSV virus is a (−)ssRNA virus belonging to group V of the Baltimore classification. It is a pneumovirus which is part of the Paramyxoviridae family, which belongs to the Mononegavirales order. Among other viruses of the Mononegavirales order, those which are particularly considered by the invention include: measles virus, mumps virus, Nipah virus, rabies virus, and human parainfluenza virus (which includes HPIV-1, HPIV-2, HPIV-3 and HPIV-4). Of note, the Paramyxovirinae subfamily was conventionally merged into the Paramyxoviridae family, by reference to the taxonomy of the Mononegavirales order updated in 2016.

The virus genus which are particularly considered within the Paramyxoviridae family include: Aquaparamyxovirus, Avulavirus, Ferlavirus, Henipavirus, Morbillivirus, Respirovirus and Rubulavirus genus.

Viruses of the Orthomyxoviridae family are also particularly considered by the invention. The Orthomyxoviridae family belongs to an "Unassigned" order according to the 2017 Virus Taxonomy. The virus genus which are particularly considered within the Orthomyxoviridae family include: Alphainfluenzavirus, Betainfluenzavirus, Deltainfluenzavirus, Gammainfluenzavirus, Isavirus, Quaranjavirus, and Thogotovirus.

Influenzavirus A, Influenzavirus B, Influenzavirus C may in particular be considered by the invention and pertain to the Group V RNA viruses and the Orthomyxoviridae family, which can be defined as a negative-sense single-stranded RNA or (−)ss RNA viruses. Isavirus and Thogotovirus also belong to the Orthomyxoviridae order.

DETAILED DESCRIPTION OF THE INVENTION

The inventors have surprisingly found that aryl-N-aryl compounds are endowed with a broad-spectrum activity against RNA viruses, and more particularly single-stranded RNA viruses belonging to Group IV or V of the Baltimore classification. Groups IV and V include respectively (+)ssRNA viruses and (−)ssRNA viruses; which also refer to positive-sense single-stranded RNA viruses and negative-sense single-stranded RNA viruses.

For reference, the content of the «Baltimore classification» is considered in light of the Classification and Nomenclature of viruses as set forth in the 10th report on Virus Taxonomy dated 2017.

The present document discloses a compound of formula (I)

(I)

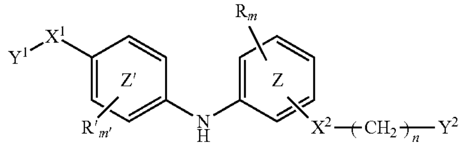

wherein:

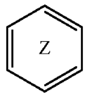

ring and

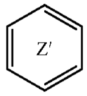

ring independently mean a phenylene or a pyridylene group, wherein the group $$-X^2-(CH_2)_n-Y^2$$

is in meta or para position on the

ring, in particular in meta position, with respect to the —NH— group,

- $X^1$ represents an alkenylene group, in particular an ethenylene group, a —NH—CO— group, a —CO—NH— group, a $—CR_aR_bO—$ group,
- $Y^1$ represents an aryl group selected from a 2-pyridyl group or a pyrimidinyl group, wherein one of the nitrogen atom of the pyrimidinyl group is in ortho position with respect to $X^1$,
- or alternatively $X^1—Y^1$ represents a group (A) of formula (A)

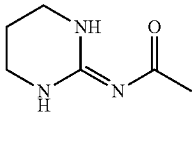

- $X^2$ represents a —CO—NH— group, a —NH—CO—NH— group, a $—OCH_2—$ group, a —NH—CO— group or a $—SO_2—NH—$ group,
- n is 0, 1, 2 or 3,
- m and m' are independently 0, 1 or 2,
- $Y^2$ represents a hydrogen atom, a hydroxyl group or a $—CR^1R^2R^3$ group, wherein $R^1$, $R^2$ and $R^3$ independently represent a hydrogen atom, a fluorine atom or a ($C_1$-$C_4$)alkyl group, being understood that no more than one of $R^1$, $R^2$ and $R^3$ is a hydrogen atom, or $R^1$ and $R^2$ form together with the carbon atom bearing them a ($C_3$-$C_8$)cycloalkyl group, said ($C_3$-$C_8$)cycloalkyl group being optionally substituted by one or two ($C_1$-$C_4$)alkyl group, halogen atom or ($C_1$-$C_4$)alkoxy group and said ($C_3$-$C_5$)cycloalkyl group being optionally interrupted on said $R^1$ and/or $R^2$ by an oxygen atom, R and R' independently represent a halogen atom, a ($C_1$-$C_4$)alkyl group, a ($C_3$-$C_6$)cycloalkyl group, a ($C_1$-$C_5$)alkoxy group, a —$SO_2$—$NR_aR_b$ group, a —$SO_3H$ group, a —OH group, a —O—$SO_2$—$OR_c$ group or a —O—P(═O)—($OR_c$)($OR_d$) group, $R_a$, $R_b$, $R_c$ and $R_d$ independently represent a hydrogen atom or a ($C_1$-$C_4$) alkyl group, provided that when $X^1$ is a —$CR_aR_bO$— group, $Y^1$ may further be a 3-pyridyl, a 4-pyridyl or a phenyl group optionally substituted by one or two substituent(s) selected from a halogen atom, a ($C_1$-$C_4$)alkyl group, a cyano group, a ($C_1$-$C_5$)alkoxy group, a trifluoromethyl group, a trifluoromethoxy group, a —$SO_2$—$NR_aR_b$ group, a —$SO_3H$ group, a —OH group, a —O—$SO_2$—$OR_c$ group or a —O—P(═O)—($OR_c$)($OR_d$) group, or any of its pharmaceutically acceptable salt, for use in the treatment and/or prevention of a RNA virus infection caused by a RNA virus belonging to group IV or V of the Baltimore classification and in particular a Chikungunya viral infection, a Dengue viral infection, an Influenza viral infection or a RSV viral infection or a virus-related condition.

According to a first aspect, the present invention relates to a compound of formula (Ie), (Ie)

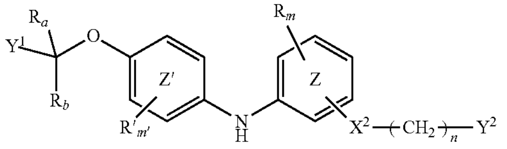

wherein $Y^1$, R, R', $R_a$, $R_b$, m, m',

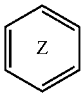

ring,

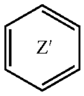

ring, $X^2$, n and $Y^2$ are as defined above for formula (I)

or any of its pharmaceutically acceptable salt.

Still according to said first aspect, the present invention further relates to compounds of formula (Ie), wherein the group

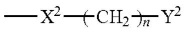

is in meta or para position and preferably in meta position on the

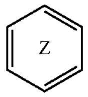

ring, with respect to the —NH— group, m is 0, n is 0, 1, 2 or 3, $Y^1$ represents a pyridyl or a phenyl group optionally substituted by one or two substituent(s) selected from a halogen atom, a ($C_1$-$C_4$)alkyl group and a cyano group, a ($C_1$-$C_5$)alkoxy group, a trifluoromethyl group, a trifluoromethoxy group, a —$SO_2$—$NR_aR_b$ group, a —$SO_3H$ group, a —OH group, a —O—$SO_2$—$OR_c$ group or a —O—P(═O)—($OR_c$)($OR_d$) group, $Y^2$ represents a hydrogen atom, a hydroxyl group or a —$CR^1R^2R^3$ group, wherein $R^1$, $R^2$ and $R^3$ independently represent a hydrogen atom or a ($C_1$-$C_2$)alkyl group, being understood that no more than one of $R^1$, $R^2$ and $R^3$ is a hydrogen atom, or $R^1$ and $R^2$ form together with the carbon atom bearing them a ($C_3$-$C_6$) cycloalkyl group, said ($C_3$-$C_6$)cycloalkyl group being optionally substituted by one or two halogen atom(s) and said ($C_3$-$C_6$)cycloalkyl group being optionally interrupted on said $R^1$ and/or $R^2$ by an oxygen atom, or any of its pharmaceutically acceptable salt.

According to a second aspect, the present invention relates to compounds of formula (Ie) as defined above for use in the treatment and/or prevention of a RNA virus infection caused by a RNA virus belonging to group IV or V of the Baltimore classification, and in particular a Chikungunya viral infection, a Dengue viral infection, an Influenza viral infection or a RSV viral infection or a virus-related condition.

According to a third aspect, the present invention relates to a compound of formula (Ie)

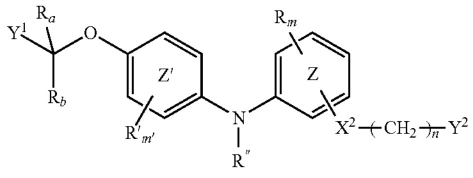

wherein

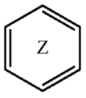

ring and

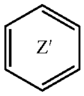

ring independently mean a phenylene or a pyridylene group,

Y represents an aryl group selected from a phenyl group, a pyridyl group, a pyrazinyl group, a pyridazinyl or a pyrimidinyl group, said aryl group being optionally substituted by one or two substituent(s) selected from a halogen atom, a $(C_1\text{-}C_4)$alkyl group, a cyano group, a $(C_1\text{-}C_5)$alkoxy group, a trifluoromethyl group, a trifluoromethoxy group, a $—SO_2—NR_aR_b$ group, a $—SO_3H$ group, a —OH group, a $—O—SO_2—OR_c$ group or a $—O—P(=O)—(OR_c)(OR_d)$ group, $X^2$ represents a —O— group, a —NH— group, a —S— group, a —CO—NH— group, a —NH—CO—NH— group, a —NH—CO— group, a —CH(OH)— group, a —CH(COOH)NH— group, a $—CH(COOCH_3)NH—$ group, a $—C(OH)(CH_2OH)—$, a

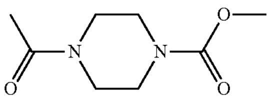

group, a divalent 5-membered heteroaromatic ring comprising 1, 2, 3 or heteroatoms such as a triazole, a tetrazole or an oxadiazole, a $—SO_2—$ group, or a $—SO_2—NH—$ group, n is 0, 1, 2 or 3, m and m' are independently 0, 1 or 2, $Y^2$ represents a hydrogen atom, a hydroxyl group, a $(C_1\text{-}C_4)$alkoxy group, a $—CHC(OH)_2$, a $COOR_f$, wherein $R_f$ represents a hydrogen atom or a $(C_1\text{-}C_4)$alkyl group, a morpholinyl group, a dihydropyranyl group, a

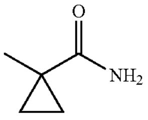

group, a

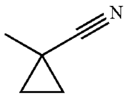

group, a $—PO(OR_f)(OR'_f)$ group, wherein $R_f$ and $R'_f$ independently represents a hydrogen atom or a $(C_1\text{-}C_4)$alkyl group, an oxetanyl group, a $—Si(CH_3)_3$ group, a $—NHCOO—(C_1\text{-}C_4)$alkyl group, or a $—CR^1R^2R^3$ group, wherein $R^1$, $R^2$ and $R^3$ independently represent a hydrogen atom, a fluorine atom or a $(C_1\text{-}C_4)$alkyl group, being understood that no more than one of $R^1$, $R^2$ and $R^3$ is a hydrogen atom, or $R^1$ and $R^2$ form together with the carbon atom bearing them a $(C_3\text{-}C_8)$cycloalkyl group, said $(C_3\text{-}C_8)$cycloalkyl group being optionally substituted by one or two $(C_1\text{-}C_4)$alkyl group, halogen atom or $(C_1\text{-}C_4)$ alkoxy group and said $(C_3\text{-}C_8)$cycloalkyl group being optionally interrupted on said $R^1$ and/or $R^2$ by an oxygen atom, or alternatively $X^2—Y^2$ represents a group $—CONR_cR_d$, wherein $R_c$ and $R_d$ form, together with the nitrogen atom a heterocyclic group, optionally substituted by a hydroxy group or a $(C_1\text{-}C_4)$alkyl group, R and R' independently represent a $(C_1\text{-}C_4)$alkyl group, a $—S—(C_1\text{-}C_4)$alkyl group, a $(C_3\text{-}C_6)$cycloalkyl group, a halogen atom, such as a fluoro atom, a trifluoromethyl group, a $—SO_2(C_1\text{-}C_4)$alkyl group, a $(C_3\text{-}C_6)$cycloalkenyl group, a $(C_1\text{-}C_5)$alkoxy group, a $—SO_2—NR_aR_b$ group, a $—SO_3H$ or $SO_2—CH_3$ group, a —OH group, a $—CONHR_g$, wherein $R_g$ represents a hydrogen atom or a $(C_1\text{-}C_4)$alkyl group, a $—O—SO_2—OR_c$ group, a azetidinyl group, a morpholinyl group, or a cyano group, R" represents a hydrogen atom, a $(C_1\text{-}C_4)$alkyl group optionally substituted by a —COOH group, or any of its pharmaceutically acceptable salt.

According to a fourth aspect, the present invention relates to a compound of formula (Ie) as defined above for use as a medicament.

According to a fifth aspect, the present invention relates to a compound of formula (Ie) as defined above, for use in the treatment and/or prevention of a RNA virus infection caused by a RNA virus belonging to group IV or V of the Baltimore classification, and in particular a Chikungunya viral infection, a Dengue viral infection, an Influenza viral infection or a RSV viral infection or a virus-related condition.

The above-mentioned compounds (I) and (Ie) are particularly suitable for treating or preventing a virus infection or related condition, in particular a RNA virus infection caused by a RNA virus belonging to group IV or V of the Baltimore classification or related condition, and most preferably a Chikungunya viral infection, a Dengue viral infection, an Influenza viral infection or a RSV viral infection or a virus-related condition.

The above-mentioned compounds are even more particularly suitable for treating or preventing a Chikungunya viral infection, a Dengue viral infection or a RSV viral infection or a virus-related condition, most particularly a RSV viral infection.

Further aspects of the present invention will be described herein after such as the use of new compounds of formula (Ie) as a medicament, a pharmaceutical composition and a synthetic process.

According to a particular embodiment, a subject-matter of the present document describes a compound of formula (I) as defined above, wherein the alkenylene group is a (E)-alkenylene group, m and m' are independently 0 or 1, $Y^2$ represents a —$CR^1R^2R^3$ group, wherein $R^1$, $R^2$ and $R^3$ independently represent a hydrogen atom, a fluorine atom or a ($C_1$-$C_2$)alkyl group, being understood that no more than one of $R^1$, $R^2$ and $R^3$ is a hydrogen atom, or $R^1$ and $R^2$ form together with the carbon atom bearing them a ($C_3$-$C_6$)cycloalkyl group, said ($C_3$-$C_6$)cycloalkyl group being optionally substituted by one or two halogen atoms and said ($C_3$-$C_6$)cycloalkyl group being optionally interrupted on said $R^1$ and/or $R^2$ by an oxygen atom, R and R' independently represent a halogen atom, a ($C_1$-$C_2$)alkyl group, a ($C_3$-$C_6$)cycloalkyl group, or a ($C_1$-$C_2$)alkoxy group, or any of its pharmaceutically acceptable salt, for use in the treatment and/or prevention of a RNA virus infection caused by a RNA virus belonging to group IV or V of the Baltimore classification, and in particular a Chikungunya viral infection a Dengue viral infection, an Influenza viral infection or a RSV viral infection or a virus-related condition.

According to a further embodiment, the present document describes a compound of formula (I)

(I)

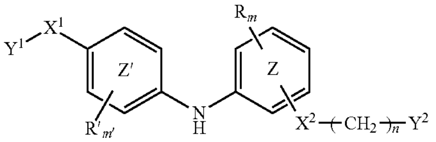

wherein:

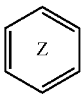

ring and

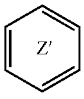

ring independently mean a phenylene or a pyridylene group, wherein the group $$-X^2-(CH_2)_n-Y^2$$

is m meta or para position on the

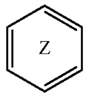

ring, with respect to the —NH— group, $X^1$ represents an alkenylene group, a —NH—CO— group, a —CO—NH— group, a —$CR_aR_bO$— group, $Y^1$ represents an aryl group selected from a 2-pyridyl group or a pyrimidinyl group, wherein one of the nitrogen atom of the pyrimidinyl group is in ortho position with respect to $X^1$, or alternatively $X^1$—$Y^1$ represents a group (A) of formula (A)

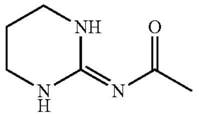

$X^2$ represents a —CO—NH— group, a —NH—CO—NH— group, a —$OCH_2$— group, a —NH—CO— group or a —$SO_2$—NH— group, n is 0, 1, 2 or 3, m and m' are independently 0, 1 or 2, $Y^2$ represents a hydrogen atom, a hydroxyl group or a —$CR^1R^2R^3$ group, wherein $R^1$, $R^2$ and $R^3$ independently represent a hydrogen atom, a fluorine atom or a ($C_1$-$C_4$)alkyl group, being understood that no more than one of $R^1$, $R^2$ and $R^3$ is a hydrogen atom, or $R^1$ and $R^2$ form together with the carbon atom bearing them a ($C_3$-$C_8$)cycloalkyl group, said ($C_3$-$C_8$)cycloalkyl group being optionally substituted by one or two ($C_1$-$C_4$)alkyl group, halogen atom or ($C_1$-$C_4$)alkoxy group and said ($C_3$-$C_5$)cycloalkyl group being optionally interrupted on said $R^1$ and/or $R^2$ by an oxygen atom, R and R' independently represent a halogen atom, a ($C_1$-$C_4$)alkyl group, a ($C_3$-$C_6$)cycloalkyl group, a ($C_1$-$C_5$)alkoxy group, a —$SO_2$—$NR_aR_b$ group, a —$SO_3H$ group, a —OH group, a —O—$SO_2$—$OR_c$ group or a —O—P(═O)—($OR_c$)($OR_d$) group, $R_a$, $R_b$, $R_c$ and $R_d$ independently represent a hydrogen atom or a ($C_1$-$C_4$)alkyl group, provided that when $X^1$ is a —$CR_aR_bO$— group, $Y^1$ may further be a 3-pyridyl, a 4-pyridyl or a phenyl group optionally substituted by one or two substituent(s) selected from a halogen atom, a ($C_1$-$C_4$)alkyl group, a cyano group, a ($C_1$-$C_5$)alkoxy group, a trifluoromethyl group, a trifluoromethoxy group, a —$SO_2$—$NR_aR_b$ group, a —$SO_3H$ group, a —OH group, a —O—$SO_2$—$OR_c$ group or a —O—P(═O)—($OR_c$)($OR_d$) group, and provided that when $Y^1$—$X^1$ represents a 2-pyridylethenylene group, $X^2$ represents a —CO—NH— group and $Y^2$ represents a —$CR^1R^2R^3$ group, wherein $R^1$, $R^2$ and $R^3$ independently represent a hydrogen atom or a ($C_1$-$C_4$)alkyl group, and m' is different from 0, or any of its pharmaceutically acceptable salt, for use in the treatment and/or prevention of a RNA virus infection caused by a RNA virus belonging to group IV or V of the Baltimore classification.

According to a particular embodiment, the present invention relates to a compound of formula (Ie) as defined above, wherein

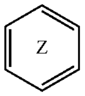

ring and

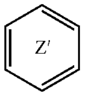

ring both represent a phenylene group or

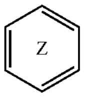

ring represents a pyridylene group and

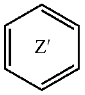

ring represents a phenylene group, or any of its pharmaceutically acceptable salt.

In another embodiment, the present invention relates to a compound of formula (Ie) as defined above, wherein m and m' are independently 0 or 1, $Y^2$ represents a —$CR^1R^2R^3$ group, wherein $R^1$, $R^2$ and $R^3$ independently represent a hydrogen atom, a fluorine atom or a ($C_1$-$C_2$)alkyl group, being understood that no more than one of $R^1$, $R^2$ and $R^3$ is a hydrogen atom, or $R^1$ and $R^2$ form together with the carbon atom bearing them a ($C_3$-$C_6$)cycloalkyl group, said ($C_3$-$C_6$)cycloalkyl group being optionally substituted by one or two halogen atom(s) and said ($C_3$-$C_6$)cycloalkyl group being optionally interrupted on said $R^1$ and/or $R^2$ by an oxygen atom, R and R' independently represent a halogen atom, a ($C_1$-$C_2$)alkyl group, a ($C_3$-$C_6$)cycloalkyl group, or a ($C_1$-$C_2$)alkoxy group, or any of its pharmaceutically acceptable salt.

In another embodiment, the present invention relates to the compound of formula (Ie), wherein R" is a hydrogen atom or any of its pharmaceutically acceptable salt.

In another embodiment, the present invention relates to the compound of formula (Ie), wherein $Y^1$ represents an aryl group selected from a phenyl group, a pyridyl group, a pyrazinyl group, a pyridazinyl or a pyrimidinyl group, said aryl group being optionally substituted by one or two substituent(s) selected from a halogen atom, a ($C_1$-$C_4$)alkyl group, a cyano group, a ($C_1$-$C_5$)alkoxy group, a trifluoromethyl group, a trifluoromethoxy group, or any of its pharmaceutically acceptable salt.

In another embodiment, the present invention relates to the compound of formula (Ie), wherein $X^2$ represents a —O— group, a —NH— group, a —S— group, a —CO—NH— group, a —NH—CO—NH— group, a —NH—CO— group, a divalent 5-membered heteroaromatic ring comprising 1, 2, 3 or 4 heteroatoms such as a triazole, a tetrazole or an oxadiazole, a —$SO_2$— group, or a —$SO_2$—NH— group, or any of its pharmaceutically acceptable salt.

In another embodiment, the present invention relates to the compound of formula (Ie), wherein $Y^2$ represents a hydrogen atom, a hydroxyl group, a —PO($OR_f$)($R'_f$) group, wherein $R_f$ and $R'_f$ independently represents a hydrogen atom or a ($C_1$-$C_4$)alkyl group, or a —$CR^1R^2R^3$ group, wherein $R^1$, $R^2$ and $R^3$ independently represent a hydrogen atom, a fluorine atom or a ($C_1$-$C_4$)alkyl group, being understood that no more than one of $R^1$, $R^2$ and $R^3$ is a hydrogen atom, or $R^1$ and $R^2$ form together with the carbon atom bearing them a ($C_3$-$C_8$)cycloalkyl group, said ($C_3$-$C_5$)cycloalkyl group being optionally substituted by one or two ($C_1$-$C_4$)alkyl group, halogen atom or ($C_1$-$C_4$)alkoxy group and said ($C_3$-$C_8$)cycloalkyl group being optionally interrupted on said $R^1$ and/or $R^2$ by an oxygen atom, or any of its pharmaceutically acceptable salt.

In another embodiment, the present invention relates to the compound of formula (Ie), wherein R and R' independently represent a ($C_1$-$C_4$)alkyl group, a ($C_3$-$C_6$)cycloalkyl group, a halogen atom, such as a fluoro atom, a trifluoromethyl group, or a —$SO_3H$ or $SO_2$—$CH_3$ group, or any of its pharmaceutically acceptable salt.

In another embodiment, the present invention relates to the compound of formula (Ie), wherein

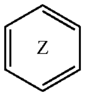

ring and

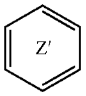

ring both represent a phenylene group,

R" is a hydrogen atom, $Y^1$ represents an aryl group selected from a phenyl group, a pyridyl group, a pyrazinyl group, a pyridazinyl or a pyrimidinyl group, said aryl group being optionally substituted by one or two substituent(s) selected from a halogen atom, a $(C_1-C_4)$alkyl group, a cyano group, a $(C_1-C_5)$alkoxy group, a trifluoromethyl group, a trifluoromethoxy group, $X^2$ represents
a —O— group,
a —CO—NH— group,
a —NH—CO—NH— group,
a —NH—CO— group,
a divalent 5-membered heteroaromatic ring comprising 1, 2, 3 or 4 heteroatoms such as a triazole, a tetrazole or an oxadiazole,
or
a $—SO_2—NH—$ group, $Y^2$ represents
a hydrogen atom,
a hydroxyl group,
a $—PO(OR_f)(R'_f)$ group, wherein $R_f$ and $R'_f$ independently represents a hydrogen atom or a $(C_1-C_4)$alkyl group,
or
a $—CR^1R^2R^3$ group, wherein $R^1$, $R^2$ and $R^3$ independently represent a hydrogen atom, a fluorine atom or a $(C_1-C_4)$alkyl group, being understood that no more than one of $R^1$, $R^2$ and $R^3$ is a hydrogen atom, or $R^1$ and $R^2$ form together with the carbon atom bearing them a $(C_3-C_8)$cycloalkyl group, said $(C_3-C_5)$cycloalkyl group being optionally substituted by one or two $(C_1-C_4)$alkyl group, halogen atom or $(C_1-C_4)$alkoxy group and said $(C_3-C_8)$cycloalkyl group being optionally interrupted on said $R^1$ and/or $R^2$ by an oxygen atom, and R and R' independently represent
a $(C_1-C_4)$alkyl group,
a $(C_3-C_6)$cycloalkyl group,
a halogen atom, such as a fluoro atom,
a trifluoromethyl group,
a $—SO_3H$ or $SO_2—CH_3$ group, or
a morpholinyl group, or any of its pharmaceutically acceptable salt.

In another embodiment, the present invention relates to the compound of formula (Ie), wherein

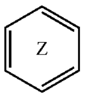

ring and

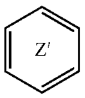

ring both represent a phenylene group,

R" is a hydrogen atom, $Y^1$ represents a phenyl group or a pyridyl group, $X^2$ represents
a —O— group,
a —CO—NH— group,
a —NH—CO— group,
or
a divalent 5-membered heteroaromatic ring comprising 1, 2, 3 or 4 heteroatoms such as a triazole, tetrazole or an oxadiazole, $Y^2$ represents
a $—PO(OR_f)(R'_f)$ group, wherein $R_f$ and $R'_f$ independently represents a hydrogen atom or a $(C_1-C_4)$alkyl group,
or
a $—CR^1R^2R^3$ group, wherein $R^1$, $R^2$ and $R^3$ independently represent a hydrogen atom, a fluorine atom or a $(C_1-C_4)$alkyl group, being understood that no more than one of $R^1$, $R^2$ and $R^3$ is a hydrogen atom, or $R^1$ and $R^2$ form together with the carbon atom bearing them a $(C_3-C_5)$cycloalkyl group, and R and R' independently represent
a $(C_1-C_4)$alkyl group,
a $(C_3-C_6)$cycloalkyl group, or
a morpholinyl group, or any of its pharmaceutically acceptable salt.

Any combination of the above-defined embodiments for R, R', R", m, m',

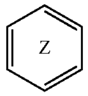

ring,

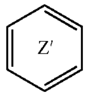

ring, $X^1$, $X^2$, n, $Y^1$, $Y^2$, $R_a$ and $R_b$ with each other does form part of the instant invention.

According to a preferred embodiment of the present invention, the compound of formula (Ie) is chosen from:

(36) N-(2-cyclopentylethyl)-3-((4-(pyridin-2-ylmethoxy)phenyl)amino)benzamide
(37) N-isopentyl-3-((4-(pyridin-2-ylmethoxy)phenyl)amino)benzamide
(38) N-(2-cyclohexylethyl)-3-((4-(pyridin-2-ylmethoxy)phenyl)amino)benzamide
(39) N-(2-cyclopentylethyl)-3-((2-methyl-4-(pyridin-2-ylmethoxy)phenyl)amino)benzamide
(40) N-(2-cyclopentylethyl)-3-((3-methyl-4-(pyridin-2-ylmethoxy)phenyl)amino)benzamide
(41) N-(2-cyclopentylethyl)-3-((6-(pyridin-2-ylmethoxy)pyridin-3-yl)amino)benzamide
(42) N-(2-cyclopentylethyl)-6-((4-(pyridin-2-ylmethoxy)phenyl)amino)picolinamide
(43) N-(2-cyclopentylethyl)-3-((3-methoxy-4-(pyridin-2-ylmethoxy)phenyl)amino)benzamide
(44) N-(2-cyclopentylethyl)-3-((5-(pyridin-2-ylmethoxy)pyridin-2-yl)amino)benzamide
(45) N-(2-cyclopropylethyl)-3-((2-methyl-4-(pyridin-2-ylmethoxy)phenyl)amino)benzamide
(46) N-(2-cyclobutylethyl)-3-((2-methyl-4-(pyridin-2-ylmethoxy)phenyl)amino)benzamide
(47) N-(2-cyclohexylethyl)-3-((2-methyl-4-(pyridin-2-ylmethoxy)phenyl)amino)benzamide
(48) N-(2-cyclobutylethyl)-3-((4-(pyridin-2-ylmethoxy)phenyl)amino)benzamide

(49) N-(2-cyclopropylethyl)-3-((4-(pyridin-2-ylmethoxy)phenyl)amino)benzamide
(50) N-(2-cyclopentylethyl)-3-((4-((2-fluorobenzyl)oxy)phenyl)amino)benzamide
(51) 3-((4-((2-cyanobenzyl)oxy)phenyl)amino)-N-(2-cyclopentylethyl)benzamide
(52) 3-((4-(benzyloxy)phenyl)amino)-N-(2-cyclopentylethyl)benzamide
(53) N-(2-cyclopentylethyl)-3-((3-hydroxy-4-(pyridin-2-ylmethoxy)phenyl)amino)benzamide
(54) N-isopentyl-3-((2-methyl-4-(pyridin-2-ylmethoxy)phenyl)amino)benzamide
(55) N-(2-cyclopentylethyl)-3-((4-(pyridin-2-ylmethoxy)phenyl)amino)benzenesulfonamide
(56) N-(2-cyclohexylethyl)-3-((4-(pyridin-2-ylmethoxy)phenyl)amino)benzenesulfonamide
(57) 3-((2-ethyl-4-(pyridin-2-ylmethoxy)phenyl)amino)-N-isopentylbenzamide
(58) N-(2-cyclopentylethyl)-3-((2-ethyl-4-(pyridin-2-ylmethoxy)phenyl)amino)benzamide
(59) N-(2-cyclopropylethyl)-3-((4-(pyridin-2-ylmethoxy)phenyl)amino)benzenesulfonamide
(60) N-(2-cyclopentylethyl)-3-((2-cyclopropyl-4-(pyridin-2-ylmethoxy)phenyl)amino)benzamide
(61) 3-((2-cyclopropyl-4-(pyridin-2-ylmethoxy)phenyl)amino)-N-isopentylbenzamide
(62) N-(cyclopentylmethyl)-3-((4-(pyridin-2-ylmethoxy)phenyl)amino)benzamide
(63) N-((3-methyloxetan-3-yl)methyl)-3-((4-(pyridin-2-ylmethoxy)phenyl)amino)benzamide
(64) N-(pentan-2-yl)-3-((4-(pyridin-2-ylmethoxy)phenyl)amino)benzamide
(65) 3-((4-(pyridin-2-ylmethoxy)phenyl)amino)-N-(3,3,3-trifluoropropyl)benzamide
(66) N-(2-cyclopentylethyl)-3-((2-methyl-4-(1-(pyridin-2-yl)ethoxy)phenyl)amino)benzamide
(67) N-isopentyl-3-((2-methyl-4-(1-(pyridin-2-yl)ethoxy)phenyl)amino)benzamide
(68) 1-isopentyl-3-(3-((2-methyl-4-(pyridin-2-ylmethoxy)phenyl)amino)phenyl)urea
(69) 3-((2-methyl-4-(pyridin-2-ylmethoxy)phenyl)amino)-N-(oxetan-3-yl)benzamide
(70) N-(2-(3,3-difluorocyclobutyl)ethyl)-3-((2-methyl-4-(pyridin-2-ylmethoxy)phenyl)amino)benzamide
(71) N-cyclopentyl-3-((2-methyl-4-(pyridin-2-ylmethoxy)phenyl)amino)benzamide
(72) 3-((2-methyl-4-(pyridin-2-ylmethoxy)phenyl)amino)-N-(4-methylpentyl)benzamide
(73) 3-(3-cyclopentylpropoxy)-N-(4-(pyridin-2-ylmethoxy)phenyl)aniline
(74) 3-((2-methylpentyl)oxy)-N-(4-(pyridin-2-ylmethoxy)phenyl)aniline
(75) N-(2-(cyclohexyl)ethyl)-3-((2-ethyl-4-(pyridin-2-ylmethoxy)phenyl)amino)benzamide
(76) N-(2-(cyclohexyl)ethyl)-3-((2-cyclopropyl-4-(pyridin-2-ylmethoxy)phenyl)amino)benzamide
(77) N-(1-methylbutyl)-3-((2-methyl-4-(pyridin-2-ylmethoxy)phenyl)amino)benzamide
(78) N-(1-methylbutyl)-3-((2-ethyl-4-(pyridin-2-ylmethoxy)phenyl)amino)benzamide
(79) N-(2-(cyclohexyl)ethyl)-3-((2-cyclopropyl-4-(pyridin-2-ylmethoxy)phenyl)amino)benzenesulfonamide
(80) (3-(cyclohexyl)propanamide), N-[3-([2-cyclopropyl-4-(pyridin-2-ylmethoxy)phenyl]amino)phenyl]-(81) N-(3-methylbutyl)-4-((2-cyclopropyl-4-(pyridin-2-ylmethoxy)phenyl)amino)benzamide
(82) N-(2-(cyclopentyl)ethyl)-3-((2-cyclopropyl-4-(phenylmethoxy)phenyl)amino)benzamide
(83) 3-(3-cyclohexylpropoxy)-N-(2-cyclopropyl-4-(pyridin-2-ylmethoxy)phenyl)aniline
(84) 3-((2-cyclopropyl-4-(pyridin-2-ylmethoxy)phenyl)amino)benzamide
(85) N-(2-cyclohexylethyl)-3-((2-cyclopropyl-4-(pyridin-3-ylmethoxy)phenyl)amino)benzamide
(86) N-(2-cyclohexylethyl)-6-((2-cyclopropyl-4-(pyridin-2-ylmethoxy)phenyl)amino)picolinamide
(87) 3-((2-cyclopropyl-4-(pyridin-2-ylmethoxy)phenyl)amino)benzenesulfonamide
(88) N-(2-cyclohexylethyl)-5-((2-cyclopropyl-4-(pyridin-2-ylmethoxy)phenyl)amino)nicotinamide
(89) N-(2-cyclopentylethyl)-3-((2-cyclopropyl-4-(pyridin-4-ylmethoxy)phenyl)amino)benzamide
(90) N-(2-cyclohexylethyl)-2-((2-cyclopropyl-4-(pyridin-2-ylmethoxy)phenyl)amino)isonicotinamide
(91) N-(3-{[4-(benzyloxy)-2-tert-butylphenyl]amino}phenyl)-3-cyclohexylpropanamide
(92) N-(3-{[4-(benzyloxy)-2-(cyclopent-1-en-1-yl)phenyl]amino}phenyl)-3-cyclohexylpropanamide
(93) N-(3-{[4-(benzyloxy)-2-cyclopentylphenyl]amino}phenyl)-3-cyclohexylpropanamide
(94) N-(3-{[4-(benzyloxy)-2-(methylsulfanyl)phenyl]amino}phenyl)-3-cyclohexylpropanamide
(95) N1-[4-(benzyloxy)-2-cyclopropylphenyl]-N3-(3-cyclohexylpropyl)benzene-1,3-diamine
(96) 1-(2-cyclohexylethyl)-3-[3-({2-cyclopropyl-4-[(pyridin-2-yl)methoxy]phenyl}amino)phenyl]urea
(97) 1-(3-{[4-(benzyloxy)-2-cyclopropylphenyl]amino}phenyl)-4-cyclohexylbutan-1-ol
(98) N-(3-{[4-(benzyloxy)-2-(trifluoromethyl)phenyl]amino}phenyl)-3-cyclohexylpropanamide
(99) 3-cyclohexyl-N-[3-({4-[(4-fluorophenyl)methoxy]-2-(trifluoromethyl)phenyl}amino)phenyl]propanamide
(100) N-{3-[4-(cyclohexylmethyl)-1H-1,2,3-triazol-1-yl]phenyl}-2-cyclopropyl-4-[(pyridin-2-yl)methoxy]aniline
(101) 2-{[4-(benzyloxy)-2-tert-butylphenyl]amino}-N-(2-cyclohexylethyl)benzamide
(102) 1-cyano-N-[3-({2-cyclopropyl-4-[(pyridin-2-yl)methoxy]phenyl}amino)-2-methylphenyl]cyclopropane-1-carboxamide
(103) 2-{[4-(benzyloxy)-2-cyclopropylphenyl]amino}-N-(3-cyclohexylpropyl)benzamide
(104) 3-{[4-(benzyloxy)-2-(trifluoromethyl)phenyl]amino}-N-(2-cyclopentylethyl)benzamide
(105) 4-(benzyloxy)-N-[3-(3-cyclohexylpropoxy)-2-methylphenyl]-2-cyclopropylaniline
(106) 2-cyclopropyl-N-{3-[(4-methylpentyl)oxy]phenyl}-4-[(pyridin-2-yl)methoxy]aniline
(107) N-(3-{[4-(benzyloxy)-2-methanesulfonylphenyl]amino}phenyl)-3-cyclohexylpropanamide
(108) N'1-[3-({2-cyclopropyl-4-[(pyridin-2-yl)methoxy]phenyl}amino)-2-methylphenyl]cyclopropane-1,1-dicarboxamide
(109) [3-({2-cyclopropyl-4-[(pyridin-2-yl)methoxy]phenyl}amino)-2-methylphenoxy]phosphonic acid
(110) 2-{[4-(benzyloxy)-2-cyclopropylphenyl]amino}-N-(cyclohexylmethyl)benzamide
(111) N-(2-cyclohexylethyl)-3-({2-cyclopropyl-4-[(pyridin-2-yl)methoxy]phenyl}(methyl)amino)benzamide
(112) 2-cyclopropyl-N-{3-[4-(3-methylbutyl)-1H-1,2,3-triazol-1-yl]phenyl}-4-[(pyridin-2-yl)methoxy]aniline
(113) N-(cyclopentylmethyl)-2-({2-cyclopropyl-4-[(pyridin-2-yl)methoxy]phenyl}amino)benzamide (114) 4-(benzyloxy)-N-[3-(3-cyclohexylpropoxy)phenyl]-2-(morpholin-4-yl)aniline (115) 2-{[4-(benzyloxy)-2-cyclopropylphenyl]amino}-N-(2-cyclohexylethyl)benzamide (116) N-(5-{[4-(benzyloxy)-2-(trifluoromethyl)phenyl]amino}-2-fluorophenyl)-3-cyclohexylpropanamide (117) N-(2-cyclohexylethyl)-4-({2-cyclopropyl-4-[(pyridin-2-yl)methoxy]phenyl}amino)pyridine-2-carboxamide (118) N-{3-[1-(3-cyclohexylpropyl)-1H-1,2,3,4-tetrazol-5-yl]phenyl}-2-cyclopropyl-4-[(pyridin-2-yl)methoxy]aniline (119) 4-(benzyloxy)-N-[3-(3-cyclohexylpropoxy)phenyl]-2-(propan-2-yl)aniline (120) 2-({2-cyclopropyl-4-[(pyridin-2-yl)methoxy]phenyl}amino)-N-(3,3,3-trifluoropropyl)benzamide (121) 3-cyclohexyl-N-[2-fluoro-5-({4-[(4-fluorophenyl)methoxy]-2-methylphenyl}amino)phenyl]propanamide (122) 4-(benzyloxy)-N-[2-(3-cyclohexylpropanesulfonyl)phenyl]-2-cyclopropylaniline (123) 2-({2-cyclopropyl-4-[(pyridin-2-yl)methoxy]phenyl}amino)-N-(3-methylbutyl)benzamide (124) 3-{[4-(benzyloxy)-2-(trifluoromethyl)phenyl]amino}-N-(2-cyclohexylethyl)benzene-1-sulfonamide (125) 3-cyclohexyl-N-[2-fluoro-5-({4-[(4-fluorophenyl)methoxy]-2-(trifluoromethyl)phenyl}amino)phenyl]propanamide (126) 2-cyclopropyl-N-{3-[1-(4-methylpentyl)-1H-1,2,3,4-tetrazol-5-yl]phenyl}-4-[(pyridin-2-yl)methoxy]aniline (127) 2-cyclopropyl-N-{3-[5-(3-methylbutyl)-1,2,4-oxadiazol-3-yl]phenyl}-4-[(pyridin-2-yl)methoxy]aniline (128) 2-{[4-(benzyloxy)-2-cyclopropylphenyl]amino}-6-cyano-N-(propan-2-yl)benzamide (129) N-{3-[5-(2-cyclohexylethyl)-1,2,4-oxadiazol-3-yl]phenyl}-2-cyclopropyl-4-[(pyridin-2-yl)methoxy]aniline (130) N-{3-[5-(2-cyclohexylethyl)-1,3,4-oxadiazol-2-yl]phenyl}-2-cyclopropyl-4-[(pyridin-2-yl)methoxy]aniline (131) 2-(azetidin-1-yl)-4-(benzyloxy)-N-[3-(3-cyclohexylpropoxy)phenyl]aniline (132) N-(3-{[4-(benzyloxy)-2-methylphenyl]amino}phenyl)-3-cyclohexylpropanamide (133) [3-({2-cyclopropyl-4-[(pyridin-2-yl)methoxy]phenyl}amino)phenoxy]phosphonic acid (134) tert-butyl 4-[3-({2-cyclopropyl-4-[(pyridin-2-yl)methoxy]phenyl}amino)benzoyl]piperazine-1-carboxylate (135) 2-(3-{[4-(benzyloxy)-2-cyclopropylphenyl]amino}phenyl)-2-[(2-cyclohexylethyl)amino]aceticacid (136) N-(1-cyanocyclopropyl)-2-({2-cyclopropyl-4-[(pyridin-2-yl)methoxy]phenyl}amino)benzamide (137) N-(3-cyclobutoxyphenyl)-2-cyclopropyl-4-[(pyridin-2-yl)methoxy]aniline (138)methyl 2-(3-{[4-(benzyloxy)-2-cyclopropylphenyl]amino}phenyl)-2-[(2-cyclohexylethyl)amino]acetate (139) 2-{[4-(benzyloxy)-2-methylphenyl]amino}-N-(2-cyclohexylethyl)benzamide (140) 3-cyclohexyl-N-[3-({4-[(4-fluorophenyl)methoxy]-2-methylphenyl}amino)phenyl]propanamide (141) 2-cyclopropyl-4-[(pyridin-2-yl)methoxy]-N-{3-[(trimethylsilyl)oxy]phenyl}aniline (142) 4-(benzyloxy)-N-[3-(3-cyclohexylpropanesulfonyl)phenyl]-2-cyclopropylaniline (143) N-(2-cyclohexylethyl)-2-[(2-cyclopropyl-4-{[4-(trifluoromethoxy)phenyl]methoxy}phenyl)amino]pyridine-4-carboxamide (144) tert-butyl N-[2-(3-{[4-(benzyloxy)-2-methylphenyl]amino}phenoxy)ethyl]carbamate (145) 2-cyclopropyl-N-{3-[4-(2-methylpropyl)-1H-1,2,3-triazol-1-yl]phenyl}-4-[(pyridin-2-yl)methoxy]aniline (146) N-(5-{[4-(benzyloxy)-2-methylphenyl]amino}-2-fluorophenyl)-3-cyclohexylpropanamide (147) 2-cyclopropyl-N-{3-[2-(2-methylpropyl)-2H-1,2,3,4-tetrazol-5-yl]phenyl}-4-[(pyridin-2-yl)methoxy]aniline (148) N-[3-(3-cyclohexylpropoxy)phenyl]-2-methyl-4-[(pyridazin-3-yl)methoxy]aniline (149) 4-(benzyloxy)-N-{3-[(3-cyclohexylpropyl)sulfanyl]phenyl}-2-cyclopropylaniline (150) N-(3-{[4-(benzyloxy)-2-fluorophenyl]amino}phenyl)-3-cyclohexylpropanamide (151) 2-cyclopropyl-N-[3-(oxetan-3-yloxy)phenyl]-4-[(pyridin-2-yl)methoxy]aniline (152) N-[3-(3-cyclohexylpropoxy)phenyl]-2-methyl-4-[(pyrimidin-2-yl)methoxy]aniline (153) 3-cyclohexyl-N-{3-[(2-methyl-4-{[4-(trifluoromethoxy)phenyl]methoxy}phenyl)amino]phenyl}propanamide (154) 4-(benzyloxy)-N-[2-(3-cyclohexylpropoxy)phenyl]-2-cyclopropylaniline (155) 2-(3-{[4-(benzyloxy)-2-cyclopropylphenyl]amino}phenyl)-4-cyclohexylbutane-1,2-diol (156) N-[3-(3-cyclohexylpropoxy)phenyl]-2-cyclopropyl-N-methyl-4-[(pyridin-2-yl)methoxy]aniline (157) 3-({2-cyclopropyl-4-[(pyridin-2-yl)methoxy]phenyl}amino)phenyl diethyl phosphate (158) N-(2-cyclohexylethyl)-3-[(2-cyclopropyl-4-{[4-(trifluoromethoxy)phenyl]methoxy}phenyl)amino]benzene-1-sulfonamide (159) N-[3-(3-cyclohexylpropoxy)phenyl]-2-methyl-4-[(pyrimidin-4-yl)methoxy]aniline (160) 3-({2-cyclopropyl-4-[(pyridin-2-yl)methoxy]phenyl}amino)-2-methylphenyl diethyl phosphate (161) 2-cyclopropyl-N-{3-[2-(3-methylbut-2-en-1-yl)-2H-1,2,3,4-tetrazol-5-yl]phenyl}-4-[(pyridin-2-yl)methoxy]aniline (162) 2-cyclopropyl-N-{3-[2-(2-methoxyethyl)-2H-1,2,3,4-tetrazol-5-yl]phenyl}-4-[(pyridin-2-yl)methoxy]aniline (163) 2-cyclopropyl-N-{3-[1-(cyclopropylmethyl)-1H-1,2,3,4-tetrazol-5-yl]phenyl}-4-[(pyridin-2-yl)methoxy]aniline (164) 4-(benzyloxy)-N-[3-(3-cyclohexylpropoxy)phenyl]-2-(oxan-4-yl)aniline (165) 4-(benzyloxy)-N-[3-(3-cyclohexylpropoxy)phenyl]-2-(3,6-dihydro-2H-pyran-4-yl)aniline (166) 5-(3-cyclohexylpropoxy)-N-{2-cyclopropyl-4-[(pyridin-2-yl)methoxy]phenyl}pyridin-3-amine (167) 4-(benzyloxy)-N-{2-[(3-cyclohexylpropyl)sulfanyl]phenyl}-2-cyclopropylaniline (167) 5-(3-cyclohexylpropoxy)-N-{2-cyclopropyl-4-[(pyridin-2-yl)methoxy]phenyl}pyridin-3-amine (168) 5-{[4-(benzyloxy)-2-(trifluoromethyl)phenyl]amino}-2-fluorobenzamide (169) 3-cyclohexyl-N-{3-[(2-cyclopropyl-4-{[4-(trifluoromethyl)phenyl]methoxy}phenyl)amino]phenyl}propanamide (170) 3-cyclohexyl-N-[3-({2-cyclopropyl-4-[(4-methoxyphenyl)methoxy]phenyl}amino)phenyl]propanamide (171) 2-(3-{[4-(benzyloxy)-2-methylphenyl]amino}phenoxy)ethan-1-ol (172) 4-(benzyloxy)-N-[3-(3-cyclohexylpropoxy)phenyl]aniline (173) ethyl 5-(3-{[4-(benzyloxy)-2-methylphenyl]amino}phenoxy)pentanoate (174) 4-(benzyloxy)-N-[3-(2-methoxyethoxy)phenyl]-2-methylaniline (175) 4-(benzyloxy)-N-[3-(cyclopentylmethoxy)phenyl]-2-methylaniline (176) N-[3-(3-cyclohexylpropoxy)phenyl]-2-methyl-4-[(pyrimidin-5-yl)methoxy]aniline (177) 4-(benzyloxy)-N-[3-(3-cyclohexylpropoxy)phenyl]-2-methylaniline (178) 3-{1-[3-({2-cyclopropyl-4-[(pyridin-2-yl)methoxy]phenyl}amino)phenyl]-1H-1,2,3-triazol-4-yl}propan-1-ol (179) 2-cyclopropyl-N-[3-(1,3-oxazol-5-yl)phenyl]-4-[(pyridin-2-yl)methoxy]aniline (180) 2-{[4-(benzyloxy)-2-cyclopropylphenyl]amino}-6-methyl-N-(propan-2-yl)benzamide (181) 2-{[4-(benzyloxy)-2-cyclopropylphenyl]amino}-N-(propan-2-yl)-6-(trifluoromethyl)benzamide (182) [3-({2-cyclopropyl-4-[(pyridin-2-yl)methoxy]phenyl}amino)phenoxy](methoxy)phosphinic acid (183) 5-(benzyloxy)-2-{[3-(3-cyclohexylpropoxy)phenyl]amino}benzonitrile (184) 2-{[4-(benzyloxy)phenyl]amino}-N-(2-cyclohexylethyl)benzamide (185) 4-(benzyloxy)-N-[3-(3-cyclohexylpropoxy)-4-methylphenyl]-2-cyclopropylaniline (186) 4-(benzyloxy)-N-[3-(3-cyclohexylpropoxy)-5-methylphenyl]-2-cyclopropylaniline (187) 4-(benzyloxy)-N-[5-(3-cyclohexylpropoxy)-2-methylphenyl]-2-cyclopropylaniline (188) 4-{[4-(benzyloxy)-2-cyclopropylphenyl]amino}-2-(3-cyclohexylpropoxy)benzamide (189) 3-{[4-(benzyloxy)-2-cyclopropylphenyl]amino}-5-(3-cyclohexylpropoxy)benzamide (190) N-(2-{[4-(benzyloxy)-2-cyclopropylphenyl]amino}phenyl)-3-cyclohexylpropanamide (191) 3-{[4-(benzyloxy)-2-methylphenyl][3-(3-cyclohexylpropoxy)phenyl]amino}propanoic acid (192) 2-(3-{[4-(benzyloxy)-2-methylphenyl]amino}phenoxy)acetic acid (193) 5-(3-{[4-(benzyloxy)-2-methylphenyl]amino}phenoxy)pentanoic acid (194) methyl 2-(3-{[4-(benzyloxy)-2-methylphenyl]amino}phenoxy)acetate (195) 4-(benzyloxy)-2-methyl-N-[3-(trifluoromethoxy)phenyl]aniline (196) 4-(benzyloxy)-2-methyl-N-{3-[(oxan-4-yl)methoxy]phenyl}aniline (197) 4-(3-cyclohexylpropoxy)-N-{2-methyl-4-[(pyridin-3-yl)methoxy]phenyl}pyridin-2-amine (198) 6-(3-cyclohexylpropoxy)-N-{2-methyl-4-[(pyridin-3-yl)methoxy]phenyl}pyridin-2-amine (199) N-[4-(benzyloxy)-2-methylphenyl]-4-(3-cyclohexylpropoxy)pyridin-2-amine (200) N-[4-(benzyloxy)-2-methylphenyl]-6-(3-cyclohexylpropoxy)pyridin-2-amine (201) N-[3-(3-cyclohexylpropoxy)phenyl]-2-methyl-4-[(pyrazin-2-yl)methoxy]aniline (202) N-(5-{[4-(benzyloxy)-2-fluorophenyl]amino}-2-fluorophenyl)-3-cyclohexylpropanamide (203) N-[3-(morpholin-4-yl)propyl]-3-({4-[(pyridin-2-yl)methoxy]phenyl}amino)benzamide (204) 2-cyclopropyl-4-[(pyridin-2-yl)methoxy]-N-[3-(1H-1,2,3,4-tetrazol-5-yl)phenyl]aniline (205) 2-{[4-(benzyloxy)-2-cyclopropylphenyl]amino}-6-cyclopropyl-N-(propan-2-yl)benzamide (206) 2-{[4-(benzyloxy)-2-cyclopropylphenyl]amino}-6-chloro-N-(propan-2-yl)benzamide and their pharmaceutically acceptable salts.

The present invention extends to compounds (36) to (206) and their pharmaceutically acceptable salts, such as hydrobromide, tartrate, citrate, trifluoroacetate, ascorbate, hydrochloride, tosylate, triflate, maleate, mesylate, formate, acetate and fumarate.

According to another aspect, a subject-matter of the present invention relates to compounds (36) to (206) or any of its pharmaceutically acceptable salts, for use as a medicament.

According to another aspect, a subject-matter of the present invention relates to a compound of formula (Ie) as defined above or any of its pharmaceutically acceptable salts, and any of compounds (36) to (206) or any of its pharmaceutically acceptable salts, for use as an agent for preventing, inhibiting or treating a RNA virus infection caused by a RNA virus belonging to group IV or V of the Baltimore classification.

Compounds (38), (40), (43), (45), (46), (48), (49), (61), (62), (64), (35), (68), (82), (98), (119), (121), (132), (140), (150), (151), (156), (169), (175), (176) and (192) or any of its pharmaceutically acceptable salts may be particularly useful for preventing, inhibiting or treating dengue infection.

Compounds (36), (38), (39), (45), (46), (47), (54), (57), (60), (61), (64), (68), (70), (71), (72), (75)-(80), (82)-(86), (88)-(142), (147)-(156), (164)-(166) and (179) or any of its pharmaceutically acceptable salts may be particularly useful for preventing, inhibiting or treating RSV infection.

Compounds (36)-(41), (43), (45)-(52), (53), (54), (57), (58), (60)-(62), (64), (68), (70), (71) and (73) or any of its pharmaceutically acceptable salts may be particularly useful for preventing, inhibiting or treating Chikungunya infection.

The compounds of the invention may exist in the form of free bases or of addition salts with pharmaceutically acceptable acids.

«Pharmaceutically acceptable salt thereof» refers to salts which are formed from acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, naphthalene disulfonic acid, and poly-galacturonic acid.

Suitable physiologically acceptable acid addition salts of compounds of formula (Ie) include hydrobromide, tartrate, citrate, trifluoroacetate, ascorbate, hydrochloride, tosylate, triflate, maleate, mesylate, formate, acetate and fumarate.

The compounds of formula (Ie) and any of compounds (36) to (206) or any of their pharmaceutically acceptable salts may form solvates or hydrates and the invention includes all such solvates and hydrates.

The compounds of formula (Ie) may be present as well under tautomer forms and are part of the invention.

The terms "hydrates" and "solvates" simply mean that the compounds (Ie) according to the invention can be in the form of a hydrate or solvate, i.e. combined or associated with one or more water or solvent molecules. This is only a chemical characteristic of such compounds, which can be applied for all organic compounds of this type.

In the context of the present invention, the term:

"halogen" is understood to mean chlorine, fluorine, bromine, or iodine, and in particular denotes chlorine, fluorine or bromine, "$(C_1-C_x)$alkyl", as used herein, respectively refers to a $C_1-C_x$ normal, secondary or tertiary saturated hydrocarbon, for example ($C_1$-$C_6$)alkyl. Examples are, but are not limited to, methyl, ethyl, 1-propyl, 2-propyl, butyl, pentyl, an "alkenylene" means a divalent ($C_1$-$C_x$)alkyl group comprising a double bond, and more particularly a ethenylene group, also known as vinylene or 1,2-ethenediyl, "($C_3$-$C_6$)cycloalkyl", as used herein, refers to a cyclic saturated hydrocarbon. Examples are, but are not limited to, cyclopropyl, cyclobutyl, cyclopentyl, cyclohexyl, "($C_3$-$C_6$)cycloalkenyl", as used herein, refers to a cyclic non aromatic hydrocarbon comprising at least one unsaturated bond. Examples are, but not limited to, cyclopentenyl and cyclohexenyl, "($C_1$-$C_x$)alkoxy", as used herein, refers to a 0-($C_1$-$C_x$) alkyl moiety, wherein alkyl is as defined above, for example ($C_1$-$C_6$)alkoxy. Examples are, but are not limited to, methoxy, ethoxy, 1-propoxy, 2-propoxy, butoxy, pentoxy, "aryl", as used herein, refers to a monocyclic aromatic group containing 6 carbon atoms and containing between 0 and 2 heteroatoms, such as nitrogen, oxygen or sulphur, and in particular nitrogen. By way of examples of aryl groups, mention may be made of, but not limited to: phenyl, pyridine, pyrimidine, pyridazine, pyrazine and the like. In the framework of the present invention, the aryl is advantageously phenyl, pyridazine, pyrazine, pyridine, such as 2-pyridine or 3-pyridine and pyrimidine. The aryl is even more advantageously phenyl and pyridine, a "divalent 5-membered heteroaromatic ring comprising 1, 2, 3 or 4 heteroatoms" as used herein, means a divalent ring consisting of an aromatic ring comprising 5 chains and 1, 2, 3 or 4 heteroatoms selected from nitrogen and oxygen atoms. In one embodiment, it comprises at least 1 heteroatom, and preferably at least one nitrogen atom. In another embodiment, it comprises at least 2 heteroatoms, with for example at least one nitrogen atom. According to a further embodiment, it comprises 2, 3 or 4 nitrogen atoms, preferably 3 nitrogen atoms. According to an even further embodiment, it comprises one nitrogen atom and one oxygen atom or two nitrogen atoms and one oxygen atom. Examples are, but not limited to, divalent triazole, such as 1,2,3- or 1,2,4-triazoles, oxadiazoles, such as 1,2,4-oxadiazole or 1,2,3-oxadiazole and divalent diazoles such as diazole and imidazole.

The compounds of formula (Ie) can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

The compounds of the present invention can be prepared by conventional methods of organic synthesis practiced by those skilled in the art. The general reaction sequences outlined below represent a general method useful for preparing the compounds of the present invention and are not meant to be limiting in scope or utility.

The compounds of general formula (I) and (Ie) can be prepared according to scheme 1 below.

Scheme 1

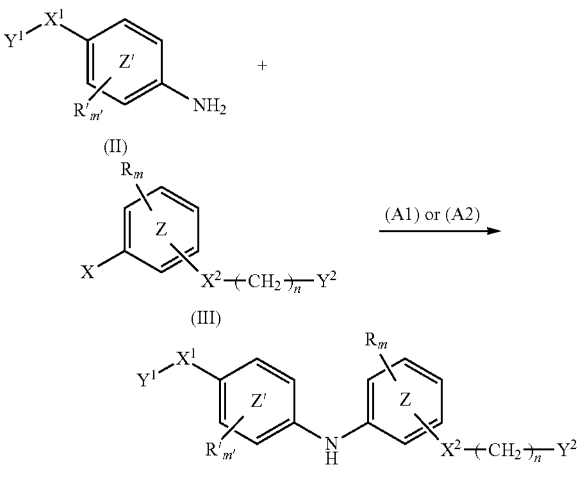

(II)
(III)
(I)

The synthesis is based on a coupling reaction starting from a halogeno aromatic compound of formula (III), wherein R, R', m, m',

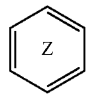

ring,

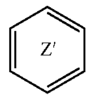

ring, $X^1$, $X^2$, n, $Y^1$, $Y^2$ are as defined above and X is a chlorine atom, an iodine atom or a bromine atom.

According to one embodiment, procedure (A1) may advantageously be used when the group $$-X^2-(CH_2)_n-Y^2$$

is meta or para position on the

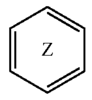

ring, with respect to the —NH— group.

According to route (A1), the compound of formula (III) may be placed in a protic solvent such as tert-butanol. The compound of formula (II) may then be added, for example in a molar ratio ranging from 1 to 1.5 with respect to the compound of formula (III) in presence of an inorganic base, such as $Cs_2CO_3$ or $K_2CO_3$, for example in a molar ratio ranging from 1 to 5 still with respect to the compound of formula (III), in the presence of a diphosphine, such as Xantphos (4,5-Bis(diphenylphosphino)-9,9-dimethylxanthine), X-Phos (2-Dicyclohexylphosphino-2',4',6'-triisopropylbiphenyl) or rac-BINAP in particular in an amount ranging from 2 mol % to 15 mol % relative to the total amount of compound of formula (III), and in the presence of an organometallic catalyst, such as $Pd(OAc)_2$, $Pd_2dba_3$ or BrettPhos Pd G3, in an amount ranging from 2 mol % to 25 mol % relative to the total amount of compound of formula (III). The reaction mixture can then be heated at a temperature ranging from 80 to 130° C., for example at 90° C., and stirred for a time ranging from 15 to 25 hours, for example during 20 hours, under inert gas and for example argon. The reaction mixture can be concentrated under reduced pressure and the residue can be diluted with an organic solvent such as ethyl acetate. The organic phase can be washed with water, decanted, dried over magnesium sulphate, filtered and then concentrated under reduced pressure to give a compound of formula (I) and (Ie).

According to one embodiment, procedure (A2) may advantageously be used when the group $$-X^2-(CH_2)_n-Y^2$$

is in ortho position on the

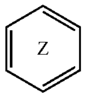

ring, with respect to the —NH— group.

According to procedure (A2), the compound of formula (II) may be placed in a polar aprotic solvent such as dimethylsulfoxide. The compound of formula (III) may then be added, for example in a molar ratio ranging from 1 to 1.5 with respect to the compound of formula (II) in presence of an inorganic base, such as $Cs_2CO_3$ or $K_2CO_3$, for example in a molar ratio ranging from 1 to 5 still with respect to the compound of formula (II), in the presence of a ligand, such as L-proline in particular in an amount ranging from 2 mol % to 25 mol % relative to the total amount of compound of formula (II), and in the presence of an organometallic catalyst, such as CuI, in an amount ranging from 2 mol % to 25 mol % relative to the total amount of compound of formula (II). The reaction mixture can then be heated at a temperature ranging from 80 to 130° C., for example at 90° C., and stirred for a time ranging from 15 to 25 hours, for example during 20 hours, under inert gas and for example argon. The reaction mixture can be diluted with an organic solvent such as ethyl acetate. The organic phase can be washed with water, decanted, dried over magnesium sulphate, filtered and then concentrated under reduced pressure to give a compound of formula (I) and (Ie).

The starting compounds of formula (II), (III) are available or can be prepared according to methods known to the person skilled in the art.

Accordingly, the present document further describes the synthesis process for manufacturing new compounds of formula (I) and (Ie) as defined above, comprising at least a step of coupling a compound of formula (II)

(II)

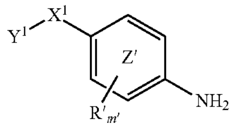

with a compound of formula (III)

(III)

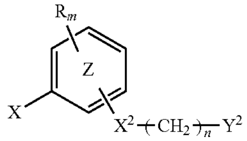

wherein $X^1$, $Y^1$, R, R', m, m',

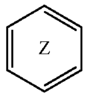

ring,

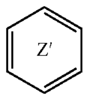

ring, $X^2$, $Y^2$ are as defined above and X is a chlorine atom, an iodine atom or a bromine atom, in presence of an inorganic base and a diphosphine and in the presence of an organometallic catalyst, to obtain a compound of formula (I) or (Ie).

The compounds of general formula (Ie) according to the invention can be prepared according to scheme 1' below.

Scheme 1'

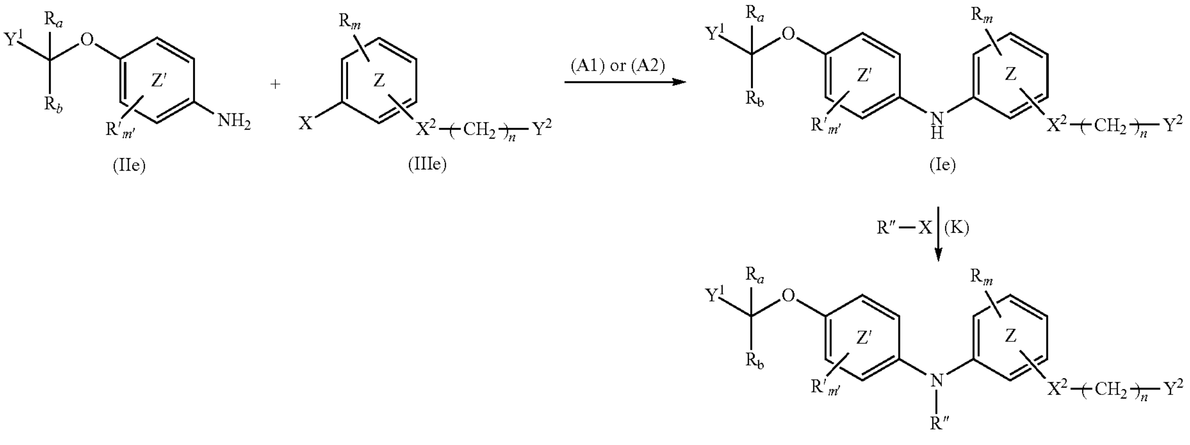

(IIe) (IIIe) (Ie)

(Ie)

For (Ic) when R'' ≠ H

The synthesis is based on a coupling reaction starting from a halogeno aromatic compound of formula (IIIe) with a compound of formula (IIe), wherein R, R', R'', m, m',

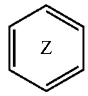

ring,

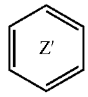

ring, $X^1$, $X^2$, n, $Y^1$, $Y^2$, $R_a$ and $R_b$ are as defined above and X is a chlorine atom, an iodine atom or a bromine atom.

More particularly, the present invention relates to the synthesis process for manufacturing the compounds of formula (Ie) as defined above, comprising at least a step of coupling a compound of formula (IIe)

(IIe)

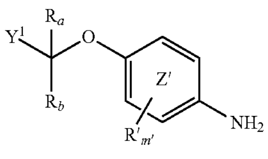

with a compound of formula (IIIe)

(IIIe)

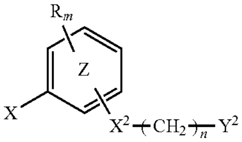

wherein $X^1$, $Y^1$, R, R', m, m',

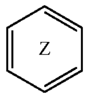

ring,

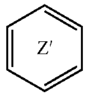

ring, $X^2$, $Y^2$ $R_a$ and $R_b$ are as defined above X is a chlorine atom, an iodine atom or a bromine atom and $Y^1$ is a phenyl group, a pyridine group, a pyrazine group, a pyridazine group or a pyrimidine group, in presence of an inorganic base and a ligand and in the presence of an organometallic catalyst, to obtain a compound of formula (Ie).

To afford (Ie) when R''≠H, an additional step (K) may be implemented, in which the compound can be placed in an anhydrous polar solvent such as anhydrous N,N-dimethylformamide in the presence of NaH in a molar ratio ranging from 2 to 5, for example 3, and the reaction mixture can be stirred at room temperature for a time ranging from 10 minutes to 50 minutes, for example 30 minutes. The halide derivative R''—X can then be added and the resulting reaction mixture can be stirred at a temperature ranging from 70 to 110° C., for example at 90° C., for a time ranging from 2 hours to 10 hours, for example 5 hours. Upon cooling to room temperature, the reaction mixture can be concentrated under reduced pressure and the resulting residue can be diluted with an organic solvent such as ethyl acetate. The organic phase can then be washed with a saturated aqueous solution of brine, dried over $MgSO_4$, filtered and concentrated under reduced pressure to give a compound of formula (Ie) where R"≠H.

More particularly, compounds of formula (IIe), when used to prepare compounds of formula (Ie) with $R_a$=$R_b$=H, can be prepared according to scheme 6 below. In the case where either $R_a$ or $R_b$≠H, a route starting from the 4-nitrophenol derivative and the suitable alcohol derivative and using classical Mitsunobu conditions can generate such compounds, and for example compounds 66 and 67 as defined in table I herein after.

Preparation of (IIe) for (Ie)

Scheme 6

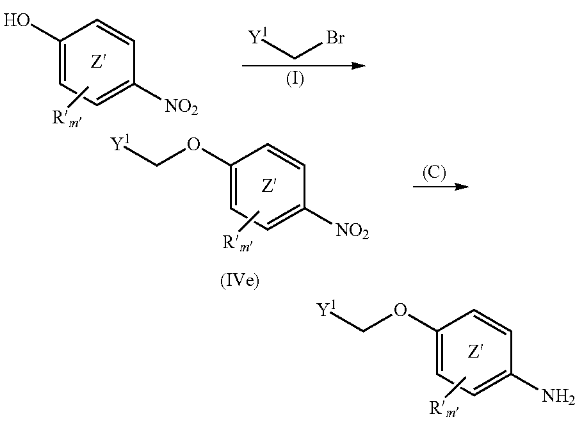

(IVe)

(IIe)

to the 4-nitrophenol derivative in presence of an inorganic base, such as $Cs_2CO_3$ or $K_2CO_3$, for example in a molar ratio ranging from 1 to 5 still with respect to the 4-nitrophenol derivative. The reaction mixture can then be heated at a temperature ranging from 50 to 150° C., for example at 90° C. and stirred for a time ranging from 15 to 30 hours, for example during 24 hours, under inert gas and for example argon. The reaction mixture can be concentrated under reduced pressure and the residue can be partitioned between an organic solvent, such as dichloromethane, and water. The organic phase can be washed with water, decanted, dried over magnesium sulphate, filtered and concentrated under reduced pressure to give a compound of formula (IVe).

According to route (C), the compound of formula (IVe) and tin (II) chloride dihydrate in a ratio ranging from 3 to 8 equivalents are placed in a protic solvent such as ethanol. The reaction mixture can then be heated at a temperature ranging from 40 to 80° C., for example at 60° C. and stirred for a time ranging from 15 to 25 hours, for example during 20 hours. The mixture can be poured into 1N NaOH aqueous solution and extracted with an organic solvent such as ethyl acetate. The organic phase can then be washed with water and a saturated aqueous solution of brine, dried over magnesium sulphate, filtered and concentrated under reduced pressure to give a compound of formula (IIe).

More particularly, compounds of formula (IIe), when used to prepare compounds of formula (Ie) with $R_a$=$R_b$=H and with one R' group (i.e. $R_c$') being different from H and Me, can be prepared according to scheme 7 below.

Preparation of (IIe) for (e), when $R_c$'≠Me and $R_c$'≠H

Scheme 7

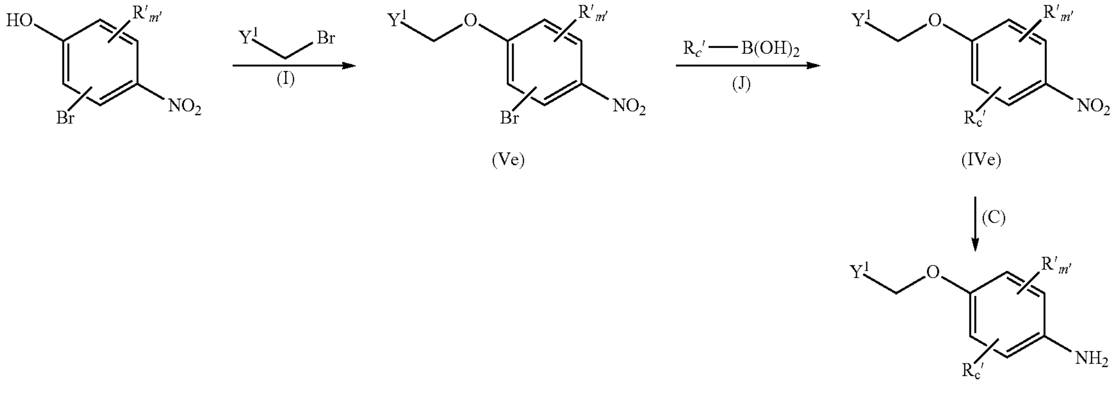

(Ve)

(IVe)

(IIe)

Intermediate compounds of formulae (IIe) and (IVe) are useful for preparing compounds of formula (Ie) according to the invention.

According to route (I), the 4-nitrophenol derivative may be placed in a polar solvent such as N,N-dimethylformamide. 2-(Bromomethyl)aryl derivative may then be added, for example in a molar ratio ranging from 1 to 2 with respect Intermediate compounds of formulae (IIe), (IVe) and (Ve) are useful for preparing compounds of formula (Ie) according to the invention.

According to route (I), the 4-nitrophenol derivative may be placed in a polar solvent such as N,N-dimethylformamide. 2-(Bromomethyl)aryl derivative may then be added, for example in a molar ratio ranging from 1 to 2 with respect to the 4-nitrophenol derivative in presence of an inorganic base, such as $Cs_2CO_3$ or $K_2CO_3$, for example in a molar ratio ranging from 1 to 5 still with respect to the 4-nitrophenol derivative. The reaction mixture can then be heated at a temperature ranging from 50 to 150° C., for example at 90° C. and stirred for a time ranging from 15 to 30 hours, for example during 24 hours, under inert gas and for example argon. The reaction mixture can be concentrated under reduced pressure and the residue can be partitioned between an organic solvent, such as dichloromethane, and water. The organic phase can be washed with water, decanted, dried over magnesium sulphate, filtered and concentrated under reduced pressure to give a compound of formula (Ve).

According to route (J), the compound of formula (Ve) and an organometallic catalyst such as $Pd(dppf)Cl_2 . CH_2Cl_2$ in an amount ranging from 2 mol % to 20 mol % relative to the amount of the compound of formula (Ve) may be placed in an apolar solvent such as 1,4-dioxane. A boronic acid $R_c'$—$B(OH)_2$ is then added, for example in a molar ratio ranging from 1 to 5 with respect to the compound of formula (Ve), in presence of an inorganic base, such as $K_3PO_4$ or $K_2CO_3$, for example in a molar ratio ranging from 2 to 5 still with respect to the compound of formula (Ve). The reaction mixture can then be heated at a temperature ranging from 50 to 150° C., for example at 100° C., and stirred for a time ranging from 10 to 70 hours, for example during 20 hours, under inert gas and for example argon. The reaction mixture can be concentrated under reduced pressure to give a compound of formula (IVe).

According to route (C), the compound of formula (IVe) and tin (II) chloride dihydrate in a ratio ranging from 3 to 8 equivalents may be placed in a protic solvent such as ethanol. The reaction mixture can then be heated at a temperature ranging from 40 to 80° C., for example at 60° C. and stirred for a time ranging from 15 to 25 hours, for example during 20 hours. The mixture can be poured into 1N NaOH aqueous solution and extracted with an organic solvent such as ethyl acetate. The organic phase can then be washed with water and a saturated aqueous solution of brine, dried over magnesium sulphate, filtered and concentrated under reduced pressure to give a compound of formula (IIe).

The chemical structures and spectroscopic data of some compounds of formula (Ie) of the invention are illustrated respectively in the following Table I and Table II.

TABLE I (Ie)

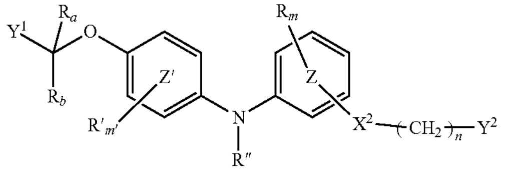

(Ie)

36

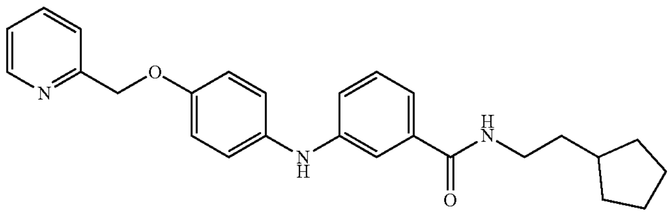 [SMILES: O=C(NCCC1CCCC1)c1cccc(Nc2ccc(OCc3ccccn3)cc2)c1]

37

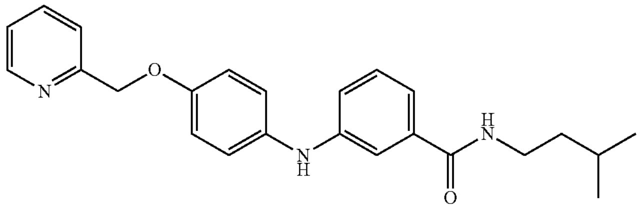 [SMILES: CC(C)CCNC(=O)c1cccc(Nc2ccc(OCc3ccccn3)cc2)c1]

38

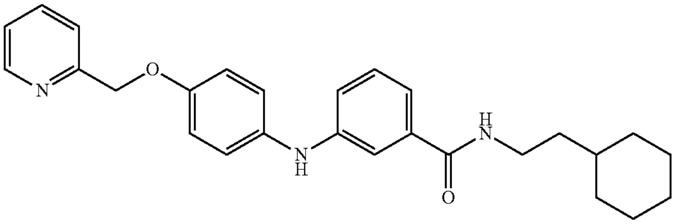 [SMILES: O=C(NCCC1CCCCC1)c1cccc(Nc2ccc(OCc3ccccn3)cc2)c1]

TABLE I-continued
(Ie)
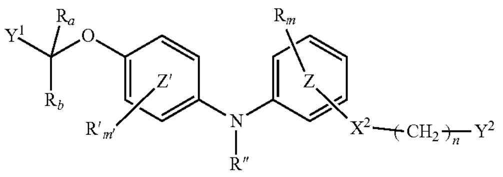
(Ie)
39
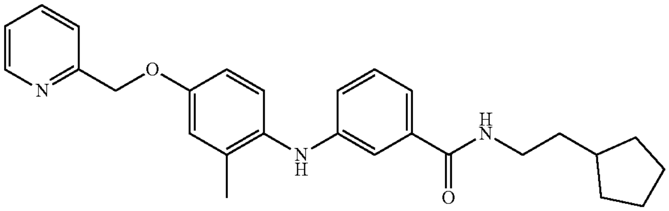 [SMILES: Cc1cc(OCc2ccccn2)ccc1Nc1cccc(C(=O)NCCC2CCCC2)c1]
40
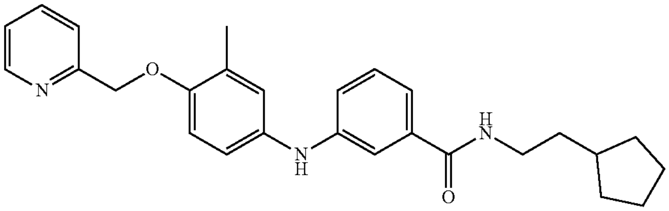 [SMILES: Cc1cc(Nc2cccc(C(=O)NCCC3CCCC3)c2)ccc1OCc1ccccn1]
41
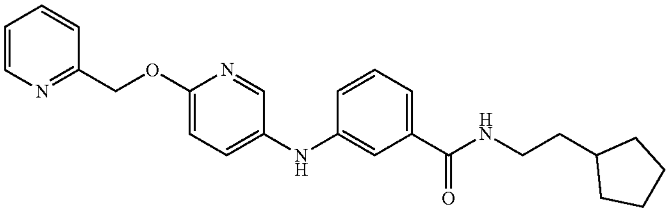 [SMILES: O=C(NCCC1CCCC1)c1cccc(Nc2ccc(OCc3ccccn3)nc2)c1]
42
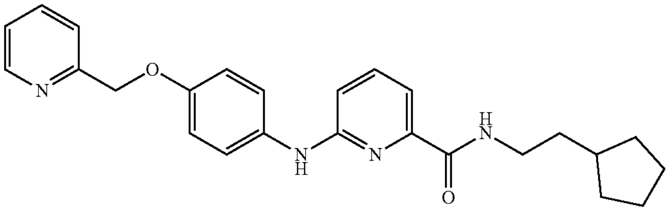 [SMILES: O=C(NCCC1CCCC1)c1cccc(Nc2ccc(OCc3ccccn3)cc2)n1]
43
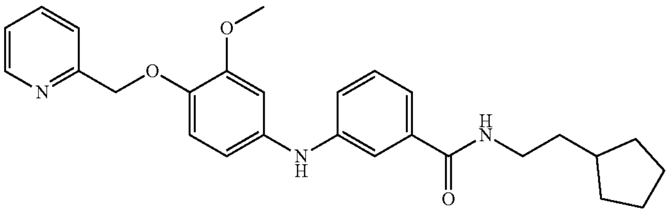 [SMILES: COc1cc(Nc2cccc(C(=O)NCCC3CCCC3)c2)ccc1OCc1ccccn1]
44
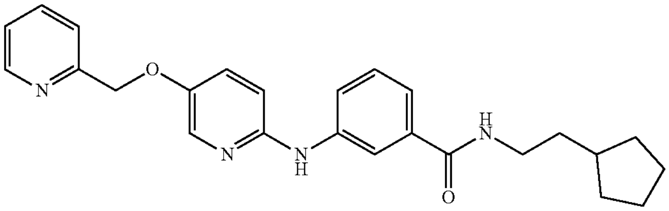 [SMILES: O=C(NCCC1CCCC1)c1cccc(Nc2ccc(OCc3ccccn3)cn2)c1]

TABLE I-continued
(Ie)
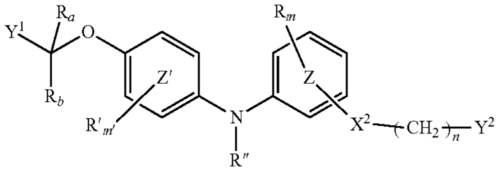
(Ie)
45
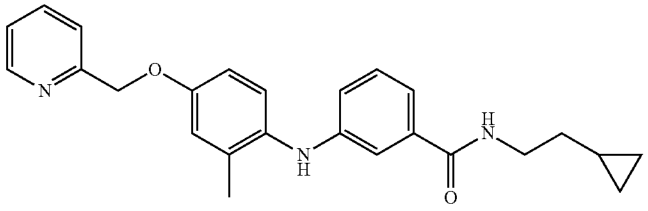
46
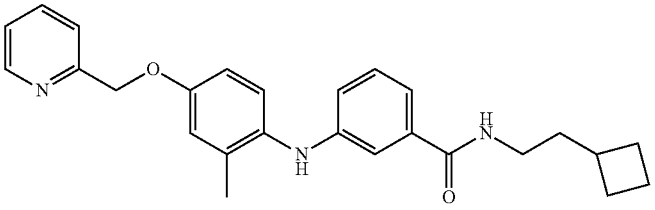 [SMILES: Cc1cc(OCc2ccccn2)ccc1Nc1cccc(C(=O)NCCC2CCC2)c1]
47
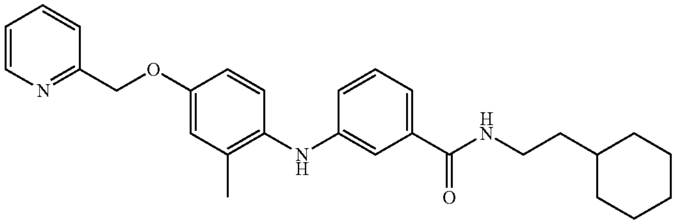 [SMILES: Cc1cc(OCc2ccccn2)ccc1Nc1cccc(C(=O)NCCC2CCCCC2)c1]
48
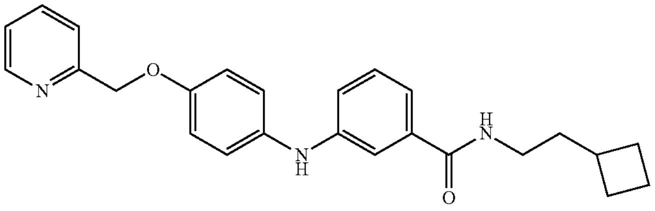 [SMILES: O=C(NCCC1CCC1)c1cccc(Nc2ccc(OCc3ccccn3)cc2)c1]
49
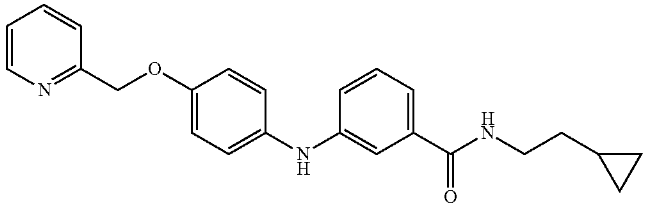 [SMILES: O=C(NCCC1CC1)c1cccc(Nc2ccc(OCc3ccccn3)cc2)c1]
50
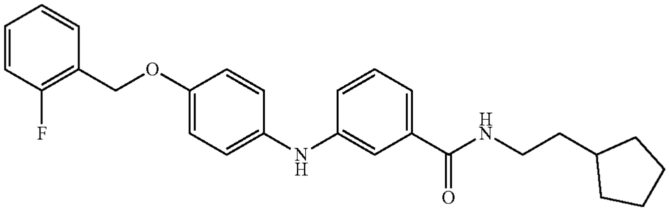 [SMILES: O=C(NCCC1CCCC1)c1cccc(Nc2ccc(OCc3ccccc3F)cc2)c1]

TABLE I-continued
(Ie)
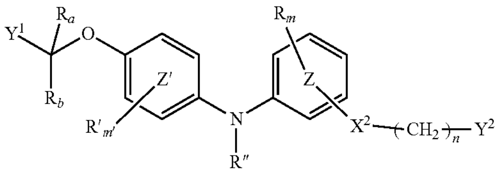
(Ie)
51
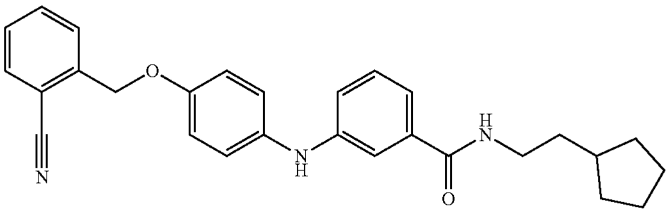 [SMILES: N#Cc1ccccc1COc1ccc(Nc2cccc(C(=O)NCCC3CCCC3)c2)cc1]
52
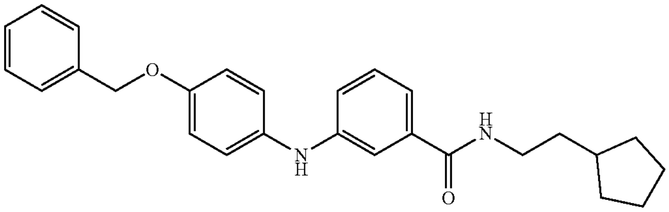 [SMILES: O=C(NCCC1CCCC1)c1cccc(Nc2ccc(OCc3ccccc3)cc2)c1]
53
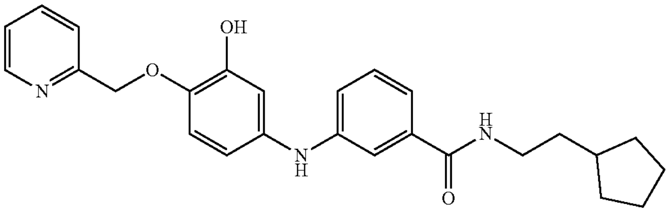 [SMILES: O=C(NCCC1CCCC1)c1cccc(Nc2ccc(OCc3ccccn3)c(O)c2)c1]
54
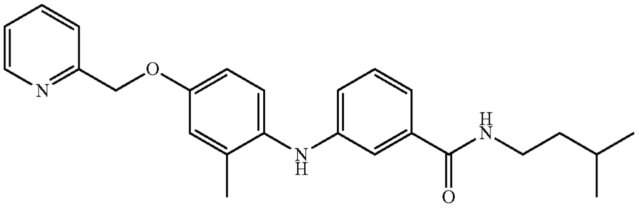 [SMILES: Cc1cc(OCc2ccccn2)ccc1Nc1cccc(C(=O)NCCC(C)C)c1]
55
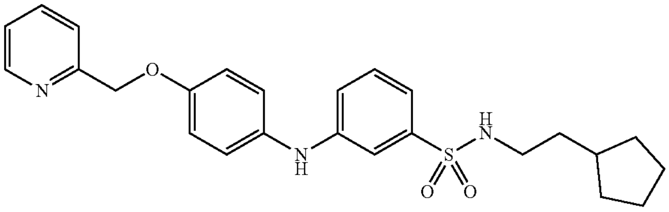 [SMILES: O=S(=O)(NCCC1CCCC1)c1cccc(Nc2ccc(OCc3ccccn3)cc2)c1]
56
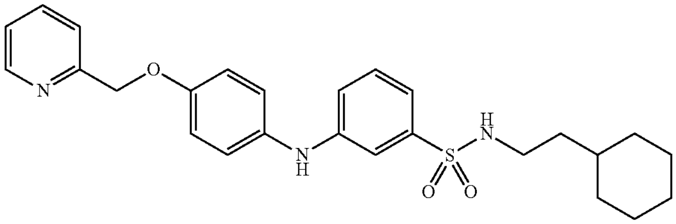 [SMILES: O=S(=O)(NCCC1CCCCC1)c1cccc(Nc2ccc(OCc3ccccn3)cc2)c1]

TABLE I-continued
(Ie)
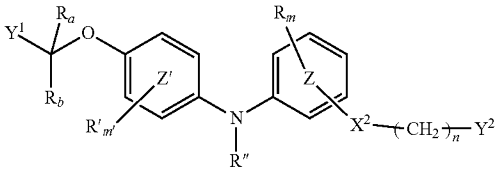
(Ie)
57
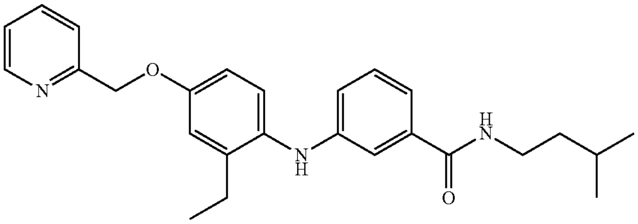 [SMILES: CCc1cc(OCc2ccccn2)ccc1Nc1cccc(C(=O)NCCC(C)C)c1]
58
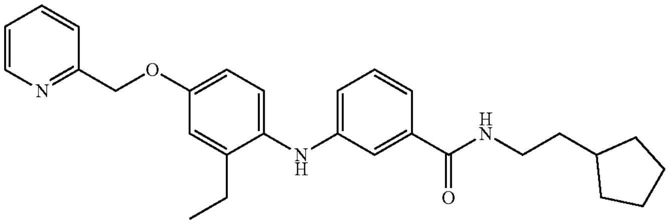 [SMILES: CCc1cc(OCc2ccccn2)ccc1Nc1cccc(C(=O)NCCC2CCCC2)c1]
59
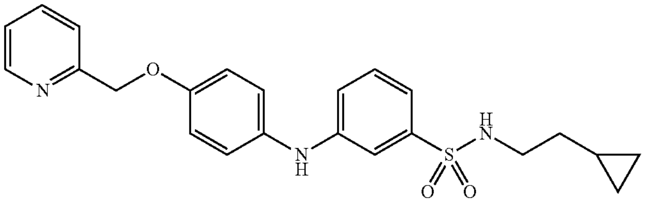 [SMILES: O=S(=O)(NCCC1CC1)c1cccc(Nc2ccc(OCc3ccccn3)cc2)c1]
60
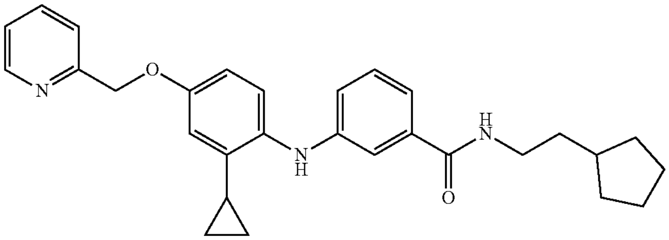 [SMILES: O=C(NCCC1CCCC1)c1cccc(Nc2ccc(OCc3ccccn3)cc2C2CC2)c1]
61
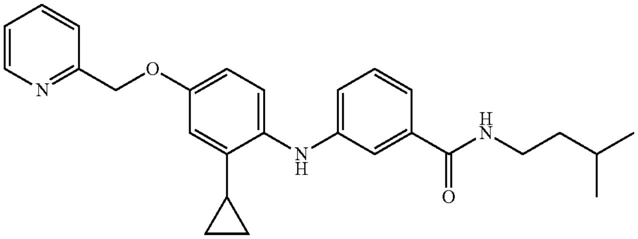 [SMILES: CC(C)CCNC(=O)c1cccc(Nc2ccc(OCc3ccccn3)cc2C2CC2)c1]
62
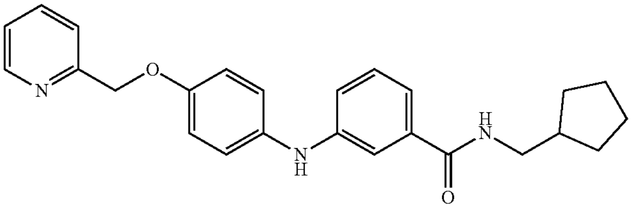 [SMILES: O=C(NCC1CCCC1)c1cccc(Nc2ccc(OCc3ccccn3)cc2)c1]

TABLE I-continued
| (Ie) |
|---|
| 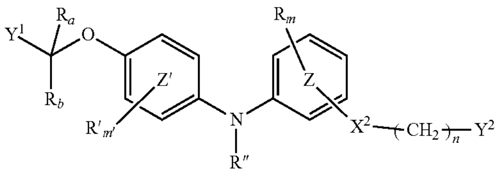 |
| (Ie) |
| | |
|---|---|
| 63 | 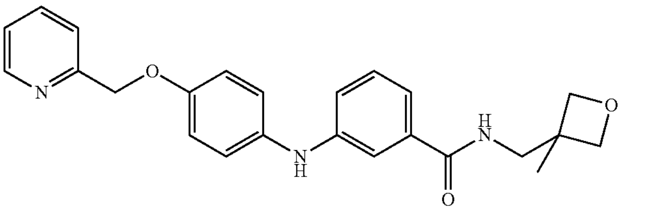 [SMILES: CC1(CNC(=O)c2cccc(Nc3ccc(OCc4ccccn4)cc3)c2)COC1] |
| 64 | 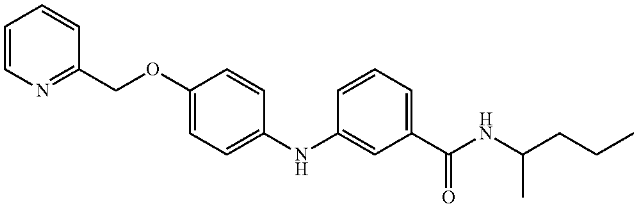 [SMILES: CCCC(C)NC(=O)c1cccc(Nc2ccc(OCc3ccccn3)cc2)c1] |
| 65 | 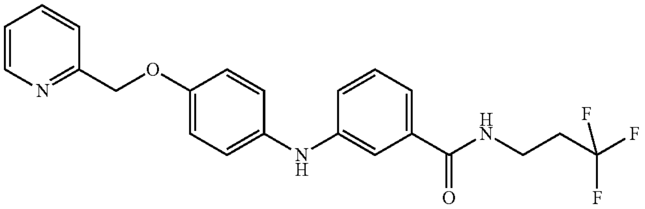 [SMILES: O=C(NCCC(F)(F)F)c1cccc(Nc2ccc(OCc3ccccn3)cc2)c1] |
| 66 | 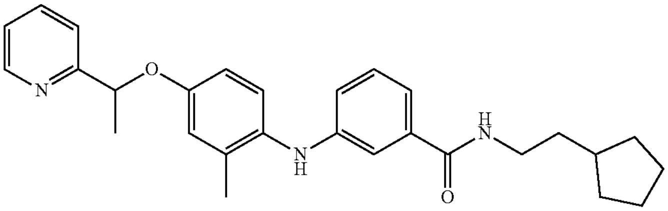 [SMILES: Cc1cc(OC(C)c2ccccn2)ccc1Nc1cccc(C(=O)NCCC2CCCC2)c1] |
| 67 | 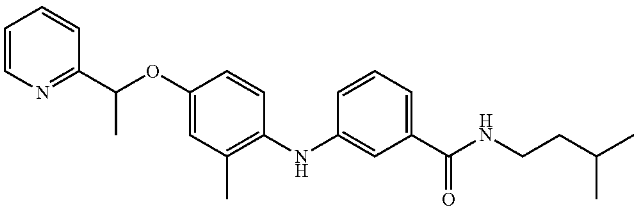 [SMILES: Cc1cc(OC(C)c2ccccn2)ccc1Nc1cccc(C(=O)NCCC(C)C)c1] |
| 68 | 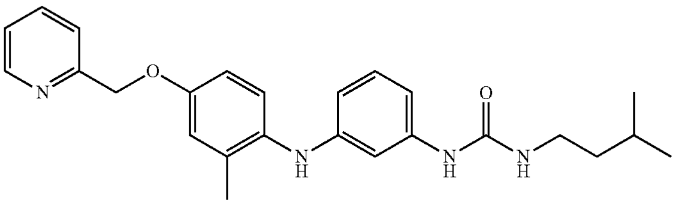 [SMILES: Cc1cc(OCc2ccccn2)ccc1Nc1cccc(NC(=O)NCCC(C)C)c1] |

TABLE I-continued
(Ie)
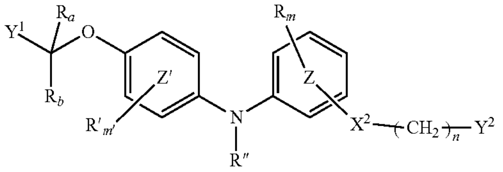
(Ie)
69
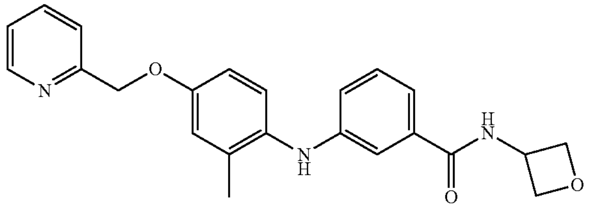 [SMILES: Cc1cc(OCc2ccccn2)ccc1Nc1cccc(C(=O)NC2COC2)c1]
70
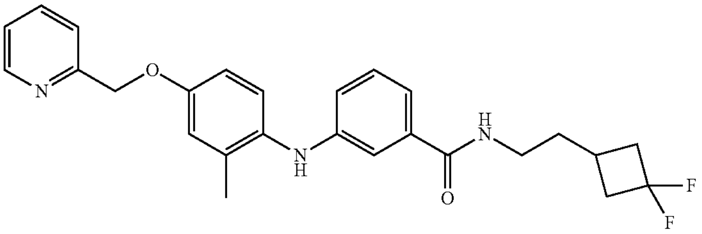 [SMILES: Cc1cc(OCc2ccccn2)ccc1Nc1cccc(C(=O)NCCC2CC(F)(F)C2)c1]
71
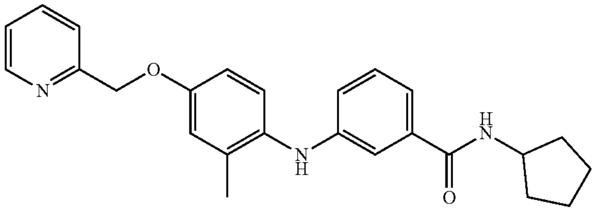 [SMILES: Cc1cc(OCc2ccccn2)ccc1Nc1cccc(C(=O)NC2CCCC2)c1]
72
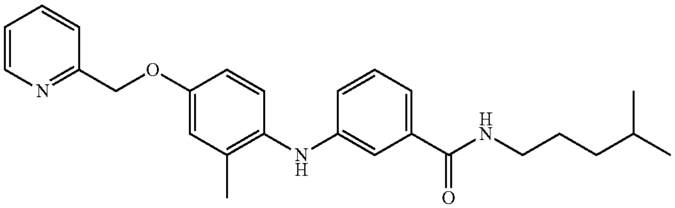 [SMILES: Cc1cc(OCc2ccccn2)ccc1Nc1cccc(C(=O)NCCCC(C)C)c1]
73
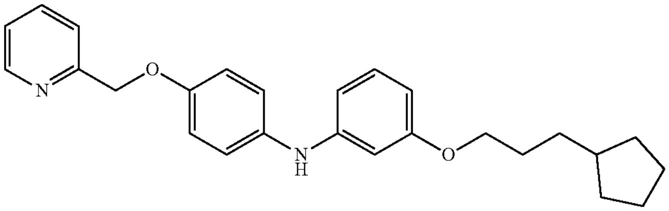 [SMILES: c1ccc(COc2ccc(Nc3cccc(OCCCC4CCCC4)c3)cc2)nc1]
74
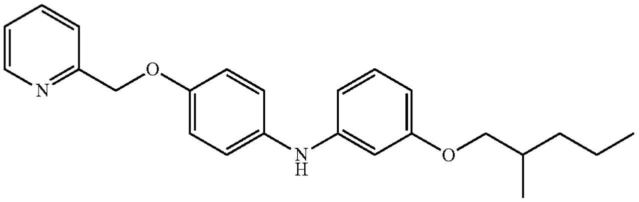 [SMILES: CCCC(C)COc1cccc(Nc2ccc(OCc3ccccn3)cc2)c1]

TABLE I-continued
(Ie)
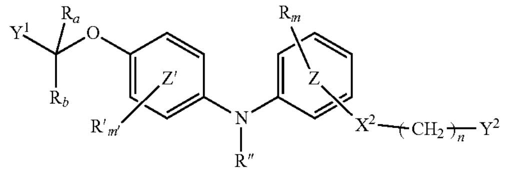
(Ie)
75
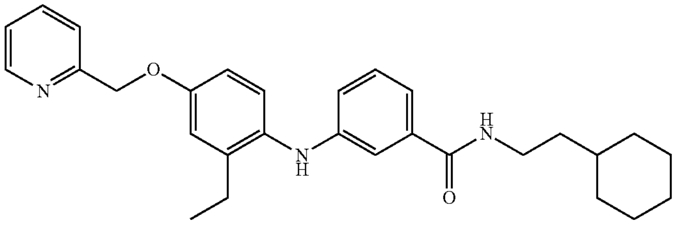 [SMILES: CCc1cc(OCc2ccccn2)ccc1Nc1cccc(C(=O)NCCC2CCCCC2)c1]
76
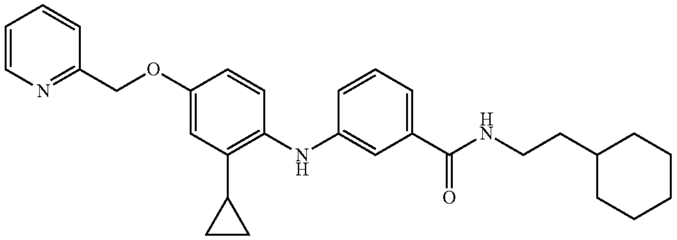 [SMILES: O=C(NCCC1CCCCC1)c1cccc(Nc2ccc(OCc3ccccn3)cc2C2CC2)c1]
77
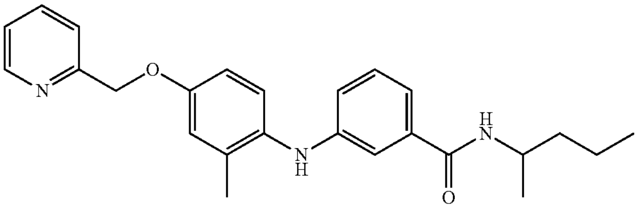 [SMILES: CCCC(C)NC(=O)c1cccc(Nc2ccc(OCc3ccccn3)cc2C)c1]
78
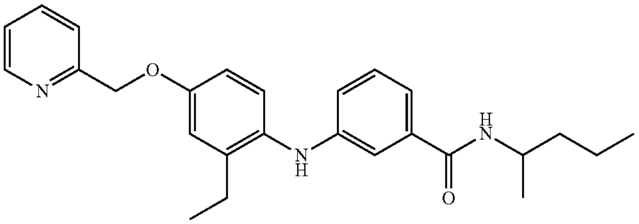 [SMILES: CCCC(C)NC(=O)c1cccc(Nc2ccc(OCc3ccccn3)cc2CC)c1]
79
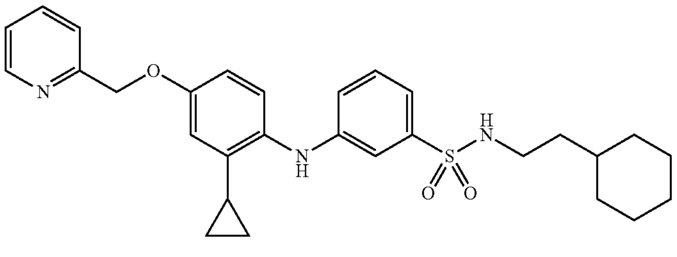 [SMILES: O=S(=O)(NCCC1CCCCC1)c1cccc(Nc2ccc(OCc3ccccn3)cc2C2CC2)c1]
80
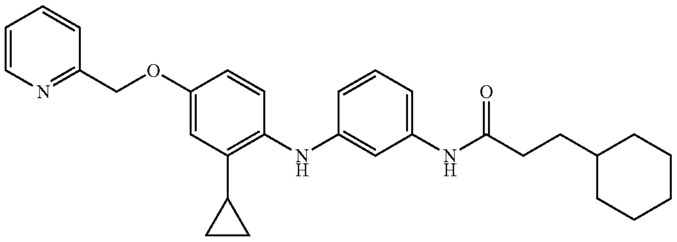 [SMILES: O=C(CCC1CCCCC1)Nc1cccc(Nc2ccc(OCc3ccccn3)cc2C2CC2)c1]

TABLE I-continued
(Ie)
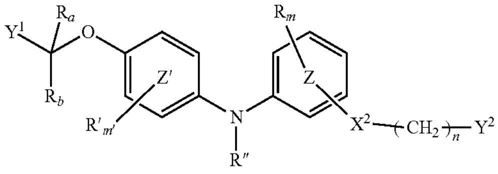
(Ie)
81
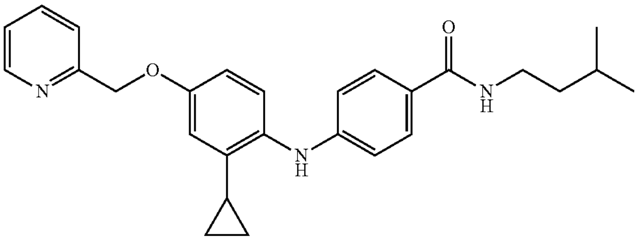 [SMILES: CC(C)CCNC(=O)c1ccc(Nc2ccc(OCc3ccccn3)cc2C2CC2)cc1]
82
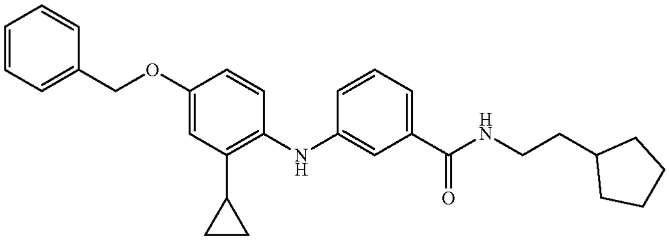 [SMILES: O=C(NCCC1CCCC1)c1cccc(Nc2ccc(OCc3ccccc3)cc2C2CC2)c1]
83
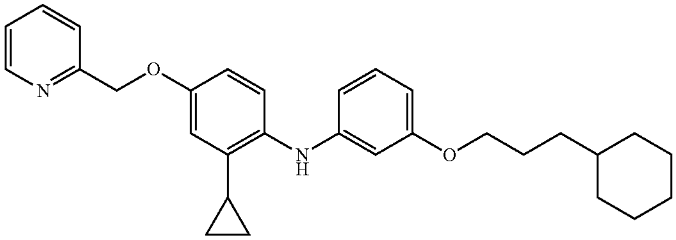 [SMILES: c1ccc(COc2ccc(Nc3cccc(OCCCC4CCCCC4)c3)c(C3CC3)c2)nc1]
84
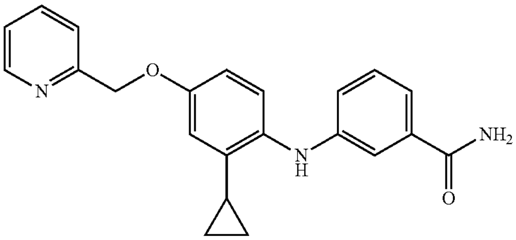 [SMILES: NC(=O)c1cccc(Nc2ccc(OCc3ccccn3)cc2C2CC2)c1]
85
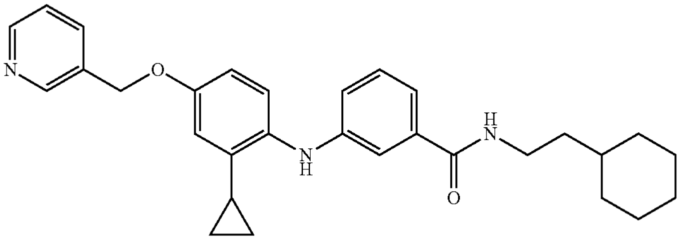 [SMILES: O=C(NCCC1CCCCC1)c1cccc(Nc2ccc(OCc3cccnc3)cc2C2CC2)c1]

TABLE I-continued
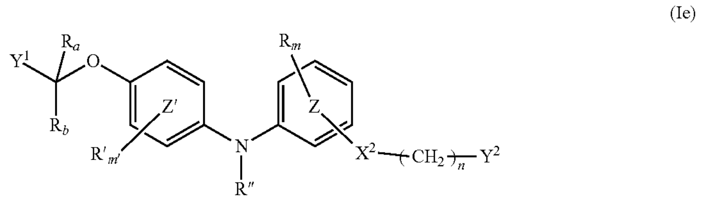
(Ie)
86
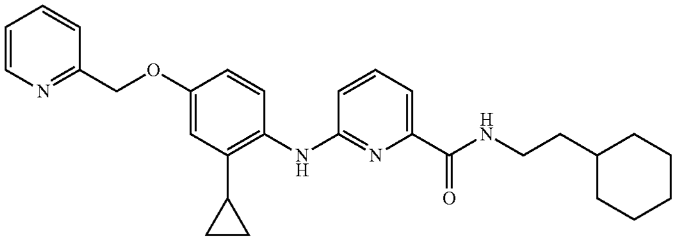 [SMILES: O=C(NCCC1CCCCC1)c1cccc(Nc2ccc(OCc3ccccn3)cc2C2CC2)n1]
87
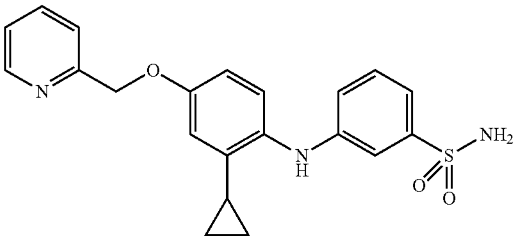 [SMILES: NS(=O)(=O)c1cccc(Nc2ccc(OCc3ccccn3)cc2C2CC2)c1]
88
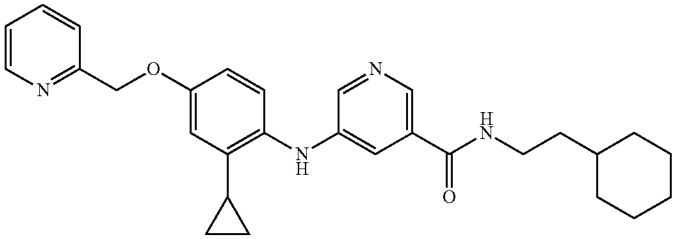
89
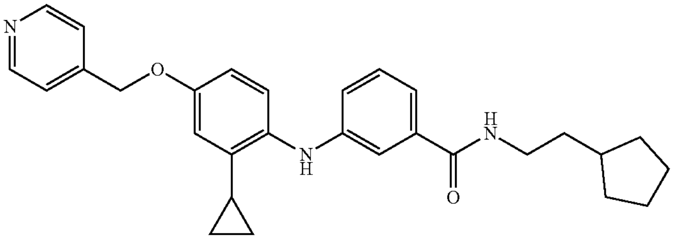 [SMILES: O=C(NCCC1CCCC1)c1cccc(Nc2ccc(OCc3ccncc3)cc2C2CC2)c1]
90
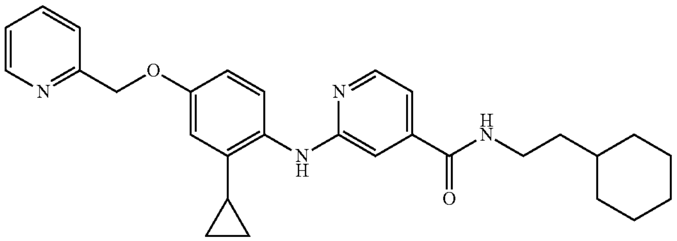

TABLE I-continued
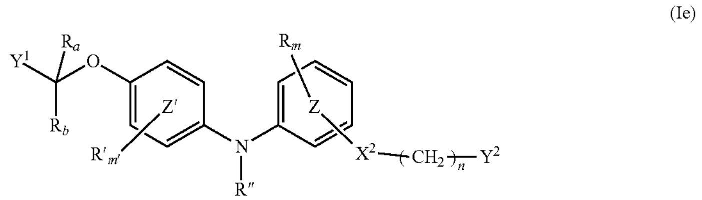
(Ie)
91 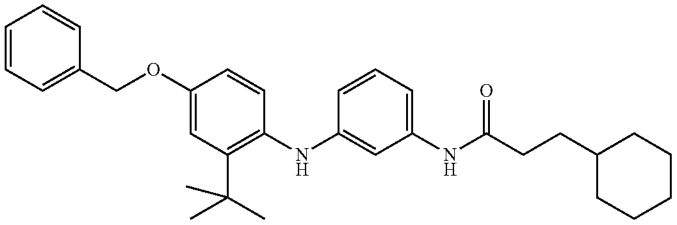 [SMILES: CC(C)(C)c1cc(OCc2ccccc2)ccc1Nc1cccc(NC(=O)CCC2CCCCC2)c1]
92 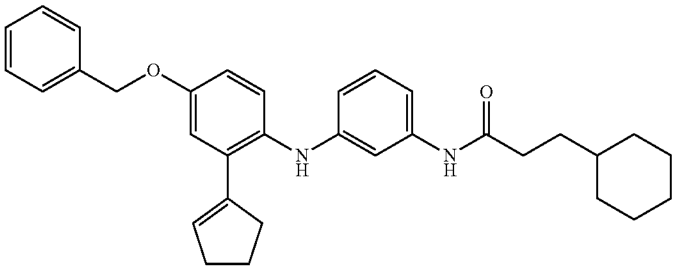 [SMILES: O=C(CCC1CCCCC1)Nc1cccc(Nc2ccc(OCc3ccccc3)cc2C2=CCCC2)c1]
93 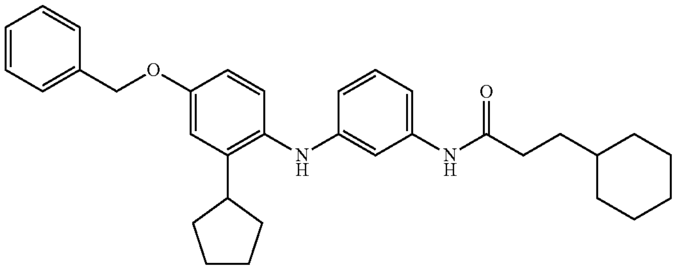 [SMILES: O=C(CCC1CCCCC1)Nc1cccc(Nc2ccc(OCc3ccccc3)cc2C2CCCC2)c1]
94 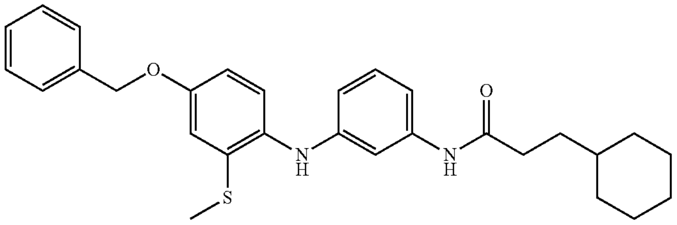 [SMILES: CSc1cc(OCc2ccccc2)ccc1Nc1cccc(NC(=O)CCC2CCCCC2)c1]
95 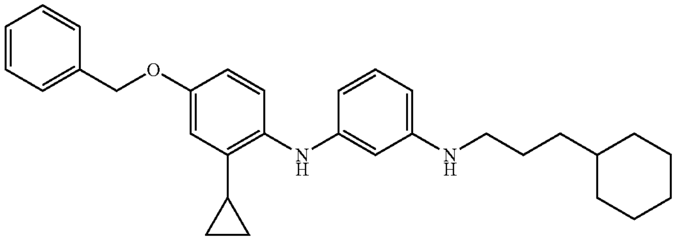 [SMILES: c1ccc(COc2ccc(Nc3cccc(NCCCC4CCCCC4)c3)c(C3CC3)c2)cc1]

TABLE I-continued
(Ie)
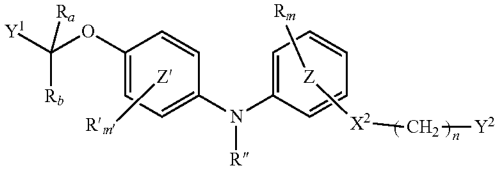
(Ie)
96
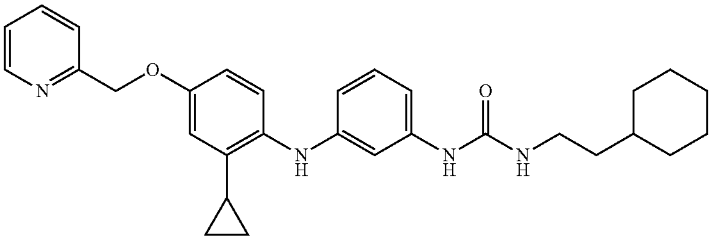 [SMILES: O=C(NCCC1CCCCC1)Nc1cccc(Nc2ccc(OCc3ccccn3)cc2C2CC2)c1]
97
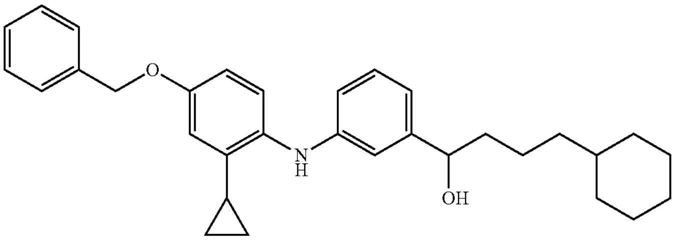 [SMILES: OC(CCCC1CCCCC1)c1cccc(Nc2ccc(OCc3ccccc3)cc2C2CC2)c1]
98
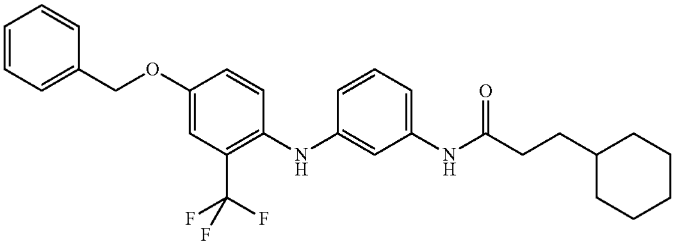 [SMILES: O=C(CCC1CCCCC1)Nc1cccc(Nc2ccc(OCc3ccccc3)cc2C(F)(F)F)c1]
99
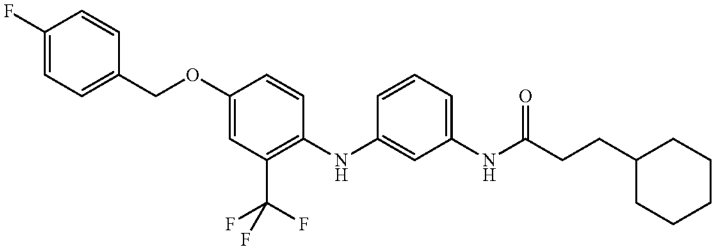 [SMILES: O=C(CCC1CCCCC1)Nc1cccc(Nc2ccc(OCc3ccc(F)cc3)cc2C(F)(F)F)c1]
100
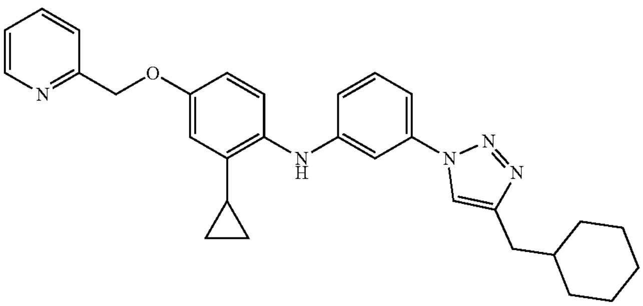 [SMILES: c1ccc(COc2ccc(Nc3cccc(-n4cc(CC5CCCCC5)nn4)c3)c(C3CC3)c2)nc1]

TABLE I-continued
(Ie)
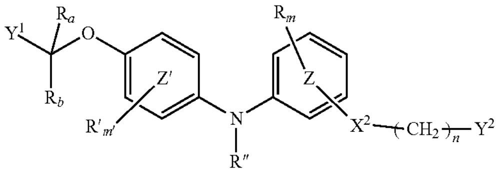
(Ie)
101
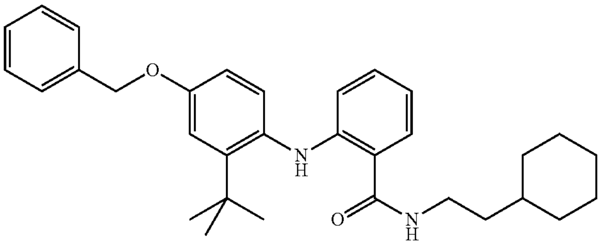 [SMILES: CC(C)(C)c1cc(OCc2ccccc2)ccc1Nc1ccccc1C(=O)NCCC1CCCCC1]
102
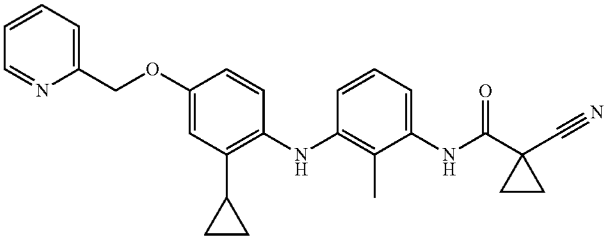 [SMILES: Cc1c(NC(=O)C2(C#N)CC2)cccc1Nc1ccc(OCc2ccccn2)cc1C1CC1]
103
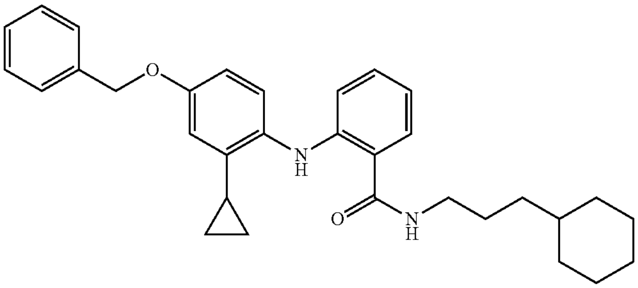 [SMILES: O=C(NCCCC1CCCCC1)c1ccccc1Nc1ccc(OCc2ccccc2)cc1C1CC1]
104
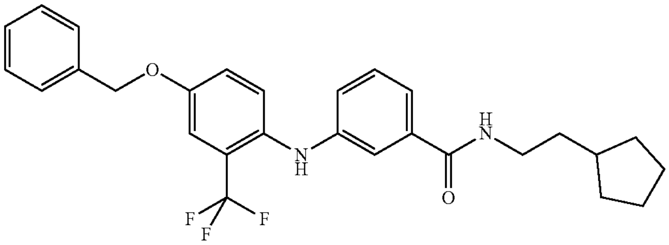 [SMILES: O=C(NCCC1CCCC1)c1cccc(Nc2ccc(OCc3ccccc3)cc2C(F)(F)F)c1]
105
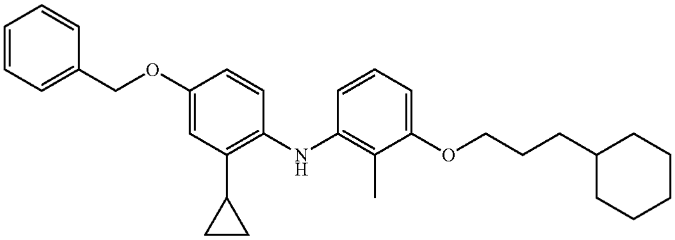 [SMILES: Cc1c(Nc2ccc(OCc3ccccc3)cc2C2CC2)cccc1OCCCC1CCCCC1]

TABLE I-continued
(Ie)
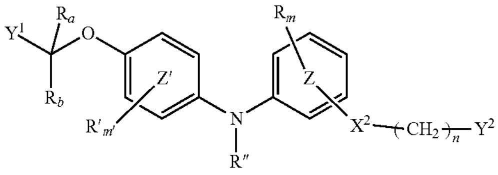
(Ie)
106
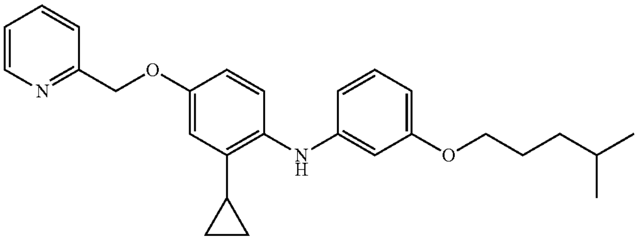 [SMILES: CC(C)CCCOc1cccc(Nc2ccc(OCc3ccccn3)cc2C2CC2)c1]
107
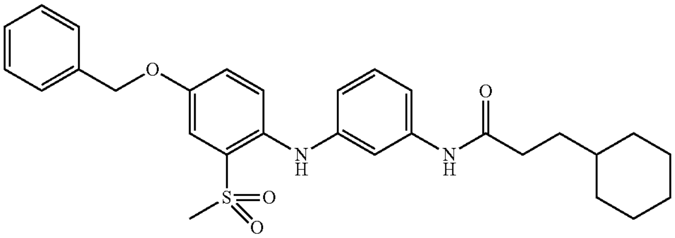 [SMILES: CS(=O)(=O)c1cc(OCc2ccccc2)ccc1Nc1cccc(NC(=O)CCC2CCCCC2)c1]
108
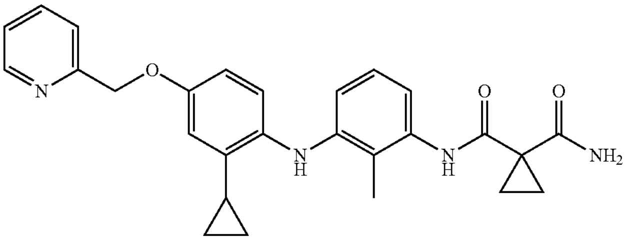 [SMILES: Cc1c(NC(=O)C2(C(N)=O)CC2)cccc1Nc1ccc(OCc2ccccn2)cc1C1CC1]
109
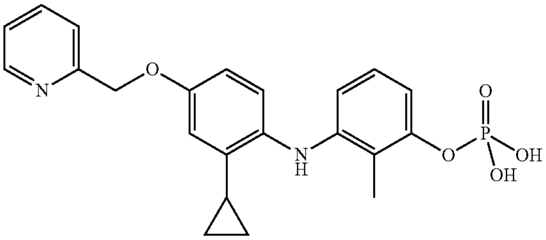 [SMILES: Cc1c(Nc2ccc(OCc3ccccn3)cc2C2CC2)cccc1OP(=O)(O)O]
110
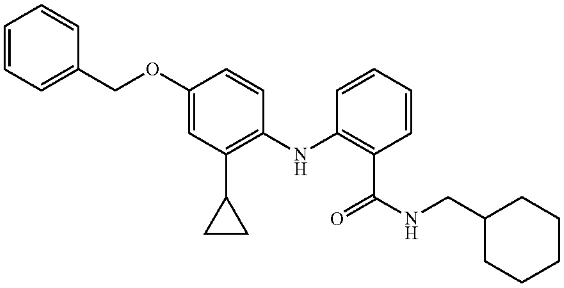 [SMILES: O=C(NCC1CCCCC1)c1ccccc1Nc1ccc(OCc2ccccc2)cc1C1CC1]

TABLE I-continued
(Ie)
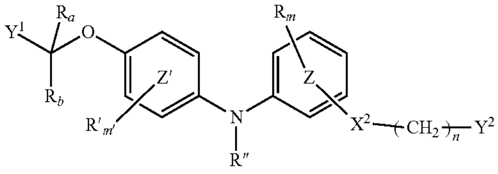
(Ie)
111
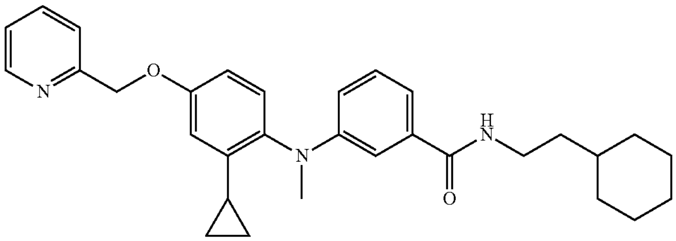 [SMILES: CN(c1cccc(C(=O)NCCC2CCCCC2)c1)c1ccc(OCc2ccccn2)cc1C1CC1]
112
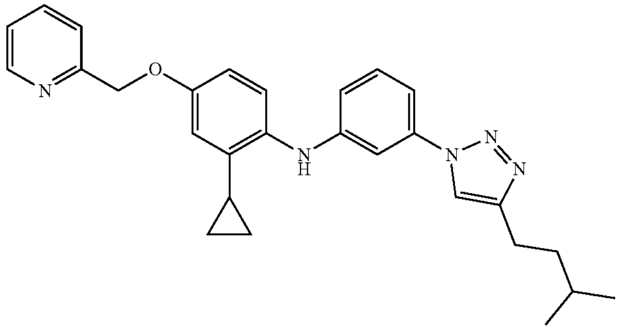 [SMILES: CC(C)CCc1cn(-c2cccc(Nc3ccc(OCc4ccccn4)cc3C3CC3)c2)nn1]
113
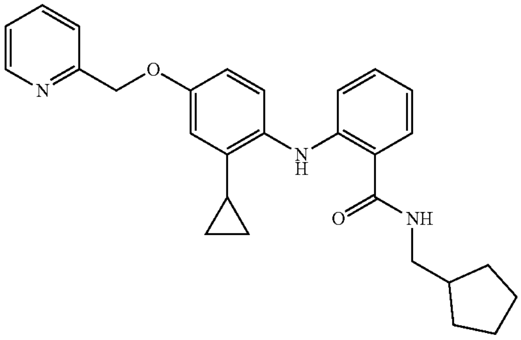 [SMILES: O=C(NCC1CCCC1)c1ccccc1Nc1ccc(OCc2ccccn2)cc1C1CC1]
114
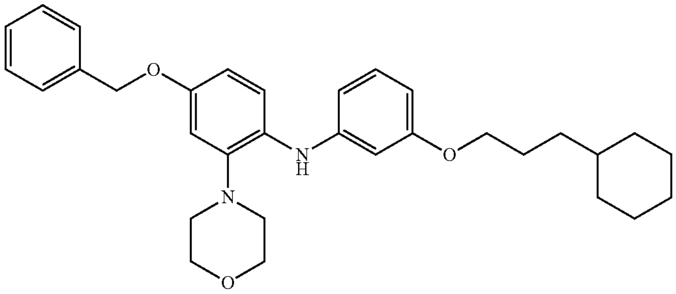 [SMILES: c1ccc(COc2ccc(Nc3cccc(OCCCC4CCCCC4)c3)c(N3CCOCC3)c2)cc1]

TABLE I-continued
(Ie)
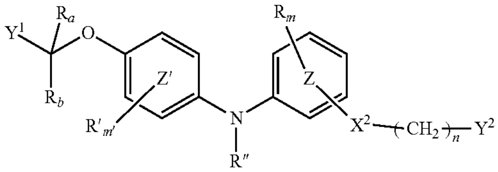
(Ie)
115
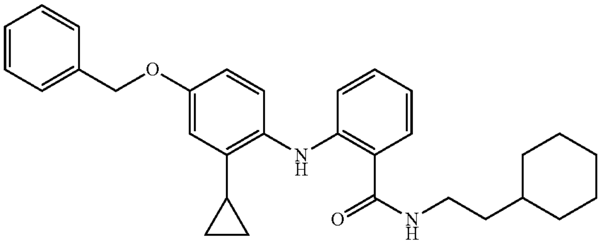 [SMILES: O=C(NCCC1CCCCC1)c1ccccc1Nc1ccc(OCc2ccccc2)cc1C1CC1]
116
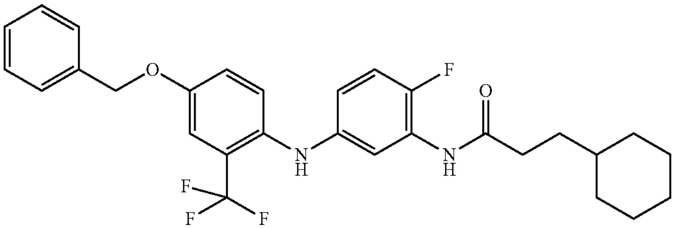 [SMILES: O=C(CCC1CCCCC1)Nc1cc(Nc2ccc(OCc3ccccc3)cc2C(F)(F)F)ccc1F]
117
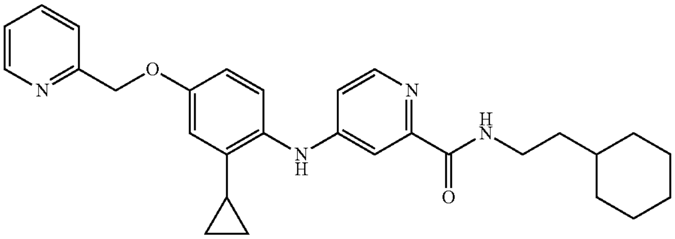
118
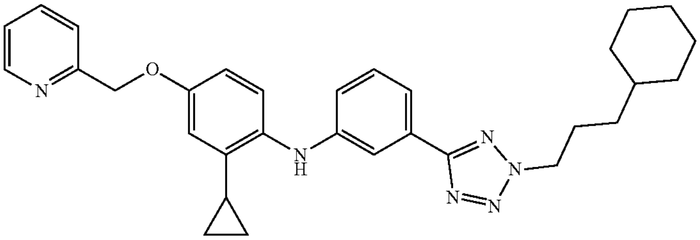 [SMILES: c1ccc(COc2ccc(Nc3cccc(-c4nnn(CCCC5CCCCC5)n4)c3)c(C3CC3)c2)nc1]
119
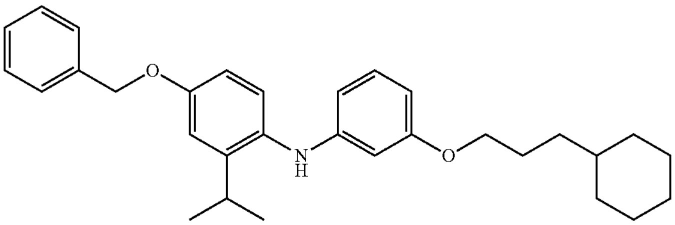 [SMILES: CC(C)c1cc(OCc2ccccc2)ccc1Nc1cccc(OCCCC2CCCCC2)c1]

TABLE I-continued
(Ie)
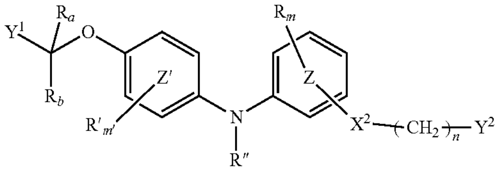
(Ie)
120
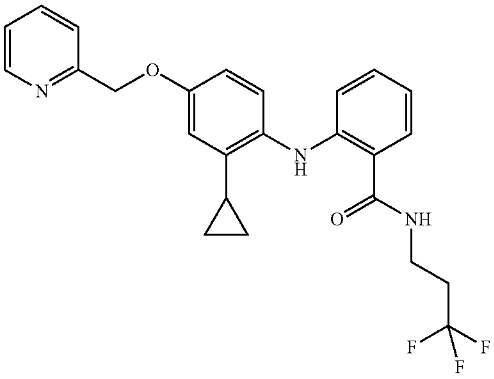 [SMILES: O=C(NCCC(F)(F)F)c1ccccc1Nc1ccc(OCc2ccccn2)cc1C1CC1]
121
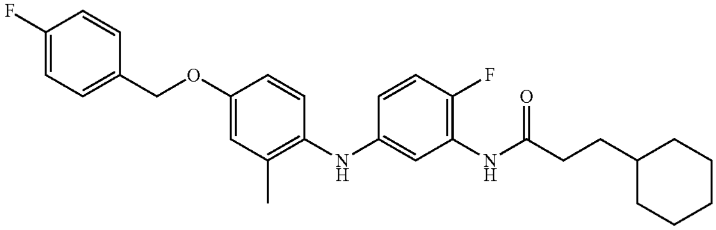 [SMILES: Cc1cc(OCc2ccc(F)cc2)ccc1Nc1ccc(F)c(NC(=O)CCC2CCCCC2)c1]
122
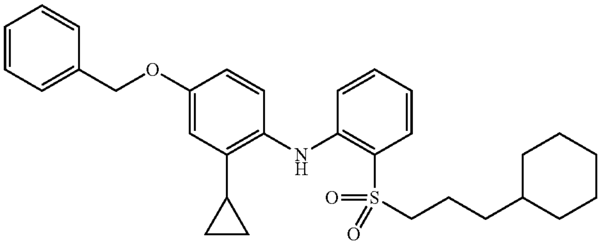 [SMILES: O=S(=O)(CCCC1CCCCC1)c1ccccc1Nc1ccc(OCc2ccccc2)cc1C1CC1]
123
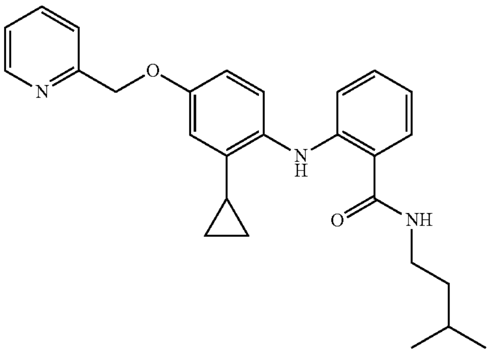 [SMILES: CC(C)CCNC(=O)c1ccccc1Nc1ccc(OCc2ccccn2)cc1C1CC1]

TABLE I-continued
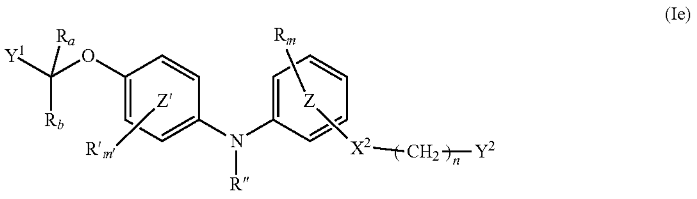
(Ie)
124
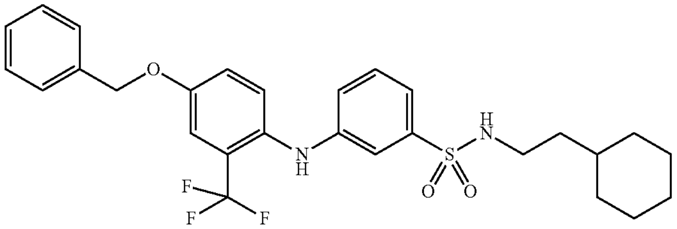 [SMILES: O=S(=O)(NCCC1CCCCC1)c1cccc(Nc2ccc(OCc3ccccc3)cc2C(F)(F)F)c1]
125
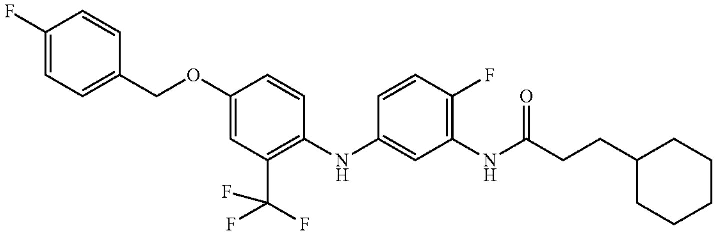 [SMILES: O=C(CCC1CCCCC1)Nc1cc(Nc2ccc(OCc3ccc(F)cc3)cc2C(F)(F)F)ccc1F]
126
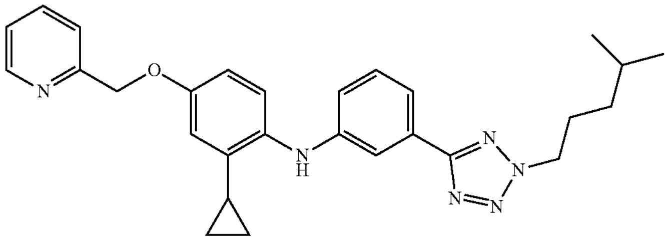 [SMILES: CC(C)CCCn1nnc(-c2cccc(Nc3ccc(OCc4ccccn4)cc3C3CC3)c2)n1]
127
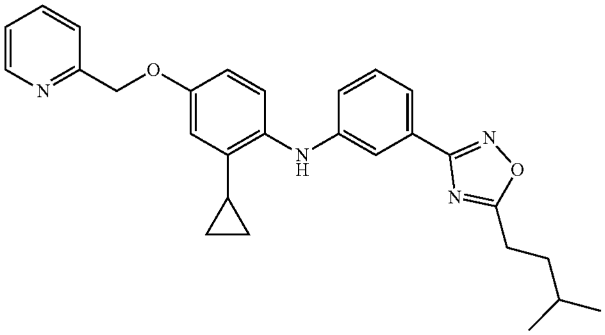 [SMILES: CC(C)CCc1nc(-c2cccc(Nc3ccc(OCc4ccccn4)cc3C3CC3)c2)no1]
128
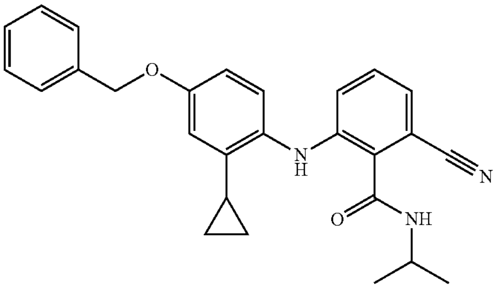 [SMILES: CC(C)NC(=O)c1c(C#N)cccc1Nc1ccc(OCc2ccccc2)cc1C1CC1]

TABLE I-continued
(Ie)
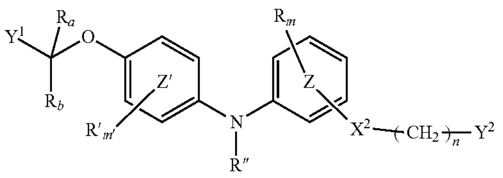
(Ie)
129
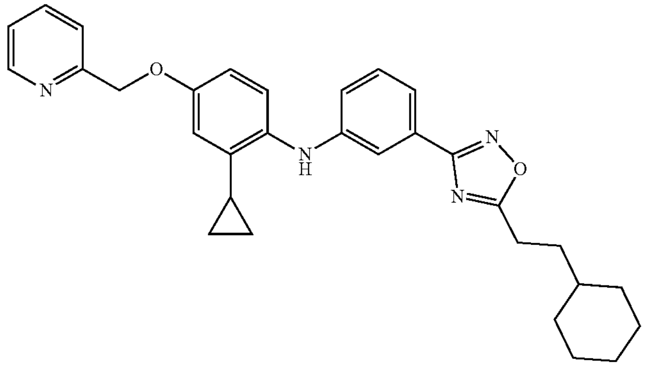 [SMILES: c1ccc(COc2ccc(Nc3cccc(-c4noc(CCC5CCCCC5)n4)c3)c(C3CC3)c2)nc1]
130
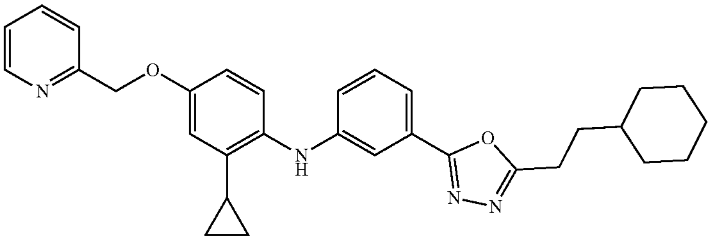 [SMILES: c1ccc(COc2ccc(Nc3cccc(-c4nnc(CCC5CCCCC5)o4)c3)c(C3CC3)c2)nc1]
131
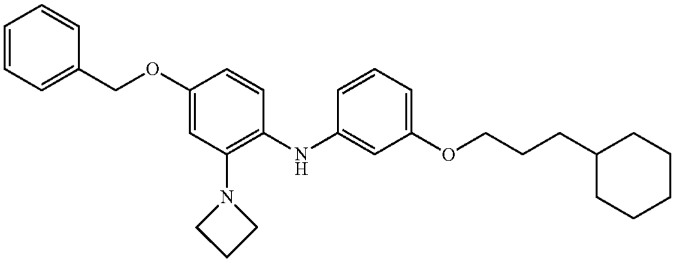 [SMILES: c1ccc(COc2ccc(Nc3cccc(OCCCC4CCCCC4)c3)c(N3CCC3)c2)cc1]
132
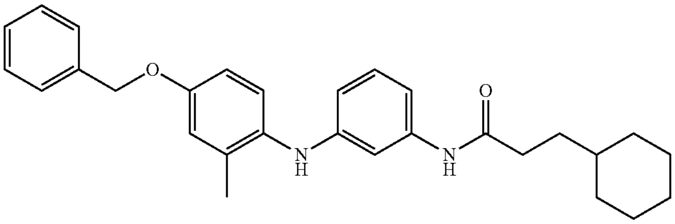 [SMILES: Cc1cc(OCc2ccccc2)ccc1Nc1cccc(NC(=O)CCC2CCCCC2)c1]
133
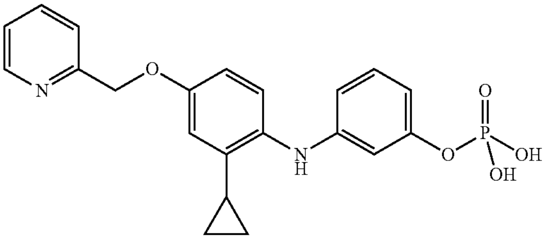 [SMILES: O=P(O)(O)Oc1cccc(Nc2ccc(OCc3ccccn3)cc2C2CC2)c1]

TABLE I-continued
(Ie)
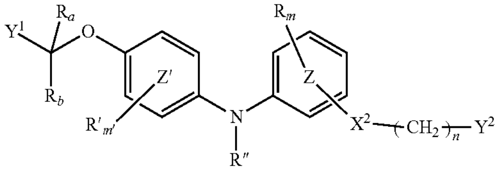
(Ie)
134
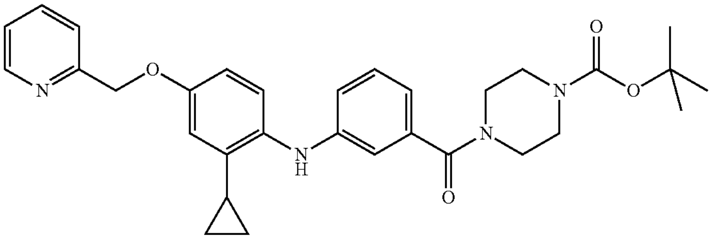 [SMILES: CC(C)(C)OC(=O)N1CCN(C(=O)c2cccc(Nc3ccc(OCc4ccccn4)cc3C3CC3)c2)CC1]
135
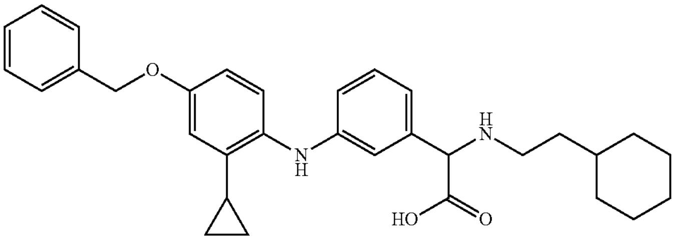 [SMILES: O=C(O)C(NCCC1CCCCC1)c1cccc(Nc2ccc(OCc3ccccc3)cc2C2CC2)c1]
136
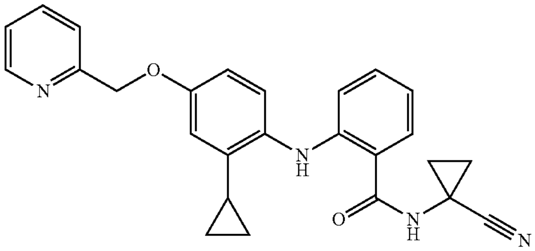 [SMILES: N#CC1(NC(=O)c2ccccc2Nc2ccc(OCc3ccccn3)cc2C2CC2)CC1]
137
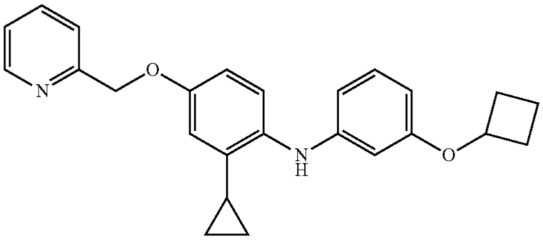 [SMILES: c1ccc(COc2ccc(Nc3cccc(OC4CCC4)c3)c(C3CC3)c2)nc1]
138
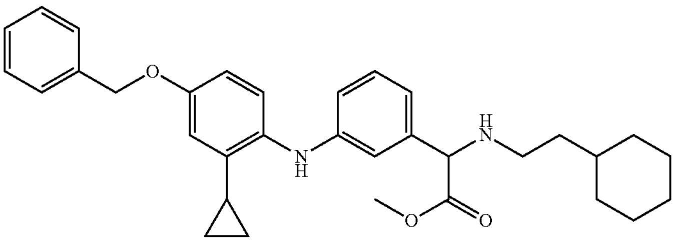 [SMILES: COC(=O)C(NCCC1CCCCC1)c1cccc(Nc2ccc(OCc3ccccc3)cc2C2CC2)c1]

TABLE I-continued
(Ie)
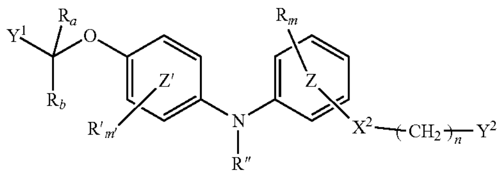
(Ie)
| | |
|---|---|
| 139 | 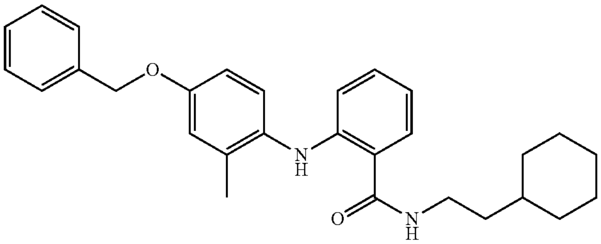 [SMILES: Cc1cc(OCc2ccccc2)ccc1Nc1ccccc1C(=O)NCCC1CCCCC1] |
| 140 | 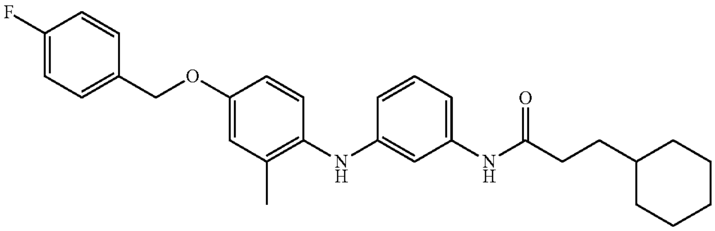 [SMILES: Cc1cc(OCc2ccc(F)cc2)ccc1Nc1cccc(NC(=O)CCC2CCCCC2)c1] |
| 141 | 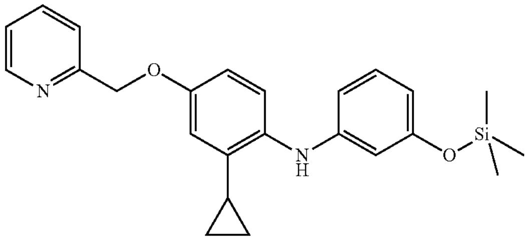 [SMILES: C[Si](C)(C)Oc1cccc(Nc2ccc(OCc3ccccn3)cc2C2CC2)c1] |
| 142 | 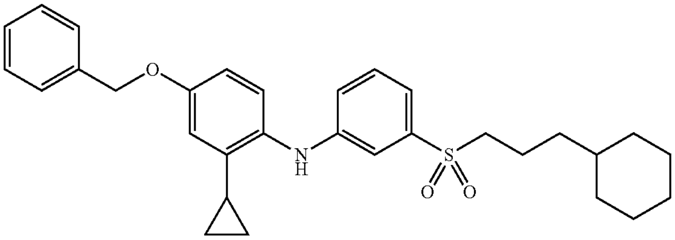 [SMILES: O=S(=O)(CCCC1CCCCC1)c1cccc(Nc2ccc(OCc3ccccc3)cc2C2CC2)c1] |
| 143 | 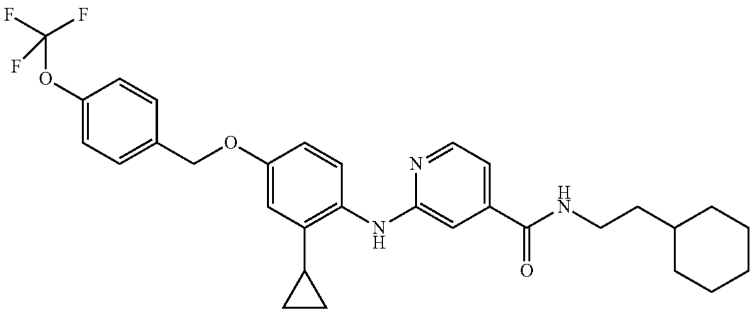 [SMILES: O=C(NCCC1CCCCC1)c1ccnc(Nc2ccc(OCc3ccc(OC(F)(F)F)cc3)cc2C2CC2)c1] |

TABLE I-continued
(Ie)
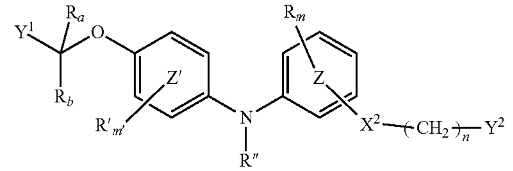
(Ie)
144
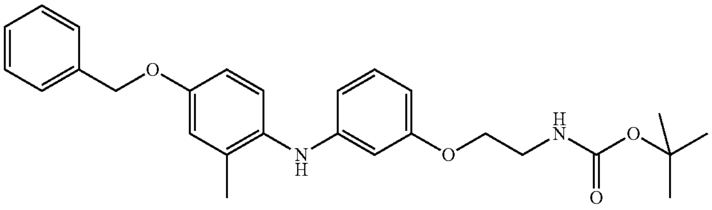 [SMILES: Cc1cc(OCc2ccccc2)ccc1Nc1cccc(OCCNC(=O)OC(C)(C)C)c1]
145
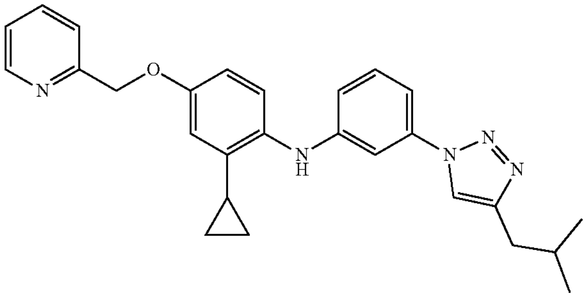 [SMILES: CC(C)Cc1cn(-c2cccc(Nc3ccc(OCc4ccccn4)cc3C3CC3)c2)nn1]
146
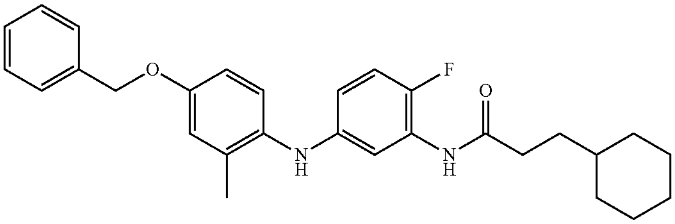 [SMILES: Cc1cc(OCc2ccccc2)ccc1Nc1ccc(F)c(NC(=O)CCC2CCCCC2)c1]
147
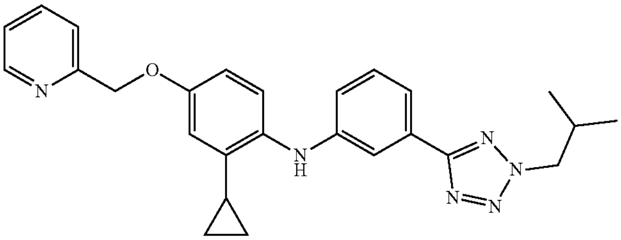 [SMILES: CC(C)Cn1nnc(-c2cccc(Nc3ccc(OCc4ccccn4)cc3C3CC3)c2)n1]
148
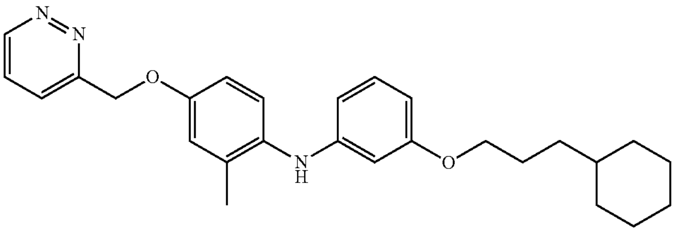 [SMILES: Cc1cc(OCc2cccnn2)ccc1Nc1cccc(OCCCC2CCCCC2)c1]

TABLE I-continued
(Ie)
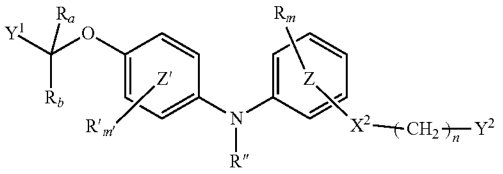
(Ie)
149
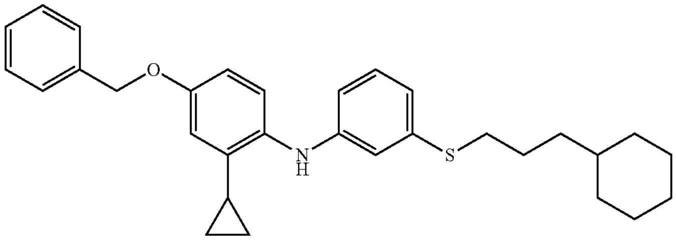 [SMILES: c1ccc(COc2ccc(Nc3cccc(SCCCC4CCCCC4)c3)c(C3CC3)c2)cc1]
150
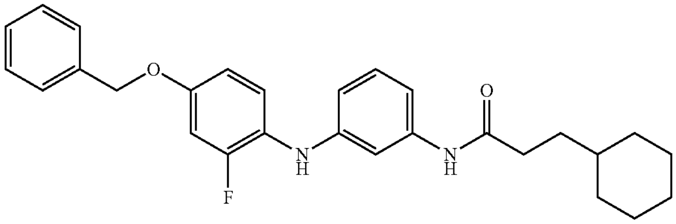
151
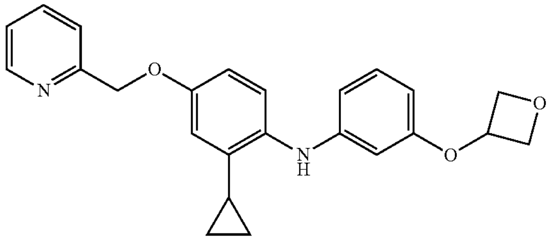 [SMILES: c1ccc(COc2ccc(Nc3cccc(OC4COC4)c3)c(C3CC3)c2)nc1]
152
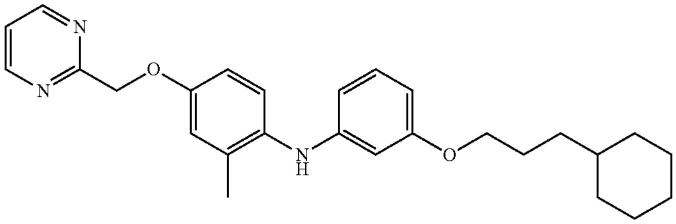 [SMILES: Cc1cc(OCc2ncccn2)ccc1Nc1cccc(OCCCC2CCCCC2)c1]
153
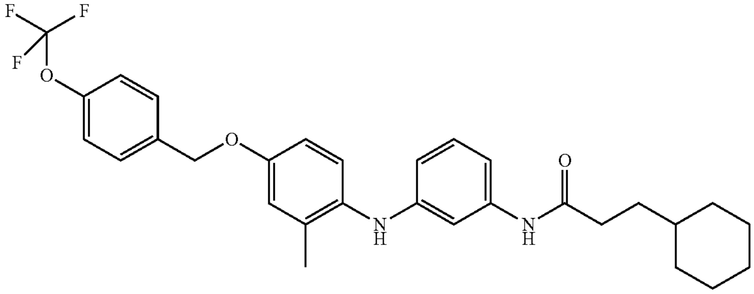 [SMILES: Cc1cc(OCc2ccc(OC(F)(F)F)cc2)ccc1Nc1cccc(NC(=O)CCC2CCCCC2)c1]

TABLE I-continued
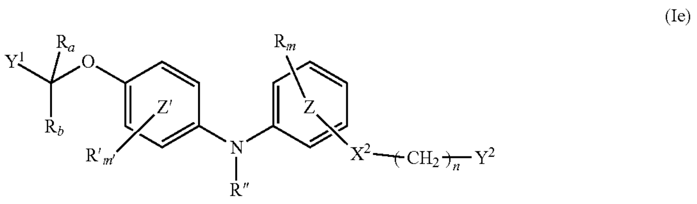
(Ie)
154
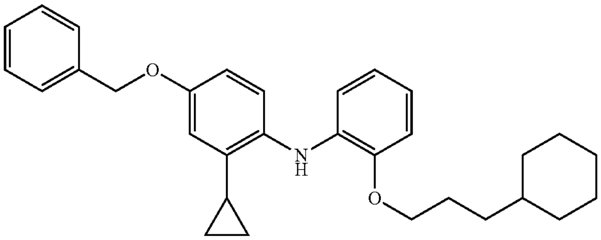 [SMILES: c1ccc(COc2ccc(Nc3ccccc3OCCCC3CCCCC3)c(C3CC3)c2)cc1]
155
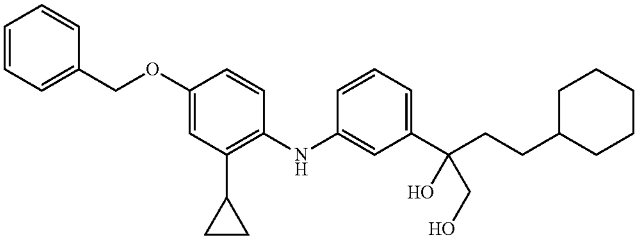 [SMILES: OCC(O)(CCC1CCCCC1)c1cccc(Nc2ccc(OCc3ccccc3)cc2C2CC2)c1]
156
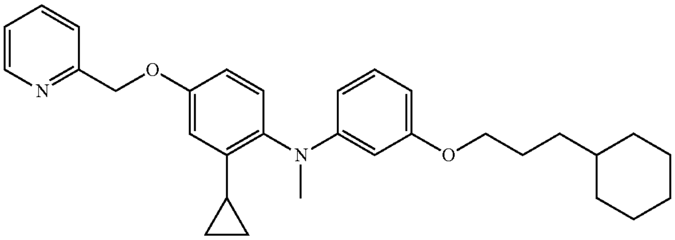 [SMILES: CN(c1cccc(OCCCC2CCCCC2)c1)c1ccc(OCc2ccccn2)cc1C1CC1]
157
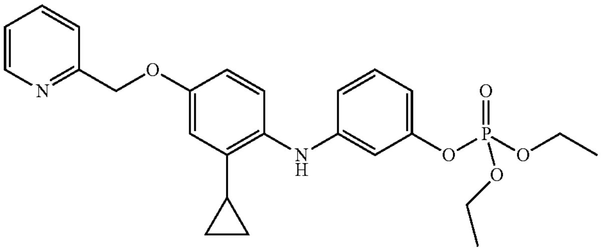 [SMILES: CCOP(=O)(OCC)Oc1cccc(Nc2ccc(OCc3ccccn3)cc2C2CC2)c1]
158
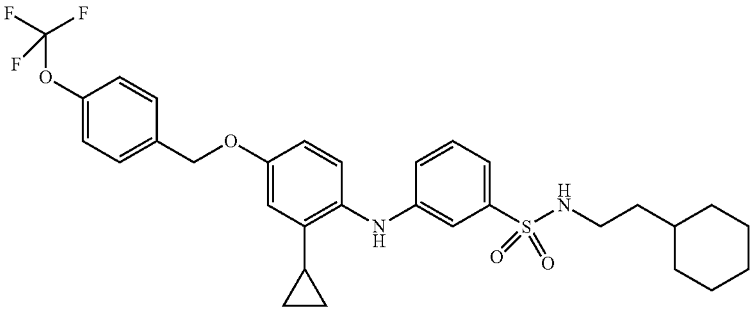 [SMILES: O=S(=O)(NCCC1CCCCC1)c1cccc(Nc2ccc(OCc3ccc(OC(F)(F)F)cc3)cc2C2CC2)c1]

TABLE I-continued
(Ie)
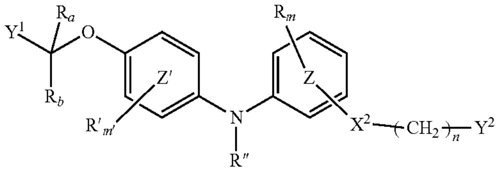
(Ie)
159
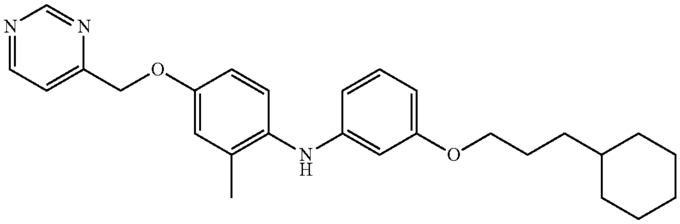 [SMILES: Cc1cc(OCc2ccncn2)ccc1Nc1cccc(OCCCC2CCCCC2)c1]
160
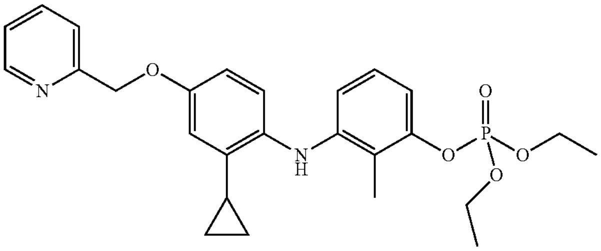 [SMILES: CCOP(=O)(OCC)Oc1cccc(Nc2ccc(OCc3ccccn3)cc2C2CC2)c1C]
161
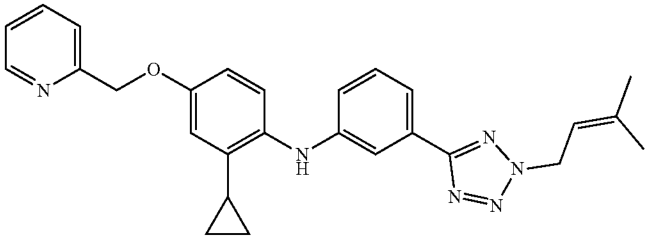 [SMILES: CC(C)=CCn1nnc(-c2cccc(Nc3ccc(OCc4ccccn4)cc3C3CC3)c2)n1]
162
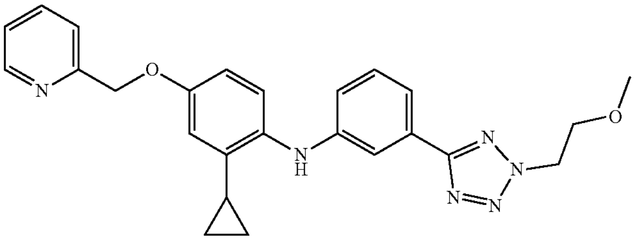 [SMILES: COCCn1nnc(-c2cccc(Nc3ccc(OCc4ccccn4)cc3C3CC3)c2)n1]
163
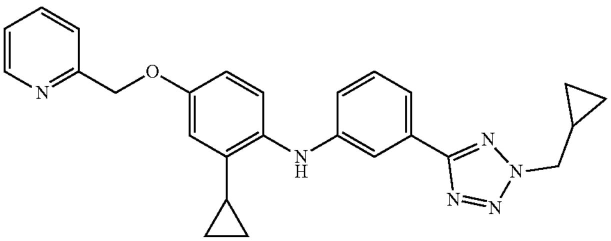 [SMILES: c1ccc(COc2ccc(Nc3cccc(-c4nnn(CC5CC5)n4)c3)c(C3CC3)c2)nc1]

TABLE I-continued
(Ie)
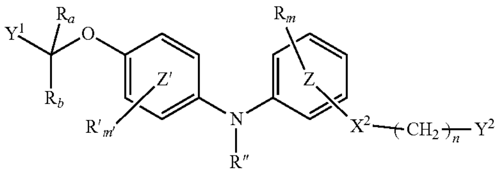
(Ie)
164
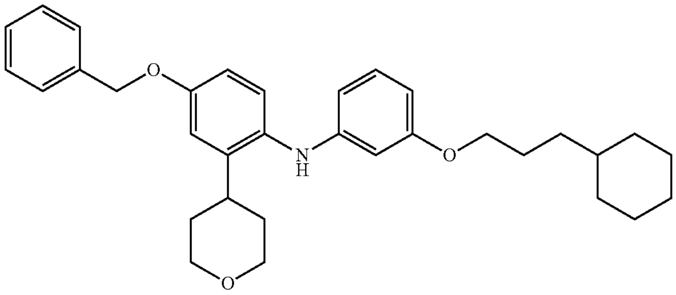
165
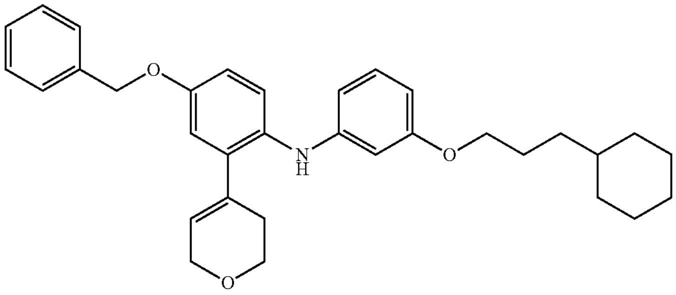 [SMILES: C1=C(c2cc(OCc3ccccc3)ccc2Nc2cccc(OCCCC3CCCCC3)c2)CCOC1]
166
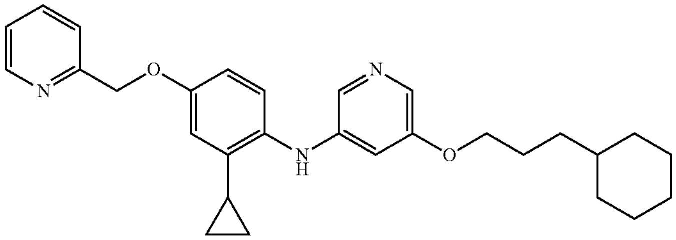 [SMILES: c1ccc(COc2ccc(Nc3cncc(OCCCC4CCCCC4)c3)c(C3CC3)c2)nc1]
167
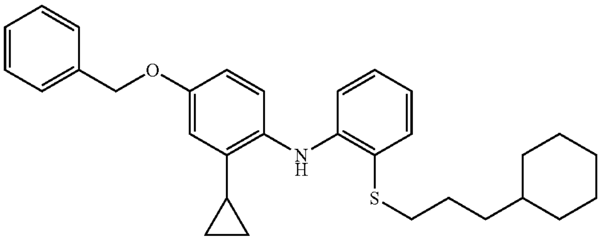 [SMILES: c1ccc(COc2ccc(Nc3ccccc3SCCCC3CCCCC3)c(C3CC3)c2)cc1]
168
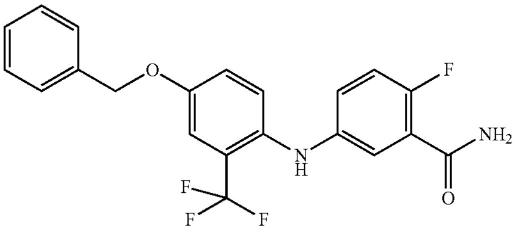 [SMILES: NC(=O)c1cc(Nc2ccc(OCc3ccccc3)cc2C(F)(F)F)ccc1F]

TABLE I-continued
(Ie)
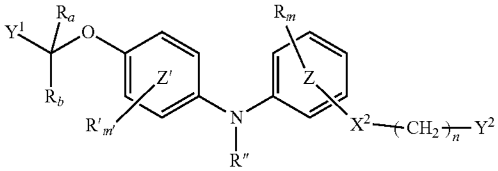
(Ie)
169
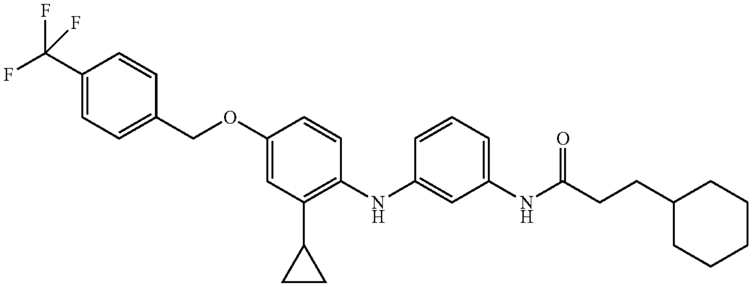 [SMILES: O=C(CCC1CCCCC1)Nc1cccc(Nc2ccc(OCc3ccc(C(F)(F)F)cc3)cc2C2CC2)c1]
170
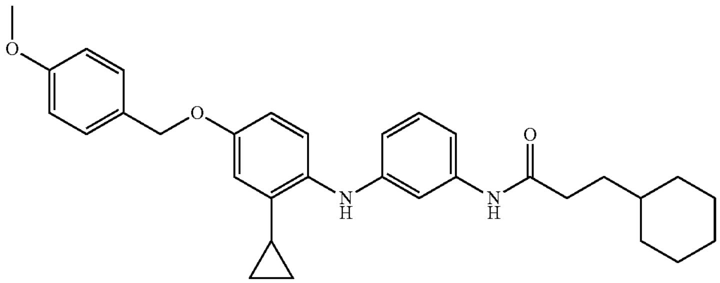 [SMILES: COc1ccc(COc2ccc(Nc3cccc(NC(=O)CCC4CCCCC4)c3)c(C3CC3)c2)cc1]
171
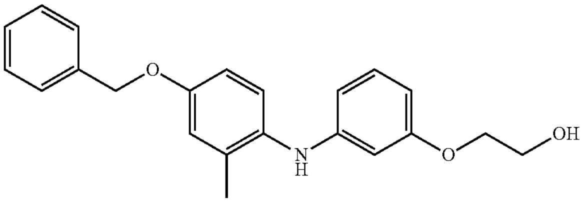 [SMILES: Cc1cc(OCc2ccccc2)ccc1Nc1cccc(OCCO)c1]
172
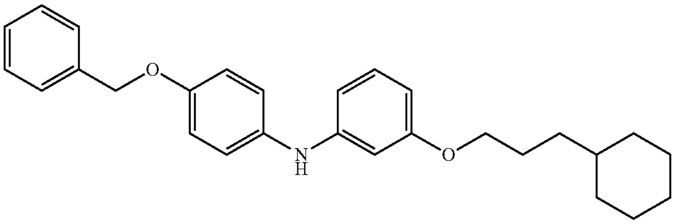 [SMILES: c1ccc(COc2ccc(Nc3cccc(OCCCC4CCCCC4)c3)cc2)cc1]
173
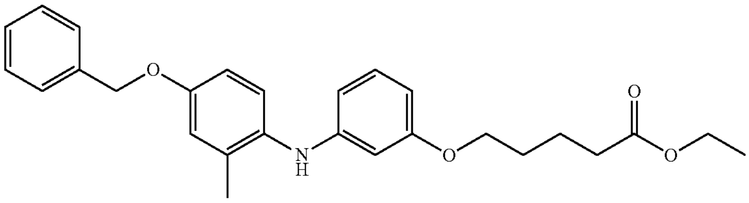 [SMILES: CCOC(=O)CCCCOc1cccc(Nc2ccc(OCc3ccccc3)cc2C)c1]

TABLE I-continued
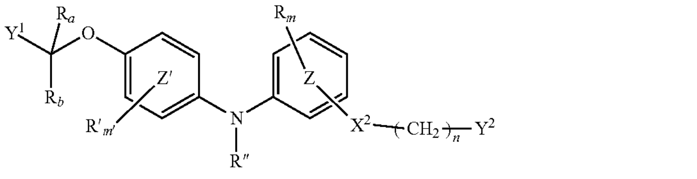
(Ie)
174
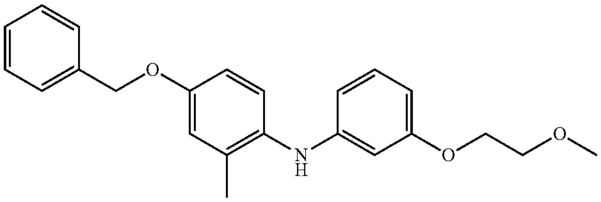 [SMILES: COCCOc1cccc(Nc2ccc(OCc3ccccc3)cc2C)c1]
175
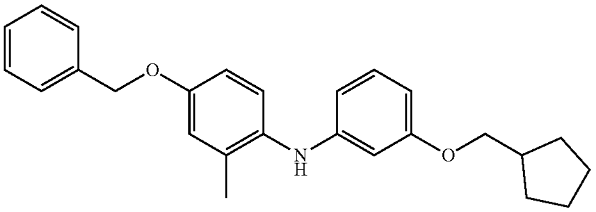 [SMILES: Cc1cc(OCc2ccccc2)ccc1Nc1cccc(OCC2CCCC2)c1]
176
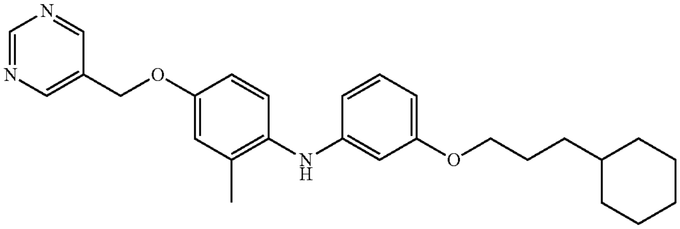 [SMILES: Cc1cc(OCc2cncnc2)ccc1Nc1cccc(OCCCC2CCCCC2)c1]
177
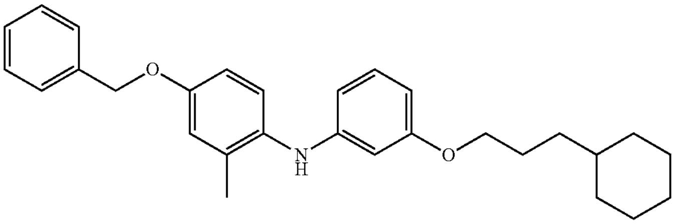 [SMILES: Cc1cc(OCc2ccccc2)ccc1Nc1cccc(OCCCC2CCCCC2)c1]
178
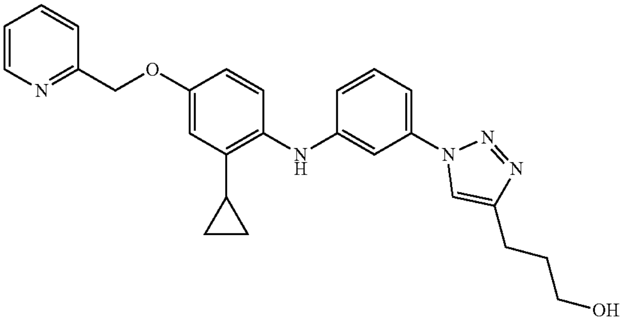 [SMILES: OCCCc1cn(-c2cccc(Nc3ccc(OCc4ccccn4)cc3C3CC3)c2)nn1]

TABLE I-continued
(Ie)
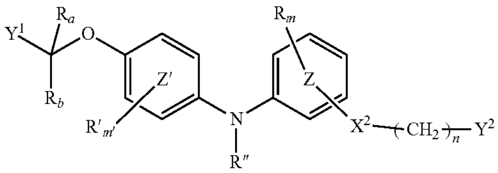
(Ie)
179
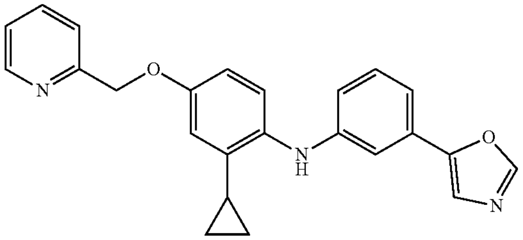 [SMILES: c1ccc(COc2ccc(Nc3cccc(-c4cnco4)c3)c(C3CC3)c2)nc1]
180
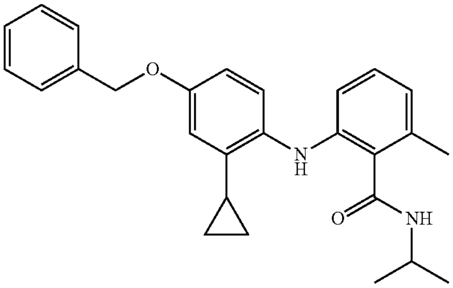 [SMILES: Cc1cccc(Nc2ccc(OCc3ccccc3)cc2C2CC2)c1C(=O)NC(C)C]
181
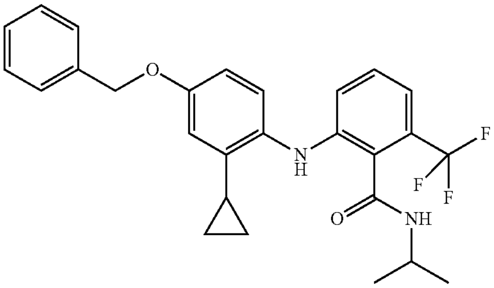 [SMILES: CC(C)NC(=O)c1c(Nc2ccc(OCc3ccccc3)cc2C2CC2)cccc1C(F)(F)F]
182
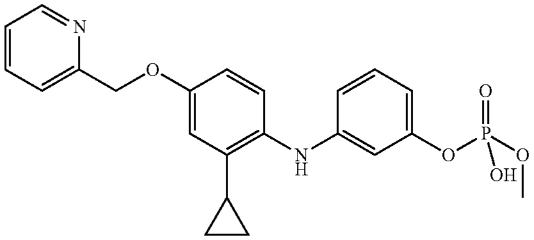 [SMILES: COP(=O)(O)Oc1cccc(Nc2ccc(OCc3ccccn3)cc2C2CC2)c1]
183
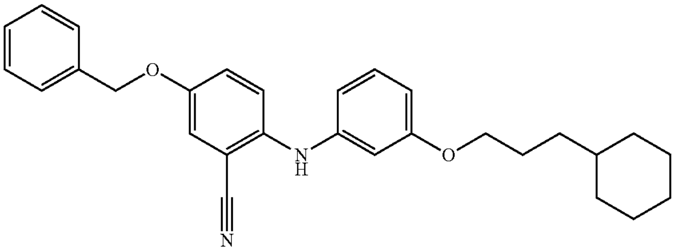 [SMILES: N#Cc1cc(OCc2ccccc2)ccc1Nc1cccc(OCCCC2CCCCC2)c1]

TABLE I-continued
(Ie)
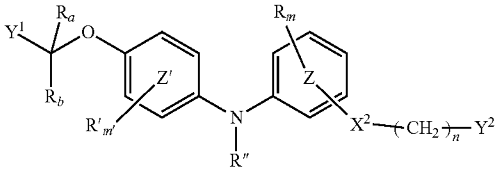
(Ie)
184
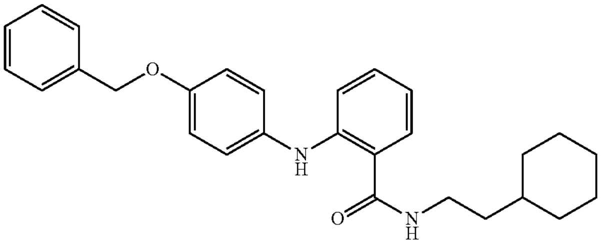 [SMILES: O=C(NCCC1CCCCC1)c1ccccc1Nc1ccc(OCc2ccccc2)cc1]
185
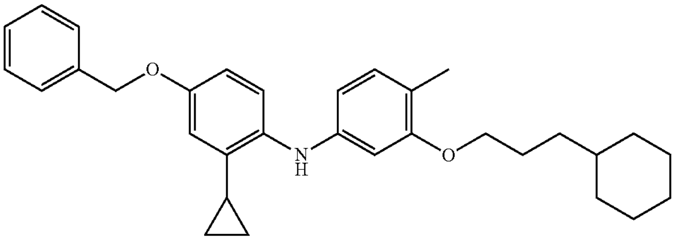 [SMILES: Cc1ccc(Nc2ccc(OCc3ccccc3)cc2C2CC2)cc1OCCCC1CCCCC1]
186
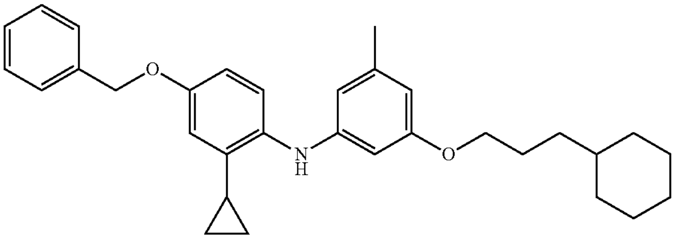 [SMILES: Cc1cc(Nc2ccc(OCc3ccccc3)cc2C2CC2)cc(OCCCC2CCCCC2)c1]
187
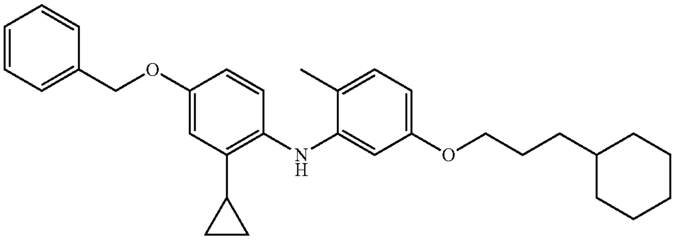 [SMILES: Cc1ccc(OCCCC2CCCCC2)cc1Nc1ccc(OCc2ccccc2)cc1C1CC1]
188
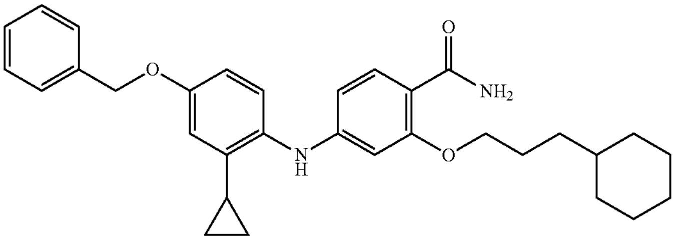 [SMILES: NC(=O)c1ccc(Nc2ccc(OCc3ccccc3)cc2C2CC2)cc1OCCCC1CCCCC1]

TABLE I-continued
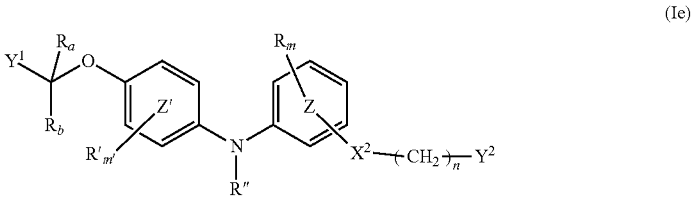
(Ie)
189
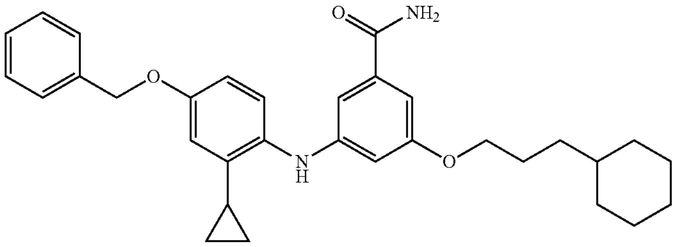 [SMILES: NC(=O)c1cc(Nc2ccc(OCc3ccccc3)cc2C2CC2)cc(OCCCC2CCCCC2)c1]
190
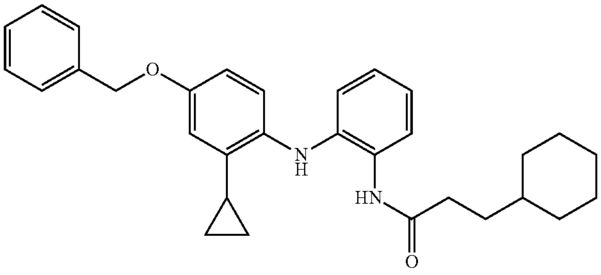 [SMILES: O=C(CCC1CCCCC1)Nc1ccccc1Nc1ccc(OCc2ccccc2)cc1C1CC1]
191
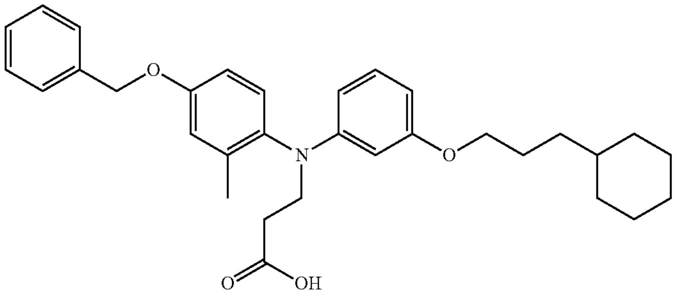 [SMILES: Cc1cc(OCc2ccccc2)ccc1N(CCC(=O)O)c1cccc(OCCCC2CCCCC2)c1]
192
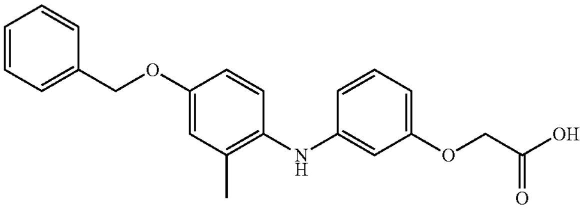 [SMILES: Cc1cc(OCc2ccccc2)ccc1Nc1cccc(OCC(=O)O)c1]
193
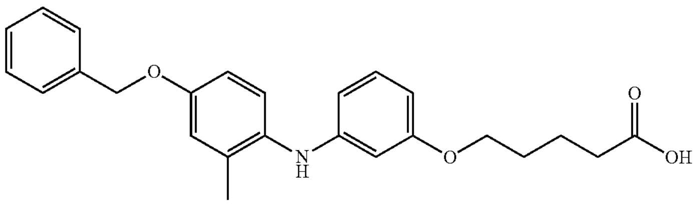 [SMILES: Cc1cc(OCc2ccccc2)ccc1Nc1cccc(OCCCCC(=O)O)c1]

TABLE I-continued
(Ie)
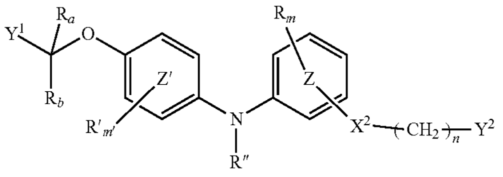
(Ie)
194
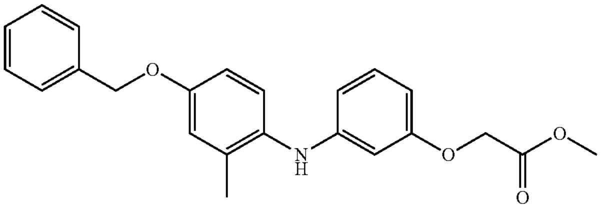 [SMILES: COC(=O)COc1cccc(Nc2ccc(OCc3ccccc3)cc2C)c1]
195
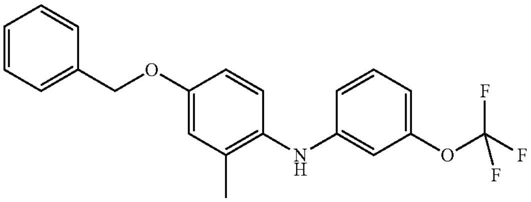 [SMILES: Cc1cc(OCc2ccccc2)ccc1Nc1cccc(OC(F)(F)F)c1]
196
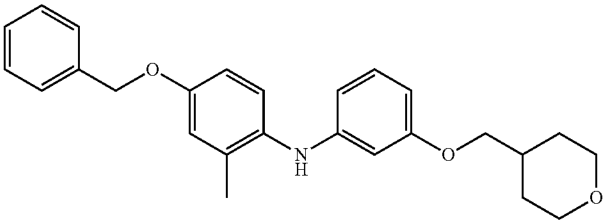 [SMILES: Cc1cc(OCc2ccccc2)ccc1Nc1cccc(OCC2CCOCC2)c1]
197
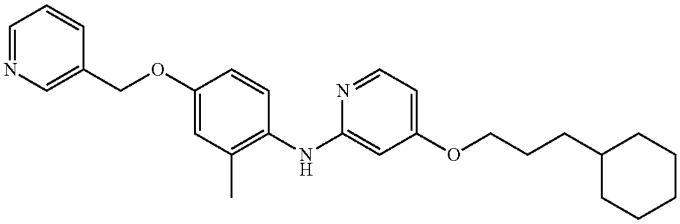 [SMILES: Cc1cc(OCc2cccnc2)ccc1Nc1cc(OCCCC2CCCCC2)ccn1]
198
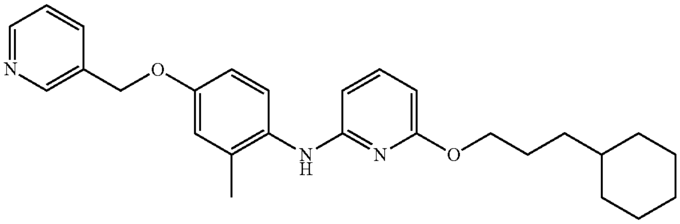 [SMILES: Cc1cc(OCc2cccnc2)ccc1Nc1cccc(OCCCC2CCCCC2)n1]
199
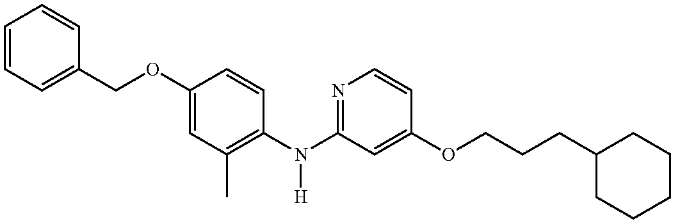 [SMILES: Cc1cc(OCc2ccccc2)ccc1Nc1cc(OCCCC2CCCCC2)ccn1]

TABLE I-continued
(Ie)
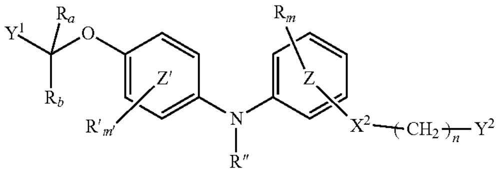
(Ie)
200
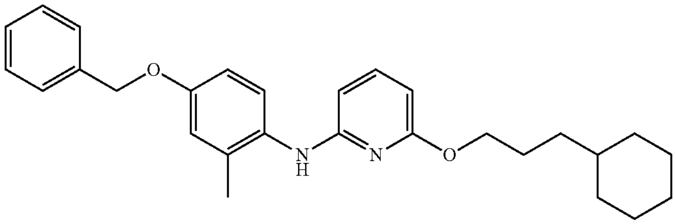 [SMILES: Cc1cc(OCc2ccccc2)ccc1Nc1cccc(OCCCC2CCCCC2)n1]
201
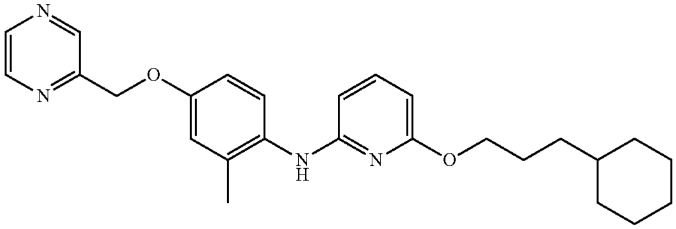 [SMILES: Cc1cc(OCc2cnccn2)ccc1Nc1cccc(OCCCC2CCCCC2)n1]
202
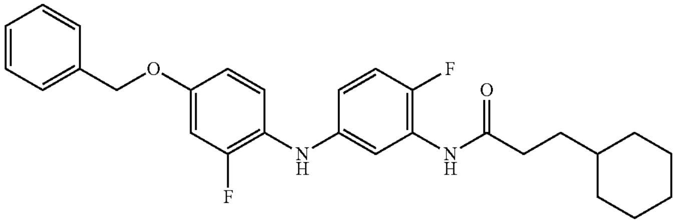 [SMILES: O=C(CCC1CCCCC1)Nc1cc(Nc2ccc(OCc3ccccc3)cc2F)ccc1F]
203
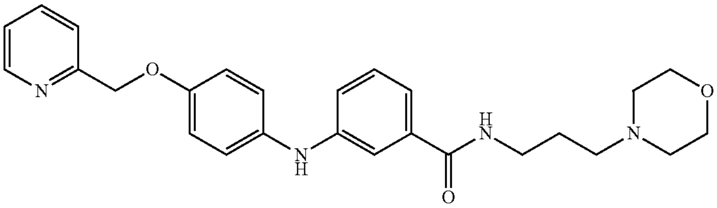 [SMILES: O=C(NCCCN1CCOCC1)c1cccc(Nc2ccc(OCc3ccccn3)cc2)c1]
204
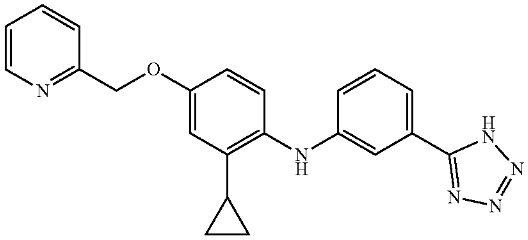 [SMILES: c1ccc(COc2ccc(Nc3cccc(-c4nnn[nH]4)c3)c(C3CC3)c2)nc1]

TABLE I-continued

| | |
|---|---|
| | (Ie)<br>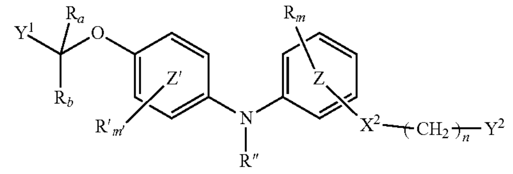<br>(Ie) |
| 205 | 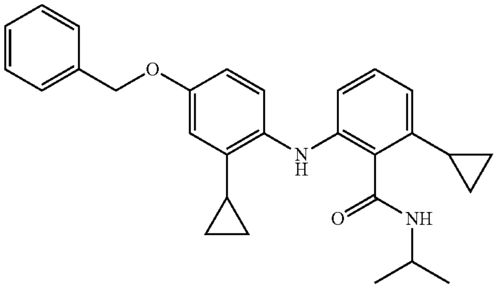 [SMILES: CC(C)NC(=O)c1c(Nc2ccc(OCc3ccccc3)cc2C2CC2)cccc1C1CC1] |
| 206 | 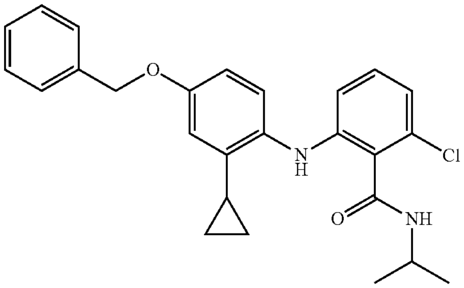 [SMILES: CC(C)NC(=O)c1c(Cl)cccc1Nc1ccc(OCc2ccccc2)cc1C1CC1] |

TABLE II

| Ex | Characterization |
|---|---|
| 36 | $^1$H NMR (300 MHz, $d_6$-DMSO) δ 8.58 (d, J = 4.2 Hz, 1H), 8.30 (t, J = 5.4 Hz, 1H), 8.03 (s, 1H), 7.84 (td, J = 7.7, 1.7 Hz, 1H), 7.53 (d, J = 7.8 Hz, 1H), 7.39-7.32 (m, 2H), 7.20 (d, J = 7.8 Hz, 1H), 7.14 (d, J = 7.7 Hz, 1H), 7.06 (d, J = 9.0 Hz, 3H), 6.97 (d, J = 9.0 Hz, 2H), 5.14 (s, 2H), 3.22 (dd, J = 13.3, 6.8 Hz, 2H), 1.86-1.70 (m, 3H), 1.62-1.42 (m, 7H), 1.10-1.07 (m, 2H). [M + H]$^+$ = 416.0 |
| 37 | $^1$H NMR (300 MHz, $d_6$-DMSO) δ 8.58 (d, J = 4.1 Hz, 1H), 8.28 (t, J = 5.2 Hz, 1H), 8.03 (s, 1H), 7.84 (td, J = 7.7, 1.6 Hz, 1H), 7.52 (d, J = 7.8 Hz, 1H), 7.39-7.31 (m, 2H), 7.20 (d, J = 7.7 Hz, 1H), 7.14 (d, J = 7.6 Hz, 1H), 7.05 (d, J = 9.0 Hz, 2H), 6.97 (d, J = 9.0 Hz, 2H), 5.13 (s, 2H), 3.23 (dd, J = 13.2, 6.6 Hz, 2H), 1.59 (d, J = 6.6 Hz, 1H), 1.39 (dd, J = 13.2, 6.6 Hz, 2H), 0.89 (d, J = 6.6 Hz, 6H). [M + H]$^+$ = 390.0 |
| 38 | $^1$H NMR (300 MHz, $d_6$-DMSO) δ 8.58 (d, J = 4.2 Hz, 1H), 8.26 (t, J = 5.4 Hz, 1H), 8.03 (s, 1H), 7.84 (td, J = 7.7, 1.7 Hz, 1H), 7.52 (d, J = 7.9 Hz, 1H), 7.39-7.31 (m, 2H), 7.20 (d, J = 7.8 Hz, 1H), 7.13 (d, J = 7.7 Hz, 1H), 7.06 (d, J = 9.0 Hz, 2H), 7.03 (s, 1H), 6.97 (d, J = 9.0 Hz, 2H), 5.13 (s, 2H), 3.23 (dd, J = 13.2, 6.8 Hz, 2H), 1.77-1.55 (m, 5H), 1.39 (dd, J = 14.1, 6.8 Hz, 2H), 1.31-1.12 (m, 4H), 0.97-0.79 (m, 2H). [M + H]$^+$ = 430.3 |
| 39 | $^1$H NMR (300 MHz, $d_6$-DMSO) δ 8.59 (d, J = 4.3 Hz, 1H), 8.26 (t, J = 5.5 Hz, 1H), 7.85 (td, J = 7.7, 1.6 Hz, 1H), 7.54 (d, J = 7.7 Hz, 1H), 7.47 (s, 1H), 7.35 (dd, J = 6.9, 5.5 Hz, 1H), 7.20-7.05 |

TABLE II-continued

| Ex | Characterization |
|---|---|
| | (m, 4H), 6.97 (d, J = 2.7 Hz, 1H), 6.85 (dd, J = 8.6, 2.7 Hz, 1H), 6.75 (d, J = 7.7 Hz, 1H), 5.16 (s, 2H), 3.21 (dd, J = 13.4, 6.5 Hz, 2H), 2.14 (s, 3H), 1.82-1.70 (m, 2H), 1.64-1.39 (m, 6H), 1.12-1.07 (m, 3H). $^{13}$C NMR (75 MHz, $d_6$-DMSO) δ 165.1, 155.5, 153.2, 147.6, 145.4, 135.5, 134.4, 132.7, 132.3, 127.3, 123.6, 121.5, 120.1, 117.8, 115.6, 114.6, 114.2, 111.3, 111.2, 35.9, 34.0, 30.7, 23.2, 16.6 [M + H]$^+$ = 430.3 |
| 40 | $^1$H NMR (300 MHz, $CDCl_3$) δ 8.59 (d, J = 4.8 Hz, 1H), 7.73 (td, J = 7.7, 1.7 Hz, 1H), 7.56 (d, J = 7.8 Hz, 1H), 7.36-7.31 (m, 1H), 7.24-7.17 (m, 2H), 7.10 (d, J = 7.7 Hz, 1H), 7.03-6.98 (m, 1H), 6.95 (d, J = 2.4 Hz, 1H), 6.90 (dd, J = 8.6, 2.6 Hz, 1H), 6.78 (d, J = 8.6 Hz, 1H), 6.25 (t, J = 5.3 Hz, 1H), 5.78 (s, 2H), 5.18 (s, 1H), 3.42 (dd, J = 14.5, 6.0 Hz, 2H), 2.30 (s, 3H), 1.88-1.73 (m, 3H), 1.63-1.47 (m, 6H), 1.15-1.10 (m, 2H). |
| 41 | $^1$H NMR (300 MHz, $d_6$-DMSO) δ 8.56 (d, J = 4.1 Hz, 1H), 8.32 (t, J = 5.7 Hz, 1H), 8.13 (s, 1H), 7.97 (d, J = 2.7 Hz, 1H), 7.81 (td, J = 7.7, 1.7 Hz, 1H), 7.57 (dd, J = 8.8, 2.8 Hz, 1H), 7.46 (d, J = 7.9 Hz, 1H), 7.34 (s, 1H), 7.33-7.29 (m, 1H), 7.23 (d, J = 7.7 Hz, 1H), 7.18 (d, J = 7.6 Hz, 1H), 7.01 (d, J = 8.6 Hz, 1H), 6.93 (d, J = 8.8 Hz, 1H), 5.38 (s, 1H), 3.22 (dd, J = 13.8, 6.3 Hz, 1H), 1.83-1.70 (m, 1H), 1.62-1.40 (m, 1H). |
| 42 | $^1$H NMR (300 MHz, $CDCl_3$) δ 8.61 (d, J = 4.8 Hz, 1H), 7.85 (t, J = 5.5 Hz, 1H), 7.73 (td, J = 7.7, 1.7 Hz, 1H), 7.61-7.51 (m, 3H), 7.24 (d, J = 9.0 Hz, 3H), 6.99 (d, J = 8.9 Hz, 2H), 6.77 (dd, J = 6.5, 2.7 Hz, 1H), 6.43 (s, 1H), 5.21 (s, 2H), 3.44 |

TABLE II-continued

| Ex | Characterization |
|---|---|
| | (dd, J = 14.1, 6.4 Hz, 2H), 1.89-1.79 (m, 3H), 1.66-1.53 (m, 6H), 1.18-1.12 (m, 2H). |
| 43 | $^{1}$H NMR (300 MHz, $CDCl_3$) δ 8.58 (d, J = 4.2 Hz, 1H), 7.71 (td, J = 7.7, 1.7 Hz, 1H), 7.58 (d, J = 7.7 Hz, 1H), 7.36 (s, 1H), 7.25-7.17 (m, 2H), 7.11 (d, J = 7.7 Hz, 1H), 7.04 (dd, J = 8.0, 1.5 Hz, 1H), 6.82 (d, J = 8.5 Hz, 1H), 6.73 (d, J = 2.4 Hz, 1H), 6.61 (dd, J = 8.5, 2.5 Hz, 1H), 6.03 (s, 1H), 5.65 (s, 1H), 5.26 (s, 2H), 3.87 (s, 3H), 3.44 (dd, J = 14.5, 6.0 Hz, 2H), 1.86-1.76 (m, 3H), 1.57-1.52 (m, 5H), 1.18-1.08 (m, 2H). $[M + H]^+$ = 446.4 |
| 44 | $^{1}$H NMR (300 MHz, $d_6$-DMSO) δ 8.99 (s, 1H), 8.58 (d, J = 4.1 Hz, 1H), 8.31 (t, J = 5.6 Hz, 1H), 7.97 (d, J = 3.1 Hz, 1H), 7.94 (s, 1H), 7.84 (tt, J = 4.7, 2.4 Hz, 2H), 7.54 (d, J = 7.8 Hz, 1H), 7.41 (dd, J = 9.0, 3.1 Hz, 1H), 7.35 (dd, J = 7.0, 5.3 Hz, 1H), 7.30-7.21 (m, 2H), 6.84 (d, J = 9.0 Hz, 1H), 5.17 (s, 2H), 3.24 (dd, J = 13.9, 6.3 Hz, 2H), 1.84-1.72 (m, 3H), 1.64-1.43 (m, 6H), 1.18-1.02 (m, 2H). $[M + H]^+$ = 417.4 |
| 45 | $^{1}$H NMR (300 MHz, $CDCl_3$) δ 8.59 (d, J = 4.8 Hz, 1H), 7.72 (td, J = 7.7, 1.7 Hz, 1H), 7.53 (d, J = 7.8 Hz, 1H), 7.27-7.22 (m, 1H), 7.19 (d, J = 7.8 Hz, 1H), 7.15-7.12 (m, 1H), 7.11 (d, J = 8.6 Hz, 1H), 7.06 (d, J = 7.7 Hz, 1H), 6.89 (d, J = 2.8 Hz, 1H), 6.81-6.76 (m, 1H), 6.36 (t, J = 5.3 Hz, 1H), 5.45 (s, 1H), 5.17 (s, 1H), 3.49 (dd, J = 12.9, 6.8 Hz, 2H), 2.18 (s, 3H), 1.48 (dd, J = 12.9, 6.8 Hz, 2H), 0.76-0.62 (m, 1H), 0.45 (dt, J = 8.0, 5.0 Hz, 1H), 0.07 (dt, J = 8.0, 5.0 Hz, 1H). $[M + H]^+$ = 402.3 |
| 46 | $^{1}$H NMR (300 MHz, $CDCl_3$) δ 8.61 (d, J = 4.3 Hz, 1H), 7.73 (td, J = 7.7, 1.7 Hz, 1H), 7.54 (d, J = 7.8 Hz, 1H), 7.26-7.23 (m, 1H), 7.19 (t, J = 7.8 Hz, 1H), 7.14-7.11 (m, 2H), 7.04 (d, J = 7.7 Hz, 1H), 6.90 (d, J = 2.9 Hz, 1H), 6.80 (dd, J = 9.3, 3.0 Hz, 2H), 5.98 (s, 1H), 5.32 (s, 1H), 5.20 (s, 2H), 3.35 (dd, J = 13.4, 6.7 Hz, 1H), 2.35 (dt, J = 15.5, 7.8 Hz, 1H), 2.20 (s, 3H), 2.15-2.02 (m, 2H), 1.94-1.79 (m, 2H), 1.68-1.63 (m, 4H). $[M + H]^+$ = 416.3 |
| 47 | $^{1}$H NMR (300 MHz, $d_6$-DMSO) δ 8.59 (d, J = 4.3 Hz, 1H), 8.22 (t, J = 5.6 Hz, 1H), 7.85 (td, J = 7.7, 1.6 Hz, 1H), 7.54 (d, J = 7.8 Hz, 1H), 7.45 (s, 1H), 7.35 (dd, J = 6.9, 5.2 Hz, 1H), 7.14 (d, J = 7.8 Hz, 1H), 7.11-7.04 (m, 3H), 6.97 (d, J = 2.7 Hz, 1H), 6.85 (dd, J = 8.6, 2.8 Hz, 1H), 6.75 (d, J = 7.7 Hz, 1H), 5.16 (s, 2H), 3.22 (dd, J = 13.2, 6.6 Hz, 2H), 2.14 (s, 3H), 1.73-1.63 (m, 5H), 1.42-1.35 (m, 2H), 1.32-1.11 (m, 4H), 0.94-0.83 (m, 2H). $[M + H]^+$ = 444.4 |
| 48 | $^{1}$H NMR (300 MHz, $CDCl_3$) δ 8.61 (d, J = 4.3 Hz, 1H), 7.73 (td, J = 7.7, 1.7 Hz, 1H), 7.54 (d, J = 7.8 Hz, 1H), 7.35-7.28 (m, 1H), 7.25-7.19 (m, 2H), 7.08 (d, J = 8.9 Hz, 2H), 7.00 (dd, J = 8.4, 1.9 Hz, 1H), 6.95 (d, J = 8.9 Hz, 2H), 5.98 (s, 1H), 5.61 (s, 1H), 5.20 (s, 2H), 3.35 (dd, J = 13.5, 6.5 Hz, 2H), 2.36 (dt, J = 15.6, 7.9 Hz, 1H), 2.16-2.00 (m, 2H), 1.97-1.79 (m, 2H), 1.72-1.65 (m, 4H). $[M + H]^+$ = 402.3 |
| 49 | $^{1}$H NMR (300 MHz, $d_6$-DMSO) δ 8.58 (d, J = 4.1 Hz, 1H), 8.31 (t, J = 5.6 Hz, 1H), 8.02 (s, 1H), 7.84 (td, J = 7.7, 1.8 Hz, 1H), 7.52 (d, J = 7.8 Hz, 1H), 7.37 (d, J = 1.9 Hz, 1H), 7.36-7.31 (m, 1H), 7.20 (d, J = 7.7 Hz, 1H), 7.14 (d, J = 7.7 Hz, 1H), 7.06 (d, J = 9.0 Hz, 1H), 6.97 (d, J = 9.0 Hz, 2H), 5.13 (s, 2H), 3.27 (dd, J = 14.3, 7.1 Hz, 2H), 1.40 (dd, J = 14.3, 7.1 Hz, 2H), 0.70 (m, 1H), 0.39 (dd, J = 12.0, 3.9 Hz, 2H), 0.04 (dd, J = 12.0, 3.9 Hz, 2H). $[M + H]^+$ = 388.3 |
| 50 | $^{1}$H NMR (300 MHz, $d_6$-DMSO) δ 8.31 (t, J = 5.6 Hz, 1H), 8.05 (s, 1H), 7.57 (td, J = 7.4, 1.5 Hz, 1H), 7.47-7.36 (m, 2H), 7.30-7.19 (m, 3H), 7.15 (d, J = 7.7 Hz, 1H), 7.07 (d, J = 9.0 Hz, 2H), 7.05-7.0 (m, 1H), 6.98 (d, J = 9.0 Hz, 2H), 5.10 (s, 2H), 3.23 (dd, J = 13.8, 6.3 Hz, 2H), 1.86-1.72 (m, 3H), 1.62-1.45 (m, 6H), 1.11-1.04 (m, 2H). $^{13}$C NMR (75 MHz, $d_6$-DMSO) δ 164.6, 160.2, 156.9, 151.1, 143.3, 134.4, 134.2, 128.9, 128.8, 128.4, 127.1, 122.7, 122.7, 122.4, 122.2, 118.7, 117.4, 115.3, 114.9, 113.8, 113.4, 111.8, 62.0, 35.6, 33.7, 30.4, 22.9 |
| 51 | $^{1}$H NMR (300 MHz, $d_6$-DMSO) δ 8.30 (t, J = 5.5 Hz, 1H), 8.07 (s, 1H), 7.92 (d, J = 7.6 Hz, 1H), 7.81-7.72 (m, 2H), 7.62-7.55 (m, 1H), 7.40 (s, 1H), 7.22 (d, J = 7.7 Hz, 1H), 7.16 (d, J = 7.7 Hz, 1H), 7.08 (d, J = 9.0 Hz, 2H), 7.01 (d, J = 9.1 Hz, 2H), 5.21 (s, 2H), 3.23 (dd, J = 13.9, 6.2 Hz, 2H), 1.79-1.70 (m, 3H), 1.60-1.49 (m, 7H). |
| 52 | $^{1}$H NMR (300 MHz, $d_6$-DMSO) δ 8.29 (t, J = 5.6 Hz, 1H), 8.01 (s, 1H), 7.44 (dd, J = 9.5, 4.1 Hz, 3H), 7.41-7.30 (m, 4H), 7.20 (d, J = 7.7 Hz, 1H), 7.14 (d, J = 7.7 Hz, 1H), 7.06 (d, J = 9.0 Hz, 2H), 7.00 (s, 1H), 6.97 (d, J = 9.0 Hz, 2H), 5.07 (s, 2H), 3.23 (dd, J = 13.7, 6.2 Hz, 2H), 1.79-1.70 (m, 3H), 1.63-1.46 (m, 6H). |
| 53 | $^{1}$H NMR (300 MHz, $d_6$-DMSO) δ 8.76 (d, J = 5.0 Hz, 1H), 8.32 (t, J = 5.3 Hz, 1H), 8.25 (t, J = 6.7 Hz, 1H), 7.90 (d, J = 7.8 Hz, 1H), 7.70 (s, 1H), 7.44 (s, 1H), 7.31-7.14 (m, 2H), 7.07 (d, J = 7.1 Hz, 1H), 6.93 (d, J = 8.6 Hz, 1H), 6.67 (d, J = 2.4 Hz, 1H), 6.49 (dd, J = 8.6, 2.3 Hz, 1H), 5.27 (s, 2H), 3.23 (dd, J = 13.4, 6.4 Hz, 2H), 1.82-1.73 (m, 3H), 1.62-1.43 (m, 6H), 1.12-1.04 (m, 2H). $[M + H]^+$ = 432.3 |
| 54 | $^{1}$H NMR (300 MHz, $d_6$-DMSO) δ 8.59 (d, J = 4.0 Hz, 1H), 8.23 (t, J = 5.6 Hz, 1H), 7.85 (td, J = 7.7, 1.8 Hz, 1H), 7.54 (d, J = 7.8 Hz, 1H), 7.45 (s, 1H), 7.36 (dd, J = 6.9, 5.3 Hz, 1H), 7.16 (t, J = 7.8 Hz, 1H), 7.12-7.04 (m, 3H), 6.97 (d, J = 2.8 Hz, 1H), 6.85 (dd, J = 8.6, 2.9 Hz, 1H), 6.74 (dd, J = 7.9, 1.5 Hz, 1H), 5.16 (s, 2H), 3.22 (dd, J = 13.8, 6.3 Hz, 2H), 2.14 (s, 3H), 1.68-1.51 (m, 1H), 1.38 (dd, J = 14.4, 6.9 Hz, 2H), 0.89 (d, J = 6.6 Hz, 6H). $[M + H]^+$ = 404.3 |
| 55 | $^{1}$H NMR (300 MHz, $CDCl_3$) δ 8.60 (d, J = 4.2 Hz, 1H), 7.73 (td, J = 7.7, 1.7 Hz, 1H), 7.54 (d, J = 7.8 Hz, 1H), 7.34 (d, J = 1.7 Hz, 1H), 7.29-7.21 (m, 3H), 7.07 (d, J = 8.9 Hz, 2H), 7.05-7.01 (m, 1H), 6.95 (d, J = 8.9 Hz, 2H), 5.89 (s, 1H), 5.19 (s, 2H), 4.67 (t, J = 6.1 Hz, 1H), 2.95 (dd, J = 14.3, 6.6 Hz, 2H), 1.78-1.62 (m, 3H), 1.60-1.42 (m, 6H), 1.05-0.94 (m, 2H). $[M + H]^+$ = 452.3 |
| 56 | $^{1}$H NMR (300 MHz, $d_6$-DMSO) δ 8.59 (d, J = 4.2 Hz, 1H), 8.29 (s, 1H), 7.85 (td, J = 7.7, 1.8 Hz, 1H), 7.53 (d, J = 7.7 Hz, 1H), 7.42 (t, J = 5.6 Hz, 1H), 7.38-7.27 (m, 3H), 7.10-7.06 (m, 4H), 7.01 (d, J = 9.0 Hz, 2H), 5.16 (s, 2H), 2.81-2.69 (m, 2H), 1.64-1.53 (m, 5H), 1.26-1.10 (m, 6H), 0.83-0.69 (m, 2H). $[M + H]^+$ = 466.3 |
| 57 | $^{1}$H NMR (300 MHz, $CDCl_3$) δ 8.59 (d, J = 4.5 Hz, 1H), 7.72 (td, J = 7.7, 1.7 Hz, 1H), 7.55 (d, J = 7.8 Hz, 1H), 7.28-7.16 (m, 2H), 7.16-7.09 (m, 2H), 7.04 (d, J = 7.7 Hz, 1H), 6.92 (d, J = 2.8 Hz, 1H), 6.81-6.72 (m, 2H), 6.23 (t, J = 5.3 Hz, 1H), 5.44 (s, 1H), 5.18 (s, 2H), 3.41 (dd, J = 14.6, 6.0 Hz, 2H), 2.54 (q, J = 7.5 Hz, 2H), 1.72-1.57 (m, 1H), 1.46 (dd, J = 14.7, 7.1 Hz, 2H), 1.14 (t, J = 7.5 Hz, 3H), 0.92 (d, J = 6.6 Hz, 6H). $[M + H]^+$ = 418.3 |
| 58 | $^{1}$H NMR (300 MHz, $CDCl_3$) δ 8.60 (d, J = 4.8 Hz, 1H), 7.73 (td, J = 7.7, 1.7 Hz, 1H), 7.55 (d, J = 7.8 Hz, 1H), 7.27-7.19 (m, 1H), 7.17-7.11 (m, 3H), 7.04 (d, J = 7.8 Hz, 1H), 6.93 (d, J = 2.9 Hz, 1H), 6.83-6.73 (m, 2H), 6.13 (t, J = 5.2 Hz, 1H), |

TABLE II-continued

| Ex | Characterization |
|---|---|
| | 5.38 (s, 1H), 5.20 (s, 2H), 3.42 (dd, J = 14.4, 6.1 Hz, 2H), 2.56 (q, J = 7.5 Hz, 2H), 1.86-1.75 (m, 3H), 1.66-1.49 (m, 6H), 1.15 (t, J = 7.5 Hz, 3H), 1.11-1.07 (m, 2H). [M + H]$^+$ = 444.2 |
| 59 | $^1$H NMR (300 MHz, $d_6$-DMSO) δ 8.58 (d, J = 4.1 Hz, 1H), 8.29 (s, 1H), 7.84 (td, J = 7.7, 1.8 Hz, 1H), 7.53 (d, J = 7.8 Hz, 1H), 7.47 (t, J = 5.8 Hz, 1H), 7.39-7.28 (m, 3H), 7.12-7.06 (m, 4H), 7.00 (d, J = 9.0 Hz, 2H), 5.15 (s, 2H), 2.78 (dd, J = 13.4, 7.0 Hz, 2H), 1.28-1.20 (m, 2H), 0.71-0.57 (m, 1H), 0.37-0.29 (m, 2H), −0.02-−0.08 (m, 2H). [M + H]$^+$ = 424.2 |
| 60 | $^1$H NMR (300 MHz, $CDCl_3$) δ 8.61 (d, J = 4.2 Hz, 1H), 7.73 (td, J = 7.7, 1.7 Hz, 1H), 7.54 (d, J = 7.7 Hz, 1H), 7.26-7.19 (m, 3H), 7.16 (d, J = 8.6 Hz, 1H), 7.08 (d, J = 7.7 Hz, 1H), 6.95 (dd, J = 7.7, 1.7 Hz, 1H), 6.78 (dd, J = 8.6, 2.9 Hz, 1H), 6.68 (d, J = 2.9 Hz, 1H), 6.03 (s, 1H), 5.71 (s, 1H), 5.18 (s, 2H), 3.43 (dd, J = 9.8, 4.7 Hz, 2H), 1.90-1.78 (m, 5H), 1.66-1.51 (m, 4H), 1.17-1.09 (m, 3H), 0.94-0.87 (m, 2H), 0.67-0.59 (m, 2H). $^{13}$C NMR (75 MHz, $CDCl_3$) δ 165.4, 155.1, 152.7, 146.9, 143.9, 135.4, 134.5, 133.8, 132.2, 127.0, 120.9, 120.3, 119.0, 115.3, 114.4, 111.8, 111.2, 110.0, 68.6, 37.2, 35.6, 33.6, 30.4, 22.8, 9.3, 4.9 [M + H]$^+$ = 456.4 |
| 61 | $^1$H NMR (300 MHz, $CDCl_3$) δ 8.60 (d, J = 4.5 Hz, 1H), 7.72 (td, J = 7.7, 1.6 Hz, 1H), 7.53 (d, J = 7.8 Hz, 1H), 7.28-7.18 m, 3H), 7.15 (d, J = 8.7 Hz, 1H), 7.08 (d, J = 7.7 Hz, 1H), 6.93 (dd, J = 7.9, 1.7 Hz, 1H), 6.77 (dd, J = 8.6, 2.9 Hz, 1H), 6.67 (d, J = 2.8 Hz, 1H), 6.11 (s, 1H), 5.74 (s, 1H), 5.17 (s, 2H), 3.44 (dd, J = 14.5, 6.0 Hz, 2H), 1.91-1.82 (m, 1H), 1.71-1.60 (m, 1H), 1.48 (dd, J = 14.7, 7.1 Hz, 2H), 0.94 (d, J = 6.6 Hz, 6H), 0.92-0.85 (m, 2H), 0.66-0.56 (m, 2H). [M + H]$^+$ = 430.3 |
| 62 | $^1$H NMR (300 MHz, $d_6$-DMSO) δ 8.58 (d, J = 4.2 Hz, 1H), 8.34 (t, J = 5.6 Hz, 1H), 8.04 (s, 1H), 7.85 (td, J = 7.7, 1.7 Hz, 1H), 7.53 (d, J = 7.8 Hz, 1H), 7.37-1.33 (m, 2H), 7.21 (d, J = 7.7 Hz, 1H), 7.15 (d, J = 7.6 Hz, 1H), 7.07 (d, J = 9.0 Hz, 2H), 7.10-7.01 (m, 1H), 6.98 (d, J = 9.0 Hz, 2H), 5.14 (s, 2H), 3.15 (t, J = 6.3 Hz, 2H), 2.19-2.07 (m, 1H), 1.72-1.44 (m, 6H), 1.30-1.18 (m, 2H). [M + H]$^+$ = 402.3 |
| 63 | $^1$H NMR (300 MHz, $d_6$-DMSO) δ 8.58 (d, J = 4.1 Hz, 1H), 8.52 (t, J = 6.0 Hz, 1H), 8.07 (s, 1H), 7.85 (td, J = 7.7, 1.7 Hz, 1H), 7.53 (d, J = 7.8 Hz, 1H), 7.39 (s, 1H), 7.35 (dd, J = 7.3, 5.7 Hz, 1H), 7.23 (d, J = 7.7 Hz, 1H), 7.18 (d, J = 7.7 Hz, 1H), 7.07 (d, J = 8.9 Hz, 2H), 7.09-7.03 (m, 1H), 6.98 (d, J = 9.0 Hz, 2H), 5.14 (s, 2H), 4.47 (d, J = 5.7 Hz, 2H), 4.19 (d, J = 5.7 Hz, 2H), 3.42 (d, J = 6.1 Hz, 2H), 1.24 (s, 3H). [M + H]$^+$ = 404.2 |
| 64 | $^1$H NMR (300 MHz, $d_6$-DMSO) δ 8.58 (d, J = 4.1 Hz, 1H), 8.04-8.01 (m, 2H), 7.85 (td, J = 7.7, 1.8 Hz, 1H), 7.53 (d, J = 7.8 Hz, 1H), 7.37-7.33 (m, 2H), 7.21 (d, J = 7.7 Hz, 1H), 7.16 (d, J = 7.6 Hz, 1H), 7.06 (d, J = 9.0 Hz, 2H), 7.02-7.00 (m, 1H), 6.98 (d, J = 9.0 Hz, 2H), 5.14 (s, 2H), 4.05-3.92 (m, 1H), 1.57-1.25 (m, 4H), 1.11 (d, J = 6.6 Hz, 3H), 0.87 (t, J = 7.2 Hz, 3H). [M + H]$^+$ = 390.1 |
| 65 | $^1$H NMR (300 MHz, $d_6$-DMSO) δ 8.58 (d, J = 4.1 Hz, 1H), 8.54 (d, J = 5.7 Hz, 1H), 8.08 (s, 1H), 7.85 (td, J = 7.7, 1.8 Hz, 1H), 7.53 (d, J = 7.9 Hz, 1H), 7.38 (d, J = 2.0 Hz, 1H), 7.37-7.32 (m, 1H), 7.23 (d, J = 7.8 Hz, 1H), 7.14 (d, J = 7.7 Hz, 1H), 7.07 (d, J = 9.0 Hz, 2H), 7.03-7.01 (m, 1H), 6.98 (d, J = 9.0 Hz, 2H), 5.14 (s, 2H), 3.46 (dd, J = 12.6, 6.8 Hz, 2H), 2.50 (dd, J = 12.6, 6.8 Hz, 2H). [M + H]$^+$ = 416.1 |

TABLE II-continued

| Ex | Characterization |
|---|---|
| 66 | $^1$H NMR (300 MHz, $d_6$-DMSO) δ 8.56 (d, J = 4.2 Hz, 1H), 8.25 (t, J = 5.7 Hz, 1H), 7.80 (td, J = 7.7, 1.7 Hz, 1H), 7.46 (d, J = 7.9 Hz, 1H), 7.40 (s, 1H), 7.30 (dd, J = 6.9, 5.4 Hz, 1H), 7.12 (d, J = 7.7 Hz, 1H), 7.09-7.05 (m, 2H), 7.02 (d, J = 10.0 Hz, 1H), 6.95 (d, J = 11.7 Hz, 1H), 6.84 (d, J = 2.8 Hz, 1H), 6.69 (dd, J = 8.6, 2.9 Hz, 2H), 5.41 (q, J = 6.5 Hz, 1H), 3.20 (dd, J = 13.6, 6.4 Hz, 1H), 2.08 (s, 3H), 1.82-1.70 (m, 4H), 1.58 (d, J = 6.5 Hz, 3H), 1.54-1.42 (m, 5H), 1.09 (t, J = 7.0 Hz, 3H). [M + H]$^+$ = 444.2 |
| 67 | $^1$H NMR (300 MHz, $d_6$-DMSO) δ 8.56 (d, J = 4.2 Hz, 1H), 8.23 (t, J = 5.6 Hz, 1H), 7.80 (td, J = 7.7, 1.7 Hz, 1H), 7.46 (d, J = 7.9 Hz, 1H), 7.40 (s, 1H), 7.30 (ddd, J = 7.5, 4.8, 1.0 Hz, 1H), 7.12 (d, J = 7.8 Hz, 1H), 7.09-7.05 (m, 2H), 7.02 (d, J = 9.5 Hz, 1H), 6.95 (d, J = 11.8 Hz, 1H), 6.85 (d, J = 2.8 Hz, 1H), 6.73-6.65 (m, 2H), 5.42 (q, J = 6.4 Hz, 1H), 3.21 (dd, J = 13.7, 6.4 Hz, 2H), 2.08 (s, 3H), 1.58 (d, J = 6.5 Hz, 4H), 1.37 (dd, J = 14.4, 6.9 Hz, 2H), 0.88 (d, J = 6.6 Hz, 6H). [M + H]$^+$ = 418.3 |
| 68 | $^1$H NMR (300 MHz, $d_6$-DMSO) δ 8.59 (d, J = 4.5 Hz, 1H), 8.15 (s, 1H), 7.85 (td, J = 7.9, 1.5 Hz, 1H), 7.54 (d, J = 7.9 Hz, 1H), 7.39-7.31 (m, 1H), 7.18 (s, 1H), 7.06 (d, J = 8.6 Hz, 1H), 6.96-6.90 (m, 2H), 6.82 (dd, J = 8.6, 2.8 Hz, 1H), 6.73 (s, 1H), 6.67 (d, J = 7.9 Hz, 1H), 6.21 (d, J = 7.9 Hz, 1H), 5.92 (t, J = 5.4 Hz, 1H), 5.14 (s, 2H), 3.06 (dd, J = 13.3, 6.7 Hz, 2H), 2.14 (s, 3H), 1.57 (td, J = 13.3, 6.7 Hz, 1H), 1.33-1.25 (m, 2H), 0.88 (d, J = 6.7 Hz, 6H). [M + H]$^+$ = 419.4 |
| 69 | $^1$H NMR (300 MHz, $d_6$-DMSO) δ 8.93 (d, J = 6.4 Hz, 1H), 8.59 (d, J = 4.8 Hz, 1H), 7.85 (td, J = 7.8, 1.8 Hz, 1H), 7.54 (d, J = 7.8 Hz, 1H), 7.49 (s, 1H), 7.36 (dd, J = 6.7, 5.0 Hz, 1H), 7.23-7.12 (m, 3H), 7.08 (d, J = 8.6 Hz, 1H), 6.97 (d, J = 2.8 Hz, 1H), 6.85 (dd, J = 8.6, 2.9 Hz, 1H), 6.77 (d, J = 7.5 Hz, 1H), 5.16 (s, 2H), 4.96 (dd, J = 14.0, 7.1 Hz, 1H), 4.74 (t, J = 6.9 Hz, 2H), 4.57 (t, J = 6.4 Hz, 2H), 2.14 (s, 3H). [M + H]$^+$ = 490.3 |
| 70 | $^1$H NMR (300 MHz, $d_6$-DMSO) δ 8.59 (d, J = 4.5 Hz, 1H), 8.29 (t, J = 5.7 Hz, 1H), 7.85 (dd, J = 7.7, 6.1 Hz, 1H), 7.54 (d, J = 7.8 Hz, 1H), 7.47 (s, 1H), 7.40-7.32 (m, 1H), 7.17 (s, 1H), 7.12-7.04 (m, 3H), 6.97 (d, J = 2.7 Hz, 1H), 6.85 (dd, J = 8.6, 2.7 Hz, 1H), 6.75 (d, J = 7.8 Hz, 1H), 5.16 (s, 2H), 3.19 (dd, J = 12.5, 6.4 Hz, 2H), 2.76-2.57 (m, 3H), 2.33-2.15 (m, 2H), 2.14 (s, 3H), 1.68 (q, J = 6.8 Hz, 2H). [M + H]$^+$ = 452.3 |
| 71 | $^1$H NMR (300 MHz, $d_6$-DMSO) δ 8.59 (d, J = 4.6 Hz, 1H), 8.11 (d, J = 7.3 Hz, 1H), 7.85 (td, J = 7.7, 1.6 Hz, 1H), 7.54 (d, J = 7.8 Hz, 1H), 7.44 (s, 1H), 7.36 (dd, J = 7.3, 4.8 Hz, 1H), 7.14 (dd, J = 14.1, 6.3 Hz, 2H), 7.07 (d, J = 8.8 Hz, 2H), 6.97 (d, J = 2.7 Hz, 1H), 6.85 (dd, J = 8.6, 2.8 Hz, 1H), 6.73 (d, J = 7.5 Hz, 1H), 5.16 (s, 2H), 4.17 (dd, J = 14.0, 7.1 Hz, 1H), 2.14 (s, 3H), 1.93-1.79 (m, 2H), 1.71-1.62 (m, 2H), 1.58-1.46 (m, 4H). [M + H]$^+$ = 402.3 |
| 72 | [$^1$H NMR (300 MHz, $CDCl_3$) δ 8.60 (d, J = 4.8 Hz, 1H), 7.73 (td, J = 7.7, 1.7 Hz, 1H), 7.54 (d, J = 7.8 Hz, 1H), 7.27-7.21 (m, 1H), 7.20 (d, J = 7.6 Hz, 1H), 7.16 (s, 1H), 7.12 (d, J = 8.6 Hz, 1H), 7.05 (d, J = 7.6 Hz, 1H), 6.90 (d, J = 2.7 Hz, 1H), 6.83-6.73 (m, 2H), 6.14 (s, 1H), 5.39 (s, 1H), 5.18 (s, 2H), 3.39 (dd, J = 13.2, 7.1 Hz, 2H), 2.19 (s, 3H), 1.63-1.50 (m, 3H), 1.27-1.20 (m, 2H), 0.88 (d, J = 6.6 Hz, 6H). [M + H]$^+$ = 418.3 |
| 73 | $^1$H NMR (300 MHz, $CDCl_3$) δ 8.59 (d, J = 5.2 Hz, 1H), 7.71 (td, J = 7.7, 1.7 Hz, 1H), 7.53 (d, J = 7.7 Hz, 1H), 7.21 (dd, J = 7.0, 5.2 Hz, 1H), 7.12-7.03 (m, 3H), 6.96-6.89 (m, 2H), 6.50-6.44 |

TABLE II-continued

| Ex | Characterization |
|---|---|
| | (m, 2H), 6.38 (dd, J = 7.7, 1.7 Hz, 1H), 5.55 (br s, 1H), 5.18 (s, 2H), 3.88 (t, J = 6.6 Hz, 2H), 1.82-1.68 (m, 7H), 1.66-1.46 (m, 5H), 1.17-1.04 (m, 3H). $[M + H]^+$ = 403.4 |
| 74 | $^1H$ NMR (300 MHz, $CDCl_3$) δ 8.60 (d, J = 4.8 Hz, 1H), 7.73 (td, J = 7.7, 1.6 Hz, 1H), 7.54 (d, J = 7.9 Hz, 1H), 7.22 (d, J = 7.0 Hz, 1H), 7.14-7.04 (m, 3H), 6.98-6.93 (m, 2H), 6.51-6.45 (m, 2H), 6.42-6.35 (m, 1H), 5.49 (s, 1H), 5.19 (s, 2H), 3.76 (dd, J = 9.0, 5.8 Hz, 1H), 3.66 (dd, J = 9.0, 5.8 Hz, 1H), 1.94-1.83 (m, 1H), 1.51-1.32 (m, 4H), 1.21-1.13 (m, 2H), 0.99 (d, J = 6.7 Hz, 3H), 0.91 (t, J = 7.1 Hz, 3H). $[M + H]^+$ = 377.3 |
| 75 | $^1H$ NMR (300 MHz, $CDCl_3$) δ 8.61 (d, J = 4.8 Hz, 1H), 7.74 (td, J = 7.7, 1.7 Hz, 1H), 7.56 (d, J = 7.8 Hz, 1H), 7.22 (dd, J = 7.5, 1.6 Hz, 1H), 7.19-7.12 (m, 3H), 7.03 (d, J = 7.7 Hz, 1H), 6.94 (d, J = 2.9 Hz, 1H), 6.81 (dd, J = 8.6, 2.9 Hz, 1H), 6.77 (dd, J = 8.0, 1.8 Hz, 1H), 5.99 (s, 1H), 5.33 (s, 1H), 5.21 (s, 2H), 3.44 (dd, J = 14.4, 6.1 Hz, 2H), 2.56 (q, J = 7.5 Hz, 2H), 1.81-1.65 (m, 6H), 1.48 (dd, J = 14.6, 7.0 Hz, 2H), 1.37-1.27 (m, 2H), 1.16 (t, J = 7.5 Hz, 4H), 0.99-0.91 (m, 2H). $[M + H]^+$ = 458.1 |
| 76 | $^1H$ NMR (300 MHz, $CDCl_3$) δ 8.60 (d, J = 4.1 Hz, 1H), 7.73 (t, J = 7.8 Hz, 1H), 7.54 (d, J = 7.6 Hz, 1H), 7.25-7.20 (m, 2H), 7.16 (d, J = 8.6 Hz, 1H), 7.08 (d, J = 7.6 Hz, 1H), 6.96 (t, J = 7.8 Hz, 1H), 6.78 (dd, J = 8.7, 2.9 Hz, 1H), 6.68 (d, J = 2.8 Hz, 1H), 5.99 (s, 1H), 5.71 (s, 1H), 5.18 (s, 2H), 3.45 (dd, J = 14.6, 7.0 Hz, 2H), 1.91-1.82 (m, 1H), 1.77-1.72 (m, 5H), 1.49 (dd, J = 14.6, 7.0 Hz, 2H), 1.30-1.17 (m, 3H), 1.02-0.83 (m, 5H), 0.63 (q, J = 5.8 Hz, 2H). $[M + H]^+$ = 470.4 |
| 77 | $^1H$ NMR (300 MHz, $CDCl_3$) δ 8.61 (d, J = 4.2 Hz, 1H), 7.73 (td, J = 7.7, 1.7 Hz, 1H), 7.54 (d, J = 7.8 Hz, 1H), 7.25-7.16 (m, 3H), 7.13 (d, J = 8.6 Hz, 1H), 7.03 (d, J = 7.7 Hz, 1H), 6.90 (d, J = 2.7 Hz, 1H), 6.83-6.75 (m, 2H), 5.81 (d, J = 8.1 Hz, 1H), 5.33 (s, 1H), 5.20 (s, 2H), 4.23-4.08 (m, 1H), 2.20 (s, 3H), 1.55-1.45 (m, 2H), 1.44-1.32 (m, 2H), 1.21 (d, J = 6.6 Hz, 3H), 0.93 (t, J = 7.1 Hz, 3H). $[M + H]^+$ = 404.4 |
| 78 | $^1H$ NMR (300 MHz, $CDCl_3$) δ 8.61 (d, J = 4.8 Hz, 1H), 7.74 (td, J = 7.7, 1.7 Hz, 1H), 7.56 (d, J = 7.7 Hz, 1H), 7.22 (dd, J = 8.1, 2.5 Hz, 1H), 7.18-7.12 (m, 3H), 7.01 (d, J = 7.9 Hz, 1H), 6.94 (d, J = 2.9 Hz, 1H), 6.81 (dd, J = 8.7, 3.0 Hz, 1H), 6.76 (dd, J = 8.1, 1.7 Hz, 1H), 5.80 (d, J = 8.7 Hz, 1H), 5.32 (s, 1H), 5.21 (s, 2H), 4.23-4.14 (m, 1H), 2.57 (q, J = 7.5 Hz, 2H), 1.55-1.34 (m, 4H), 1.21 (d, J = 6.6 Hz, 3H), 1.17 (t, J = 7.6 Hz, 3H), 0.93 (t, J = 7.1 Hz, 3H). $[M + H]^+$ = 418.4 |
| 79 | $^1H$ NMR (300 MHz, $CDCl_3$) δ 8.62 (d, J = 4.8 Hz, 1H), 7.74 (td, J = 7.7, 1.7 Hz, 1H), 7.54 (d, J = 7.7 Hz, 1H), 7.34-7.28 (m, 1H), 7.27-7.21 (m, 3H), 7.16 (d, J = 8.7 Hz, 1H), 7.00-6.94 (m, 1H), 6.80 (dd, J = 8.7, 2.8 Hz, 1H), 6.68 (d, J = 2.8 Hz, 1H), 5.77 (s, 1H), 5.19 (s, 2H), 4.23 (t, J = 6.0 Hz, 1H), 2.99 (dd, J = 14.0, 7.0 Hz, 2H), 1.93-1.87 (m, 1H), 1.70-1.56 (m, 5H), 1.35 (dd, J = 14.0, 7.0 Hz, 2H), 1.22-1.10 (m, 4H), 0.94-0.88 (m, 2H), 0.87-0.80 (m, 2H), 0.67-0.59 (m, 2H). $[M + H]^+$ = 506.4 |
| 80 | $^1H$ NMR (300 MHz, $CDCl_3$) δ 8.60 (d, J = 4.4 Hz, 1H), 7.72 (td, J = 7.7, 1.6 Hz, 1H), 7.53 (d, J = 7.8 Hz, 1H), 7.26-7.08 (m, 5H), 6.83 (d, J = 7.9 Hz, 1H), 6.78 (dd, J = 8.7, 2.9 Hz, 1H), 6.68 (d, J = 2.8 Hz, 1H), 6.60 (d, J = 7.2 Hz, 1H), 5.64 (s, 1H), 5.17 (s, 2H), 2.37-2.28 (m, 2H), 1.87 (dq, J = 8.3, 5.2 Hz, 1H), 1.73-1.56 (m, 10H), 1.31-1.14 (m, 8H), 0.99-0.83 (m, 5H), 0.61 (q, J = 5.2 Hz, 2H). $[M + H]^+$ = 470.4 |
| 81 | $^1H$ NMR (300 MHz, $CDCl_3$) δ 8.61 (d, J = 4.8 Hz, 1H), 7.74 (td, J = 7.7, 1.8 Hz, 1H), 7.62 (d, J = 8.4 Hz, 2H), 7.54 (d, J = 7.7 Hz, 1H), 7.24 (d, J = 6.6 Hz, 1H), 7.18 (d, J = 8.7 Hz, 1H), 6.85-6.74 (m, 3H), 6.67 (d, J = 2.9 Hz, 1H), 5.93 (t, J = 5.2 Hz, 1H), 5.80 (s, 1H), 5.19 (s, 2H), 3.51-3.40 (m, 2H), 1.93-1.82 (m, 1H), 1.76-1.66 (m, 1H), 1.50 (dd, J = 14.7, 7.1 Hz, 2H), 0.95 (d, J = 6.6 Hz, 6H), 0.93-0.87 (m, 2H), 0.67-0.57 (m, 2H). $[M + H]^+$ = 430.3 |
| 82 | $^1H$ NMR (300 MHz, $CDCl_3$) δ 7.45-7.33 (m, 5H), 7.21 (d, J = 7.8 Hz, 1H), 7.16 (d, J = 8.6 Hz, 1H), 7.08 (d, J = 7.6 Hz, 1H), 6.94 (d, J = 6.5 Hz, 1H), 6.78 (dd, J = 8.7, 2.9 Hz, 1H), 6.66 (d, J = 2.7 Hz, 1H), 6.02 (s, 1H), 5.70 (s, 1H), 5.03 (s, 2H), 3.48 (dd, J = 14.0, 7.0 Hz, 2H), 1.92-1.76 (m, 5H), 1.61 (dd, J = 14.2, 7.1 Hz, 5H), 1.17-1.10 (m, 2H), 0.94-0.87 (m, 2H), 0.67-0.59 (m, 2H). $[M + H]^+$ = 455.3 |
| 83 | $^1H$ NMR (300 MHz, $CDCl_3$) δ 8.60 (d, J = 4.2 Hz, 1H), 7.72 (td, J = 7.7, 1.7 Hz, 1H), 7.53 (d, J = 7.8 Hz, 1H), 7.25-7.20 (m, 1H), 7.18 (d, J = 8.7 Hz, 1H), 7.09 (t, J = 8.0 Hz, 1H), 6.77 (dd, J = 8.7, 2.9 Hz, 1H), 6.68 (d, J = 2.9 Hz, 1H), 6.45 (d, J = 8.0 Hz, 1H), 6.42 (t, J = 2.1 Hz, 1H), 6.37 (d, J = 8.1 Hz, 1H), 5.60 (s, 1H), 5.17 (s, 2H), 3.88 (t, J = 6.6 Hz, 2H), 1.88 (tt, J = 8.4, 5.4 Hz, 1H), 1.80-1.62 (m, 8H), 1.26 (ddt, J = 24.7, 14.6, 6.6 Hz, 7H), 0.91 (dd, J = 12.6, 6.2 Hz, 4H), 0.62 (q, J = 5.9 Hz, 2H). $[M + H]^+$ = 457.4 |
| 84 | $^1H$ NMR (300 MHz, $CDCl_3$) δ 8.60 (d, J = 4.6 Hz, 1H), 7.73 (td, J = 7.7, 1.7 Hz, 1H), 7.53 (d, J = 7.8 Hz, 1H), 7.34-7.30 (m, 1H), 7.28-7.21 (m, 2H), 7.17-7.14 (m, 2H), 6.98 (dd, J = 7.9, 1.8 Hz, 1H), 6.79 (dd, J = 8.6, 2.9 Hz, 1H), 6.68 (d, J = 2.9 Hz, 1H), 6.07 (s, 1H), 5.73 (s, 2H), 5.17 (s, 2H), 1.91-1.82 (m, 1H), 0.95-0.86 (m, 2H), 0.66-0.58 (m, 2H). $[M + H]^+$ = 360.0 |
| 85 | $^1H$ NMR (300 MHz, $CDCl_3$) δ 8.69 (d, J = 1.6 Hz, 1H), 8.59 (dd, J = 4.8, 1.4 Hz, 1H), 7.79 (d, J = 7.9 Hz, 1H), 7.34 (dd, J = 7.8, 4.9 Hz, 1H), 7.30-7.29 (m, 1H), 7.22 (d, J = 7.8 Hz, 1H), 7.18 (d, J = 8.7 Hz, 1H), 7.08 (d, J = 7.7 Hz, 1H), 6.96 (dd, J = 8.0, 1.7 Hz, 1H), 6.78 (dd, J = 8.7, 2.9 Hz, 1H), 6.66 (d, J = 2.8 Hz, 1H), 6.01 (s, 1H), 5.74 (s, 1H), 5.05 (s, 2H), 3.45 (dd, J = 14.6, 7.0 Hz, 2H), 1.92-1.82 (m, 1H), 1.79-1.59 (m, 6H), 1.49 (dd, J = 14.6, 7.0 Hz, 2H), 1.41-1.29 (m, 1H), 1.19-1.13 (m, 2H), 1.01-0.87 (m, 4H), 0.67-0.60 (m, 2H). $[M + H]^+$ = 470.4 |
| 86 | $^1H$ NMR (300 MHz, $CDCl_3$) δ 8.61 (d, J = 4.3 Hz, 1H), 7.86-7.82 (m, 1H), 7.74 (t, J = 7.7 Hz, 1H), 7.60-7.51 (m, 3H), 7.33 (d, J = 8.7 Hz, 1H), 7.25-7.22 (m, 1H), 6.82 (dd, J = 8.7, 2.9 Hz, 1H), 6.68 (d, J = 2.8 Hz, 1H), 6.65 (dd, J = 6.6, 2.6 Hz, 1H), 6.39 (s, 1H), 5.19 (s, 2H), 3.46 (dd, J = 14.6, 7.0 Hz, 2H), 1.97-1.87 (m, 1H), 1.81-1.61 (m, 7H), 1.52 (dd, J = 14.6, 7.0 Hz, 2H), 1.43-1.29 (m, 1H), 1.29-1.12 (m, 3H), 1.02-0.90 (m, 4H), 0.68-0.61 (m, 2H). $[M + H]^+$ = 471.3 |
| 87 | $^1H$ NMR (300 MHz, $CDCl_3$) δ 8.61 (d, J = 4.2 Hz, 1H), 7.74 (td, J = 7.7, 1.8 Hz, 1H), 7.54 (d, J = 7.8 Hz, 1H), 7.32-7.29 (m, 3H), 7.24-7.22 (m, 1H), 7.15 (d, J = 8.6 Hz, 1H), 7.00-6.94 (m, 1H), 6.80 (dd, J = 8.6, 2.9 Hz, 1H), 6.67 (d, J = 2.9 Hz, 1H), 5.76 (s, 1H), 5.18 (s, 2H), 4.74 (s, 2H), 1.90-1.81 (m, 1H), 0.95-0.87 (m, 2H), 0.66-0.60 (m, 2H). $[M + H]^+$ = 396.2 |

TABLE II-continued

| Ex | Characterization |
|---|---|
| 88 | $^1$H NMR (300 MHz, $CDCl_3$) δ 8.61 (d, J = 4.8 Hz, 1H), 8.29 (d, J = 1.7 Hz, 1H), 8.27 (d, J = 2.8 Hz, 1H), 7.74 (td, J = 7.7, 1.7 Hz, 1H), 7.53 (d, J = 7.9 Hz, 1H), 7.51-7.48 (m, 1H), 7.23 (d, J = 7.0 Hz, 1H), 7.14 (d, J = 8.6 Hz, 1H), 6.80 (dd, J = 8.7, 2.9 Hz, 1H), 6.68 (d, J = 2.8 Hz, 1H), 6.08 (s, 1H), 5.74 (s, 1H), 5.18 (s, 2H), 3.47 (dd, J = 14.7, 7.0 Hz, 2H), 1.90-1.80 (m, 1H), 1.78-1.61 (m, 6H), 1.50 (dd, J = 14.7, 7.0 Hz, 2H), 1.38-1.30 (m, 2H), 1.01-0.86 (m, 4H), 0.67-0.60 (m, 2H). [M + H]$^+$ = 471.3 |
| 89 | $^1$H NMR (300 MHz, $CDCl_3$) δ 8.62 (d, J = 6.0 Hz, 2H), 7.36 (d, J = 6.0 Hz, 2H), 7.32-7.29 (m, 1H), 7.23 (t, J = 7.9 Hz, 1H), 7.17 (d, J = 8.6 Hz, 1H), 7.08 (d, J = 7.8 Hz, 1H), 6.96 (dd, J = 8.0, 1.6 Hz, 1H), 6.74 (dd, J = 8.6, 2.9 Hz, 1H), 6.66 (d, J = 2.8 Hz, 1H), 6.07 (s, 1H), 5.74 (s, 1H), 5.05 (s, 2H), 3.44 (dd, J = 14.5, 6.0 Hz, 2H), 1.92-1.77 (m, 4H), 1.71-1.50 (m, 7H), 1.18-1.10 (m, 2H), 0.96-0.86 (m, 2H), 0.68-0.59 (m, 2H). [M + H]$^+$ = 456.4 |
| 90 | $^1$H NMR (300 MHz, $CDCl_3$) δ 8.61 (d, J = 5.5 Hz, 1H), 8.22 (d, J = 5.5 Hz, 1H), 7.73 (td, J = 7.7, 1.6 Hz, 1H), 7.53 (d, J = 7.9 Hz, 1H), 7.38 (d, J = 8.7 Hz, 1H), 7.23 (d, J = 7.9 Hz, 1H), 6.90-6.79 (m, 3H), 6.68 (d, J = 2.8 Hz, 1H), 6.56 (s, 1H), 5.96 (s, 1H), 5.19 (s, 2H), 3.43 (dd, J = 14.8, 7.0 Hz, 2H), 1.94-1.84 (m, 1H), 1.78-1.61 (m, 6H), 1.48 (dd, J = 14.8, 7.0 Hz, 2H), 1.38-1.14 (m, 4H), 1.01-0.88 (m, 3H), 0.66-0.61 (m, 2H). [M + H]$^+$ = 471.3 |
| 91 | $^1$H NMR (400 MHz, DMSO-d6) δ 9.52 (s, 1H), 7.48 (d, J = 7.1 Hz, 2H), 7.41 (t, J = 7.4 Hz, 2H), 7.37-7.32 (m, 1H), 7.01-6.96 (m, 2H), 6.96-6.85 (m, 4H), 6.71 (s, 1H), 6.21 (d, J = 8.2 Hz, 1H), 5.08 (s, 2H), 2.26-2.17 (m, 2H), 1.64 (dt, J = 17.6, 10.7 Hz, 5H), 1.43 (q, J = 7.0 Hz, 2H), 1.32 (s, 9H), 1.17 (qd, J = 19.9, 17.7, 8.0 Hz, 4H), 0.86 (q, J = 10.4, 9.1 Hz, 2H) [M + H]$^+$ = 485.3 |
| 92 | $^1$H NMR (400 MHz, DMSO-d6) δ 7.52-7.22 (m, 5H), 6.76-6.53 (m, 3H), 6.01 (s, 1H), 4.97 (s, 2H), 4.50 (s, 2H), 2.62 (t, J = 6.6 Hz, 2H), 1.89 (p, J = 7.5 Hz, 2H) [M + H]$^+$ = 495.3 |
| 93 | $^1$H NMR (400 MHz, DMSO-d6) δ 9.55 (s, 1H), 7.55-7.27 (m, 5H), 7.17 (s, 1H), 7.08-6.73 (m, 6H), 6.27 (d, J = 8.9 Hz, 1H), 5.08 (s, 2H), 3.26-3.13 (m, 1H), 2.28-2.15 (m, 2H), 1.89 (d, J = 6.1 Hz, 2H), 1.79-1.36 (m, 14H), 1.28-1.04 (m, 4H), 0.87 (q, J = 10.4, 8.9 Hz, 2H) $^{13}$C NMR (151 MHz, DMSO) δ 171.6, 156.2, 149.1, 144.4, 140.5, 137.8, 133.5, 129.3, 128.8, 128.2, 128.2, 127.9, 113.5, 112.9, 109.1, 108.5, 104.4, 69.8, 37.2, 34.4, 34.2, 33.1, 33.0, 26.6, 26.2, 25.6 [M + H]$^+$ = 497.3 |
| 94 | $^1$H NMR (400 MHz, DMSO-d6) δ 9.57 (s, 1H), 7.49 (d, J = 7.1 Hz, 2H), 7.42 (t, J = 7.3 Hz, 2H), 7.38-7.32 (m, 1H), 7.16 (s, 1H), 7.07 (d, J = 8.6 Hz, 1H), 6.97 (t, J = 7.9 Hz, 1H), 6.92 (d, J = 8.1 Hz, 1H), 6.89-6.85 (m, 2H), 6.81 (dd, J = 8.5, 2.8 Hz, 1H), 6.30 (d, J = 7.6 Hz, 1H), 5.13 (s, 2H), 2.35 (s, 3H), 2.27-2.21 (m, 2H), 1.72-1.59 (m, 5H), 1.45 (q, J = 7.1 Hz, 2H), 1.25-1.11 (m, 4H), 0.93-0.81 (m, 2H) [M + H]$^+$ = 475.2 |
| 95 | $^1$H NMR (400 MHz, DMSO-d6) δ 7.44 (d, J = 6.9 Hz, 2H), 7.39 (t, J = 7.3 Hz, 2H), 7.35-7.29 (m, 1H), 7.01 (d, J = 8.6 Hz, 2H), 6.82 (t, J = 7.5 Hz, 1H), 6.76 (dd, J = 8.6, 2.9 Hz, 1H), 6.46 (d, J = 2.9 Hz, 1H), 5.97 (s, 3H), 5.03 (s, 2H), 2.88 (t, J = 7.1 Hz, 2H), 1.97 (s, 1H), 1.65 (d, J = 10.9 Hz, 5H), 1.48 (q, J = 7.4 Hz, 2H), 1.23-1.07 (m, 6H), 0.90-0.79 (m, 4H), 0.64-0.55 (m, 2H) [M + H]$^+$ = 455.3 |
| 96 | $^1$H NMR (300 MHz, $CDCl_3$) δ 8.60 (d, J = 4.4 Hz, 1H), 7.73 (td, J = 7.7, 1.7 Hz, 1H), 7.53 (d, J = 7.9 Hz, 1H), 7.28-7.20 (m, 1H), 7.15 (d, J = 8.6 Hz, 1H), 7.11 (t, J = 8.1 Hz, 1H), 6.81 (t, J = 2.0 Hz, 1H), 6.76 (dd, J = 8.7, 2.9 Hz, 1H), 6.67-6.63 (m, 2H), 6.57 (dd, J = 8.0, 1.6 Hz, 1H), 6.33 (s, 1H), 5.16 (s, 2H), 4.81 (t, J = 5.5 Hz, 1H), 3.24 (dd, J = 13.9, 6.4 Hz, 2H), 1.92-1.79 (m, 1H), 1.72-1.57 (m, 5H), 1.38 (dd, J = 13.9, 6.9 Hz, 2H), 1.29-1.12 (m, 4H), 0.97-0.81 (m, 4H), 0.66-0.55 (m, 2H) [M + H]$^+$ = 485.5 |
| 97 | $^1$H NMR (400 MHz, DMSO-d6) δ 7.45 (d, J = 7.1 Hz, 2H), 7.40 (t, J = 7.4 Hz, 2H), 7.36-7.30 (m, 1H), 7.28 (s, 1H), 7.01 (t, J = 8.7 Hz, 2H), 6.77 (dd, J = 8.6, 2.9 Hz, 1H), 6.67 (s, 1H), 6.56 (d, J = 7.5 Hz, 1H), 6.52 (dd, J = 8.0, 1.7 Hz, 1H), 6.48 (d, J = 2.8 Hz, 1H), 5.05 (s, 2H), 4.91 (d, J = 4.1 Hz, 1H), 4.33 (q, J = 5.2 Hz, 1H), 1.95 (ddd, J = 13.7, 8.4, 5.3 Hz, 1H), 1.68-1.57 (m, 5H), 1.54-1.40 (m, 2H), 1.38-1.26 (m, 1H), 1.26-1.06 (m, 7H), 0.88-0.75 (m, 4H), 0.66-0.57 (m, 2H) [M + H]$^+$ = 470.3 |
| 98 | $^1$H NMR (400 MHz, DMSO-d6) δ 9.61 (s, 1H), 7.48 (d, J = 7.2 Hz, 2H), 7.42 (t, J = 7.4 Hz, 2H), 7.36 (d, J = 7.1 Hz, 1H), 7.30 (dd, J = 6.8, 3.7 Hz, 4H), 7.03 (d, J = 2.6 Hz, 1H), 7.01 (d, J = 8.0 Hz, 1H), 6.95 (d, J = 8.1 Hz, 1H), 6.42 (d, J = 7.8 Hz, 1H), 5.17 (s, 2H), 2.28-2.20 (m, 2H), 1.72-1.56 (m, 5H), 1.44 (q, J = 7.1 Hz, 2H), 1.25-1.09 (m, 4H), 0.93-0.81 (m, 2H) [M + H]$^+$ = 497.1 |
| 99 | $^1$H NMR (400 MHz, DMSO-d6) δ 9.61 (s, 1H), 7.53 (dd, J = 8.5, 5.7 Hz, 2H), 7.34-7.27 (m, 4H), 7.24 (t, J = 8.9 Hz, 2H), 7.06-6.99 (m, 2H), 6.94 (d, J = 8.1 Hz, 1H), 6.42 (d, J = 8.8 Hz, 1H), 5.15 (s, 2H), 2.28-2.20 (m, 2H), 1.72-1.56 (m, 5H), 1.44 (q, J = 7.1 Hz, 2H), 1.25-1.07 (m, 4H), 0.87 (s, 2H) [M + H]$^+$ = 515.1 |
| 100 | $^1$H NMR (300 MHz, $CDCl_3$) δ 8.61 (d, J = 4.2 Hz, 1H), 7.73 (td, J = 7.7, 1.7 Hz, 1H), 7.63 (s, 1H), 7.54 (d, J = 7.8 Hz, 1H), 7.32-7.26 (m, 1H), 7.26-7.22 (m, 2H), 7.20 (d, J = 8.7 Hz, 1H), 7.04 (dd, J = 7.9, 1.2 Hz, 1H), 6.86-6.77 (m, 2H), 6.69 (d, J = 2.9 Hz, 1H), 5.18 (s, 2H), 2.65 (d, J = 6.8 Hz, 2H), 1.96-1.85 (m, 1H), 1.79-1.64 (m, 6H), 1.29-1.17 (m, 3H), 1.04-0.97 (m, 2H), 0.95-0.89 (m, 2H), 0.66-0.61 (m, 2H) [M + H]$^+$ = 480.6 |
| 101 | $^1$H NMR (400 MHz, DMSO-d6) δ 9.47 (s, 1H), 8.40 (s, 1H), 7.61 (d, J = 6.9 Hz, 1H), 7.48 (d, J = 7.1 Hz, 2H), 7.41 (t, J = 7.4 Hz, 2H), 7.34 (t, J = 7.2 Hz, 1H), 7.16 (t, J = 7.7 Hz, 1H), 7.06 (d, J = 8.6 Hz, 1H), 7.00 (d, J = 2.8 Hz, 1H), 6.90 (dd, J = 8.6, 2.8 Hz, 1H), 6.61 (t, J = 7.4 Hz, 1H), 6.49 (d, J = 8.4 Hz, 1H), 5.09 (s, 2H), 3.27 (d, J = 6.8 Hz, 2H), 1.74 (d, J = 12.2 Hz, 2H), 1.64 (dd, J = 20.5, 11.1 Hz, 3H), 1.44 (q, J = 6.9 Hz, 2H), 1.31 (s, 9H), 1.26-1.13 (m, 4H), 0.90 (q, J = 13.3, 12.5 Hz, 2H) $^{13}$C NMR (151 MHz, DMSO) δ 169.5, 156.0, 148.9, 147.5, 137.7, 132.5, 132.3, 130.2, 128.9, 128.8, 128.3, 128.2, 116.1, 115.7, 114.6, 113.4, 112.7, 69.8, 37.2, 37.0, 35.2, 35.1, 33.2, 30.5, 26.6, 26.2 [M + H]$^+$ = 485.3 |
| 102 | 1H NMR (300 MHz, $CDCl_3$) δ 8.60 (d, J = 4.4 Hz, 1H), 7.99 (s, 1H), 7.73 (td, J = 7.7, 1.8 Hz, 1H), 7.54 (d, J = 7.8 Hz, 1H), 7.22 (d, J = 6.8 Hz, 1H), 7.13 (dd, J = 7.9, 1.4 Hz, 1H), 7.08 (t, J = 7.9 Hz, 1H), 6.93 (d, J = 8.5 Hz, 1H), 6.82 (dd, J = 7.7, 1.4 Hz, 1H), 6.77-6.73 (m, 2H), 5.51 (bs, 1H), 5.17 (s, 2H), 2.20 (s, 3H), 1.81 (dd, J = 8.2, 4.5 Hz, 2H), 1.62 (dd, J = 8.1, 4.5 Hz, 2H), 0.90 (dt, J = 6.1, 4.2 Hz, 2H), 0.64 (td, J = 5.9, 4.2 Hz, 2H) |

TABLE II-continued

| Ex | Characterization |
|---|---|
| 103 | $^{1}$H NMR (400 MHz, DMSO-d6) δ 9.52 (s, 1H), 8.43 (t, J = 5.6 Hz, 1H), 7.64-7.56 (m, 1H), 7.45 (d, J = 7.1 Hz, 2H), 7.40 (t, J = 7.4 Hz, 2H), 7.33 (dd, J = 8.3, 6.0 Hz, 1H), 7.20 (t, J = 7.2 Hz, 1H), 7.12 (d, J = 8.6 Hz, 1H), 6.83 (dd, J = 8.7, 2.9 Hz, 1H), 6.75 (d, J = 8.3 Hz, 1H), 6.67 (t, J = 7.4 Hz, 1H), 6.60 (d, J = 2.9 Hz, 1H), 5.07 (s, 2H), 3.22 (q, J = 6.8 Hz, 2H), 1.90-1.78 (m, 1H), 1.67 (t, J = 13.7 Hz, 4H), 1.58 (d, J = 7.0 Hz, 1H), 1.53 (q, J = 7.3 Hz, 2H), 1.27-1.08 (m, 6H), 0.87 (ddd, J = 8.4, 6.2, 4.3 Hz, 4H), 0.65-0.59 (m, 2H)<br>$[M + H]^+$ = 483.2 |
| 104 | $^{1}$H NMR (400 MHz, DMSO-d6) δ 8.25 (t, J = 5.6 Hz, 1H), 7.48 (d, J = 5.9 Hz, 3H), 7.45-7.28 (m, 6H), 7.23-7.11 (m, 3H), 6.87-6.80 (m, 1H), 5.18 (s, 2H), 3.21 (q, J = 6.3 Hz, 2H), 1.76 (s, 3H), 1.52 (ddq, J = 27.4, 13.0, 7.2 Hz, 6H), 1.08 (d, J = 3.5 Hz, 2H)<br>$[M + H]^+$ = 483.1 |
| 105 | $^{1}$H NMR (400 MHz, DMSO-d6) δ 7.44 (d, J = 7.1 Hz, 2H), 7.39 (t, J = 7.4 Hz, 2H), 7.35-7.30 (m, 1H), 6.90-6.84 (m, 2H), 6.76 (dd, J = 8.6, 2.8 Hz, 1H), 6.53-6.48 (m, 2H), 6.38 (d, J = 8.1 Hz, 1H), 6.11 (d, J = 8.1 Hz, 1H), 5.04 (s, 2H), 3.90 (t, J = 6.3 Hz, 2H), 2.07 (s, 3H), 1.89 (ddd, J = 13.7, 8.4, 5.3 Hz, 1H), 1.75-1.60 (m, 7H), 1.36-1.12 (m, 6H), 0.89 (q, J = 10.6, 9.6 Hz, 2H), 0.83-0.77 (m, 2H), 0.62-0.56 (m, 2H)<br>$[M + H]^+$ = 470.4 |
| 106 | $^{1}$H NMR (300 MHz, $CDCl_3$) δ 8.60 (d, J = 4.3 Hz, 1H), 7.72 (td, J = 7.7, 1.7 Hz, 1H), 7.54 (d, J = 7.9 Hz, 1H), 7.25-7.20 (m, 1H), 7.18 (d, J = 8.7 Hz, 1H), 7.10 (t, J = 8.0 Hz, 1H), 6.77 (dd, J = 8.7, 2.9 Hz, 1H), 6.68 (d, J = 2.9 Hz, 1H), 6.48-6.44 (m, 1H), 6.42 (t, J = 2.1 Hz, 1H), 6.37 (dd, J = 8.0, 1.8 Hz, 1H), 5.17 (s, 2H), 3.89 (t, J = 6.7 Hz, 2H), 1.94-1.82 (m, 1H), 1.80-1.70 (m, 2H), 1.65-1.52 (m, 1H), 1.35-1.26 (m, 2H), 0.95-(m, 2H)<br>$[M + H]^+$ = 417.4 |
| 107 | $^{1}$H NMR (400 MHz, DMSO-d6) δ 9.76 (s, 1H), 7.48 (d, J = 7.1 Hz, 2H), 7.45-7.39 (m, 4H), 7.38-7.34 (m, 3H), 7.32 (dd, J = 8.9, 2.7 Hz, 1H), 7.15 (t, J = 8.0 Hz, 1H), 7.10 (d, J = 8.4 Hz, 1H), 6.69 (d, J = 7.4 Hz, 1H), 5.15 (s, 2H), 3.19 (s, 3H), 2.31-(q, J = 7.1 Hz, 2H), 1.23-1.08 (m, 4H), 0.95-0.82 (m, 2H)<br>$[M + H]^+$ = 507.2 |
| 108 | $^{1}$H NMR (300 MHz, $CDCl_3$) δ 10.11 (s, 1H), 8.52 (d, J = 4.2 Hz, 1H), 7.65 (td, J = 7.7, 1.7 Hz, 1H), 7.46 (d, J = 7.9 Hz, 1H), 7.25 (d, J = 8.0 Hz, 1H), 7.15 (dd, J = 7.1, 5.2 Hz, 1H), 7.00 (t, J = 8.0 Hz, 1H), 6.83 (dd, J = 7.2, 2.1 Hz, 1H), 6.71 (d, J = 8.8 Hz, 1H), 6.68-6.66 (m, 2H), 5.09 (s, 2H), 2.14 (s, 3H), 1.80-1.69 (m, 3H), 1.37 (dd, J = 7.8, 4.6 Hz, 2H), 0.86-0.76 (m, 2H), 0.60-0.53 (m, 2H)<br>$[M + H]^+$ = 457.3 |
| 109 | $^{1}$H NMR (300 MHz, DMSO) δ 8.59 (d, J = 4.8 Hz, 1H), 7.85 (td, J = 7.7, 1.6 Hz, 1H), 7.54 (d, J = 7.8 Hz, 1H), 7.36 (dd, J = 7.0, 5.3 Hz, 1H), 6.94-6.85 (m, 1H), 6.80 (dd, J = 8.6, 2.8 Hz, 1H), 6.72-2.7 Hz, 1H), 6.20 (d, J = 8.1 Hz, 1H), 5.14 (s, 2H), 2.14 (s, 3H), 1.94-1.85 (m, 1H), 0.87-2H)<br>$^{13}$C NMR (151 MHz, DMSO) δ 157.4, 155.5, 150.7, 149.5, 147.0, 140.0, 137.4, 135.5, 126.2, 126.0, 123.3, 122.2, 116.1, 116.0, 112.6, 111.5, 110.8, 110.3, 70.9, 11.5, 11.0, 8.9<br>$[M + H]^+$ = 427.2 |
| 110 | 1H NMR (400 MHz, DMSO-d6) δ 9.49 (s, 1H), 8.43 (s, 1H), 7.61 (d, J = 7.7 Hz, 1H), 7.45 (d, J = 7.2 Hz, 2H), 7.40 (t, J = 7.4 Hz, 2H), 7.33 (t, J = 7.1 Hz, 1H), 7.20 (t, J = 7.8 Hz, 1H), 7.13 (d, J = 8.6 Hz, 1H), 6.83 (dd, J = 8.6, 2.8 Hz, 1H), 6.75 (d, J = 8.4 Hz, 1H), 6.68 (t, J = 7.4 Hz, 1H), 6.60 (d, J = 2.8 Hz, 1H), 5.07 (s, 2H), 3.11 (t, J = 6.3 Hz, 2H), 1.84 (s, 1H), 1.71 (t, J = 13.5 Hz, 4H), 1.60 (d, J = 26.4 Hz, 2H), 1.20 (dd, J = 23.1, 8.6 Hz, 3H), 1.00-0.91 (m, 2H), 0.91-0.84 (m, 2H), 0.62 (d, J = 5.1 Hz, 2H)<br>$[M + H]^+$ = 455.2 |

TABLE II-continued

| Ex | Characterization |
|---|---|
| 111 | $^{1}$H NMR (300 MHz, $CDCl_3$) δ 8.61 (d, J = 4.2 Hz, 1H), 7.74 (td, J = 7.7, 1.8 Hz, 1H), 7.55 (d, J = 7.8 Hz, 1H), 7.27-7.22 (m, 1H), 7.15 (t, J = 7.9 Hz, 1H), 7.09-7.06 (m, 1H), 7.02 (d, J = 8.6 Hz, 1H), 6.94 (d, J = 7.8 Hz, 1H), 6.80 (dd, J = 8.6, 2.9 Hz, 1H), 6.59 (dd, J = 8.3, 2.1 Hz, 1H), 6.54 (d, J = 2.9 Hz, 1H), 5.98 (t, J = 6.0 Hz, 1H), 5.18 (s, 2H), 3.44 (dd, J = 14.6, 7.0 Hz, 2H), 3.28 (s, 3H), 1.88-1.79 (m, 1H), 1.77-1.61 (m, 7H), 1.48 (dd, J = 14.6, 7.0 Hz, 2H), 1.23-1.14 (m, 2H), 1.00-0.91 (m, 2H), 0.86-0.78 (m, 2H), 0.65-0.58 (m, 2H)<br>$[M + H]^+$ = 484.4 |
| 112 | $^{1}$H NMR (300 MHz, $CDCl_3$) δ 8.61 (d, J = 4.2 Hz, 1H), 7.73 (td, J = 7.7, 1.7 Hz, 1H), 7.64 (s, 1H), 7.54 (d, J = 7.8 Hz, 1H), 7.29 (d, J = 8.0 Hz, 1H), 7.25-7.21 (m, 2H), 7.19 (d, J = 6.4 Hz, 1H), 7.03 (dd, J = 7.9, 1.2 Hz, 1H), 6.85-6.78 (m, 2H), 6.69 (d, J = 2.9 Hz, 1H), 5.18 (s, 2H), 2.85-2.74 (m, 2H), 1.95-1.86 (m, 1H), 1.67-1.58 (m, 3H), 0.96 (d, J = 6.2 Hz, 6H), 0.94-0.88 (m, 2H), 0.67-0.61 (m, 2H)<br>$[M + H]^+$ = 454.5 |
| 113 | $^{1}$H NMR (300 MHz, $CDCl_3$) δ 9.14 (s, 1H), 8.60 (d, J = 4.8 Hz, 1H), 7.72 (td, J = 7.7, 1.7 Hz, 1H), 7.54 (d, J = 7.8 Hz, 1H), 7.37 (dd, J = 7.8, 1.4 Hz, 1H), 7.23 (d, J = 7.5 Hz, 1H), 7.18 (d, J = 8.6 Hz, 2H), 6.89 (d, J = 7.8 Hz, 1H), 6.77 (dd, J = 8.7, 2.9 Hz, 1H), 6.69-6.63 (m, 2H), 6.13 (bs, 1H), 5.18 (s, 2H), 3.38 (dd, J = 7.2, 5.8 Hz, 2H), 2.16 (dt, J = 15.0, 7.5 Hz, 1H), 2.02-1.91 (m, 1H), 1.88-1.77 (m, 2H), 1.72-1.58 (m, 4H), 1.35-1.22 (m, 2H), 0.97-0.89 (m, 2H), 0.65-0.58 (m, 2H)<br>$[M + H]^+$ = 442.4 |
| 114 | 1H NMR (500 MHz, DMSO-d6) δ 7.46 (d, J = 7.2 Hz, 2H), 7.40 (t, J = 7.4 Hz, 2H), 7.36-7.30 (m, 1H), 7.12-7.06 (m, 1H), 7.00 (t, J = 8.1 Hz, 1H), 6.93 (s, 1H), 6.66 (dd, J = 6.5, 2.8 Hz, 2H), 6.46 (dd, J = 7.9, 1.8 Hz, 1H), 6.41 (t, J = 2.2 Hz, 1H), 6.25 (dd, J = 8.1, 2.3 Hz, 1H), 5.06 (s, 2H), 3.84 (t, J = 6.5 Hz, 2H), 3.67-3.59 (m, 4H), 2.87-2.80 (m, 4H), 1.72-1.58 (m, 7H), 1.30-1.09 (m, 6H), 0.87 (q, J = 10.0, 9.5 Hz, 2H)<br>$^{13}$C NMR (151 MHz, DMSO) δ 160.0, 154.9, 147.0, 146.0, 137.8, 130.0, 129.2, 128.8, 128.2, 128.2, 123.4, 108.8, 107.7, 107.2, 104.5, 101.4, 69.9, 67.8, 66.7, 51.1, 37.3, 33.7, 33.3, 26.6, 26.6, 26.3<br>$[M + H]^+$ = 501.2 |
| 115 | $^{1}$H NMR (400 MHz, DMSO-d6) δ 9.52 (s, 1H), 8.40 (t, J = 5.6 Hz, 1H), 7.59 (dd, J = 7.9, 1.4 Hz, 1H), 7.49-7.43 (m, 2H), 7.42-7.37 (m, 2H), 7.36-7.30 (m, 1H), 7.20 (s, 1H), 7.12 (d, J = 8.7 Hz, 1H), 6.83 (dd, J = 8.7, 2.9 Hz, 1H), 6.78-6.71 (m, 1H), 6.70-6.64 (m, 1H), 6.59 (d, J = 2.9 Hz, 1H), 5.07 (s, 2H), 3.30-3.23 (m, 2H), 1.84 (ddd, J = 13.8, 8.4, 5.3 Hz, 1H), 1.73 (d, J = 13.0 Hz, 2H), 1.69-1.57 (m, 3H), 1.44 (q, J = 6.9 Hz, 2H), 1.31 (ddt, J = 10.8, 7.3, 3.6 Hz, 1H), 1.26-1.09 (m, 3H), 0.97-0.84 (m, 4H), 0.66-0.58 (m, 2H)<br>$[M + H]^+$ = 469.2 |
| 116 | $^{1}$H NMR (400 MHz, DMSO-d6) δ 9.45 (s, 1H), 7.47 (d, J = 7.2 Hz, 2H), 7.41 (t, J = 7.4 Hz, 2H), 7.36 (d, J = 7.1 Hz, 2H), 7.27 (d, J = 3.2 Hz, 4H), 7.00 (dd, J = 10.4, 9.0 Hz, 1H), 6.46 (dt, J = 8.6, 3.4 Hz, 1H), 5.16 (s, 2H), 2.34 (t, J = 7.6 Hz, 2H), 1.73-1.55 (m, 5H), 1.45 (q, J = 7.1 Hz, 2H), 1.24-1.09 (m, 4H), 0.94-0.80 (m, 2H)<br>$[M + H]^+$ = 515.1 |
| 117 | $^{1}$H NMR (300 MHz, $CDCl_3$) δ 8.61 (d, J = 4.9 Hz, 1H), 8.12 (d, J = 5.6 Hz, 1H), 7.99 (t, J = 5.7 Hz, 1H), 7.73 (td, J = 7.7, 1.7 Hz, 1H), 7.55-7.51 (m, 2H), 7.28-7.21 (m, 1H), 7.16 (d, J = 8.6 Hz, 1H), 6.81 (dd, J = 8.6, 2.9 Hz, 1H), 6.67-6.61 (m, 2H), 5.19 (s, 2H), 3.45 (dd, J = 14.5, 6.2 Hz, 2H), 1.84 (td, J = 8.4, 4.2 Hz, 1H), 1.77-1.65 (m, 6H), |

TABLE II-continued

| Ex | Characterization |
|---|---|
| | 1.51 (dd, J = 14.6, 6.2 Hz, 2H), 1.21-1.16 (m, 2H), 1.00-0.94 (m, 1H), 0.93-0.86 (m, 4H), 0.64-0.59 (m, 2H)<br>$[M + H]^+$ = 471.4 |
| 118 | $^1$H NMR (300 MHz, $CDCl_3$) δ 8.60 (d, J = 4.3 Hz, 1H), 7.73 (td, J = 7.7, 1.7 Hz, 1H), 7.65 (t, J = 1.5 Hz, 1H), 7.56 (t, J = 8.9 Hz, 2H), 7.31 (t, J = 7.9 Hz, 1H), 7.26-7.20 (m, 2H), 6.95 (dd, J = 8.1, 1.7 Hz, 1H), 6.80 (dd, J = 8.7, 2.9 Hz, 1H), 6.71 (d, J = 2.9 Hz, 1H), 5.19 (s, 2H), 4.60 (t, J = 7.2 Hz, 2H), 2.10-2.00 (m, 2H), 1.95-1.85 (m, 1H), 1.73-1.67 (m, 6H), 1.31-1.13 (m, 5H), 0.96-0.89 (m, 4H), 0.67-0.61 (m, 2H)<br>$[M + H]^+$ = 509.6 |
| 119 | $^1$H NMR (400 MHz, DMSO-d6) δ 7.47 (d, J = 7.2 Hz, 2H), 7.41 (t, J = 7.4 Hz, 2H), 7.36 1H), 7.19 (s, 1H), 7.03 (d, J = 8.6 Hz, 1H), 6.97-6.91 (m, 2H), 6.84 (dd, J = 8.6, 2.9 Hz, 1H), 6.15 (d, J = 8.0 Hz, 2H), 6.06 (t, J = 2.1 Hz, 1H), 5.08 (s, 2H), 3.80 (t, J = 6.5 Hz, 2H), 3.15 (p, J = 6.8 Hz, 1H), 1.73-1.55 (m, 7H), 1.28-1.12 (m, 6H), 1.10 (d, J = 6.9 Hz, 6H), 0.92-0.80 (m, 2H)<br>$[M + H]^+$ = 458.3 |
| 120 | $^1$H NMR (300 MHz, $CDCl_3$) δ 9.12 (s, 1H), 8.60 (d, J = 4.1 Hz, 1H), 7.73 (td, J = 7.7, 1.7 Hz, 1H), 7.54 (d, J = 7.9 Hz, 1H), 7.36 (dd, J = 7.9, 1.3 Hz, 1H), 7.26-7.21 (m, 2H), 7.17 (d, J = 8.5 Hz, 1H), 6.88 (d, J = 7.8 Hz, 1H), 6.78 (dd, J = 8.6, 2.9 Hz, 1H), 6.70-6.63 (m, 2H), 6.36 (t, J = 5.5 Hz, 1H), 5.18 (s, 2H), 3.71 (dd, J = 12.7, 6.3 Hz, 2H), 2.56-2.39 (m, 2H), 2.01-1.89 (m, 1H), 0.96-0.88 (m, 2H), 0.66-0.57 (m, 2H)<br>$[M + H]^+$ = 456.3 |
| 121 | $^1$H NMR (400 MHz, DMSO-d6) δ 9.41 (s, 1H), 7.50 (dd, J = 8.5, 5.7 Hz, 2H), 7.26-7.18 (m, 4H), 7.02 (d, J = 8.6 Hz, 1H), 6.96 (dd, J = 10.4, 9.0 Hz, 1H), 6.91 (d, J = 2.8 Hz, 1H), 6.80 (dd, J = 8.6, 2.9 Hz, 1H), 6.39-6.31 (m, 1H), 5.04 (s, 2H), 2.33 (t, J = 7.6 Hz, 2H), 2.13 (s, 3H), 1.65 (dt, J = 18.2, 10.5 Hz, 5H), 1.45 (q, J = 7.1 Hz, 2H), 1.16 (td, J = 20.4, 19.2, 11.1 Hz, 4H), 0.87 (q, J = 10.6, 9.5 Hz, 2H)<br>$[M + H]^+$ = 479.2 |
| 122 | $^1$H NMR (400 MHz, DMSO-d6) δ 7.79 (s, 1H), 7.67 (dd, J = 7.9, 1.4 Hz, 1H), 7.43 (dt, J = 19.3, 7.3 Hz, 5H), 7.37-7.30 (m, 1H), 7.15 (d, J = 8.6 Hz, 1H), 6.92-6.86 (m, 2H), 6.73 (d, J = 8.4 Hz, 1H), 6.67 (d, J = 2.8 Hz, 1H), 5.10 (s, 2H), 3.36-3.32 (m, 2H), 1.78 (ddd, J = 13.7, 8.4, 5.3 Hz, 1H), 1.66-1.48 (m, 7H), 1.22-1.03 (m, 6H), 0.87-0.70 (m, 4H), 0.68-0.59 (m, 2H)<br>$[M + H]^+$ = 504.3 |
| 123 | $^1$H NMR (300 MHz, $CDCl_3$) δ 9.16 (s, 1H), 8.60 (d, J = 4.8 Hz, 1H), 7.72 (td, J = 7.7, 1.6 Hz, 1H), 7.54 (d, J = 7.8 Hz, 1H), 7.36 (d, J = 6.7 Hz, 1H), 7.26-7.21 (m, 1H), 7.18 (d, J = 8.6 Hz, 2H), 6.88 (d, J = 8.3 Hz, 1H), 6.77 (dd, J = 8.6, 2.9 Hz, 1H), 6.68-6.63 (m, 2H), 6.05 (t, J = 5.6 Hz), 1H), 5.18 (s, 2H), 3.46 (dd, J = 14.6, 7.1 Hz, 2H), 2.03-1.92 (m, 1H), 1.78-1.63 (m, 1H), 1.52 (dd, J = 14.7, 7.1 Hz, 2H), 0.99-0.90 (m, 8H), 0.64-0.58 (m, 2H)<br>$[M + H]^+$ = 430.4 |
| 124 | $^1$H NMR (400 MHz, DMSO-d6) δ 7.82 (s, 1H), 7.48 (d, J = 7.1 Hz, 2H), 7.42 (s, 2H), 7.39-7.26 (m, 6H), 7.08-7.03 (m, 2H), 6.90-6.84 (m, 1H), 5.20 (s, 2H), 2.73 (d, J = 6.3 Hz, 2 H), 1.65-1.49 (m, 5H), 1.22 (t, J = 5.7 Hz, 3H), 1.19-1.05 (m, 3H), 0.76 (d, J = 10.6 Hz, 2H)<br>$[M + H]^+$ = 533.2 |
| 125 | $^1$H NMR (400 MHz, DMSO-d6) δ 9.45 (s, 1H), 7.53 (dd, J = 8.5, 5.7 Hz, 2H), 7.37 (d, J = 4.5 Hz, 1H), 7.27 (s, 4H), 7.24 (t, J = 8.9 Hz, 2H), 7.00 (dd, J = 10.5, 9.0 Hz, 1H), 6.46 (dt, J = 8.7, 3.3 Hz, 1H), 5.14 (s, 2H), 2.34 (t, J = 7.6 Hz, 2H), 1.73-1.58 (m, 5H), 1.45 (q, J = 7.1 Hz, 2H), 1.24-1.09 (m, 4H), 0.94-0.80 (m, 2H)<br>$[M + H]^+$ = 533.1 |

TABLE II-continued

| Ex | Characterization |
|---|---|
| 126 | $^1$H NMR (300 MHz, $CDCl_3$) δ 8.60 (d, J = 4.8 Hz, 1H), 7.73 (td, J = 7.7, 1.8 Hz, 1H), 7.68-7.64 (m, 1H), 7.58 (d, J = 7.8 Hz, 1H), 7.54 (d, J = 7.9 Hz, 1H), 7.31 (t, J = 7.9 Hz, 1H), 7.22 (d, J = 8.6 Hz, 2H), 6.95 (dd, J = 8.1, 1.6 Hz, 1H), 6.80 (dd, J = 8.7, 2.9 Hz, 1H), 6.71 (d, J = 2.9 Hz, 1H), 5.19 (s, 2H), 4.61 (t, J = 7.2 Hz, 2H), 2.11-1.99 (m, 2H), 1.96-1.85 (m, 1H), 1.68-1.55 (m, 2H), 1.28-1.21 (m, 2H), 0.96-0.85 (m, 8H), 0.68-0.60 (m, 2H)<br>$[M + H]^+$ = 469.5 |
| 127 | $^1$H NMR (300 MHz, $CDCl_3$) δ 8.60 (d, J = 4.3 Hz, 1H), 7.73 (td, J = 7.7, 1.7 Hz, 1H), 7.54 (d, J = 8.1 Hz, 2H), 7.50 (d, J = 7.7 Hz, 1H), 7.32-7.26 (m, 1H), 7.26-7.22 (m, 1H), 7.20 (d, J = 8.6 Hz, 1H), 6.97 (dd, J = 7.8, 2.0 Hz, 1H), 6.80 (dd, J = 8.7, 2.9 Hz, 1H), 6.70 (d, J = 2.9 Hz, 1H), 5.18 (s, 2H), 2.99-2.89 (m, 2H), 1.89 (It, J = 8.4, 5.4 Hz, 1H), 1.80-1.67 (m, 3H), 0.97 (d, J = 6.4 Hz, 6H), 0.95-0.87 (m, 2H), 0.67-0.60 (m, 2H)<br>$[M + H]^+$ = 455.5 |
| 128 | $^1$H NMR (500 MHz, DMSO-d6) δ ppm 0.57-0.64 (m, 2 H), 0.81-0.90 (m, 2 H), 1.18 (d, J = 6.6 Hz, 6 H), 1.76-1.83 (m, 1 H), 4.12 (dq, J = 13.8, 6.7 Hz, 1 H), 5.07 (s, 2 H), 6.62 (d, J = 2.7 Hz, 1 H), 6.84 (dd, J = 8.6, 2.9 Hz, 1 H), 6.90 (d, J = 8.5 Hz, 1 H), 7.08 (d, J = 8.5 Hz, 1 H), 7.11-7.16 (m, 1 H), 7.29 (d, J = 8.0 Hz, 1 H), 7.32-7.36 (m, 1 H), 7.37-7.42 (m, 2 H), 7.42-7.47 (m, 2 H), 7.52 (s, 1 H), 8.79 (d, J = 7.7 Hz, 1 H)<br>$[M + H]^+$ = 426.2 |
| 129 | $^1$H NMR (300 MHz, $CDCl_3$) δ 8.60 (d, J = 4.2 Hz, 1H), 7.73 (td, J = 7.7, 1.7 Hz, 1H), 7.55-7.52 (m, 2H), 7.52-7.48 (m, 1H), 7.32-7.26 (m, 1H), 7.26-7.22 (m, 1H), 7.20 (d, J = 8.6 Hz, 1H), 6.97 (dd, J = 7.6, 2.1 Hz, 1H), 6.80 (dd, J = 8.7, 2.9 Hz, 1H), 6.70 (d, J = 2.9 Hz, 1H), 5.18 (s, 2H), 2.99-2.90 (m, 2H), 1.93-1.84 (m, 1H), 1.80-1.64 (m, 8H), 1.32-1.11 (m, 3H), 1.02-0.87 (m, 4H), 0.67-0.59 (m, 2H)<br>$[M + H]^+$ = 495.5 |
| 130 | $^1$H NMR (300 MHz, $CDCl_3$) δ 8.61 (d, J = 4.3 Hz, 1H), 7.73 (td, J = 7.7, 1.7 Hz, 1H), 7.54 (d, J = 7.8 Hz, 1H), 7.51-7.49 (m, 1H), 7.43 (d, J = 7.8 Hz, 1H), 7.30 (t, J = 7.9 Hz, 1H), 7.27-7.21 (m, 2H), 7.19 (d, J = 8.7 Hz, 1H), 6.97 (dd, J = 8.1, 1.6 Hz, 1H), 6.81 (dd, J = 8.6, 2.9 Hz, 1H), 6.70 (d, J = 2.8 Hz, 1H), 5.19 (s, 2H), 2.94-2.88 (m, 2H), 1.95-1.84 (m, 1H), 1.72 (dt, J = 16.7, 9.3 Hz, 8H), 1.30-1.16 (m, 3H), 1.00-0.95 (t, J = 8.7 Hz, 2H), 0.93-0.88 (m, 2H), 0.67-0.61 (m, 2H)<br>$[M + H]^+$ = 495.4 |
| 131 | $^1$H NMR (500 MHz, DMSO-d6) δ 7.48-7.43 (m, 2H), 7.40 (dd, J = 8.1, 6.7 Hz, 2H), 7.33 (t, J = 7.3 Hz, 1H), 6.96-6.88 (m, 2H), 6.85 (d, J = 8.5 Hz, 1H), 6.37 (dd, J = 8.5, 2.8 Hz, 1H), 6.11 (dq, J = 5.1, 2.7, 2.3 Hz, 3H), 6.00 (t, J = 2.2 Hz, 1H), 5.05 (s, 2H), 3.80 (t, J = 6.5 Hz, 2H), 3.73 (d, J = 7.3 Hz, 4H), 2.07 (p, J = 7.2 Hz, 2H)<br>$[M + H]^+$ = 471.2 |
| 132 | $^1$H NMR (400 MHz, DMSO-d6) δ 9.57 (s, 1H), 7.46 (d, J = 7.2 Hz, 2H), 7.40 (t, J = 7.4 Hz, 2H), 7.33 (t, J = 7.2 Hz, 1H), 7.24 (s, 1H), 7.04 (d, J = 8.6 Hz, 1H), 6.98 (t, J = 8.0 Hz, 1H), 6.92 (d, J = 2.2 Hz, 2H), 6.88 (d, J = 8.1 Hz, 1H), 6.82 (dd, J = 8.6, 2.9 Hz, 1H), 6.32 (d, J = 9.3 Hz, 1H), 5.06 (s, 2H), 2.27-2.18 (m, 2H), 2.14 (s, 3H), 1.73-1.55 (m, 5H), 1.45 (q, J = 7.0 Hz, 2H), 1.27-1.07 (m, 4H), 0.93-0.81 (m, 2H)<br>$[M + H]^+$ = 443.2 |
| 133 | $^1$H NMR (300 MHz, DMSO) δ 8.60 (d, J = 4.5 Hz, 1H), 7.87 (t, J = 6.9 Hz, 1H), 7.55 (d, J = 7.8 Hz, 2H), 7.40-7.33 (m, 1H), 7.05 (d, J = 8.6 Hz, 1H), 7.02 (t, J = 8.0 Hz, 1H), 6.81 (dd, J = 8.7, 2.8 Hz, 1H), 6.51 (d, J = 2.8 Hz, 1H), 6.49 (s, 1H), 6.42 (t, J = 8.5 Hz, 2H), 5.15 (s, 2H), 1.96 (ddd, |

TABLE II-continued

| Ex | Characterization |
|---|---|
| | J = 14.4, 8.6, 5.4 Hz, 1H), 0.86 (q, J = 5.7 Hz, 2H), 0.62 (q, J = 5.7 Hz, 2H) $[M + H]^+$ = 413.4 |
| 134 | $^1$H NMR (300 MHz, $CDCl_3$) δ 8.60 (d, J = 4.2 Hz, 1H), 7.72 (td, J = 7.7, 1.7 Hz, 1H), 7.53 (d, J = 7.8 Hz, 1H), 7.25-7.21 (m, 2H), 7.15 (d, J = 8.7 Hz, 1H), 6.87 (dd, J = 8.1, 1.6 Hz, 1H), 6.83 (s, 1H), 6.80-6.74 (m, 2H), 6.67 (d, J = 2.9 Hz, 1H), 5.17 (s, 2H), 3.69 (bs, 2H), 3.42 (bs, 6H) 1.93-1.82 (m, 1H), 1.47 (s, 9H), 0.94-0.87 (m, 2H), 0.65-0.58 (m, 2H) $[M + H]^+$ = 529.5 |
| 135 | $^1$H NMR (400 MHz, DMSO-d6) δ 7.45 (d, J = 7.0 Hz, 2H), 7.39 (t, J = 7.4 Hz, 2H), 7.36-7.30 (m, 1H), 7.09 (d, J = 20.6 Hz, 2H), 7.02 (d, J = 8.7 Hz, 1H), 6.93 (t, J = 7.8 Hz, 1H), 6.84 (d, J = 7.3 Hz, 1H), 6.74 (dd, J = 8.6, 2.9 Hz, 1H), 6.47 (d, J = 2.8 Hz, 1H), 6.42 (d, J = 7.6 Hz, 1H), 5.04 (s, 2H), 1.97 (td, J = 8.4, 4.2 Hz, 1H), 1.90-1.80 (m, 2H), 1.67-1.53 (m, 5H), 1.19-1.02 (m, 6H), 0.88-0.72 (m, 5H), 0.65-0.56 (m, 2H) $[M + H]^+$ = 499.3 |
| 136 | $^1$H NMR (300 MHz, $CDCl_3$) δ 9.23 (s, 1H), 8.60 (d, J = 4.2 Hz, 1H), 7.73 (t, J = 7.6 Hz, 1H), 7.54 (d, J = 8.0 Hz, 1H), 7.33-7.21 (m, 3H), 7.15 (d, J = 8.5 Hz, 1H), 6.83 (d, J = 8.0 Hz, 1H), 6.78 (dd, J = 8.7, 2.8 Hz, 1H), 6.67-6.59 (m, 3H), 5.18 (s, 2H), 2.00-1.90 (m, 1H), 1.65 (dd, J = 8.2, 5.7 Hz, 2H), 1.35 (dd, J = 8.2, 5.9 Hz, 2H), 0.93 (dd, J = 13.7, 5.2 Hz, 2H), 0.62 (dd, J = 13.7, 5.2 Hz, 2H) $[M + H]^+$ = 425.3 |
| 137 | $^1$H NMR (300 MHz, $CDCl_3$) δ 8.60 (d, J = 4.2 Hz, 1H), 7.72 (td, J = 7.7, 1.7 Hz, 1H), 7.53 (d, J = 7.8 Hz, 1H), 7.26-7.20 (m, 1H), 7.17 (d, J = 8.7 Hz, 1H), 7.08 (t, J = 8.1 Hz, 1H), 6.77 (dd, J = 8.7, 2.9 Hz, 1H), 6.68 (d, J = 2.9 Hz, 1H), 6.44 (dd, J = 8.0, 1.5 Hz, 1H), 6.34 (t, J = 2.2 Hz, 1H), 6.28 (dd, J = 7.9, 2.0 Hz, 1H), 5.17 (s, 2H), 4.57 (p, J = 7.1 Hz, 1H), 2.44-2.33 (m, 2H), 2.22-2.06 (m, 2H), 1.91-1.85 (m, 1H), 1.70-1.57 (m, 2H), 0.95-0.86 (m, 2H), 0.65-0.55 (m, 2H) $[M + H]^+$ = 387.2 |
| 138 | $^1$H NMR (400 MHz, DMSO-d6) δ 7.45 (d, J = 7.0 Hz, 2H), 7.39 (t, J = 7.4 Hz, 2H), 7.34 (d, J = 10.0 Hz, 2H), 7.06-6.99 (m, 2H), 6.83 (s, 1H), 6.77 (dd, J = 8.6, 2.8 Hz, 1H), 6.70 (d, J = 7.8 Hz, 1H), 6.53 (d, J = 7.9 Hz, 1H), 6.48 (d, J = 2.8 Hz, 1H), 5.05 (s, 2H), 3.56 (s, 3H), 2.25-2.00 (m, 2H), 1.98-1.87 (m, 2H), 1.84-1.74 (m, 1H), 1.67-1.54 (m, 5H), 1.22-1.01 (m, 6H), 0.87-0.75 (m, 4H), 0.61 (q, J = 5.8 Hz, 2H) $[M + H]^+$ = 513.4 |
| 139 | $^1$H NMR (400 MHz, DMSO-d6) δ 9.36 (s, 1H), 8.42 (t, J = 5.6 Hz, 1H), 7.60 (dd, J = 7.9, 1.4 Hz, 1H), 7.46 (d, J = 7.0 Hz, 2H), 7.43-7.38 (m, 2H), 7.36-7.31 (m, 1H), 7.23-7.16 (m, 1H), 7.12 (d, J = 8.6 Hz, 1H), 6.98 (d, J = 2.9 Hz, 1H), 6.85 (dd, J = 8.6, 2.9 Hz, 1H), 6.66 (dd, J = 12.9, 7.8 Hz, 2H), 5.08 (s, 2H), 3.30-3.24 (m, 2H), 2.14 (s, 3H), 1.73 (d, J = 13.0 Hz, 2H), 1.64 (dd, J = 21.4, 11.2 Hz, 3H), 1.44 (q, J = 6.9 Hz, 2H), 1.31 (ddt, J = 10.7, 7.1, 3.5 Hz, 1H), 1.19 (dt, J = 17.8, 8.5 Hz, 3H), 0.90 (q, J = 11.7 Hz, 2H) $[M + H]^+$ = 443.2 |
| 140 | $^1$H NMR (400 MHz, DMSO-d6) δ 9.57 (s, 1H), 7.51 (dd, J = 8.5, 5.7 Hz, 2H), 7.26-7.19 (m, 3H), 7.05 (d, J = 8.6 Hz, 1H), 6.98 (t, J = 8.0 Hz, 1H), 6.95-6.90 (m, 2H), 6.87 (d, J = 8.1 Hz, 1H), 6.81 (dd, J = 8.6, 2.9 Hz, 1H), 6.32 (d, J = 9.4 Hz, 1H), 5.05 (s, 2H), 2.27-2.19 (m, 2H), 2.14 (s, 3H), 1.64 (dt, J = 18.1, 10.2 Hz, 5H), 1.45 (q, J = 7.1 Hz, 2H), 1.16 (h, J = 11.8, 11.3 Hz, 4H), 0.87 (q, J = 10.5, 9.3 Hz, 2H) $[M + H]^+$ = 461.2 |
| 141 | $^1$H NMR (300 MHz, $CDCl_3$) δ 8.60 (d, J = 4.2 Hz, 1H), 7.72 (td, J = 7.7, 1.7 Hz, 1H), 7.53 (d, J = 7.9 Hz, 1H), 7.22 (dd, J = 6.9, 5.2 Hz, 1H), 7.17 (d, |

TABLE II-continued

| Ex | Characterization |
|---|---|
| | J = 8.7 Hz, 1H), 7.05 (t, J = 8.0 Hz, 1H), 6.77 (dd, J = 8.7, 2.9 Hz, 1H), 6.69 (d, J = 2.9 Hz, 1H), 6.49 (dd, J = 8.0, 1.5 Hz, 1H), 6.36 (t, J = 2.2 Hz, 1H), 6.31 (dd, J = 8.0, 1.5 Hz, 1H), 5.57 (s, 1H), 5.17 (s, 2H), 1.95-1.82 (m, 1H), 0.95-0.87 (m, 2H), 0.65-0.57 (m, 2H), 0.24 (s, 9H) $[M + H]^+$ = 405.4 |
| 142 | $^1$H NMR (400 MHz, DMSO-d6) δ 7.98 (s, 1H), 7.46 (d, J = 7.1 Hz, 2H), 7.40 (t, J = 7.3 Hz, 2H), 7.37-7.31 (m, 2H), 7.09-7.01 (m, 3H), 6.92 (dd, J = 8.1, 2.2 Hz, 1H), 6.83 (dd, J = 8.6, 2.8 Hz, 1H), 6.53 (d, J = 2.8 Hz, 1H), 5.08 (s, 2H), 3.17-3.09 (m, 2H), 1.90 (ddd, J = 13.5, 8.4, 5.3 Hz, 1H), 1.65-1.47 (m, 7H), 1.21-1.08 (m, 6H), 0.85-0.75 (m, 4H), 0.67-0.62 (m, 2H) $[M + H]^+$ = 504.3 |
| 143 | $^1$H NMR (400 MHz, DMSO-d6) δ 8.43 (t, J = 5.6 Hz, 1H), 8.29 (s, 1H), 8.07 (d, J = 5.2 Hz, 1H), 7.59 (d, J = 8.5 Hz, 2H), 7.40 (d, J = 8.2 Hz, 2H), 7.27 (d, J = 8.7 Hz, 1H), 6.92 (d, J = 5.3 Hz, 1H), 6.87 (s, 1H), 6.81 (dd, J = 8.7, 2.8 Hz, 1H), 6.53 (d, J = 2.8 Hz, 1H), 5.12 (s, 2H), 3.23 (q, J = 6.6 Hz, 2H), 1.97-1.90 (m, 1H), 1.74-1.57 (m, 5H), 1.39 (d, J = 7.3 Hz, 2H), 1.26 (s, 1H), 1.16 (d, J = 8.8 Hz, 3H), 0.93-0.84 (m, 2H), 0.84-0.79 (m, 2H), 0.60 (d, J = 4.1 Hz, 2H) $[M + H]^+$ = 554.2 |
| 144 | $^1$H NMR (400 MHz, DMSO-d6) δ 7.45 (d, J = 7.1 Hz, 2H), 7.40 (t, J = 7.4 Hz, 2H), 7.33 (t, J = 7.1 Hz, 1H), 7.25 (s, 1H), 7.05 (d, J = 8.6 Hz, 1H), 6.98 (t, J = 8.1 Hz, 1H), 6.96-6.91 (m, 2H), 6.82 (dd, J = 8.6, 2.9 Hz, 1H), 6.24 (dd, J = 8.1, 1.6 Hz, 1H), 6.20 (dd, J = 8.1, 2.1 Hz, 1H), 6.13 (t, J = 2.0 Hz, 1H), 5.07 (s, 2H), 3.82 (t, J = 5.8 Hz, 2H), 3.23 (q, J = 5.7 Hz, 2H), 2.13 (s, 3H), 1.37 (s, 9H) $[M + H]^+$ = 449.3 |
| 145 | $^1$H NMR (300 MHz, $CDCl_3$) δ 8.61 (d, J = 4.4 Hz, 1H), 7.73 (td, J = 7.7, 1.7 Hz, 1H), 7.64 (s, 1H), 7.54 (d, J = 7.8 Hz, 1H), 7.32-7.22 (m, 3H), 7.20 (d, J = 8.8 Hz, 1H), 7.04 (dd, J = 7.9, 1.3 Hz, 1H), 6.86-6.78 (m, 2H), 6.68 (d, J = 2.8 Hz, 1H), 5.79 (s, 1H), 5.18 (s, 1H), 2.65 (d, J = 7.0 Hz, 2H), 2.03 (dq, J = 13.4, 6.7 Hz, 1H), 1.91 (It, J = 8.4, 5.6 Hz, 1H), 0.97 (d, J = 6.6 Hz, 6H), 0.95-0.88 (m, 2H), 0.68-0.61 (m, 2H) $[M + H]^+$ = 440.5 |
| 146 | $^1$H NMR (400 MHz, DMSO-d6) δ 9.41 (s, 1H), 7.45 (d, J = 7.2 Hz, 2H), 7.40 (t, J = 7.4 Hz, 2H), 7.33 (t, J = 7.1 Hz, 1H), 7.25-7.18 (m, 2H), 7.02 (d, J = 8.6 Hz, 1H), 6.95 (dd, J = 10.4, 9.0 Hz, 1H), 6.91 (d, J = 2.8 Hz, 1H), 6.80 (dd, J = 8.6, 2.9 Hz, 1H), 6.35 (dt, J = 8.5, 3.3 Hz, 1H), 5.06 (s, 2H), 2.33 (t, J = 7.6 Hz, 2H), 2.13 (s, 3H), 1.65 (dt, J = 18.1, 11.1 Hz, 5H), 1.45 (q, J = 7.1 Hz, 2H), 1.17 (dq, J = 16.0, 8.5, 7.1 Hz, 4H), 0.87 (q, J = 10.6, 9.5 Hz, 2H) $[M + H]^+$ = 461.2 |
| 147 | $^1$H NMR (300 MHz, $CDCl_3$) δ 8.61 (d, J = 4.3 Hz, 1H), 7.73 (td, J = 7.6, 1.7 Hz, 1H), 7.66 (t, J = 1.5 Hz, 1H), 7.58 (d, J = 7.7 Hz, 1H), 7.54 (d, J = 7.9 Hz, 1H), 7.31 (t, J = 7.8 Hz, 1H), 7.22 (d, J = 8.6 Hz, 2H), 6.95 (dd, J = 7.6, 2.2 Hz, 1H), 6.80 (dd, J = 8.6, 2.9 Hz, 1H), 6.71 (d, J = 2.9 Hz, 1H), 5.19 (s, 2H), 4.45 (d, J = 7.2 Hz, 2H), 1.95-1.85 (m, 1H), 1.95-1.85 (m, 1H), 0.99 (d, J = 6.7 Hz, 6H), 0.92 (dt, J = 6.0, 4.3 Hz, 2H), 0.67-0.60 (m, 2H) $[M + H]^+$ = 441.4 |
| 148 | $^1$H NMR (400 MHz, DMSO-d6) δ 9.22 (dd, J = 4.9, 1.7 Hz, 1H), 7.83 (dd, J = 8.5, 1.7 Hz, 1H), 7.76 (dd, J = 8.5, 4.9 Hz, 1H), 7.24 (s, 1H), 7.08 (d, J = 8.6 Hz, 1H), 7.02-6.93 (m, 2H), 6.87 (dd, J = 8.6, 3.0 Hz, 1H), 6.22 (ddd, J = 10.8, 8.1, 1.9 Hz, 2H), 6.16 (t, J = 2.2 Hz, 1H), 5.37 (s, 2H), 3.82 (t, J = 6.5 Hz, 2H), 2.14 (s, 3H), 1.65 (td, J = 17.0, 14.4, 7.0 Hz, 7H), 1.30-1.08 (m, 6H), 0.86 (q, J = 10.4, 9.1 Hz, 2H) $[M + H]^+$ = 432.3 |

TABLE II-continued

| Ex | Characterization |
|---|---|
| 149 | $^1$H NMR (400 MHz, DMSO-d6) δ 7.47-7.43 (m, 3H), 7.40 (t, J = 7.4 Hz, 2H), 7.36-7.30 (m, 1H), 7.02 (t, J = 8.5 Hz, 2H), 6.79 (dd, J = 8.6, 2.9 Hz, 1H), 6.54 (dd, J = 4.0, 2.1 Hz, 2H), 6.50-6.44 (m, 2H), 5.06 (s, 2H), 2.80 (t, J = 7.3 Hz, 2H), 1.94 (ddd, J = 13.7, 8.5, 5.3 Hz, 1H), 1.68-1.58 (m, 5H), 1.54 (dt, J = 15.1, 7.5 Hz, 2H), 1.27-1.06 (m, 6H), 0.88-0.76 (m, 4H), 0.67-0.58 (m, 2H) [M + H]$^+$ = 472.4 |
| 150 | $^1$H NMR (400 MHz, DMSO-d6) δ 9.63 (s, 1H), 7.57 (s, 1H), 7.46 (d, J = 7.2 Hz, 2H), 7.41 (t, J = 7.3 Hz, 2H), 7.38-7.31 (m, 1H), 7.19 (t, J = 9.2 Hz, 1H), 7.07 (s, 1H), 7.04-6.92 (m, 3H), 6.83 (dd, J = 8.8, 2.5 Hz, 1H), 6.42 (d, J = 8.0 Hz, 1H), 5.09 (s, 2H), 2.28-2.21 (m, 2H), 1.65 (dt, J = 18.4, 10.9 Hz, 5H), 1.45 (q, J = 7.1 Hz, 2H), 1.26-1.09 (m, 4H), 0.87 (q, J = 10.6, 9.5 Hz, 2H) [M + H]$^+$ = 447.2 |
| 151 | $^1$H NMR (300 MHz, $CDCl_3$) δ 8.60 (d, J = 4.3 Hz, 1H), 7.73 (td, J = 7.7, 1.7 Hz, 1H), 7.53 (d, J = 7.8 Hz, 1H), 7.27-7.21 (m, 1H), 7.15 (d, J = 8.6 Hz, 1H), 7.08 (t, J = 8.1 Hz, 1H), 6.78 (dd, J = 8.7, 2.9 Hz, 1H), 6.67 (d, J = 2.9 Hz, 1H), 6.47 (dd, J = 8.0, 1.7 Hz, 1H), 6.21 (t, J = 2.2 Hz, 1H), 6.09 (dd, J = 8.0, 2.1 Hz, 1H), 5.18 (s, 2H), 5.16-5.10 (m, 1H), 4.90 (t, J = 6.8 Hz, 2H), 4.76 (t, J = 6.8 Hz, 2H), 1.94-1.83 (m, 1H), 0.95-0.87 (m, 2H), 0.66-0.59 (m, 2H) [M + H]$^+$ = 389.3 |
| 152 | $^1$H NMR (400 MHz, DMSO-d6) δ 8.85 (d, J = 4.9 Hz, 2H), 7.47 (t, J = 4.9 Hz, 1H), 7.21 (s, 1H), 7.03 (d, J = 8.6 Hz, 1H), 6.97 (t, J = 8.1 Hz, 1H), 6.89 (d, J = 2.9 Hz, 1H), 6.77 (dd, J = 8.6, 3.0 Hz, 1H), 6.20 (td, J = 8.1, 2.0 Hz, 2H), 6.14 (t, J = 2.2 Hz, 1H), 5.22 (s, 2H), 3.81 (t, J = 6.5 Hz, 2H), 2.12 (s, 3H), 1.66 (td, J = 14.8, 13.2, 5.2 Hz, 7H), 1.29-1.06 (m, 6H), 0.93-0.79 (m, 2H) [M + H]$^+$ = 432.3 |
| 153 | $^1$H NMR (400 MHz, DMSO-d6) δ 9.57 (s, 1H), 7.59 (d, J = 8.6 Hz, 2H), 7.40 (d, J = 8.2 Hz, 2H), 7.25 (s, 1H), 7.05 (d, J = 8.6 Hz, 1H), 6.98 (t, J = 8.0 Hz, 1H), 6.95-6.92 (m, 2H), 6.87 (d, J = 8.0 Hz, 1H), 6.82 (dd, J = 8.6, 2.9 Hz, 1H), 6.33 (d, J = 7.9 Hz, 1H), 5.10 (s, 2H), 2.28-2.20 (m, 2H), 2.14 (s, 3H), 1.65 (dt, J = 18.0, 10.7 Hz, 5H), 1.44 (q, J = 7.1 Hz, 2H), 1.17 (dt, J = 17.1, 9.3 Hz, 4H), 0.87 (q, J = 10.5, 9.4 Hz, 2H) [M + H]$^+$ = 527.1 |
| 154 | $^1$H NMR (400 MHz, DMSO-d6) δ 7.45 (d, J = 6.9 Hz, 2H), 7.42-7.36 (m, 2H), 7.36-7.30 (m, 1H), 7.11 (d, J = 8.7 Hz, 1H), 6.92 (d, J = 7.5 Hz, 1H), 6.81 (dd, J = 8.7, 2.9 Hz, 1H), 6.74 (d, J = 3.0 Hz, 2H), 6.70-6.65 (m, 1H), 6.63 (d, J = 2.9 Hz, 1H), 6.49 (s, 1H), 5.05 (s, 2H), 4.01 (t, J = 6.4 Hz, 2H), 1.89-1.82 (m, 1H), 1.82-1.74 (m, 2H), 1.66 (q, J = 17.2, 15.6 Hz, 5H), 1.38-1.30 (m, 2H), 1.26-1.10 (m, 4H), 0.86 (ddd, J = 8.4, 6.2, 4.1 Hz, 4H), 0.65-0.59 (m, 2H) [M + H]$^+$ = 456.3 |
| 155 | $^1$H NMR (400 MHz, DMSO-d6) δ 7.45 (d, J = 7.0 Hz, 2H), 7.40 (t, J = 7.4 Hz, 2H), 7.34 (d, J = 7.1 Hz, 1H), 7.21 (s, 1H), 7.06-6.97 (m, 2H), 6.84 (s, 1H), 6.76 (dd, J = 8.7, 2.9 Hz, 1H), 6.67 (d, J = 7.6 Hz, 1H), 6.51 (d, J = 7.9 Hz, 1H), 6.48 (d, J = 2.7 Hz, 1H), 5.05 (s, 2H), 4.52 (t, J = 5.7 Hz, 1H), 4.32 (s, 1H), 3.38 (d, J = 5.7 Hz, 2H), 1.97 (s, 1H), 1.63 (d, J = 27.6 Hz, 7H), 1.19-1.01 (m, 5H), 0.84 (d, J = 8.0 Hz, 3H), 0.78 (d, J = 11.1 Hz, 2H), 0.61 (d, J = 3.7 Hz, 2H) [M + H]$^+$ = 486.2 |
| 156 | $^1$H NMR (400 MHz, DMSO-d6) δ 8.59 (d, J = 4.7 Hz, 1H), 7.85 (td, J = 7.7, 1.6 Hz, 1H), 7.54 (d, J = 7.8 Hz, 1H), 7.35 (dd, J = 7.4, 4.9 Hz, 1H), 7.07-6.94 (m, 2H), 6.90-6.81 (m, 1H), 6.55 (d, J = 2.8 Hz, 1H), 6.20 (dd, J = 8.0, 1.9 Hz, 1H), 6.05 (dd, J = 8.2, 1.9 Hz, 1H), 5.97 (s, 1H), 5.16 (s, 2H), 3.81 (t, J = 6.5 Hz, 2H), 3.15 (s, 3H), 1.77 (ddd, J = 13.7, 8.5, 5.3 Hz, 1H), 1.65 (q, J = 9.3, 5.8 Hz, 6H), 1.29-1.09 (m, 7H), 0.91-0.77 (m, 4H), 0.63 (d, J = 3.6 Hz, 2H) [M + H]$^+$ = 471.1 |
| 157 | $^1$H NMR (300 MHz, $CDCl_3$) δ 8.60 (d, J = 4.5 Hz, 1H), 7.72 (td, J = 7.7, 1.7 Hz, 1H), 7.53 (d, J = 7.8 Hz, 1H), 7.23 (dd, J = 7.1, 5.2 Hz, 1H), 7.18-7.09 (m, 2H), 6.78 (dd, J = 8.7, 2.9 Hz, 1H), 6.71-6.59 (m, 4H), 5.17 (s, 2H), 4.25-4.14 (m, 4H), 1.94-1.81 (m, 1H), 1.33 (td, J = 7.1, 0.6 Hz, 6H), 0.95-0.87 (m, 2H), 0.65-0.57 (m, 2H) [M + H]$^+$ = 469.5 |
| 158 | $^1$H NMR (400 MHz, DMSO-d6) δ 7.87 (s, 1H), 7.59 (d, J = 8.6 Hz, 2H), 7.40 (d, J = 8.2 Hz, 2H), 7.34 (t, J = 5.8 Hz, 1H), 7.27 (t, J = 7.9 Hz, 1H), 7.07 (d, J = 8.6 Hz, 1H), 7.00 (d, J = 2.4 Hz, 2H), 6.85-6.80 (m, 2H), 6.52 (d, J = 2.8 Hz, 1H), 5.11 (s, 2H), 2.73 (q, J = 6.7 Hz, 2H), 1.96-1.88 (m, 1H), 1.63-1.50 (m, 5H), 1.22 (t, J = 5.7 Hz, 3H), 1.17-1.03 (m, 3H), 0.87-0.81 (m, 2H), 0.80-0.69 (m, 2H), 0.67-0.61 (m, 2H) [M + H]$^+$ = 589.2 |
| 159 | $^1$H NMR (400 MHz, DMSO-d6) δ 9.18 (d, J = 1.3 Hz, 1H), 8.84 (d, J = 5.2 Hz, 1H), 7.63 (dd, J = 5.2, 1.1 Hz, 1H), 7.24 (s, 1H), 7.08 (d, J = 8.7 Hz, 1H), 7.02-6.93 (m, 2H), 6.84 (dd, J = 8.6, 3.0 Hz, 1H), 6.22 (ddd, J = 12.1, 8.1, 1.9 Hz, 2H), 6.16 (t, J = 2.2 Hz, 1H), 5.19 (s, 2H), 3.82 (t, J = 6.5 Hz, 2H), 2.14 (s, 3H), 1.65 (td, J = 16.9, 14.3, 6.9 Hz, 7H), 1.29-1.06 (m, 6H), 0.86 (q, J = 10.5, 9.2 Hz, 2H) [M + H]$^+$ = 432.3 |
| 160 | $^1$H NMR (300 MHz, $CDCl_3$) δ 8.60 (d, J = 4.8 Hz, 1H), 7.73 (td, J = 7.7, 1.6 Hz, 1H), 7.55 (d, J = 7.8 Hz, 1H), 7.23 (d, J = 6.7 Hz, 1H), 7.03-6.97 (m, 2H), 6.85 (d, J = 8.2 Hz, 1H), 6.77 (dd, J = 8.6, 2.8 Hz, 1H), 6.71 (s, 1H), 6.70 (d, J = 8.6 Hz, 1H), 5.51 (s, 1H), 5.18 (s, 2H), 4.30-4.18 (m, 4H), 2.23 (s, 3H), 1.88-1.79 (m, 1H), 1.37 (t, J = 7.1 Hz, 6H), 0.90 (dt, J = 10.0, 5.1 Hz, 2H), 0.64 (dt, J = 10.0, 5.1 Hz, 2H) |
| 161 | $^1$H NMR (300 MHz, $CDCl_3$) δ 8.60 (d, J = 4.5 Hz, 1H), 7.73 (td, J = 7.7, 1.7 Hz, 1H), 7.65 (t, J = 1.9 Hz, 1H), 7.56 (t, J = 8.6 Hz, 2H), 7.30 (t, J = 7.9 Hz, 1H), 7.21 (d, J = 8.6 Hz, 2H), 6.95 (dd, J = 8.1, 1.6 Hz, 1H), 6.80 (dd, J = 8.7, 2.9 Hz, 1H), 6.71 (d, J = 2.8 Hz, 1H), 5.54 (t, J = 7.2 Hz, 1H), 5.22 (d, J = 7.3 Hz, 2H), 5.18 (s, 2H), 1.95-1.87 (m, 1H), 1.85 (s, 3H), 1.80 (s, 3H), 0.95-0.88 (m, 2H), 0.67-0.61 (m, 2H) [M + H]$^+$ = 453.3 |
| 162 | $^1$H NMR (300 MHz, $CDCl_3$) δ 8.61 (d, J = 4.7 Hz, 1H), 7.73 (td, J = 7.7, 1.6 Hz, 1H), 7.66 (t, J = 1.6 Hz, 1H), 7.59 (d, J = 7.6 Hz, 1H), 7.55 (d, J = 7.8 Hz, 1H), 7.31 (t, J = 7.9 Hz, 1H), 7.22 (d, J = 8.6 Hz, 2H), 6.96 (dd, J = 7.8, 1.8 Hz, 1H), 6.80 (dd, J = 8.7, 2.9 Hz, 1H), 6.71 (d, J = 2.8 Hz, 1H), 5.19 (s, 2H), 4.81 (t, J = 5.5 Hz, 2H), 3.97 (t, J = 5.5 Hz, 2H), 3.36 (s, 3H), 1.96-1.84 (m, 1H), 0.96-0.88 (m, 2H), 0.64 (q, J = 5.9 Hz, 2H) [M + H]$^+$ = 443.3 |
| 163 | $^1$H NMR (300 MHz, $CDCl_3$) δ 8.61 (d, J = 4.2 Hz, 1H), 7.73 (td, J = 7.7, 1.8 Hz, 1H), 7.68-7.65 (m, 1H), 7.59 (d, J = 7.7 Hz, 1H), 7.55 (d, J = 7.8 Hz, 1H), 7.31 (t, J = 7.9 Hz, 1H), 7.26-7.21 (m, 2H), 6.95 (dd, J = 8.2, 1.5 Hz, 1H), 6.81 (dd, J = 8.7, 2.9 Hz, 1H), 6.71 (d, J = 2.9 Hz, 1H), 5.19 (s, 2H), 4.48 (d, J = 7.4 Hz, 2H), 1.96-1.85 (m, 1H), 1.53-1.45 (m, 1H), 0.97-0.86 (m, 2H), 0.71-0.68 (m, 2H), 0.65-0.63 (m, 2H), 0.55-0.49 (m, 2H) [M + H]$^+$ = 439.4 |
| 164 | $^1$H NMR (400 MHz, DMSO-d6) δ 7.48 (d, J = 7.1 Hz, 2H), 7.41 (t, J = 7.3 Hz, 2H), 7.35 (d, J = 7.2 Hz, 1H), 7.21 (s, 1H), 7.06 (d, J = 8.6 Hz, 1H), 7.00-6.91 (m, 2H), 6.86 (dd, J = 8.6, 2.9 Hz, 1H), 6.22-6.14 (m, 2H), 6.10 (t, J = 2.1 Hz, 1H), 5.10 (s, 2H), 3.90 (dd, J = 10.8, 3.6 Hz, 2H), 3.81 (t, J = 6.5 Hz, 2H), 3.12-3.01 (m, 1H), 1.62 (ddd, J = 28.5, |

TABLE II-continued

| Ex | Characterization |
|---|---|
| | 24.4, 11.6 Hz, 12H), 1.30-1.08 (m, 7H), 0.93-0.82 (m, 2H)<br>[M + H]+ = 500.2 |
| 165 | 1H NMR (400 MHz, DMSO-d6) δ 7.49-7.31 (m, 5H), 7.16 (s, 1H), 7.10 (d, J = 8.6 Hz, 1H), 6.99-6.89 (m, 2H), 6.87 (d, J = 3.0 Hz, 1H), 6.26 (d, J = 7.4 Hz, 1H), 6.19 (dd, J = 4.6, 2.3 Hz, 2H), 5.78 (s, 1H), 5.09 (s, 2H), 4.11 (d, J = 2.5 Hz, 2H), 3.81 (t, J = 6.5 Hz, 2H), 3.64 (t, J = 5.3 Hz, 2H), 2.27 (s, 2H), 1.72-1.58 (m, 7H), 1.29-1.09 (m, 6H), 0.93-0.82 (m, 2H)<br>[M + H]+ = 498.2 |
| 166 | 1H NMR (400 MHz, DMSO-d6) δ 8.58 (d, J = 4.8 Hz, 1H), 7.84 (td, J = 7.7, 1.5 Hz, 1H), 7.65 (d, J = 2.4 Hz, 2H), 7.56 (d, J = 2.3 Hz, 1H), 7.52 (d, J = 7.8 Hz, 1H), 7.35 (dd, J = 7.4, 4.9 Hz, 1H), 7.06 (d, J = 8.6 Hz, 1H), 6.82 (dd, J = 8.6, 2.8 Hz, 1H), 6.52 (d, J = 2.8 Hz, 1H), 6.41 (t, J = 2.1 Hz, 1H), 5.14 (s, 2H), 3.88 (t, J = 6.5 Hz, 2H), 1.92 (ddd, J = 13.7, 8.5, 5.3 Hz, 1H), 1.64 (dt, J = 21.1, 11.5 Hz, 7H), 1.29-1.11 (m, 6H), 0.87 (td, J = 9.3, 8.4, 3.8 Hz, 4H), 0.63 (q, J = 5.8 Hz, 2H)<br>[M + H]+ = 458.2 |
| 167 | 1H NMR (400 MHz, DMSO-d6) δ 7.45 (d, J = 7.1 Hz, 2H), 7.40 (t, J = 7.4 Hz, 3H), 7.36-7.30 (m, 1H), 7.12-7.06 (m, 2H), 6.98 (s, 1H), 6.83 (dd, J = 8.6, 2.9 Hz, 1H), 6.73-6.64 (m, 1H), 6.62 (d, J = 2.9 Hz, 1H), 6.60 (d, J = 8.2 Hz, 1H), 5.07 (s, 2H), 2.79 (t, J = 7.2 Hz, 2H), 1.84 (ddd, J = 13.7, 8.4, 5.3 Hz, 1H), 1.63-1.55 (m, 5H), 1.54-1.47 (m, 2H), 1.28-1.21 (m, 2H), 1.19-1.05 (m, 4H), 0.85-0.73 (m, 4H), 0.67-0.61 (m, 2H)<br>[M + H]+ = 472.4 |
| 168 | 1H NMR (400 MHz, DMSO-d6) δ 7.53 (d, J = 11.4 Hz, 2H), 7.50-7.45 (m, 2H), 7.45-7.38 (m, 3H), 7.38-7.32 (m, 1H), 7.31 (s, 3H), 7.05 (dd, J = 10.2, 9.0 Hz, 1H), 7.00 (dd, J = 6.1, 3.0 Hz, 1H), 6.83 (dt, J = 8.8, 4.0 Hz, 1H), 5.18 (s, 2H)<br>[M + H]+ = 405.0 |
| 169 | 1H NMR (400 MHz, DMSO-d6) δ 9.57 (s, 1H), 7.77 (d, J = 8.2 Hz, 2H), 7.68 (d, J = 8.0 Hz, 2H), 7.34 (s, 1H), 7.04 (d, J = 8.6 Hz, 1H), 7.01-6.94 (m, 2H), 6.88 (d, J = 8.1 Hz, 1H), 6.80 (dd, J = 8.6, 2.9 Hz, 1H), 6.51 (d, J = 2.8 Hz, 1H), 6.34 (d, J = 9.6 Hz, 1H), 5.18 (s, 2H), 2.28-2.20 (m, 2H), 1.97 (tt, J = 8.5, 5.2 Hz, 1H), 1.73-1.57 (m, 5H), 1.45 (q, J = 7.0 Hz, 2H), 1.21-1.10 (m, 4H), 0.90-0.80 (m, 4H), 0.66-0.57 (m, 2H)<br>[M + H]+ = 537.2 |
| 170 | 1H NMR (400 MHz, DMSO-d6) δ 9.56 (s, 1H), 7.37 (d, J = 8.6 Hz, 2H), 7.32 (s, 1H), 7.02 (d, J = 8.6 Hz, 1H), 6.96 (dd, J = 11.4, 8.3 Hz, 4H), 6.89 (d, J = 8.3 Hz, 1H), 6.77 (dd, J = 8.6, 2.8 Hz, 1H), 6.47 (d, J = 2.8 Hz, 1H), 6.33 (d, J = 9.1 Hz, 1H), 4.96 (s, 2H), 3.76 (s, 3H), 2.27-2.20 (m, 2H), 1.96 (ddd, J = 13.8, 8.5, 5.4 Hz, 1H), 1.72-1.57 (m, 5H), 1.45 (q, J = 7.1 Hz, 2H), 1.23-1.09 (m, 4H), 0.92-0.80 (m, 4H), 0.66-0.57 (m, 2H)<br>[M + H]+ = 499.2 |
| 171 | 1H NMR (400 MHz, DMSO-d6) δ 7.46 (d, J = 7.3 Hz, 2H), 7.40 (t, J = 7.4 Hz, 2H), 7.33 (t, J = 7.1 Hz, 1H), 7.24 (s, 1H), 7.06 (d, J = 8.6 Hz, 1H), 6.98 (t, J = 8.1 Hz, 1H), 6.93 (d, J = 2.7 Hz, 1H), 6.82 (dd, J = 8.6, 2.8 Hz, 1H), 6.27-6.17 (m, 2H), 6.15 (s, 1H), 5.07 (s, 2H), 4.78 (t, J = 5.6 Hz, 1H), 3.85 (t, J = 5.0 Hz, 2H), 3.65 (q, J = 5.2 Hz, 2H), 2.14 (s, 3H)<br>[M + H]+ = 350.3 |
| 172 | 1H NMR (400 MHz, DMSO-d6) δ 7.81 (s, 1H), 7.45 (d, J = 7.2 Hz, 2H), 7.39 (t, J = 7.4 Hz, 2H), 7.33 (t, J = 7.1 Hz, 1H), 7.06-7.00 (m, 3H), 6.94 (d, J = 8.9 Hz, 2H), 6.47 (d, J = 8.1 Hz, 1H), 6.42 (s, 1H), 6.27 (dd, J = 8.1, 1.8 Hz, 1H), 5.05 (s, 2H), 3.85 (t, J = 6.5 Hz, 2H), 1.74-1.57 (m, 7H), 1.30-1.10 (m, 6H), 0.87 (q, J = 10.3, 9.5 Hz, 2H)<br>[M + H]+ = 416.4 |
| 173 | 1H NMR (400 MHz, DMSO-d6) δ 7.45 (d, J = 7.2 Hz, 2H), 7.40 (t, J = 7.4 Hz, 2H), 7.33 (t, J = 7.1 Hz, 1H), 7.23 (s, 1H), 7.06 (d, J = 8.7 Hz, 1H), 6.97 (t, J = 8.1 Hz, 1H), 6.92 (d, J = 2.8 Hz, 1H), 6.82 (dd, J = 8.6, 2.9 Hz, 1H), 6.26-6.16 (m, 2H), 6.16-6.12 (m, 1H), 5.07 (s, 2H), 4.04 (q, J = 7.1 Hz, 2H), 3.85 (t, J = 5.8 Hz, 2H), 2.34 (t, J = 6.9 Hz, 2H), 2.13 (s, 3H), 1.72-1.59 (m, 4H), 1.17 (t, J = 7.1 Hz, 3H)<br>[M + H]+ = 434.2 |
| 174 | 1H NMR (400 MHz, DMSO-d6) δ 7.46 (d, J = 7.1 Hz, 2H), 7.40 (t, J = 7.4 Hz, 2H), 7.33 (t, J = 7.1 Hz, 1H), 7.25 (s, 1H), 7.06 (d, J = 8.7 Hz, 1H), 6.98 (t, J = 8.1 Hz, 1H), 6.93 (d, J = 2.8 Hz, 1H), 6.82 (dd, J = 8.6, 2.9 Hz, 1H), 6.26-6.19 (m, 2H), 6.14 (t, J = 2.1 Hz, 1H), 5.07 (s, 2H), 3.99-3.92 (m, 2H), 3.64-3.57 (m, 2H), 3.28 (s, 3H), 2.14 (s, 3H)<br>[M + H]+ = 364.2 |
| 175 | 1H NMR (400 MHz, DMSO-d6) δ 7.45 (d, J = 7.2 Hz, 2H), 7.40 (t, J = 7.4 Hz, 2H), 7.33 (t, J = 7.2 Hz, 1H), 7.22 (s, 1H), 7.06 (d, J = 8.6 Hz, 1H), 6.97 (t, J = 8.1 Hz, 1H), 6.92 (d, J = 2.8 Hz, 1H), 6.82 (dd, J = 8.6, 2.9 Hz, 1H), 6.23-6.18 (m, 2H), 6.18-6.14 (m, 1H), 5.07 (s, 2H), 3.72 (d, J = 6.9 Hz, 2H), 2.24 (dt, J = 14.8, 7.4 Hz, 1H), 2.13 (s, 3H), 1.73 (dq, J = 11.8, 6.4 Hz, 2H), 1.64-1.47 (m, 4H), 1.28 (dq, J = 14.1, 7.4, 7.0 Hz, 2H)<br>[M + H]+ = 388.2 |
| 176 | 1H NMR (400 MHz, DMSO-d6) δ 9.18 (s, 1H), 8.91 (s, 2H), 7.25 (s, 1H), 7.08 (d, J = 8.6 Hz, 1H), 7.02-6.93 (m, 2H), 6.86 (dd, J = 8.6, 3.0 Hz, 1H), 6.22 (ddd, J = 10.5, 8.1, 2.0 Hz, 2H), 6.15 (t, J = 2.2 Hz, 1H), 5.16 (s, 2H), 3.82 (t, J = 6.5 Hz, 2H), 2.15 (s, 3H), 1.73-1.57 (m, 7H), 1.30-1.08 (m, 6H), 0.86 (q, J = 10.3, 9.0 Hz, 2H)<br>[M + H]+ = 432.3 |
| 177 | 1H NMR (400 MHz, DMSO-d6) δ 7.45 (d, J = 7.1 Hz, 2H), 7.40 (t, J = 7.4 Hz, 2H), 7.33 (t, J = 7.2 Hz, 1H), 7.22 (s, 1H), 7.05 (d, J = 8.6 Hz, 1H), 6.97 (t, J = 8.1 Hz, 1H), 6.92 (d, J = 2.8 Hz, 1H), 6.82 (dd, J = 8.6, 2.9 Hz, 1H), 6.24-6.17 (m, 2H), 6.13 (t, J = 2.1 Hz, 1H), 5.06 (s, 2H), 3.82 (t, J = 6.5 Hz, 2H), 2.13 (s, 3H), 1.73-1.56 (m, 7H), 1.28-1.10 (m, 6H), 0.86 (q, J = 10.3, 9.0 Hz, 2H)<br>[M + H]+ = 430.2 |
| 178 | 1H NMR (300 MHz, $CDCl_3$) δ 8.60 (d, J = 4.8 Hz, 1H), 7.73 (td, J = 7.7, 1.7 Hz, 1H), 7.68 (s, 1H), 7.54 (d, J = 7.9 Hz, 1H), 7.32-7.26 (m, 2H), 7.26-7.17 (m, 3H), 7.03 (dd, J = 7.9, 1.2 Hz, 1H), 6.87-6.77 (m, 2H), 6.68 (d, J = 2.8 Hz, 1H), 5.18 (s, 2H), 3.72 (t, J = 7.3 Hz, 2H), 2.90 (t, J = 7.3 Hz, 2H), 1.99 (quint, J = 7.3 Hz, 2H), 1.95-1.86 (m, 1H), 0.96-0.88 (m, 2H), 0.67-0.60 (m, 2H)<br>[M + H]+ = 442.6 |
| 179 | 1H NMR (300 MHz, $CDCl_3$) δ 8.61 (d, J = 4.2 Hz, 1H), 7.88 (s, 1H), 7.73 (td, J = 7.7, 1.8 Hz, 1H), 7.54 (d, J = 7.7 Hz, 1H), 7.29 (s, 1H), 7.28-7.22 (m, 2H), 7.19 (d, J = 8.7 Hz, 1H), 7.13-7.09 (m, 2H), 6.84-6.78 (m, 2H), 6.70 (d, J = 2.9 Hz, 1H), 5.19 (s, 2H), 1.96-1.85 (m, 1H), 0.96-0.88 (m, 2H), 0.68-0.61 (m, 2H)<br>[M + H]+ = 384.4 |
| 180 | 1H NMR (500 MHz, DMSO-d6) δ ppm 0.52-0.66 (m, 2 H), 0.81-0.97 (m, 2 H), 1.14 (d, J = 6.6 Hz, 6 H), 1.78 (lt, J = 8.3, 5.4 Hz, 1 H), 2.25 (s, 3 H), 4.11 (dt, J = 7.6, 6.6 Hz, 1 H), 5.05 (s, 2 H), 6.59-6.66 (m, 3 H), 6.78-6.84 (m, 2 H), 7.02-7.08 (m, 2 H), 7.31 (br d, J = 1.4 Hz, 1 H), 7.37-7.41 (m, 2 H), 7.42-7.48 (m, 2 H), 8.36 (d, J = 7.7 Hz, 1 H)<br>[M + H]+ = 415.2 |
| 181 | 1H NMR (400MHz, DMSO-d6) δ 8.49 (d, J = 7.9 Hz, 1H), 7.47-7.27 (m, 6H), 7.10-7.02 (m, 2H), 6.88-6.82 (m, 2H), 6.69 (s, 1H), 6.61 (d, J = 2.9 Hz, 1H), 5.07 (s, 2H), 4.15-4.04 (m, 1H), 1.89-1.80 (m, 1H), 1.12 (d, J = 6.6 Hz, 6H), 0.88-0.81 (m, 2H), 0.64-0.57 (m, 2H)<br>[M + H]+ = 469.1 |

TABLE II-continued

| Ex | Characterization |
|---|---|
| 182 | $^1$H NMR (400 MHz, Methanol-d4) δ 8.56 (d, J = 4.5 Hz, 1H), 7.90 (t, J = 7.7 Hz, 1H), 7.62 (d, J = 7.8 Hz, 1H), 7.42-7.37 (m, 1H), 7.13 (d, J = 8.7 Hz, 1H), 7.02 (t, J = 8.1 Hz, 1H), 6.80 (dd, J = 8.6, 2.9 Hz, 1H), 6.64 (s, 1H), 6.59 (d, J = 3.1 Hz, 2H), 6.46 (d, J = 8.1 Hz, 1H), 5.16 (s, 2H), 3.63 (d, J = 11.1 Hz, 3H), 2.07-1.92 (m, 1H), 0.93-0.87 (m, 2H), 0.62-0.57 (m, 2H) $[M + H]^+$ = 427.0 |
| 183 | $^1$H NMR (500 MHz, DMSO-d6) δ 8.12 (s, 1H), 7.45 (d, J = 7.2 Hz, 2H), 7.42 (s, 3H), 7.35 (t, J = 7.2 Hz, 1H), 7.30-7.24 (m, 2H), 7.09 (t, J = 8.1 Hz, 1H), 6.48 (d, J = 8.0 Hz, 1H), 6.44 (t, J = 2.1 Hz, 1H), 6.40 (dd, J = 8.1, 2.2 Hz, 1H), 5.12 (s, 2H), 3.87 (t, J = 6.5 Hz, 2H), 1.74-1.56 (m, 7H), 1.29-1.08 (m, 6H), 0.87 (q, J = 9.8, 9.4 Hz, 2H) $[M + H]^+$ = 441.1 |
| 184 | $^1$H NMR (400 MHz, DMSO-d6) δ 9.52 (s, 1H), 8.43 (t, J = 5.5 Hz, 1H), 7.63-7.57 (m, 1H), 7.45 (s, 2H), 7.40 (s, 2H), 7.33 (t, J = 7.1 Hz, 1H), 7.24 (t, J = 7.8 Hz, 1H), 7.10 (d, J = 8.9 Hz, 2H), 7.00 (t, J = 8.9 Hz, 3H), 6.72 (t, J = 7.4 Hz, 1H), 5.08 (s, 2H), 3.27 (q, J = 6.5 Hz, 2H), 1.72 (d, J = 12.7 Hz, 2H), 1.63 (dd, J = 19.8, 11.2 Hz, 3H), 1.42 (q, J = 6.9 Hz, 2H), 1.30 (ddt, J = 10.6, 7.1, 3.5 Hz, 1H), 1.17 (h, J = 11.9 Hz, 3H), 0.91 (t, J = 11.6 Hz, 2H) $[M + H]^+$ = 429.2 |
| 185 | $^1$H NMR (400 MHz, DMSO-d6) δ 7.44 (d, J = 7.0 Hz, 2H), 7.39 (t, J = 7.4 Hz, 2H), 7.35-7.30 (m, 1H), 7.14 (s, 1H), 7.02 (d, J = 8.6 Hz, 1H), 6.82 (d, J = 8.1 Hz, 1H), 6.76 (dd, J = 8.6, 2.9 Hz, 1H), 6.47 (d, J = 2.8 Hz, 1H), 6.31 (d, J = 1.8 Hz, 1H), 6.16 (dd, J = 8.0, 1.9 Hz, 1H), 5.04 (s, 2H), 3.80 (t, J = 6.4 Hz, 2H), 2.00 (s, 3H), 1.95 (ddd, J = 13.7, 8.5, 5.4 Hz, 1H), 1.72-1.59 (m, 7H), 1.32-1.10 (m, 6H), 0.92-0.82 (m, 4H), 0.63-0.58 (m, 2H) $[M + H]^+$ = 470.4 |
| 186 | $^1$H NMR (400 MHz, DMSO-d6) δ 7.45 (d, J = 7.0 Hz, 2H), 7.39 (t, J = 7.4 Hz, 2H), 7.35-7.31 (m, 1H), 7.23 (s, 1H), 7.02 (d, J = 8.6 Hz, 1H), 6.78 (dd, J = 8.6, 2.8 Hz, 1H), 6.47 (d, J = 2.8 Hz, 1H), 6.08 (s, 1H), 6.02 (s, 1H), 5.97 (s, 1H), 5.05 (s, 2H), 3.79 (t, J = 6.5 Hz, 2H), 2.12 (s, 3H), 1.95 (ddd, J = 13.8, 8.5, 5.4 Hz, 1H), 1.72-1.59 (m, 7H), 1.28-1.09 (m, 6H), 0.91-0.82 (m, 4H), 0.63-0.59 (m, 2H) $[M + H]^+$ = 470.4 |
| 187 | $^1$H NMR (400 MHz, DMSO-d6) δ 7.45 (d, J = 7.1 Hz, 2H), 7.39 (t, J = 7.4 Hz, 2H), 7.33 (t, J = 7.1 Hz, 1H), 6.93 (dd, J = 12.8, 8.4 Hz, 2H), 6.80 (dd, J = 8.6, 2.8 Hz, 1H), 6.55-6.50 (m, 2H), 6.18 (dd, J = 8.1, 2.5 Hz, 1H), 5.90 (d, J = 2.4 Hz, 1H), 5.06 (s, 2H), 3.73 (t, J = 6.5 Hz, 2H), 2.15 (s, 3H), 1.89 (ddd, J = 13.7, 8.4, 5.3 Hz, 1H), 1.67-1.56 (m, 7H), 1.22-1.07 (m, 6H), 0.87-0.78 (m, 4H), 0.63-0.58 (m, 2H) $[M + H]^+$ = 470.4 |
| 188 | $^1$H NMR (400 MHz, DMSO-d6) δ 7.94 (s, 1H), 7.69 (d, J = 8.6 Hz, 1H), 7.45 (d, J = 7.1 Hz, 2H), 7.40 (t, J = 7.3 Hz, 2H), 7.36-7.29 (m, 2H), 7.17-7.13 (m, 1H), 7.07 (d, J = 8.6 Hz, 1H), 6.82 (dd, J = 8.6, 2.9 Hz, 1H), 6.49 (d, J = 2.8 Hz, 1H), 6.27 (d, J = 1.7 Hz, 1H), 6.23 (dd, J = 8.6, 1.8 Hz, 1H), 5.07 (s, 2H), 3.94 (t, J = 6.5 Hz, 2H), 1.95-1.89 (m, 1H), 1.80-1.73 (m, 2H), 1.72-1.59 (m, 5H), 1.29-1.13 (m, 6H), 0.91-0.81 (m, 4H), 0.67-0.62 (m, 2H) $[M + H]^+$ = 499.4 |
| 189 | $^1$H NMR (400 MHz, DMSO-d6) δ 7.73 (s, 1H), 7.49 (s, 1H), 7.45 (d, J = 7.1 Hz, 2H), 7.40 (t, J = 7.4 Hz, 2H), 7.33 (t, J = 7.1 Hz, 1H), 7.13 (s, 1H), 7.04 (d, J = 8.6 Hz, 1H), 6.81 (dd, J = 8.7, 2.9 Hz, 1H), 6.78 (s, 1H), 6.69 (s, 1H), 6.49 (d, J = 2.8 Hz, 1H), 6.27 (t, J = 1.9 Hz, 1H), 5.06 (s, 2H), 3.87 (t, J = 6.5 Hz, 2H), 1.97-1.90 (m, 1H), 1.73-1.58 (m, 7H), 1.29-1.12 (m, 6H), 0.92-0.81 (m, 4H), 0.66-0.57 (m, 2H) $[M + H]^+$ = 499.4 |
| 190 | $^1$H NMR (400 MHz, DMSO-d6) δ 9.50 (s, 1H), 7.43 (s, 2H), 7.39 (t, J = 7.4 Hz, 2H), 7.33 (d, J = 7.1 Hz, 1H), 7.22 (d, J = 8.0 Hz, 1H), 7.01 (t, J = 7.3 Hz, 1H), 6.91 (d, J = 8.7 Hz, 1H), 6.80-6.73 (m, 3H), 6.71 (s, 1H), 6.57 (d, J = 2.8 Hz, 1H), 5.04 (s, 2H), 2.39-2.34 (m, 2H), 1.88-1.80 (m, 1H), 1.68 (dd, J = 23.1, 12.0 Hz, 4H), 1.61 (s, 1H), 1.51 (d, J = 8.0 Hz, 2H), 1.25 (s, 1H), 1.15 (t, J = 11.4 Hz, 3H), 0.93-0.83 (m, 4H), 0.60 (q, J = 5.7 Hz, 2H) $[M + H]^+$ = 469.2 |
| 191 | $^1$H NMR (400 MHz, Chloroform-d) δ 9.00 (s, 1H), 7.46 (d, J = 7.2 Hz, 2H), 7.41 (t, J = 7.4 Hz, 2H), 7.34 (t, J = 7.1 Hz, 1H), 7.08-7.00 (m, 2H), 6.92 (d, J = 2.8 Hz, 1H), 6.86 (s, 1H), 6.27 (dd, J = 8.1, 1.9 Hz, 1H), 6.11 (d, J = 8.2 Hz, 1H), 6.07 (d, J = 2.1 Hz, 1H), 5.06 (s, 2H), 3.87 (dt, J = 13.5, 7.0 Hz, 4H), 2.76-2.69 (m, 2H), 2.09 (s, 3H), 1.72 (q, J = 13.3, 10.0 Hz, 7H), 1.30 (dd, J = 9.9, 4.8 Hz, 2H), 1.19 (dq, J = 21.1, 12.1, 10.8 Hz, 4H), 0.93-0.84 (m, 2H) $[M + H]^+$ = 502.2 |
| 192 | $^1$H NMR (400 MHz, DMSO-d6) δ 12.90 (s, 1H), 7.46 (d, J = 7.2 Hz, 2H), 7.40 (t, J = 7.4 Hz, 2H), 7.33 (t, J = 7.2 Hz, 1H), 7.30 (s, 1H), 7.06 (d, J = 8.6 Hz, 1H), 6.98 (t, J = 8.0 Hz, 1H), 6.92 (d, J = 2.7 Hz, 1H), 6.82 (dd, J = 8.6, 2.9 Hz, 1H), 6.25 (d, J = 7.6 Hz, 1H), 6.19-6.13 (m, 2H), 5.07 (s, 2H), 4.52 (s, 2H), 2.14 (s, 3H) $[M + H]^+$ = 364.3 |
| 193 | $^1$H NMR (400 MHz, DMSO-d6) δ 12.00 (s, 1H), 7.45 (d, J = 7.3 Hz, 2H), 7.40 (t, J = 7.4 Hz, 2H), 7.33 (t, J = 7.1 Hz, 1H), 7.23 (s, 1H), 7.06 (d, J = 8.6 Hz, 1H), 6.97 (t, J = 8.1 Hz, 1H), 6.92 (d, J = 2.7 Hz, 1H), 6.82 (dd, J = 8.6, 2.8 Hz, 1H), 6.25-6.17 (m, 2H), 6.15 (s, 1H), 5.07 (s, 2H), 3.85 (t, J = 6.0 Hz, 2H), 2.26 (t, J = 7.1 Hz, 2H), 2.14 (s, 3H), 1.72-1.54 (m, 4H) $[M + H]^+$ = 406.4 |
| 194 | $^1$H NMR (400 MHz, DMSO-d6) δ 7.46 (d, J = 7.3 Hz, 2H), 7.40 (t, J = 7.4 Hz, 2H), 7.34 (d, J = 7.1 Hz, 1H), 7.31 (s, 1H), 7.05 (d, J = 8.6 Hz, 1H), 6.99 (t, J = 8.1 Hz, 1H), 6.93 (d, J = 2.7 Hz, 1H), 6.82 (dd, J = 8.6, 2.8 Hz, 1H), 6.27 (d, J = 8.8 Hz, 1H), 6.18 (dd, J = 8.1, 2.0 Hz, 1H), 6.12 (s, 1H), 5.07 (s, 2H), 4.64 (s, 2H), 3.67 (s, 3H), 2.13 (s, 3H) $[M + H]^+$ = 378.3 |
| 195 | $^1$H NMR (400 MHz, DMSO-d6) δ 7.71 (s, 1H), 7.46 (d, J = 7.3 Hz, 2H), 7.40 (t, J = 7.4 Hz, 2H), 7.34 (t, J = 7.2 Hz, 1H), 7.18 (t, J = 8.2 Hz, 1H), 7.08 (d, J = 8.6 Hz, 1H), 6.97 (d, J = 2.7 Hz, 1H), 6.86 (dd, J = 8.6, 2.8 Hz, 1H), 6.59 (dd, J = 8.3, 1.3 Hz, 1H), 6.53 (d, J = 8.2 Hz, 1H), 6.45 (s, 1H), 5.08 (s, 2H), 2.13 (s, 3H) $[M + H]^+$ = 374.2 |
| 196 | $^1$H NMR (400 MHz, DMSO-d6) δ 7.45 (d, J = 7.2 Hz, 2H), 7.40 (t, J = 7.4 Hz, 2H), 7.36-7.31 (m, 1H), 7.23 (s, 1H), 7.06 (d, J = 8.6 Hz, 1H), 6.97 (t, J = 8.1 Hz, 1H), 6.92 (d, J = 2.8 Hz, 1H), 6.82 (dd, J = 8.6, 2.9 Hz, 1H), 6.25-6.18 (m, 2H), 6.18-6.14 (m, 1H), 5.07 (s, 2H), 3.86 (dd, J = 11.2, 3.5 Hz, 2H), 3.71 (d, J = 6.4 Hz, 2H), 3.35-3.27 (m, 2H), 2.13 (s, 3H), 2.00-1.88 (m, 1H), 1.63 (d, J = 12.7 Hz, 2H), 1.29 (qd, J = 11.8, 11.3, 3.8 Hz, 2H) $[M + H]^+$ = 404.2 |
| 197 | $^1$H NMR (400 MHz, DMSO-d6) δ 8.67 (s, 1H), 8.55 (d, J = 4.5 Hz, 1H), 7.88 (s, 2H), 7.80 (d, J = 5.8 Hz, 1H), 7.43 (dd, J = 7.7, 4.8 Hz, 1H), 7.29 (d, J = 8.7 Hz, 1H), 6.92 (d, J = 2.7 Hz, 1H), 6.83 (dd, J = 8.7, 2.8 Hz, 1H), 6.23 (dd, J = 5.8, 1.9 Hz, 1H), 5.97 (d, J = 1.8 Hz, 1H), 5.13 (s, 2H), 3.89 (t, J = 6.5 Hz, 2H), 2.15 (s, 3H), 1.67 (t, J = 10.8 Hz, 6H), 1.29-1.08 (m, 7H), 0.92-0.80 (m, 2H) $[M + H]^+$ = 432.1 |
| 198 | $^1$H NMR (400 MHz, DMSO-d6) δ 8.67 (d, J = 1.6 Hz, 1H), 8.55 (d, J = 4.8 Hz, 1H), 7.89 (s, 1H), 7.87 (d, J = 7.9 Hz, 1H), 7.43 (dd, J = 7.8, 4.8 Hz, 1H), 7.36-7.30 (m, 2H), 6.93 (d, J = 2.8 Hz, 1H), 6.83 (dd, J = 8.7, 2.9 Hz, 1H), 6.02 (d, J = 7.9 |

TABLE II-continued

| Ex | Characterization |
|---|---|
| | Hz, 1H), 5.97 (d, J = 7.8 Hz, 1H), 5.12 (s, 2H), 4.06 (t, J = 6.7 Hz, 2H), 2.17 (s, 3H), 1.71-1.56 (m, 7H), 1.18 (dt, J = 14.7, 9.0 Hz, 6H), 0.90-0.78 (m, 2H) $[M + H]^+$ = 432.1 |
| 199 | $^1$H NMR (400 MHz, DMSO-d6) δ 7.86 (s, 1H), 7.80 (d, J = 5.8 Hz, 1H), 7.45 (d, J = 7.3 Hz, 2H), 7.40 (t, J = 7.4 Hz, 2H), 7.33 (t, J = 7.1 Hz, 1H), 7.26 (d, J = 8.7 Hz, 1H), 6.90 (d, J = 2.6 Hz, 1H), 6.81 (dd, J = 8.7, 2.8 Hz, 1H), 6.23 (dd, J = 5.8, 1.7 Hz, 1H), 5.95 (s, 1H), 5.07 (s, 2H), 3.89 (t, J = 6.5 Hz, 2H), 2.15 (s, 3H), 1.73-1.58 (m, 7H), 1.28-1.08 (m, 6H), 0.93-0.79 (m, 2H) $[M + H]^+$ = 431.1 |
| 200 | $^1$H NMR (400 MHz, DMSO-d6) δ 7.87 (s, 1H), 7.45 (d, J = 7.2 Hz, 2H), 7.40 (t, J = 7.4 Hz, 3H), 7.38-7.26 (m, 3H), 6.90 (d, J = 2.8 Hz, 1H), 6.80 (dd, J = 8.7, 2.9 Hz, 1H), 6.01 (d, J = 7.9 Hz, 1H), 5.96 (d, J = 7.8 Hz, 1H), 5.07 (s, 2H), 4.06 (t, J = 6.8 Hz, 2H), 2.17 (s, 3H), 1.63 (dq, J = 14.6, 8.6, 6.6 Hz, 7H), 1.27-1.09 (m, 6H), 0.91-0.79 (m, 2H) $[M + H]^+$ = 431.1 |
| 201 | $^1$H NMR (400 MHz, DMSO-d6) δ 8.82 (s, 1H), 8.66 (dd, J = 16.8, 2.4 Hz, 2H), 7.24 (s, 1H), 7.08 (d, J = 8.6 Hz, 1H), 6.97 (t, 2H), 6.86 (dd, J = 8.6, 2.9 Hz, 1H), 6.22 (dd, J = 11.7, 8.5 Hz, 2H), 6.16 (d, J = 1.9 Hz, 1H), 5.23 (s, 2H), 3.82 (t, J = 6.5 Hz, 2H), 2.14 (s, 3H), 1.73-1.57 (m, 7H), 1.31-1.07 (m, 6H), 0.86 (q, J = 10.2, 8.9 Hz, 2H) $[M + H]^+$ = 432.2 |
| 202 | $^1$H NMR (400 MHz, DMSO-d6) δ 9.46 (s, 1H), 7.56 (s, 1H), 7.46 (d, J = 7.2 Hz, 2H), 7.43-7.31 (m, 4H), 7.16 (t, J = 9.2 Hz, 1H), 7.03-6.95 (m, 2H), 6.81 (dd, J = 8.8, 2.4 Hz, 1H), 6.50-6.42 (m, 1H), 5.09 (s, 2H), 2.34 (t, J = 7.6 Hz, 2H), 1.74-1.56 (m, 5H), 1.46 (q, J = 7.1 Hz, 2H), 1.26-1.08 (m, 4H), 0.94-0.81 (m, 2H) $[M + H]^+$ = 465.2 |
| 203 | $^1$H NMR (300 MHz, $CDCl_3$) δ 8.60 (d, J = 4.7 Hz, 1H), 7.81 (t, J = 3.8 Hz, 1H), 7.73 (td, J = 7.7, 1.6 Hz, 1H), 7.54 (d, J = 7.8 Hz, 1H), 7.39 (t, J = 1.6 Hz, 1H), 7.27-7.21 (m, 2H), 7.14 (d, J = 7.7 Hz, 1H), 7.08 (d, J = 8.9 Hz, 2H), 7.00 (dd, J = 8.0, 1.5 Hz, 1H), 6.95 (d, J = 8.9 Hz, 2H), 5.19 (s, 2H), 3.66 (t, J = 9.3 Hz, 4H), 3.54 (dd, J = 11.5, 5.7 Hz, 2H), 2.53 (t, J = 5.7 Hz, 2H), 2.47 (t, J = 9.3 Hz, 4H), 1.77 (dt, J = 11.5, 5.7 Hz, 3H) $[M + H]^+$ = 447.3 |
| 204 | $^1$H NMR (300 MHz, $CDCl_3$) δ 8.64 (d, J = 4.4 Hz, 1H), 7.83 (td, J = 7.7, 1.7 Hz, 1H), 7.58-7.50 (m, 2H), 7.36 (d, J = 7.0 Hz, 1H), 7.33-7.26 (m, 2H), 6.98 (d, J = 8.6 Hz, 1H), 6.93 (dd, J = 8.1, 1.6 Hz, 1H), 6.46 (dd, J = 8.6, 2.9 Hz, 1H), 6.37 (d, J = 2.8 Hz, 1H), 5.61 (bs, 1H), 5.11 (s, 2H), 1.83-1.74 (m, 1H), 0.83-0.76 (m, 2H), 0.49-0.43 (m, 2H) $[M + H]^+$ = 385.4 |
| 205 | $^1$H NMR (400 MHz, DMSO-d6) δ 8.37 (d, J = 7.8 Hz, 1H), 7.46-7.42 (m, 2H), 7.42-7.36 (m, 2H), 7.35-7.29 (m, 1H), 7.09-6.99 (m, 2H), 6.80 (dd, J = 8.7, 2.9 Hz, 1H), 6.70 (s, 1H), 6.66-6.59 (m, 2H), 6.39 (d, J = 7.7 Hz, 1H), 5.05 (s, 2H), 4.19-4.06 (m, 1H), 2.02-1.92 (m, 1H), 1.85-1.74 (m, 1H), 1.14 (d, J = 6.6 Hz, 6H), 0.91-0.81 (m, 4H), 0.66-0.61 (m, 2H), 0.61-0.56 (m, 2H) $[M + H]^+$ = 441.2 |
| 206 | $^1$H NMR (400MHz, DMSO-d6) δ 8.51 (d, J = 7.9 Hz, 1H), 7.47-7.29 (m, 5H), 7.14-7.04 (m, 2H), 6.86-6.75 (m, 3H), 6.62-6.56 (m, 2H), 5.06 (s, 2H), 4.15-4.04 (m, 1H), 1.86-1.77 (m, 1H), 1.15 (d, J = 6.6 Hz, 6H), 0.89-0.81 (m, 2H), 0.63-0.55 (m, 2H) $[M + H]^+$ = 435.2 |

The following examples are provided as illustrations and in no way limit the scope of this invention.

The following examples illustrate in detail the preparation of some compounds according to the invention. The structures of the products obtained have been confirmed by NMR spectra.

EXAMPLES

Example 1: Compound (39) in Table I

According to route (I), 4-nitro-5-methylphenol (3.06 g, 20 mmoles, 1 eq.) was placed in N,N-dimethylformamide (15 mL) with $K_2CO_3$ (8.3 g, 60 mmoles, 3 eq.). Upon addition of 2-(bromomethyl)pyridine hydrobromide (5.06 g, 20 mmoles, 1 eq.), the reaction mixture was heated at 90° C. and stirred for 24 hours under an inert atmosphere of argon. Upon cooling to room temperature, the reaction mixture was concentrated under reduced pressure and the resulting residue was partitioned between dichloromethane and water. Upon decantation, the organic phase was washed with a saturated aqueous solution of brine, dried over $MgSO_4$, filtered and concentrated under reduced pressure to give 2-(3-methyl-4-nitrophenoxymethyl)pyridine (4.5 g, 92%).

$^1$H NMR (300 MHz, $CDCl_3$) δ 8.65-8.60 (m, 1H), 8.07 (d, J=9.8 Hz, 1H), 7.75 (td, J=7.7, 1.7 Hz, 1H), 7.48 (d, J=7.7 Hz, 1H), 7.27 (t, J=6.2 Hz, 1H), 6.90-6.87 (m, 2H), 2.62 (s, 3H).

According to route (C), 2-(3-methyl-4-nitrophenoxymethyl)pyridine (4.5 g, 18.4 mmoles, 1 eq.) and tin (II) chloride dihydrate (20.8 g, 92 mmoles, 5 eq.) were placed in EtOH (184 mL). The reaction mixture was heated at 60° C. and stirred for 14 hours under an inert atmosphere of argon. The reaction mixture was then concentrated under reduced pressure and the resulting residue was diluted with dichloromethane. The organic phase was washed with a 1N NaOH aqueous solution then with a saturated aqueous solution of brine, dried over $MgSO_4$, filtered and concentrated under reduced pressure to afford 2-methyl-4-(pyridin-2-ylmethoxy)aniline (2.0 g, 51%).

$^1$H NMR (300 MHz, $CDCl_3$) δ 8.58 (d, J=4.3 Hz, 1H), 7.70 (td, J=7.7, 1.7 Hz, 1H), 7.52 (d, J=7.7 Hz, 1H), 7.20 (dd, J=6.9, 5.5 Hz, 1H), 6.76 (d, J=2.7 Hz, 1H), 6.69 (dd, J=8.5, 2.7 Hz, 1H), 6.60 (d, J=8.5 Hz, 1H), 5.13 (s, 2H), 3.37 (s, 2H), 2.15 (s, 3H).

2-Cyclopentylethan-1-amine hydrochloride (1.3 g, 8.7 mmoles, 1.1 eq.) was placed in a 3N NaOH aqueous solution (5.9 mL) and dichloromethane (1.5 mL) was added to the solution. The reaction mixture was cooled down to 0° C. with an ice bath and a solution of 3-bromobenzoyl chloride (1.0 mL, 7.9 mmoles, 1.0 eq.) in dichloromethane (2.4 mL) was added dropwise. The reaction mixture was then stirred at room temperature for 18 hours under an inert atmosphere of argon. Upon decantation, the organic phase was washed with a saturated aqueous solution of brine, dried over $MgSO_4$, filtered and concentrated under reduced pressure to afford 3-bromo-N-(2-cyclopentylethyl)benzamide (1.8 g, 77%).

$^1$H NMR (300 MHz, $CDCl_3$) δ 7.89 (t, J=1.7 Hz, 1H), 7.67 (d, J=7.9 Hz, 1H), 7.65-7.58 (m, 1H), 7.31 (t, J=7.9 Hz, 1H), 6.07 (s, 1H), 3.46 (dt, J=7.4, 5.9 Hz, 2H), 1.88-1.79 (m, 3H), 1.67-1.47 (m, 6H), 1.18-1.13 (m, 2H).

According to route (A), a reaction mixture of 3-bromo-N-(2-cyclopentylethyl)benzamide (830 mg, 2.8 mmoles, 1 eq.), 2-methyl-4-(pyridin-2-ylmethoxy)aniline (600 mg, 2.8 mmoles, 1 eq.), $Pd_2(dba)_3$ (258 mg, 282 μmoles, 10 mol %), XPhos (266 mg, 559 μmoles, 20 mol %) and $K_2CO_3$ (1.55 g, 11.2 mmoles, 4 eq.) in t-BuOH (11.2 mL) was heated at 90° C. and stirred for 88 hours under an inert atmosphere of argon. The reaction mixture was then concentrated under reduced pressure and the resulting residue was diluted with dichloromethane. The organic phase was washed with a saturated aqueous solution of brine, dried over $MgSO_4$, filtered and concentrated under reduced pressure. The resulting residue was purified by column chromatography on silica gel to afford a fraction which, after trituration in diethyl ether, gave N-(2-cyclopentylethyl)-3-{[2-methyl-4-(pyridin-2-ylmethoxy)phenyl]amino}benzamide (39) (734 mg, 61%).

$^1$H NMR (300 MHz, $d_6$-DMSO) δ 8.59 (d, J=4.3 Hz, 1H), 8.26 (t, J=5.5 Hz, 1H), 7.85 (td, J=7.7, 1.6 Hz, 1H), 7.54 (d, J=7.7 Hz, 1H), 7.47 (s, 1H), 7.35 (dd, J=6.9, 5.5 Hz, 1H), 7.20-7.05 (m, 4H), 6.97 (d, J=2.7 Hz, 1H), 6.85 (dd, J=8.6, 2.7 Hz, 1H), 6.75 (d, J=7.7 Hz, 1H), 5.16 (s, 2H), 3.21 (dd, J=13.4, 6.5 Hz, 2H), 2.14 (s, 3H), 1.82-1.70 (m, 2H), 1.64-1.39 (m, 6H), 1.12-1.07 (m, 3H).

$^{13}$C NMR (75 MHz, $d_6$-DMSO) δ 165.1, 155.5, 153.2, 147.6, 145.4, 135.5, 134.4, 132.7, 132.3, 127.3, 123.6, 121.5, 120.1, 115.6, 114.6, 114.2, 111.3, 111.2, 68.9, 37.1, 35.9, 34.0, 30.7, 23.2, 16.6.

$[M+H]^+$=430.3.

Example 2: Compound (50) in Table I

According to route (I), 4-nitrophenol (1.4 g, 10 mmoles, 1 eq.) was placed in N,N-dimethylformamide (7.7 mL) with $K_2CO_3$ (4.2 g, 30 mmoles, 3 eq.). Upon addition of 2-fluorobenzyl bromide (1.2 mL, 10 mmoles, 1 eq.), the reaction mixture was heated at 90° C. and stirred for 16 hours under an inert atmosphere of argon. Upon cooling to room temperature, the reaction mixture was concentrated under reduced pressure and the resulting residue was partitioned between ethyl acetate and water. Upon decantation, the organic phase was washed with a saturated aqueous solution of brine, dried over $MgSO_4$, filtered and concentrated under reduced pressure to give 1-fluoro-2-(4-nitrophenoxymethyl) benzene (2.0 g, 81%).

$^1$H NMR (300 MHz, $CDCl_3$) δ 8.22 (d, J=9.3 Hz, 2H), 7.47 (t, J=7.5 Hz, 1H), 7.37 (dd, J=13.6, 5.8 Hz, 1H), 7.19 (t, J=7.5 Hz, 1H), 7.16-7.10 (m, 1H), 7.05 (d, J=9.3 Hz, 2H), 5.23 (s, 2H).

According to route (C), 1-[(2-fluorophenyl)methoxy]-4-nitrobenzene (1.0 g, 4.0 mmoles, 1 eq.) and tin (II) chloride dihydrate (4.6 g, 20 mmoles, 5 eq.) were placed in EtOH (40 mL). The reaction mixture was heated at 60° C. and stirred for 14 hours under an inert atmosphere of argon. The reaction mixture was then concentrated under reduced pressure and the resulting residue was diluted with dichloromethane. The organic phase was washed with a 1N NaOH aqueous solution then with a saturated aqueous solution of brine, dried over $MgSO_4$, filtered and concentrated under reduced pressure to afford 4-[(2-fluorophenyl)methoxy]aniline (836 mg, 95%).

$^1$H NMR (300 MHz, $CDCl_3$) δ 7.50 (td, J=7.5, 1.0 Hz, 1H), 7.33-7.27 (m, 1H), 7.14 (td, J=7.5, 1.0 Hz, 1H), 7.10-7.03 (m, 1H), 6.82 (d, J=8.8 Hz, 2H), 6.64 (d, J=8.8 Hz, 2H), 5.06 (s, 2H), 3.43 (s, 2H).

2-Cyclopentylethan-1-amine hydrochloride (3.0 g, 19.1 mmoles, 1.1 eq.) was placed in a 3N NaOH aqueous solution (13 mL) and dichloromethane (3.2 mL) was added to the solution. The reaction mixture was cooled down to 0° C. with an ice bath and a solution of 3-bromobenzoyl chloride (2.3 mL, 17.4 mmoles, 1 eq.) in dichloromethane (5.5 mL) was added dropwise. The reaction mixture was then stirred at room temperature for 18 hours under an inert atmosphere of argon. Upon decantation, the organic phase was washed with a saturated aqueous solution of brine, dried over $MgSO_4$, filtered and concentrated under reduced pressure to afford 3-bromo-N-(2-cyclopentylethyl)benzamide (4.6 g, 89%).

$^1$H NMR (300 MHz, $CDCl_3$) δ 7.89 (t, J=1.7 Hz, 1H), 7.67 (d, J=7.9 Hz, 1H), 7.62 (d, J=7.9 Hz, 1H), 7.30 (t, J=7.9 Hz, 1H), 6.07 (s, 1H), 3.46 (dd, J=7.4, 5.9 Hz, 2H), 1.90-1.76 (m, 3H), 1.67-1.52 (m, 6H), 1.20-1.09 (m, 2H).

According to route (A), a reaction mixture of 3-bromo-N-(2-cyclopentylethyl)benzamide (296 mg, 1 mmole, 1 eq.), 4-[(2-fluorophenyl)methoxy]aniline (217 mg, 1 mmole, 1 eq.), $Pd_2(dba)_3$ (92 mg, 100 μmoles, 10 mol %), XPhos (95 mg, 200 μmoles, 20 mol %) and $K_2CO_3$ (553 mg, 4 mmoles, 4 eq.) in t-BuOH (4 mL) was heated at 90° C. and stirred for 14 hours under an inert atmosphere of argon. The reaction mixture was then concentrated under reduced pressure and the resulting residue was diluted with dichloromethane. The organic phase was washed with a saturated aqueous solution of brine, dried over $MgSO_4$, filtered and concentrated under reduced pressure. The resulting residue was purified by column chromatography on silica gel to afford a fraction which, after trituration in diethyl ether, gave N-(2-cyclopentylethyl)-3-({4-[(2-fluorophenyl)methoxy]phenyl}amino) benzamide (50) (168 mg, 39%).

$^1$H NMR (300 MHz, $d_6$-DMSO) δ 8.31 (t, J=5.6 Hz, 1H), 8.05 (s, 1H), 7.57 (td, J=7.4, 1.5 Hz, 1H), 7.47-7.36 (m, 2H), 7.30-7.19 (m, 3H), 7.15 (d, J=7.7 Hz, 1H), 7.07 (d, J=9.0 Hz, 2H), 7.05-7.0 (m, 1H), 6.98 (d, J=9.0 Hz, 2H), 5.10 (s, 2H), 3.23 (dd, J=13.8, 6.3 Hz, 2H), 1.86-1.72 (m, 3H), 1.62-1.45 (m, 6H), 1.11-1.04 (m, 2H).

$^{13}$C NMR (75 MHz, $d_6$-DMSO) δ 164.6, 160.2, 156.9, 151.1, 143.3, 134.4, 134.2, 128.9, 128.8, 128.4, 127.1, 122.7, 122.7, 122.4, 122.2, 118.7, 117.4, 115.3, 114.9, 113.8, 113.4, 111.8, 78.0, 62.0, 35.6, 33.7, 30.4, 22.9.

Example 3: Compound (60) in Table I

According to route (I), 3-bromo-4-nitrophenol (1.7 g, 7.9 mmoles, 1 eq.) was placed in N,N-dimethylformamide (6 mL) with $K_2CO_3$ (3.3 g, 23.7 mmoles, 3 eq.). Upon addition of 2-(bromomethyl)pyridine hydrobromide (2.0 g, 7.9 mmoles, 1 eq.), the reaction mixture was heated at 90° C. and stirred for 24 hours under an inert atmosphere of argon. Upon cooling to room temperature, the reaction mixture was concentrated under reduced pressure and the resulting residue was partitioned between dichloromethane and water. Upon decantation, the organic phase was washed with a saturated aqueous solution of brine, dried over $MgSO_4$, filtered and concentrated under reduced pressure to give 2-(3-bromo-4-nitrophenoxymethyl)pyridine (2.4 g, 98%).

$^1$H NMR (300 MHz, $CDCl_3$) δ 8.63 (d, J=4.8 Hz, 1H), 7.97 (d, J=9.1 Hz, 1H), 7.76 (td, J=7.7, 1.7 Hz, 1H), 7.47 (d, J=7.7 Hz, 1H), 7.35 (d, J=2.7 Hz, 1H), 7.32-7.27 (m, 1H), 7.01 (dd, J=9.1, 2.7 Hz, 1H), 5.27 (s, 2H).

According to route (J), 2-(3-bromo-4-nitrophenoxymethyl)pyridine (2.4 g, 7.8 mmoles, 1 eq.) was placed in 1,4-dioxane (28 mL) with $Pd(dppf)Cl_2$. $CH_2Cl_2$ (634 mg, 0.78 mmole, 0.1 eq.). Upon addition of $K_3PO_4$ (6.6 g, 31 mmoles, 4 eq.) and cyclopropylboronic acid (2.0 g, 23.3 mmoles, 3 eq.), the reaction mixture was heated at 100° C. and stirred for 20 hours under an inert atmosphere of argon. The reaction mixture was then concentrated under reduced pressure and the resulting residue was purified by column chromatography on silica gel to afford 2-(3-cyclopropyl-4-nitrophenoxymethyl)pyridine (1.5 g, 71%).

$^1$H NMR (300 MHz, $CDCl_3$) δ 8.62 (d, J=4.2 Hz, 1H), 7.94 (d, J=9.0 Hz, 1H), 7.74 (td, J=7.7, 1.7 Hz, 1H), 7.47 (d,

J=7.7 Hz, 1H), 7.30-7.22 (m, 2H), 6.84 (dd, J=9.0, 2.7 Hz, 1H), 6.72 (d, J=2.7 Hz, 1H), 5.24 (s, 2H), 2.54 (tt, J=8.5, 5.5 Hz, 1H), 1.06 (q, J=4.8 Hz, 2H), 0.67 (q, J=4.8 Hz, 2H).

According to route (C), 2-(3-cyclopropyl-4-nitrophenoxymethyl)pyridine (1.5 g, 5.6 mmoles, 1 eq.) and tin (II) chloride dihydrate (6.3 g, 28 mmoles, 5 eq.) were placed in EtOH (56 mL). The reaction mixture was heated at 60° C. and stirred for 64 hours under an inert atmosphere of argon. The reaction mixture was then concentrated under reduced pressure and the resulting residue was diluted with dichloromethane. The organic phase was washed with a 1N NaOH aqueous solution then with a saturated aqueous solution of brine, dried over $MgSO_4$, filtered and concentrated under reduced pressure to afford 2-cyclopropyl-4-(pyridin-2-ylmethoxy)aniline (1.1 g, 82%).

$^1H$ NMR (300 MHz, $CDCl_3$) δ 8.58 (d, J=4.2 Hz, 1H), 7.70 (td, J=7.7, 1.7 Hz, 1H), 7.52 (d, J=7.7 Hz, 1H), 7.20 (dd, J=6.9, 5.4 Hz, 1H), 6.73 (t, J=2.7 Hz, 1H), 6.69 (d, J=2.7 Hz, 1H), 6.61 (d, J=8.3 Hz, 1H), 5.12 (s, 2H), 3.71 (s, 2H), 1.74-1.65 (m, 1H), 0.90 (q, J=4.1 Hz, 2H), 0.58 (q, J=4.1 Hz, 2H).

2-Cyclopentylethan-1-amine hydrochloride (1.3 g, 8.7 mmoles, 1.1 eq.) was placed in a 3N NaOH aqueous solution (5.9 mL) and dichloromethane (1.5 mL) was added to the solution. The reaction mixture was cooled down to 0° C. with an ice bath and a solution of 3-bromobenzoyl chloride (1.0 mL, 7.9 mmoles, 1.0 eq.) in dichloromethane (2.4 mL) was added dropwise. The reaction mixture was then stirred at room temperature for 18 hours under an inert atmosphere of argon. Upon decantation, the organic phase was washed with a saturated aqueous solution of brine, dried over $MgSO_4$, filtered and concentrated under reduced pressure to afford 3-bromo-N-(2-cyclopentylethyl)benzamide (1.8 g, 77%).

$^1H$ NMR (300 MHz, $CDCl_3$) δ 7.89 (t, J=1.7 Hz, 1H), 7.67 (d, J=7.9 Hz, 1H), 7.65-7.58 (m, 1H), 7.31 (t, J=7.9 Hz, 1H), 6.07 (s, 1H), 3.46 (dt, J=7.4, 5.9 Hz, 2H), 1.88-1.79 (m, 3H), 1.67-1.47 (m, 6H), 1.18-1.13 (m, 2H).

According to route (A), a reaction mixture of 3-bromo-N-(2-cyclopentylethyl)benzamide (148 mg, 0.5 mmole, 1 eq.), 2-cyclopropyl-4-(pyridin-2-ylmethoxy)aniline (120 mg, 0.5 mmole, 1 eq.), $Pd_2(dba)_3$ (46 mg, 50 μmoles, 10 mol %), XPhos (48 mg, 100 μmoles, 20 mol %) and $K_2CO_3$ (277 mg, 2.0 mmoles, 4 eq.) in t-BuOH (2 mL) was heated at 90° C. and stirred for 14 hours under an inert atmosphere of argon. The reaction mixture was then concentrated under reduced pressure and the resulting residue was diluted with dichloromethane. The organic phase was washed with a saturated aqueous solution of brine, dried over $MgSO_4$, filtered and concentrated under reduced pressure. The resulting residue was purified by column chromatography on silica gel to afford N-(2-cyclopentylethyl)-3-{[2-cyclopropyl-4-(pyridin-2-ylmethoxy)phenyl]amino}benzamide (60) (190 mg, 83%).

$^1H$ NMR (300 MHz, $CDCl_3$) δ 8.61 (d, J=4.2 Hz, 1H), 7.73 (td, J=7.7, 1.7 Hz, 1H), 7.54 (d, J=7.7 Hz, 1H), 7.26-7.19 (m, 3H), 7.16 (d, J=8.6 Hz, 1H), 7.08 (d, J=7.7 Hz, 1H), 6.95 (dd, J=7.7, 1.7 Hz, 1H), 6.78 (dd, J=8.6, 2.9 Hz, 1H), 6.68 (d, J=2.9 Hz, 1H), 6.03 (s, 1H), 5.71 (s, 1H), 5.18 (s, 2H), 3.43 (dd, J=9.8, 4.7 Hz, 2H), 1.90-1.78 (m, 5H), 1.66-1.51 (m 4H), 1.17-1.09 (m 3H), 0.94-0.87 (m 2H), 0.67-0.59 (m 2H).

$^{13}C$ NMR (75 MHz, $CDCl_3$) δ 165.4, 155.1, 152.7, 146.9, 143.9, 135.4, 134.5, 133.8, 132.2, 127.0, 120.9, 120.3, 119.0, 115.3, 114.4, 111.8, 111.2, 110.0, 68.6, 37.2, 35.6, 33.6, 30.4, 22.8, 9.3, 4.9.

$[M+H]^+$=456.4.

Example 4: Compound (68) in Table I

According to route (I), 4-nitro-5-methylphenol (3.06 g, 20 mmoles, 1 eq.) was placed in N,N-dimethylformamide (15 mL) with $K_2CO_3$ (8.3 g, 60 mmoles, 3 eq.). Upon addition of 2-(bromomethyl)pyridine hydrobromide (5.06 g, 20 mmoles, 1 eq.), the reaction mixture was heated at 90° C. and stirred for 24 hours under an inert atmosphere of argon. Upon cooling to room temperature, the reaction mixture was concentrated under reduced pressure and the resulting residue was partitioned between dichloromethane and water. Upon decantation, the organic phase was washed with a saturated aqueous solution of brine, dried over $MgSO_4$, filtered and concentrated under reduced pressure to give 2-(3-methyl-4-nitrophenoxymethyl)pyridine (4.5 g, 92%).

$^1H$ NMR (300 MHz, $CDCl_3$) δ 8.65-8.60 (m, 1H), 8.07 (d, J=9.8 Hz, 1H), 7.75 (td, J=7.7, 1.7 Hz, 1H), 7.48 (d, J=7.7 Hz, 1H), 7.30-7.24 (m, 1H), 6.90-6.87 (m, 2H), 2.62 (s, 3H).

According to route (C), 2-(3-methyl-4-nitrophenoxymethyl)pyridine (4.5 g, 18.4 mmoles, 1 eq.) and tin (II) chloride dihydrate (20.8 g, 92 mmoles, 5 eq.) were placed in EtOH (184 mL). The reaction mixture was heated at 60° C. and stirred for 14 hours under an inert atmosphere of argon. The reaction mixture was then concentrated under reduced pressure and the resulting residue was diluted with dichloromethane. The organic phase was washed with a 1N NaOH aqueous solution then with a saturated aqueous solution of brine, dried over $MgSO_4$, filtered and concentrated under reduced pressure to afford 2-methyl-4-(pyridin-2-ylmethoxy)aniline (2.0 g, 51%).

$^1H$ NMR (300 MHz, $CDCl_3$) δ 8.58 (d, J=4.3 Hz, 1H), 7.70 (td, J=7.7, 1.7 Hz, 1H), 7.52 (d, J=7.7 Hz, 1H), 7.23-7.17 (m, 1H), 6.76 (d, J=2.7 Hz, 1H), 6.69 (dd, J=8.5, 2.7 Hz, 1H), 6.60 (d, J=8.5 Hz, 1H), 5.13 (s, 2H), 3.37 (s, 2H), 2.15 (s, 3H).

3-Bromophenyl isocyanate (624 μL, 5.0 mmoles, 1.0 eq.) and triethylamine (695 μL, 5.0 mmoles, 1.0 eq.) were placed in dichloromethane (5 mL) and a solution of 3-methylbutan-1-amine (580 μL, 5.0 mmoles, 1.0 eq.) in dichloromethane (2 mL) was added dropwise. The reaction mixture was then stirred at room temperature for 16 hours under an inert atmosphere of argon. The reaction mixture was concentrated under reduced pressure and the resulting residue was diluted with ethyl acetate. The organic phase was washed with a 1N HCl aqueous solution then with a saturated aqueous solution of brine, dried over $MgSO_4$, filtered and concentrated under reduced pressure. The resulting residue was purified by column chromatography on silica gel to afford 1-(3-bromophenyl)-3-(3-methylbutyl)urea (1.06 g, 74%).

$^1H$ NMR (300 MHz, $CDCl_3$) δ 7.54 (s, 1H), 7.49 (t, J=1.9 Hz, 1H), 7.18 (dt, J=7.2, 1.9 Hz, 1H), 7.13-7.03 (m, 2H), 5.56 (t, J=5.3 Hz, 1H), 3.20 (dt, J=7.5, 5.8 Hz, 2H), 1.60-1.54 (m, 1H), 1.36-1.30 (m, 2H), 0.86 (d, J=6.6 Hz, 6H).

According to route (A), a reaction mixture of 1-(3-bromophenyl)-3-(3-methylbutyl)urea (285 mg, 1.0 mmole, 1 eq.), 2-methyl-4-(pyridin-2-ylmethoxy)aniline (214 mg, 1.0 mmole, 1 eq.), $Pd_2(dba)_3$ (92 mg, 100 μmoles, 10 mol %), XPhos (95 mg, 200 μmoles, 20 mol %) and $K_2CO_3$ (553 mg, 4.0 mmoles, 4 eq.) in t-BuOH (4 mL) was heated at 90° C. and stirred for 24 hours under an inert atmosphere of argon. The reaction mixture was then concentrated under reduced pressure and the resulting residue was diluted with dichloromethane. The organic phase was washed with a saturated aqueous solution of brine, dried over $MgSO_4$, filtered and concentrated under reduced pressure. The resulting residue was purified by column chromatography on silica gel to afford a fraction which, after trituration in diethyl ether, gave 1-isopentyl-3-(3-((2-methyl-4-(pyridin-2-ylmethoxy)phenyl)amino)phenyl)urea (68) (76 mg, 18%).

$^1$H NMR (300 MHz, $d_6$-DMSO) δ 8.59 (d, J=4.5 Hz, 1H), 8.15 (s, 1H), 7.85 (td, J=7.9, 1.5 Hz, 1H), 7.54 (d, J=7.9 Hz, 1H), 7.39-7.31 (m, 1H), 7.18 (s, 1H), 7.06 (d, J=8.6 Hz, 1H), 6.96-6.90 (m, 2H), 6.82 (dd, J=8.6, 2.8 Hz, 1H), 6.73 (s, 1H), 6.67 (d, J=7.9 Hz, 1H), 6.21 (d, J=7.9 Hz, 1H), 5.92 (t, J=5.4 Hz, 1H), 5.14 (s, 2H), 3.06 (dd, J=13.3, 6.7 Hz, 2H), 2.14 (s, 3H), 1.57 (td, J=13.3, 6.7 Hz, 1H), 1.33-1.25 (m, 2H), 0.88 (d, J=6.7 Hz, 6H).

$[M+H]^+$=419.4.

Example 5: Compound (73) in Table I

According to route (I), 4-nitrophenol (2.75 g, 19.8 mmoles, 1 eq.) was placed in N,N-dimethylformamide (15 mL) with $K_2CO_3$ (8.2 g, 59.3 mmoles, 3 eq.). Upon addition of 2-(bromomethyl)pyridine hydrobromide (5.0 g, 19.8 mmoles, 1 eq.), the reaction mixture was heated at 90° C. and stirred for 16 hours under an inert atmosphere of argon. Upon cooling to room temperature, the reaction mixture was concentrated under reduced pressure and the resulting residue was partitioned between ethyl acetate and water. Upon decantation, the organic phase was washed with a saturated aqueous solution of brine, dried over $MgSO_4$, filtered and concentrated under reduced pressure. The resulting residue was purified by column chromatography on silica gel to give 2-(4-nitrophenoxymethyl)pyridine (3.1 g, 68%).

$^1$H NMR (300 MHz, $CDCl_3$) δ 8.63 (d, J=4.8 Hz, 1H), 8.25-8.16 (m, 2H), 7.75 (td, J=7.7, 1.7 Hz, 1H), 7.48 (d, J=7.7 Hz, 1H), 7.31-7.26 (m, 1H), 7.11-7.03 (m, 2H), 5.30 (s, 2H).

According to route (C), 2-(4-nitrophenoxymethyl)pyridine (2.0 g, 8.7 mmoles, 1 eq.) and tin (II) chloride dihydrate (9.8 g, 43 mmoles, 5 eq.) were placed in EtOH (87 mL). The reaction mixture was heated at 60° C. and stirred for 14 hours under an inert atmosphere of argon. The reaction mixture was then concentrated under reduced pressure and the resulting residue was diluted with ethyl acetate. The organic phase was washed with a 1N NaOH aqueous solution then with a saturated aqueous solution of brine, dried over $MgSO_4$, filtered and concentrated under reduced pressure. The resulting residue was purified by column chromatography on silica gel to afford 4-(pyridin-2-ylmethoxy) aniline (1.1 g, 63%).

$^1$H NMR (300 MHz, $CDCl_3$) δ 8.58 (d, J=4.3 Hz, 1H), 7.70 (td, J=7.7, 1.7 Hz, 1H), 7.52 (d, J=7.7 Hz, 1H), 7.20 (dd, J=7.2, 5.2 Hz, 1H), 6.85-6.79 (m, 2H), 6.67-6.61 (m, 2H), 5.13 (s, 2H), 3.43 (br s, 2H).

Cyclopentanepropanol (2.0 g, 15.6 mmoles, 1 eq.) and triethylamine (2.8 mL, 20.1 mmoles, 1.3 eq.) were placed in dichloromethane (9.1 mL). The solution was cooled down to 0° C. with an ice bath and a solution of 4-toluenesulfonyl chloride (2.6 g, 13.6 mmoles, 0.9 eq.) in dichloromethane (4.6 mL) was added dropwise. The reaction mixture was then stirred at room temperature for 24 hours under an inert atmosphere of argon. The organic phase was washed with a 1N HCl aqueous solution then with a saturated aqueous solution of $NaHCO_3$, dried over $MgSO_4$, filtered and concentrated under reduced pressure. The resulting residue was purified by column chromatography on silica gel to afford 3-cyclopentylpropyl 4-methylbenzene-1-sulfonate (3.2 g, 83%).

$^1$H NMR (300 MHz, $CDCl_3$) δ 7.79 (d, J=8.1 Hz, 2H), 7.34 (d, J=8.1 Hz, 2H), 4.02 (t, J=6.6 Hz, 1H), 2.45 (s, 2H), 1.75-1.43 (m, 11H), 1.34-1.23 (m, 2H), 1.05-0.95 (m, 2H).

3-Bromophenol (613 mg, 3.5 mmoles, 1 eq.) was placed in N,N-dimethylformamide (25 mL) with $Cs_2CO_3$ (3.5 g, 10.7 mmoles, 3 eq.). Upon addition of 3-cyclopentylpropyl 4-methylbenzene-1-sulfonate (1.0 g, 3.5 mmoles, 1 eq.), the reaction mixture was heated at 90° C. and stirred for 14 hours under an inert atmosphere of argon. Upon cooling to room temperature, the reaction mixture was concentrated under reduced pressure and the resulting residue was partitioned between ethyl acetate and water. Upon decantation, the organic phase was washed with a saturated aqueous solution of $NH_4Cl$ and then with a saturated aqueous solution of brine, dried over $MgSO_4$, filtered and concentrated under reduced pressure to give 1-bromo-3-(3-cyclopentylpropoxy)benzene (716 mg, 71%).

$^1$H NMR (300 MHz, $CDCl_3$) δ 7.14-7.10 (m, 1H), 7.07-7.03 (m, 2H), 6.82 (ddd, J=8.1, 2.3, 1.2 Hz, 1H), 3.92 (t, J=6.6 Hz, 2H), 1.86-1.70 (m, 6H), 1.69-1.40 (m, 7H), 1.18-1.03 (m, 2H).

According to route (A), a reaction mixture of 1-bromo-3-(3-cyclopentylpropoxy)benzene (282 mg, 1.0 mmole, 1 eq.), 4-(pyridin-2-ylmethoxy)aniline (200 mg, 1.0 mmole, 1 eq.), $Pd_2(dba)_3$ (92 mg, 100 μmoles, 10 mol %), XPhos (95 mg, 200 μmoles, 20 mol %) and $K_2CO_3$ (553 mg, 4.0 mmoles, 4 eq.) in t-BuOH (4 mL) was heated at 90° C. and stirred for 64 hours under an inert atmosphere of argon. The reaction mixture was then concentrated under reduced pressure and the resulting residue was diluted with dichloromethane. The organic phase was washed with a saturated aqueous solution of brine, dried over $MgSO_4$, filtered and concentrated under reduced pressure. The resulting residue was purified by column chromatography on silica gel to afford 3-(3-cyclopentylpropoxy)-N-(4-(pyridin-2-ylmethoxy)phenyl)aniline (73) (94 mg, 23%).

$^1$H NMR (300 MHz, $CDCl_3$) δ 8.59 (d, J=5.2 Hz, 1H), 7.71 (td, J=7.7, 1.7 Hz, 1H), 7.53 (d, J=7.7 Hz, 1H), 7.21 (dd, J=7.0, 5.2 Hz, 1H), 7.12-7.03 (m, 3H), 6.96-6.89 (m, 2H), 6.50-6.44 (m, 2H), 6.38 (dd, J=7.7, 1.7 Hz, 1H), 5.55 (br s, 1H), 5.18 (s, 2H), 3.88 (t, J=6.6 Hz, 2H), 1.82-1.68 (m, 7H), 1.66-1.46 (m, 5H), 1.17-1.04 (m, 3H).

Example 6: Compound (93) in Table I

According to procedure (A1), a reaction mixture of N-(3-bromophenyl)-3-cyclohexylpropanamide (113 mg, 0.423 mmole, 1.2 eq.), 4-(benzyloxy)-2-(cyclopent-1-en-1-yl)aniline (100 mg, 0.351 mmole, 1.0 eq.), BrettPhos Pd G3 (6.4 mg, 7.0 μmoles, 2 mol %) and $Cs_2CO_3$ (171 mg, 0.526 mmole, 1.5 eq.) in anhydrous DMF (1.3 mL) was degassed with argon and heated at 80° C. for 75 minutes under inert atmosphere. The reaction mixture was then cooled down to room temperature, filtered over a pad of celite and the pad was washed with EtOAc. A saturated aqueous solution of brine was then added to the filtrate and the mixture was extracted with EtOAc. The combined organic layers were dried over $MgSO_4$, filtered and concentrated under reduced pressure. The resulting residue was purified by column chromatography on silica gel to give N-(3-{[4-(benzyloxy)-2-(cyclopent-1-en-1-yl)phenyl]amino}phenyl)-3-cyclohexylpropanamide (131 mg, 76%).

$^1$H NMR (400 MHz, $d_6$-DMSO) δ 7.52-7.22 (m, 5H), 6.76-6.53 (m, 3H), 6.01 (s, 1H), 4.97 (s, 2H), 4.50 (s, 2H), 2.62 (t, J=6.6 Hz, 2H), 1.89 (p, J=7.5 Hz, 2H).

$[M+H]^+$=495.3.

A 0.025M solution of N-(3-{[4-(benzyloxy)-2-(cyclopent-1-en-1-yl)phenyl]amino}phenyl)-3-cyclohexylpropanamide (100 mg, 0.202 mmole, 1.0 eq.) in MeOH:THF (1:1) was passed through a H-cube apparatus (cartridge Pd/C 30 mm, 30° C., 2 bars, 1 m/min). The solvent was then concentrated under reduced pressure. The resulting residue was purified by column chromatography on silica gel to give N-(3-{[4-(benzyloxy)-2-cyclopentylphenyl]amino}phenyl)-3-cyclohexylpropanamide (93) (50.0 mg, 50%).

$^1$H NMR (400 MHz, $d_6$-DMSO) δ 9.55 (s, 1H), 7.55-7.27 (m, 5H), 7.17 (s, 1H), 7.08-6.73 (m, 6H), 6.27 (d, J=8.9 Hz, 1H), 5.08 (s, 2H), 3.26-3.13 (m, 1H), 2.28-2.15 (m, 2H), 1.89 (d, J=6.1 Hz, 2H), 1.79-1.36 (m, 14H), 1.28-1.04 (m, 4H), 0.87 (q, J=10.4, 8.9 Hz, 2H).

$[M+H]^+$=497.3.

Example 7: Compound (101) in Table I

According to route (I), 4-amino-3-tert-butylphenol (100 mg, 0.581 mmole, 1 eq.) was placed in anhydrous N,N-dimethylformamide (2 mL) with $Cs_2CO_3$ (227 mg, 0.697 mmole, 1.2 eq.). Upon addition of bromomethylbenzene (75.9 μL, 0.639 mmole, 1 eq.), the reaction mixture was stirred at room temperature for 16 hours under an inert atmosphere of argon. The reaction was quenched with 1M aqueous hydrochloric acid and extracted with ethyl acetate. The combined organic phases were dried over magnesium sulphate, filtered and concentrated under reduced pressure to afford a mixture of 0 and N poly-benzylated products. The residue was taken up in methanol (15 mL) and hydrogenated using a H-cube apparatus (Pd/C 10%, 1 bar hydrogen pressure, 1 mL/min flow). The solvent was then concentrated under reduced pressure. The resulting residue was purified by column chromatography on silica gel to give 4-(benzyloxy)-2-tert-butylaniline (23.8 mg, 21%).

$^1$H NMR (400 MHz, $d_6$-DMSO) δ 7.42 (d, J=6.9 Hz, 2H), 7.37 (t, J=7.3 Hz, 2H), 7.31 (d, J=7.0 Hz, 1H), 6.72 (d, J=2.7 Hz, 1H), 6.61 (d, J=2.7 Hz, 1H), 6.58 (d, J=8.5 Hz, 1H), 4.94 (s, 2H), 4.32 (s, 2H), 1.31 (s, 9H).

According to procedure (A1), a reaction mixture of methyl 2-bromobenzoate (11.0 μL, 78.3 μmoles, 1.0 eq.), 4-(benzyloxy)-2-tert-butylaniline (20.0 mg, 78.3 μmoles, 1.0 eq.), $Pd(OAc)_2$ (0.53 mg, 2.3 μmoles, 3 mol %), rac-BINAP (0.98 mg, 1.6 μmole, 2 mol %) and $K_2CO_3$ (32.5 mg, 235 μmoles, 3 eq.) in anhydrous toluene (1.0 mL) was degassed with $N_2$ and heated at 110° C. for 75 minutes under inert atmosphere. The reaction mixture was cooled down to room temperature, filtered over a pad of celite and the pad was washed with EtOAc. A saturated aqueous solution of brine was then added to the filtrate and the mixture was extracted with EtOAc. The combined organic phases were dried over $MgSO_4$, filtered and concentrated under reduced pressure to give methyl 2-{[4-(benzyloxy)-2-tert-butylphenyl]amino}benzoate (50.0 mg, 47% purity, 77%).

Methyl 2-{[4-(benzyloxy)-2-tert-butylphenyl]amino}benzoate (50.0 mg, 47% purity, 60.3 μmoles, 1 eq.) was placed in methanol (2 mL) and an aqueous solution of 2M NaOH (151 μL, 302 μmoles, 5 eq.) was added. The reaction mixture was heated at 80° C. and stirred for 3 hours. It was then concentrated under reduced pressure and, after addition of an aqueous solution of 2M HCl (10 eq.), extracted with dichloromethane. The combined organic phases were dried over magnesium sulphate, filtered and concentrated under reduced pressure to give 2-{[4-(benzyloxy)-2-tert-butylphenyl]amino}benzoic acid (28.0 mg, 42% purity, 52%).

2-{[4-(benzyloxy)-2-tert-butylphenyl]amino}benzoic acid (28.0 mg, 42% purity, 74.6 μmoles, 1 eq.) and 2-cyclohexylethanamine (12.5 μL, 89.5 μmoles, 1.2 eq.) were placed in anhydrous N,N-dimethylformamide (1.0 mL). HATU (44.3 mg, 112 μmoles, 1.5 eq.) and DIPEA (39.1 μL, 224 μmoles, 3 eq.) were added and the resulting reaction mixture was stirred at room temperature for 16 hours. The reaction was quenched with 1M aqueous hydrochloric acid and extracted with ethyl acetate. The combined organic phases were dried over magnesium sulphate, filtered and concentrated under reduced pressure. The resulting residue was purified by column chromatography on silica gel to give 2-{[4-(benzyloxy)-2-tert-butylphenyl]amino}-N-(2-cyclohexylethyl)benzamide (101) (5.1 mg, 14%).

$^1$H NMR (400 MHz, $d_6$-DMSO) δ 9.47 (s, 1H), 8.40 (s, 1H), 7.61 (d, J=6.9 Hz, 1H), 7.48 (d, J=7.1 Hz, 2H), 7.41 (t, J=7.4 Hz, 2H), 7.34 (t, J=7.2 Hz, 1H), 7.16 (t, J=7.7 Hz, 1H), 7.06 (d, J=8.6 Hz, 1H), 7.00 (d, J=2.8 Hz, 1H), 6.90 (dd, J=8.6, 2.8 Hz, 1H), 6.61 (t, J=7.4 Hz, 1H), 6.49 (d, J=8.4 Hz, 1H), 5.09 (s, 2H), 3.27 (d, J=6.8 Hz, 2H), 1.74 (d, J=12.2 Hz, 2H), 1.64 (dd, J=20.5, 11.1 Hz, 3H), 1.44 (q, J=6.9 Hz, 2H), 1.31 (s, 9H), 1.26-1.13 (m, 4H), 0.90 (q, J=13.3, 12.5 Hz, 2H).

$[M+H]^+$=485.3.

Pharmacological Data

Example 8: Chikungunya Virus

The compounds of the invention have been the subject of pharmacological tests which have demonstrated their relevance as active substances in therapy and in particular for preventing, inhibiting or treating Chikungunya virus infection.

Material and Methods Inhibition of Chikungunya Virus (CHIKV) Production in Infected HEK293T Cell Line.

The ability of the compounds to inhibit viral replication was assessed with an experiment in which infected cells were treated by compounds of formula (Ie) at 1 μM. As a positive control for inhibition of Chikungunya, Ribavirin was used. Toxicity of the compounds was assessed in parallel.

Amplification of Cells

Human embryonic kidney cells 293T (HEK293T, CRL-11268) were maintained in Dulbecco's modified Eagle's Medium (DMEM, 31966-021, Thermo Fisher Scientific) supplemented with 10% of fetal bovine serum (FBS), penicillin and streptomycin. After removal of the medium, cells were washed with $Ca^{2+}$ and $Mg^{2+}$-free salt solution to remove all traces of serum. After aspiration of wash solution, cells were dissociated with 0.25% Trypsin-EDTA solution and incubated 30 s at least in 37° C. incubator. Concentration of cell suspension was determined by an automatic cell counter (EVE, NanoEntek) and, if needed, adjusted to $0.33\times10^6$ cells/mL with DMEM medium supplemented with 10% FBS.

Preparation of the Compounds

100 μL of the cell suspension were dispatched in a ViewPlate-96 Black (6005182, PerkinElmer) and in a transparent 96-well cell culture plate (655180, Greiner bio-one). After an incubation for 24 h at 37° C. under 5% of $CO_2$, compounds were added at the proper concentration.

Screen at 1 μM

An intermediate dilution was prepared with DMSO (D8418, Sigma) at 2 mM in a 96-well V-bottom microplate from the stock solution:

Mix 1 μL of the 50 mM stock library in 25 μL of DMSO.

Mix 2 μL of the 25 mM stock library in 25 μL of DMSO.

Determination of $IC_{50}$ Values

An intermediate dilution was prepared with DMSO (D8418, Sigma) at 25 mM in a 96-well V-bottom microplate from the stock solution:

Mix 2 μL of the 50 mM stock library in 2 μL of DMSO.

Perform serial dilution in 2 μL of DMSO 13 times to reach 0.0015 mM. Proceed as follows in table III:

TABLE III

| | Concentration (mM) | Volume of DMSO 100% (μL) | Volume of solution |
|---|---|---|---|
| A | 12.5 | 2 | 2 μL of 50 mM solution |
| B | 6.25 | 2 | 2 μL of solution A |
| C | 3.125 | 2 | 2 μL of solution B |
| D | 1.56 | 2 | 2 μL of solution C |
| E | 0.78 | 2 | 2 μL of solution D |
| F | 0.39 | 2 | 2 μL of solution E |
| G | 0.195 | 2 | 2 μL of solution F |
| H | 0.0976 | 2 | 2 μL of solution G |
| I | 0.0488 | 2 | 2 μL of solution H |
| J | 0.0244 | 2 | 2 μL of solution I |
| K | 0.0122 | 2 | 2 μL of solution J |
| L | 0.0061 | 2 | 2 μL of solution K |
| M | 0.0030 | 2 | 2 μL of solution L |
| N | 0.0015 | 2 | 2 μL of solution M |

For both screen and determination of $IC_{50}$, 1 μL of each solution was added in a 1 mL Masterblock 96 wells (Greiner bio-one, 780261) containing 1 mL of DMEM medium. As a positive control, 5 μL of a 80 mM Ribavirin solution (R9644, Sigma) is added to 1 mL of DMEM. On the other hand, DMSO is used as a negative control.

Infection

Cells were infected with 30 μL of CHIKV strain of La Réunion outbreak (LR2006-OPY1) with GFP modification in 5' (CHIK 5'LR) (Tsetsarkin K, Higgs S, McGee C E, De Lamballerie X, Charrel R N, Vanlandingham D L. Infectious Clones of Chikungunya Virus (La Réunion Isolate—Ref-SKU: 001N-EVA249 (PMID: 17187566) available at the following address: https://www.european-virus-archive.com/nucleic-acid/chikv-lr-5gfp-infectious-clone) for Vector Competence Studies. Vector Borne Zoonotic Dis. 2006; 6(4)). This modified virus was used to infect cells at MOI 0.1. The LR2006-OPY1 strain of CHIKV (CHIKV-LR) was obtained from the World Reference Center for Arboviruses at the University of Texas Medical Branch, Galveston, TX. This strain was originally isolated from the serum of a febrile French patient returning from La Réunion Island.

Cell Lysis

Medium was removed after 22 h at 37° C. under 5% of $CO_2$ and cells were washed as described above. 60 μL of RIPA buffer (50 mM Tris-HCl pH8, 100 mM NaCl, 1 mM $MgCl_2$, 1% Triton X-100) was added to cells and incubated for at least 20 min before reading fluorescence signal. Pierce 660 nm Protein Assay Reagent (22660, Thermo scientific) was used to normalize fluorescence signal by protein quantity.

CellTiter 96® AQueous One Solution Cell Proliferation Assay (MTS) (G3581, Promega) was used to check the toxicity of the compounds. We added 20 μL of MTS solution and read absorbance at 492 nm one hour later.

Results

A first round of experiments has been performed wherein the results are expressed as inhibition percentage, which is calculated as follows, through the following steps:

1. Fluorescence intensity (FI)/Absorbance 660 nm (A660)=A

This ratio allows considering the infection (GFP virus) to the protein amount.

2. A'=A−background noise of non-infected plate,
3. B=Fluorescence intensity (FI)/Absorbance 660 nm (A660) of infected but non treated plates,
4. C=A'/B, which is then converted as the percentage of infection after treatment, compared to non-treated sample, and subsequently as the infection percentage. For instance, a value of 100 in Table IV here below means that, after treatment, the signal attributed to GFP fluorescence is abolished, which is correlated to the absence of infection.
5. C'=100−C This value corresponds to the inhibition's percentage.

The following Table IV encompasses said C' value for some compounds, as calculated above with a mean of 2 experiments, and corresponding standard deviation.

Some values were originally above 100. In these cases, the value has been lowered to 100. This means that some molecules also have an impact on the viability of the cells. In other words, the A value may be lower than the background noise.

Moreover, for each measure, the test was performed with Ribavirin as control. The value of the inhibition percentage was checked, giving 100%.

TABLE IV

| | % CHIKV Inhibition | |
|---|---|---|
| Ex | Mean (n = 2) | Standard deviation (n = 2) |
| 36 | 99 | 0 |
| 37 | 100 | 0 |
| 38 | 99 | 2 |
| 39 | 98 | 1 |
| 40 | 99 | 1 |
| 41 | 99 | 1 |
| 43 | 100 | 0 |
| 45 | 99 | 2 |
| 46 | 99 | 2 |
| 47 | 96 | 1 |
| 48 | 98 | 1 |
| 49 | 98 | 3 |
| 50 | 100 | 0 |
| 51 | 100 | 0 |
| 52 | 99 | 1 |
| 73 | 100 | 0 |

A second round of experiments has been performed, giving the results as $IC_{50}$ values.

The $IC_{50}$ values range between 0.1 nM and 1 μM, in particular between 0.5 and 500 nM and even more particularly between 1 and 400 nM, for example between 1 and 200 nM. For example, compounds (36)-(41), (53), (54), (57), (58), (60)-(62), (64), (68), (70) and (71) have an $IC_{50}$ value ranging between 1 and 400 nM.

Conclusion

Based on the previous results, it can be concluded that the compounds of formula (Ie) are suitable chemical compounds for treating and/or preventing RNA virus infections caused by RNA viruses of group IV, more particularly, Alphavirus infections, and most particularly Chikungunya virus infections.

Example 9: RSV Virus

The compounds of the invention have been the subject of pharmacological tests which have demonstrated their relevance as active substances in therapy and in particular for preventing, inhibiting or treating RSV virus infection.

Material and Methods

Protocol for Screening Antiviral Compounds for RSV Inhibition and Cytotoxicity Using Viral ToxGlo Assay HEp-2 cells were maintained in Eagle's minimum essential medium (EMEM) with Earle's BSS adjusted to contain 2 mM L-glutamine, 10% fetal bovine serum, 100 U/ml penicillin and 100 μg/ml streptomycin. For the purposes of the screening assay they were grown to 90% confluency, trypsinized and recovered. The trypsin was neutralised with cell culture media and cells were centrifuged at 150×g for 5 minutes before discarding the supernatant and resuspending cell pellet in assay media (EMEM with Earle's BSS adjusted to contain 2 mM L-glutamine, 2% fetal bovine serum and 100 U/ml penicillin and 100 μg/ml streptomycin). The cells were seeded into white clear-bottomed cell culture plates at a density of $1.5\times10^4$ cells/well in 50 μl and $4\times10^3$ cells/well in 25 μl for 96 well plates and 384 well plates respectively. For the media/background control column assay media only was added. Cell plates were placed in a humid chamber and incubated overnight at 37° C./5% $CO_2$. After overnight incubation cells were checked for confluency and healthy appearance.

Test articles were made up at 10× test concentration in a maximum DMSO concentration of 10% (final assay concentration maximal 1% DMSO) and added to the cell plates in volumes of 10 μl for 96 well plates and 5 μl for 384 well plates. For cell control and virus control wells the test article solvent only was added. Virus or assay media for cytotoxicity test wells and media/cell control wells was added immediately after test articles at an MOI of 0.5, 40 or 20 μl for 96 and 384 well plates respectively. Virus suspension was prepared by thawing RSV A2 frozen stocks and diluting to the required concentration of plaque forming units in assay media on ice.

Cell plates were further incubated inside a humid chamber for 72 h p.i at 37° C./5% $CO_2$. After the incubation period cells were observed under the microscope to check for characteristic cytopathic effect in virus control wells and healthy cells in the cell control wells. After plates were adjusted to room temperature 20/40 μl Viral ToxGlo (Promega) was added to each well of the 384/96 well cell plates. Plates were incubated at room temperature, protected from light on a plate rocker for 20 minutes before measuring the luminescence on a spectrophotometer (Biotek Synergy HTX).

RSV inhibition was calculated as percentage of cytopathic effect inhibition relative to the virus control and cytotoxicity as percentage of cell survival relative to cell control wells. This allowed $EC_{50}$ values to be calculated for each test article where a virus inhibition or cytotoxic dose response was identified. $EC_{50}$ values ranging between 0.001 μM and 2.5 μM were found, and more particularly for compounds (36), (38), (39), (45), (46), (47), (54), (57), (60), (61), (64), (68), (70), (71), (72), (75)-(80), (82)-(86), (88)-(142), (147)-(156), (164)-(166) and (179).

TABLE V

| Ex | $EC_{50}$ (nM) |
|---|---|
| 36 | 232 |
| 38 | 281 |
| 39 | 185 |
| 45 | 280 |
| 46 | 199 |
| 47 | 182 |
| 54 | 177 |
| 57 | 26 |

TABLE V-continued

| Ex | $EC_{50}$ (nM) |
|---|---|
| 60 | 67 |
| 61 | 54 |
| 64 | 341 |
| 68 | 144 |
| 70 | 660 |
| 71 | 185 |
| 72 | 158 |
| 75 | 25 |
| 76 | 14 |
| 77 | 124 |
| 78 | 58 |
| 79 | 33 |
| 80 | 21 |
| 82 | 4 |
| 83 | 9 |
| 84 | 637 |
| 85 | 8 |
| 86 | 567 |
| 88 | 461 |
| 89 | 140 |
| 90 | 92 |
| 91 | 2 |
| 92 | 4 |
| 93 | 4 |
| 94 | 7 |
| 95 | 8 |
| 96 | 10 |
| 97 | 10 |
| 98 | 12 |
| 99 | 13 |
| 100 | 16 |
| 101 | 21 |
| 102 | 22 |
| 103 | 24 |
| 104 | 29 |
| 105 | 31 |
| 106 | 33 |
| 107 | 36 |
| 108 | 41 |
| 109 | 48 |
| 110 | 59 |
| 111 | 62 |
| 112 | 67 |
| 113 | 69 |
| 114 | 71 |
| 115 | 83 |
| 116 | 93 |
| 117 | 98 |
| 118 | 103 |
| 119 | 107 |
| 120 | 110 |
| 121 | 116 |
| 122 | 116 |
| 123 | 120 |
| 124 | 126 |
| 125 | 130 |
| 126 | 133 |
| 127 | 148 |
| 128 | 156 |
| 129 | 175 |
| 130 | 198 |
| 131 | 204 |
| 132 | 228 |
| 133 | 230 |
| 134 | 281 |
| 135 | 292 |
| 136 | 295 |
| 137 | 300 |
| 138 | 312 |
| 139 | 329 |
| 140 | 349 |
| 141 | 352 |
| 142 | 370 |
| 147 | 414 |
| 148 | 532 |
| 149 | 555 |
| 150 | 597 |
| 151 | 671 |

TABLE V-continued

| Ex | $EC_{50}$ (nM) |
|---|---|
| 152 | 802 |
| 153 | 809 |
| 154 | 810 |
| 155 | 1031 |
| 156 | 1059 |
| 164 | 1325 |
| 165 | 2357 |
| 166 | 2490 |
| 179 | 721 |

Conclusion

Based on the previous results, it can be concluded that the compounds of formula (Ie) are suitable chemical compounds for treating and/or preventing RNA virus infections caused by RNA viruses of group V, more particularly, pneumovirus infections, and most particularly RSV virus infections.

Example 10: Dengue 2 Virus

The compounds of the invention have been the subject of pharmacological tests which have demonstrated their relevance as active substances in therapy and in particular for preventing, inhibiting or treating Dengue 2 virus infection.

Material and Methods

Protocol for Screening Antiviral Compounds for DENV-2 Inhibition and Cytotoxicity Using Viral ToxGlo Assay A549 cells were maintained in Dulbecco's Modified Eagle Medium (DMEM) supplemented with 10% fetal bovine serum, 100 U/ml penicillin and 100 μg/ml streptomycin. For the purposes of the screening assay they were grown to 90% confluency, trypsinized and recovered. The trypsin was neutralised with cell culture media and cells were centrifuged at 150×g for 5 minutes before discarding the supernatant and resuspending cell pellet in assay media (DMEM supplemented with 2% fetal bovine serum and 100 U/ml penicillin and 100 μg/ml streptomycin). The cells were seeded into 96-well white clear-bottomed cell culture plates at a density of 1.0×10 4 cells/well in 50 μl. For the media/background control column assay media only was added. Cell plates were placed in a humid chamber and incubated overnight at 37° C./5% CO2. After overnight incubation cells were checked for confluency and healthy appearance.

Test compounds were prepared at a final concentration of 10 μM in a maximum DMSO concentration of 1% (final assay concentration maximal 0.1% DMSO) and added to the cell plates in volumes of 10 μl. For cell control and virus control wells the test article solvent only was added. As a positive inhibition control, 7-Deaza-2'-C-methyladenosine was added at 100 μM in 3 wells. Virus (DENV-2 strain 16681) or assay media for cytotoxicity test wells and media/cell control wells was added immediately after test articles at an MOI of 0.5, 40 for 96 well plates respectively. Virus suspension was prepared by thawing DENV-2 frozen stocks and diluting to the required concentration of plaque forming units in assay media.

Cell plates were further incubated inside a humid chamber for 5 days p.i at 37° C./5% CO2. After the incubation period cells were observed under the microscope to check for characteristic cytopathic effect in virus control wells and healthy cells in the cell control wells. After plates were adjusted to room temperature 20 μl Viral ToxGlo (Promega) was added to each well of the 96-well cell plates. Plates were incubated at room temperature for 5 minutes before measuring the luminescence on a spectrophotometer (Envision, PerkinElmer).

DENV-2 inhibition was calculated as percentage of cytopathic effect inhibition relative to the virus control and cytotoxicity as percentage of cell survival relative to cell control wells.

TABLE VI

| Ex | % DENV-2 Inhibition Mean (n = 3) |
|---|---|
| 38 | 65 |
| 40 | 71 |
| 43 | 71 |
| 45 | 89 |
| 46 | 71 |
| 48 | 110 |
| 49 | 111 |
| 61 | 55 |
| 62 | 55 |
| 64 | 93 |
| 65 | 77 |
| 68 | 70 |
| 82 | 64 |
| 98 | 60 |
| 119 | 104 |
| 121 | 59 |
| 132 | 71 |
| 140 | 74 |
| 150 | 78 |
| 151 | 63 |
| 156 | 82 |
| 169 | 59 |
| 175 | 60 |
| 176 | 85 |
| 192 | 66 |

Conclusion

Based on the previous results, it can be concluded that the compounds of formula (Ie) are suitable chemical compounds for treating and/or preventing RNA virus infections caused by RNA viruses of group IV, more particularly, Flavivirus infections, and most particularly Dengue 2 virus infections.

The present invention further relates to a pharmaceutical composition comprising at least one new compound as defined above or any of its pharmaceutically acceptable salts, or at least any of compounds (36) to (206) as defined above or any of its pharmaceutically acceptable salts and also at least one pharmaceutically acceptable excipient.

Pharmaceutical compositions of the invention can contain one or more compound(s) of the invention in any form described herein.

Still a further object of the present invention consists of the use of at least one compound of formula (Ie), as defined above, and compounds (36) to (206) as defined above, or one of their pharmaceutically acceptable salts according to the present invention for preparing a drug to prevent or treat, in a subject, a RNA virus infection caused by a RNA virus from group IV or Group V according to the Baltimore classification, and for example a Chikungunya infection, a Dengue infection, an Influenza infection or a RSV infection.

Therefore, the present invention relates to one compound of formula (Ie), as defined above, and compounds (36) to (206) or one of their acceptable salts as an agent for inhibiting, preventing or treating a RNA virus infection, and most preferably a RNA virus infection from group IV or V, and for example a Chikungunya infection, a Dengue infection, an Influenza infection or a RSV infection.

According to a particular embodiment, the treatment is continuous or non-continuous.

A "continuous treatment" means a long-term treatment which can be implemented with various administration frequencies, such as once every day, every three days, once a week, or once every two weeks or once every month.

According to one embodiment, the compound of formula (Ie), or anyone of its pharmaceutically acceptable salts, is administered at a dose varying from 0.1 to 1000 mg, in particular varying from 0.1 to 10 mg, or for example varying from 10 to 200 mg, or for example varying from 200 to 1000 mg.

Another object of the invention relates to a therapeutic method for treating and/or preventing a subject from a RNA virus infection, and most preferably a RNA virus infection caused by a virus belonging to group IV or V of the Baltimore classification comprising the administration of a therapeutically effective quantity of a compound of formula (Ie), compounds (36) to (206), as defined above, or one of their acceptable salts.

In a specific embodiment, the invention provides a use of a compound of formula (Ie) according to the invention or a pharmaceutically acceptable salt thereof or a pharmaceutically active derivative thereof or a method according to the invention wherein the compound of formula (Ie) is to be administered in combination with a co-agent useful in the treatment of said RNA virus infection, and most preferably said RNA virus infection from group IV or V, and for example Chikungunya infection, Dengue infection, Influenza infection or RSV infection.

The compounds can be administered through any mode of administration such as, for example, intramuscular, intravenous, intranasal or oral route, etc.

Compounds of the present invention may, in appropriate cases, be administered as prodrugs, such as esters, of compounds with which the invention is concerned. "Prodrug" means a compound which is convertible in vivo by metabolic means (e.g. by hydrolysis, reduction or oxidation) to a compound of the present invention. For example, an ester prodrug of a compound of the present invention may be convertible by hydrolysis in vivo to the parent molecule. Suitable esters of compounds of the present invention are for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulphonates, ethanesulphonates, benzenesulphonates, p-toluenesulphonates, cyclohexylsulfamates and quinates. Examples of ester prodrugs are those described by F. J. Leinweber, Drug Metab. Res., 1987, 18, 379. As used herein, references to the compounds of the present invention are meant to also include any prodrug or metabolite forms.

The inventive composition can further include one or more additives such as diluents, excipients, stabilizers and preservatives. Such additives are well known to those skilled in the art and are described notably in "*Ullmann's Encyclopedia of Industrial Chemistry, 6th Ed.*" (various editors, 1989-1998, Marcel Dekker) and in "*Pharmaceutical Dosage Forms and Drug Delivery Systems*" (ANSEL et al., 1994, WILLIAMS & WILKINS).

The aforementioned excipients are selected according to the dosage form and the desired mode of administration.

Compositions of this invention may be administered in any manner, including, but not limited to, orally, parenterally, sublingually, transdermally, vaginally, rectally, transmucosally, topically, intranasally via inhalation, via buccal or intranasal administration, or combinations thereof. Parenteral administration includes, but is not limited to, intravenous, intra-arterial, intra-peritoneal, subcutaneous, intramuscular, intra-thecal, and intra-articular. The compositions of this invention may also be administered in the form of an implant, which allows slow release of the compositions as well as a slow controlled i.v. infusion.

According to another embodiment, pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For example, a compound of formula (Ie) can be present in any pharmaceutical form which is suitable for enteral or parenteral administration, in association with appropriate excipients, for example in the form of plain or coated tablets, hard gelatine, soft shell capsules and other capsules, suppositories, or drinkable, such as suspensions, syrups, or injectable solutions or suspensions, in doses which enable the daily administration of from 0.1 to 1000 mg of active substance.

In a particular embodiment, a compound of formula (Ie) according to the invention is administered orally.

Oral route of administration is in particular preferred in the prophylaxis or treatment aspect of the invention.

The invention claimed is:

1. A compound of formula (Ie):

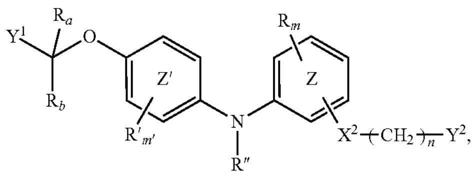

(Ie)

or a pharmaceutically acceptable salt thereof, wherein:

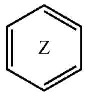

ring and

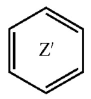

ring both represent a phenylene group, $Y^1$ represents an aryl group selected from a phenyl group, a pyridyl group, a pyrazinyl group, a pyridazinyl or a pyrimidinyl group, the aryl group being optionally substituted by one or two substituent(s) selected from a halogen atom, a ($C_1$-$C_4$)alkyl group, a cyano group, a ($C_1$-$C_5$)alkoxy group, a trifluoromethyl group, a trifluoromethoxy group, a —$SO_2$—$NR_aR_b$ group, a —$SO_3H$ group, a —OH group, a —O—$SO_2$—$OR_c$ group or a —O—P(═O)—($OR_c$)($OR_d$) group, $R_a$, $R_b$, $R_c$ and $R_d$ independently represent a hydrogen atom or a ($C_1$-$C_4$)alkyl group, $X^2$ represents a —O— group, a —NH— group, a —S— group, a —CO—NH— group, a —NH—CO— group, a —CH(OH)— group, a —CH(COOH)NH— group, a —CH($COOCH_3$)NH— group, a —C(OH)($CH_2OH$)—, a

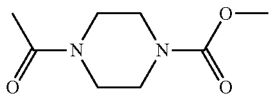

group, a divalent 5-membered heteroaromatic ring comprising 1, 2, 3 or heteroatoms, a —$SO_2$— group, or a —$SO_2$—NH— group, n is 0, 1, 2 or 3, m and m' are independently 0, 1 or 2, $Y^2$ represents a hydroxyl group, a —CHC$(OH)_2$, a morpholinyl group, a dihydropyranyl group, a

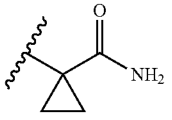 [SMILES: *C1(C(N)=O)CC1]

group, a

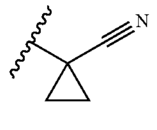 [SMILES: *C1(C#N)CC1]

group, a —PO($OR_f$)($OR'_f$) group, wherein $R_f$ and $R'_f$ independently represents a hydrogen atom or a ($C_1$-$C_4$)alkyl group, an oxetanyl group, a —$Si(CH_3)_3$ group, a —NHCOO—($C_1$-$C_4$)alkyl group, or a —$CR^1R^2R^3$ group, wherein $R^1$, $R^2$ and $R^3$ independently represent a hydrogen atom or a ($C_1$-$C_4$) alkyl group, so long as no more than one of $R^1$, $R^2$ and $R^3$ is a hydrogen atom, or $R^1$ and $R^2$ form together with the carbon atom bearing them a ($C_4$-$C_8$)cycloalkyl group, the ($C_4$-$C_8$)cycloalkyl group being optionally substituted by one or two ($C_1$-$C_4$)alkyl group, halogen atom or ($C_1$-$C_4$) alkoxy group, and the ($C_4$-$C_8$)cycloalkyl group optionally being a ($C_4$ or $C_6$-$C_8$)cycloalkyl group that is interrupted on the $R^1$ and/or $R^2$ by an oxygen atom, or alternatively, $X^2$—$(CH_2)_n$—$Y^2$ represents a —O—$(CH_2)_n$—$COOR_f$ group, wherein $R_f$ represents a hydrogen atom or a ($C_1$-$C_4$)alkyl group, or alternatively, $X^2$—$(CH_2)_n$—$Y^2$ represents a CO—NH—$(CH_2)_n$—$Y^2$ group, wherein $Y^2$ represents a cyclopropyl group, or alternatively, $X^2$—$(CH_2)_n$—$Y^2$ represents a —$SO_2$—NH—$(CH_2)_n$—$Y^2$ group, wherein $Y^2$ represents a cyclopropyl group, or alternatively, $X^2$—$(CH_2)_n$—$Y^2$ is defined by $X^2$ being a divalent 5-membered heteroaromatic ring comprising 1, 2, 3 or 4 heteroatoms, and $Y^2$ being a cyclopropyl group, a hydrogen atom, or a ($C_1$-$C_4$) alkoxy group, or alternatively, $X^2$—$(CH_2)_n$—$Y^2$ represents a —O—$(CH_2)_n$—$Y^2$ group, wherein $Y^2$ represents a ($C^1$-$C^4$) alkoxy group, or alternatively, $X^2$—$(CH_2)_n$—$Y^2$ represents a CO—NH—$(CH_2)_n$—$Y^2$ group, wherein $Y^2$ represents a —$CF_3$, or alternatively, $X^2$—$(CH_2)_n$—$Y^2$ represents a —NH—CO—NH—$(CH_2)_n$—$Y^2$ group, wherein n is 1, 2, or 3, and $Y^2$ represents a —$CR^1R^2R^3$ group, or alternatively $X^2$-$Y^2$ represents a group —$CONR_cR_d$, wherein $R_C$ and $R_d$ form, together with the nitrogen atom a heterocyclic group, optionally substituted by a hydroxy group or a ($C_1$-$C_4$)alkyl group, R and R' independently represent a ($C_1$-$C_4$)alkyl group, a —S—($C_1$-$C_4$)alkyl group, a ($C_3$-$C_6$)cycloalkyl group, a halogen atom, a trifluoromethyl group, a —$SO_2$($C_1$-$C_4$)alkyl group, a ($C_3$-$C_6$)cycloalkenyl group, a ($C_1$-$C_5$)alkoxy group, a —$SO_2$—$NR_aR_b$ group, a —$SO_3H$ or $SO_2$—$CH_3$ group, a —OH group, a —$CONHR_g$, wherein $R_g$ represents a hydrogen atom or a ($C_1$-$C_4$)alkyl group, a —O—$SO_2$—$OR_c$ group, a azetidinyl group, a morpholinyl group, or a cyano group, and R" represents a hydrogen atom, a ($C_1$-$C_4$)alkyl group optionally substituted by a —COOH group.

2. The compound of formula (Ie) according to claim 1, or a pharmaceutically acceptable salt thereof, wherein R" is a hydrogen atom.

3. The compound of formula (Ie) according to claim 1, or a pharmaceutically acceptable salt thereof, wherein $Y^1$ represents an aryl group selected from a phenyl group, a pyridyl group, a pyrazinyl group, a pyridazinyl or a pyrimidinyl group, the aryl group being optionally substituted by one or two substituent(s) selected from a halogen atom, a $(C_1-C_4)$alkyl group, a cyano group, a $(C_1-C_5)$alkoxy group, a trifluoromethyl group, a trifluoromethoxy group.

4. The compound of formula (Ie) according to claim 1, or a pharmaceutically acceptable salt thereof, wherein $X^2$ represents
a —O— group,
a —NH— group,
a —S— group,
a —CO—NH— group,
a —NH—CO— group,
a divalent 5-membered heteroaromatic ring comprising 1, 2, 3 or 4 heteroatoms,
a $—SO_2—$ group,
or
a $—SO_2—NH—$ group,
or alternatively, $X^2—(CH_2)_n—Y^2$ represents a —NH—CO—NH—$(CH_2)_n—Y^2$ group, wherein n is 1, 2, or 3, and $Y^2$ represents a $—CR^1R^2R^3$ group,
or a pharmaceutically acceptable salt thereof.

5. The compound of formula (Ie) according to claim 1, or a pharmaceutically acceptable salt thereof, wherein $Y^2$ represents
a hydroxyl group,
a $—PO(OR_f)(R'_f)$ group, wherein $R_f$ and R'f independently represents a hydrogen atom or a $(C_1-C_4)$alkyl group, or
a $—CR^1R^2R^3$ group, wherein $R^1$, $R^2$ and $R^3$ independently represent a hydrogen atom or a $(C_1-C_4)$alkyl group, being understood that no more than one of $R^1$, $R^2$ and $R^3$ is a hydrogen atom, or $R^1$ and $R^2$ form together with the carbon atom bearing them a $(C_4-C_8)$cycloalkyl group, the $(C_4-C_8)$cycloalkyl group being optionally substituted by one or two $(C_1-C_4)$ alkyl group, halogen atom or $(C_1-C_4)$alkoxy group, and the $(C_4-C_8)$cycloalkyl group optionally being a ($C_4$ or $C_6-C_8$)cycloalkyl group that is interrupted on the $R^1$ and/or $R^2$ by an oxygen atom,
or alternatively, $X^2—(CH_2)_n—Y^2$ represents a —CO—NH—$(CH_2)_n—Y^2$ group, wherein n is 0, 1, 2 or 3, and $Y^2$ represents a cyclopropyl group,
or alternatively, $X^2—(CH_2)_n—Y^2$ represents a $—SO_2—NH—(CH_2)_n—Y^2$ group, wherein n is 0, 1, 2 or 3, and $Y^2$ represents a cyclopropyl group,
or alternatively, $X^2—(CH_2)_n—Y^2$ is defined by $X^2$ being a divalent 5-membered heteroaromatic ring comprising 1, 2, 3 or 4 heteroatoms, n being 0, 1, 2 or 3, aid $Y^2$ being a cyclopropyl group,
or alternatively, $X^2—(CH_2)_n—Y^2$ represents a —CO—NH—$(CH_2)_n—Y^2$ group, wherein n is 0, 1, 2 or 3, and $Y^2$ represents a $—CF_3$.

6. The compound of formula (Ie) according to claim 1, or a pharmaceutically acceptable salt thereof, wherein R and R' independently represent
a $(C_1-C_4)$alkyl group,
a $(C_3-C_6)$cycloalkyl group,
a halogen atom,
a trifluoromethyl group, or
a $—SO_3H$ or $SO_2—CH_3$ group.

7. The compound of formula (Ie) according to claim 1, or a pharmaceutically acceptable salt thereof, wherein R" is a hydrogen atom,
$Y^1$ represents an aryl group selected from a phenyl group, a pyridyl group, a pyrazinyl group, a pyridazinyl or a pyrimidinyl group, the aryl group being optionally substituted by one or two substituent(s) selected from a halogen atom, a $(C_1-C_4)$alkyl group, a cyano group, a $(C_1-C_5)$alkoxy group, a trifluoromethyl group, a trifluoromethoxy group,
$X^2$ represents
a —O— group,
a —CO—NH— group,
a —NH—CO— group,
a divalent 5-membered heteroaromatic ring comprising 1, 2, 3 or 4 heteroatoms, or
a $—SO_2—NH—$ group,
$Y^2$ represents
a hydroxyl group,
a $—PO(OR_f)(R'_f)$ group, wherein $R_f$ and $R'_f$ independently represents a hydrogen atom or a $(C_1-C_4)$alkyl group, or
a $—CR^1R^2R^3$ group, wherein $R^1$, $R^2$ and $R^3$ independently represent a hydrogen atom, or a $(C_1-C_4)$alkyl group, being understood that no more than one of $R^1$, $R^2$ and $R^3$ is a hydrogen atom, or $R^1$ and $R^2$ form together with the carbon atom bearing them a $(C_4-C_8)$cycloalkyl group, the $(C_4-C_8)$cycloalkyl group being optionally substituted by one or two $(C_1-C_4)$ alkyl group, halogen atom or $(C_1-C_4)$alkoxy group and the $(C_4-C_8)$cycloalkyl group optionally being a ($C_4$ or $C_6-C_8$)cycloalkyl group that is interrupted on the $R^1$ and/or $R^2$ by an oxygen atom,
or alternatively, $X^2—(CH_2)_n—Y^2$ represents a —CO—NH—$(CH_2)_n—Y^2$ group, wherein n is 0, 1, 2 or 3, and $Y^2$ represents a cyclopropyl group,
or alternatively, $X^2—(CH_2)_n—Y^2$ represents a $—SO_2—NH—(CH_2)_n—Y^2$ group, wherein n is 0, 1, 2 or 3, and $Y^2$ represents a cyclopropyl group,
or alternatively, $X^2—(CH_2)_n—Y^2$ is defined by $X^2$ being a divalent 5-membered heteroaromatic ring comprising 1, 2, 3 or 4 heteroatoms, n being 0, 1, 2 or 3, and $Y^2$ being a cyclopropyl group,
or alternatively, $X^2—(CH_2)_n—Y^2$ represents a CO—NH—$(CH_2)_n—Y^2$ group, wherein n is 0, 1, 2 or 3, and $Y^2$ represents a $—CF_3$,
or alternatively, $X^2—(CH_2)_n—Y^2$ represents a —NH—CO—NH—$(CH_2)_n—Y^2$ group, wherein n is 1, 2, or 3, and $Y^2$ represents a $—CR^1R^2R^3$ group, and
R and R' independently represent
a $(C_1-C_4)$alkyl group,
a $(C_3-C_6)$cycloalkyl group,
a halogen atom,
a trifluoromethyl group,
a $—SO_3H$ or $SO_2—CH_3$ group, or
a morpholinyl group.

8. The compound of formula (Ie) according to claim 1, or a pharmaceutically acceptable salt thereof, wherein R" is a hydrogen atom,
$Y^1$ represents a phenyl group or a pyridyl group,
$X^2$ represents
a —O— group,
a —CO—NH— group,
a —NH—CO— group, or
a divalent 5-membered heteroaromatic ring comprising 1, 2, 3 or 4 heteroatoms, $Y^2$ represents a —$PO(OR_f)(R'_f)$ group, wherein $R_f$ and $R'_f$ independently represents a hydrogen atom or a $(C_1\text{-}C_4)$alkyl group, or a —$CR^1R^2R^3$ group, wherein $R^1$, $R^2$ and $R^3$ independently represent a hydrogen atom, or a $(C_1\text{-}C_4)$alkyl group, being understood that no more than one of $R^1$, $R^2$ and $R^3$ is a hydrogen atom, or $R^1$ and $R^2$ form together with the carbon atom bearing them a $(C_4\text{-}C_8)$cycloalkyl group, or alternatively, $X^2$—$(CH_2)_n$—$Y^2$ represents a —CO—NH—$(CH_2)_n$—$Y^2$ group, wherein n is 0, 1, 2 or 3, and $Y^2$ represents a cyclopropyl group, or alternatively, $X^2$—$(CH_2)_n$—$Y^2$ is defined by $X^2$ being a divalent 5-membered heteroaromatic ring comprising 1, 2, 3 or 4 heteroatoms, n being 0, 1, 2 or 3 and $Y^2$ being a cyclopropyl group, or alternatively, $X^2$—$(CH_2)_n$—$Y^2$ represents a —CO—NH—$(CH_2)_n$—$Y^2$ group, wherein n is 0, 1, 2 or 3, and $Y^2$ represents a —$CF_3$, and R and R' independently represent a $(C_1\text{-}C_4)$alkyl group, a $(C_3\text{-}C_6)$cycloalkyl group, or a morpholinyl group.

9. The compound of formula (Ie) according to claim 1, wherein the compound is selected from:

36

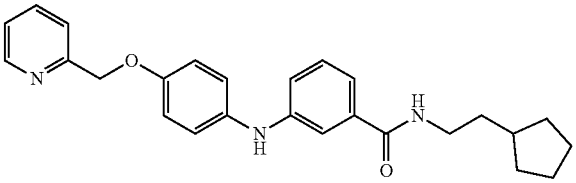

37

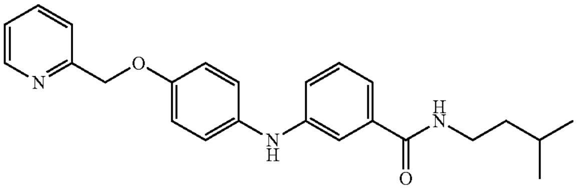

38

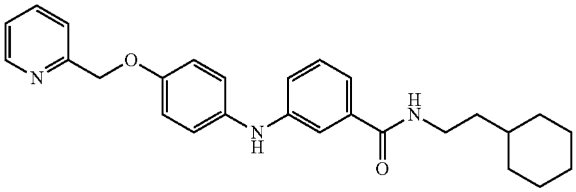

39

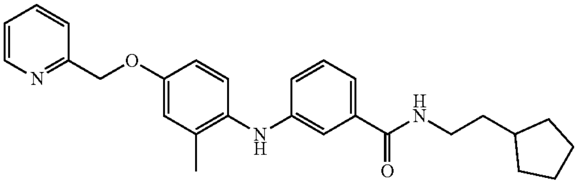

-continued

40

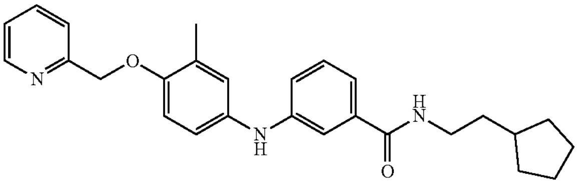

43

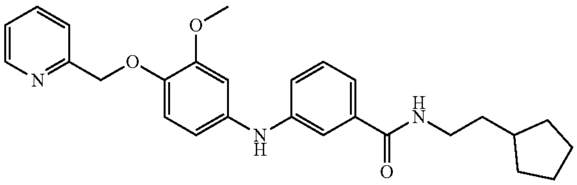

45

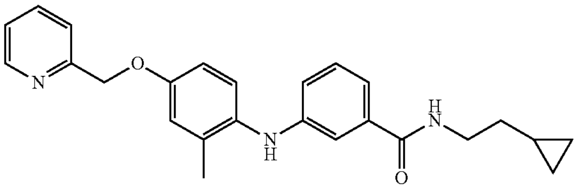

46

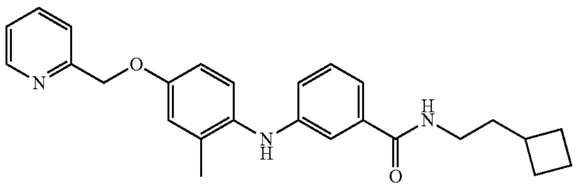

47

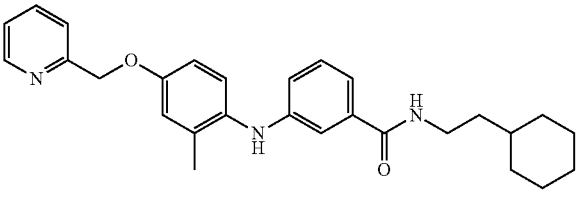

48

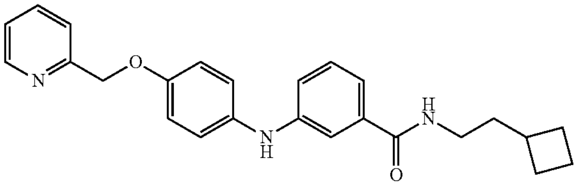

49

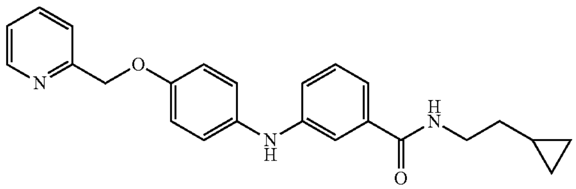

-continued
50
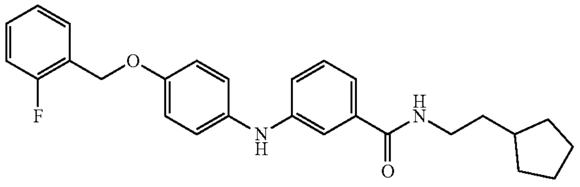
51
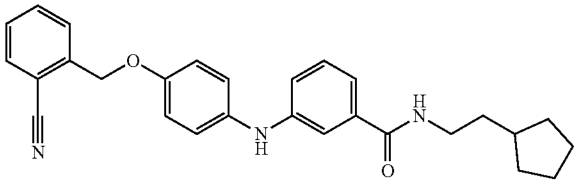
52
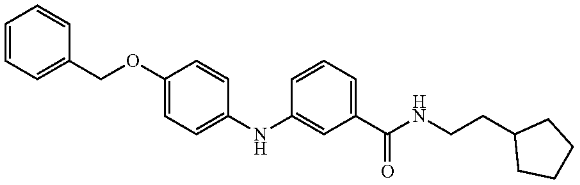
53
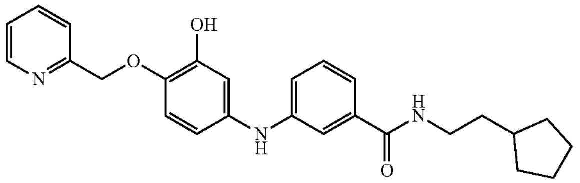
54
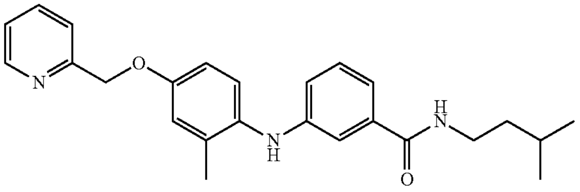
55
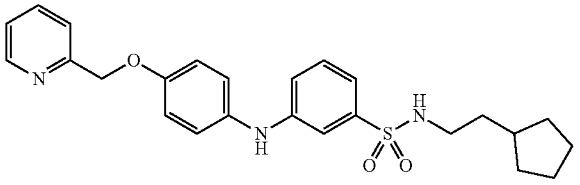
56
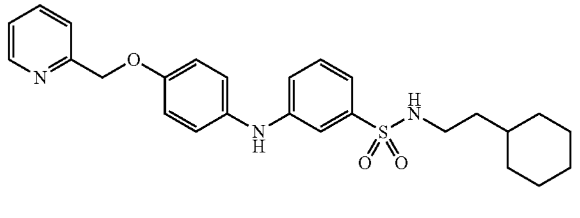
-continued
57
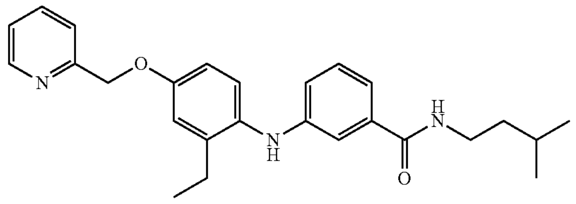
58
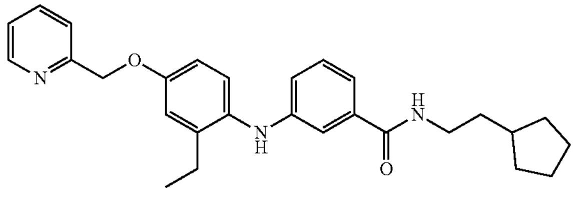
59
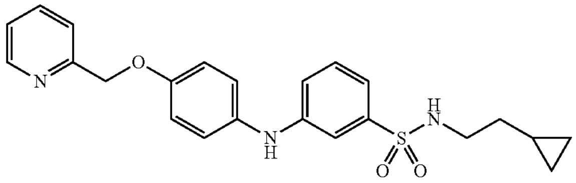
60
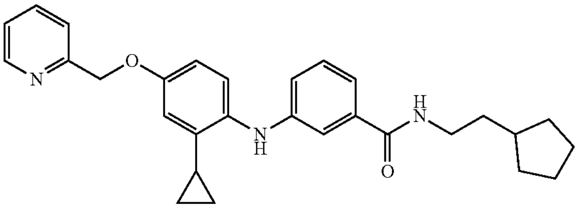
61
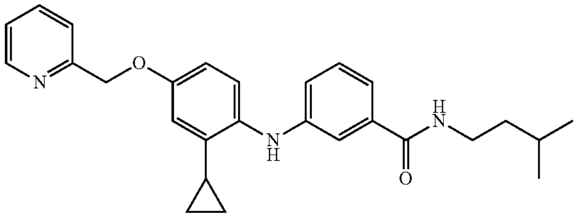
62
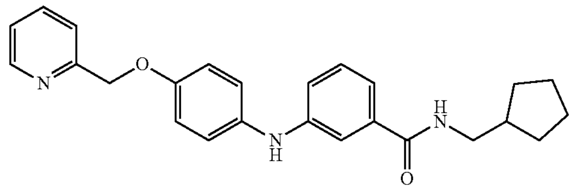
63
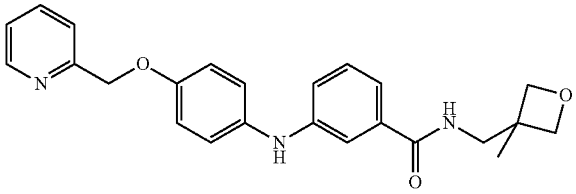

-continued
64
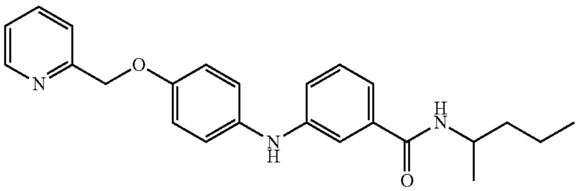
65
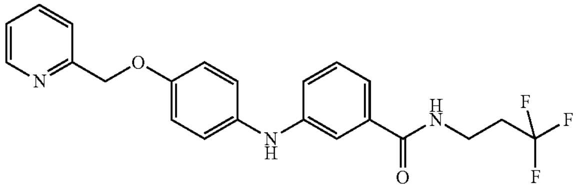
66
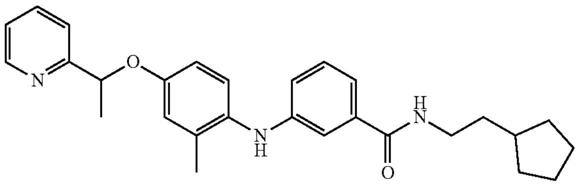
67
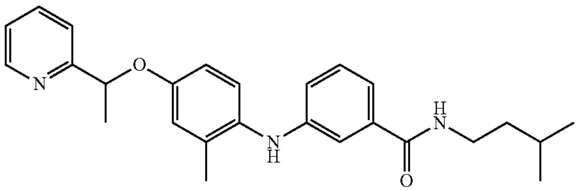
68
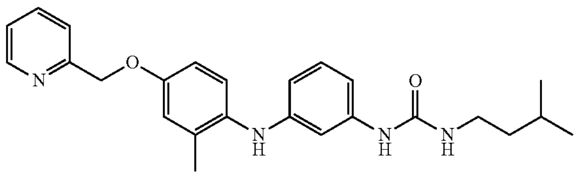
69
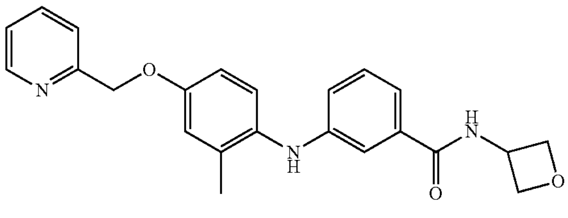
70
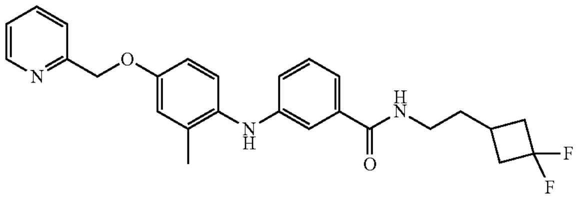
-continued
71
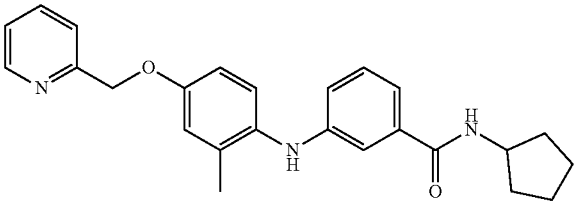
72
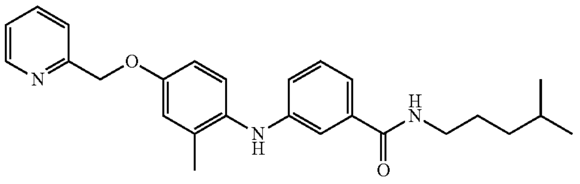
73
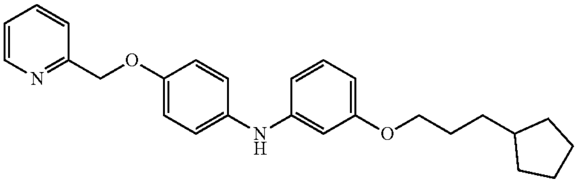
74
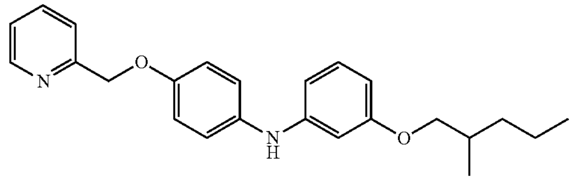
75
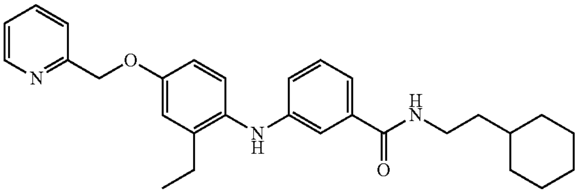
76
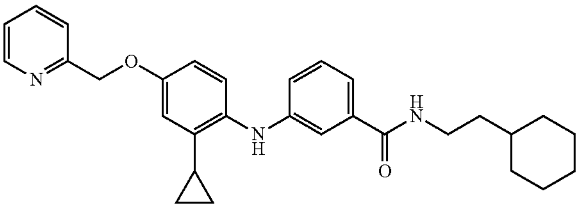
77
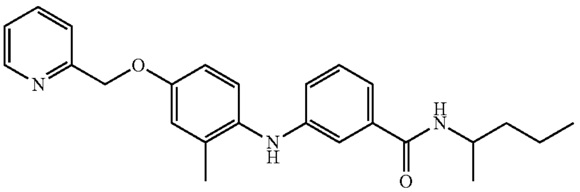

-continued
78
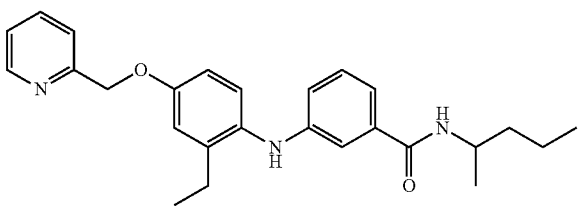
79
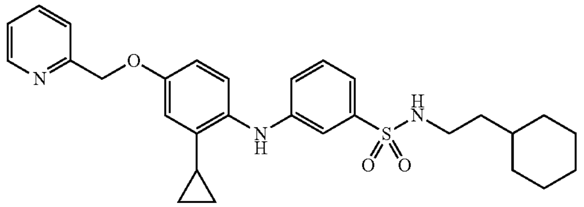
80
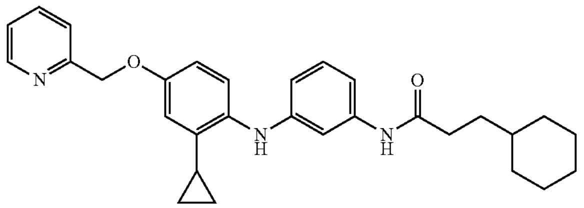
81
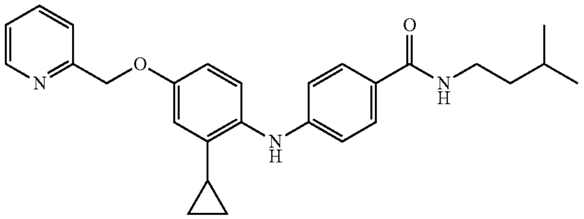
82
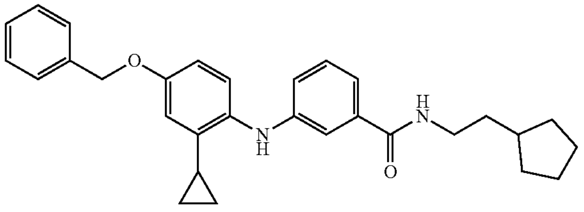
83
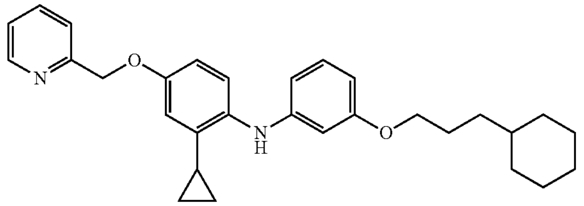
-continued
85
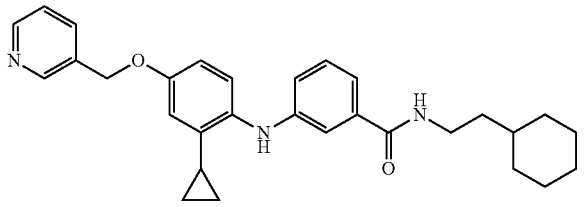
89
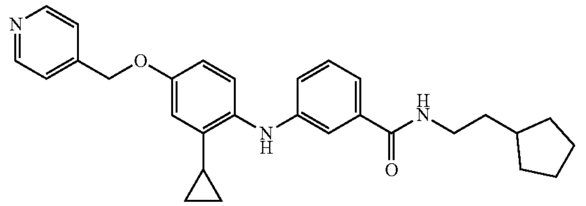
91
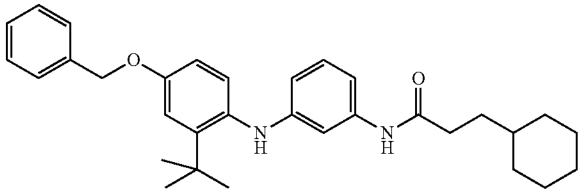
92
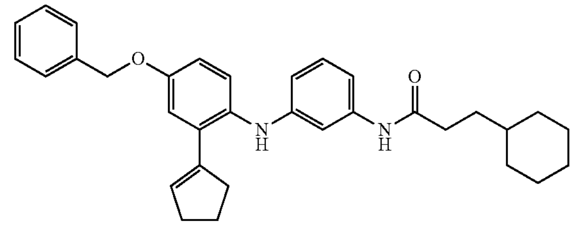
93
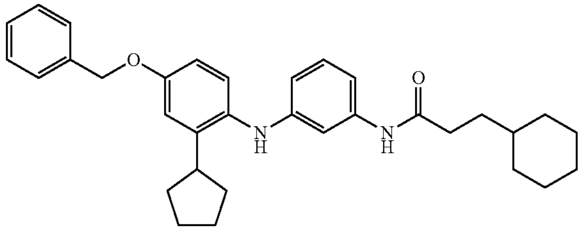
94
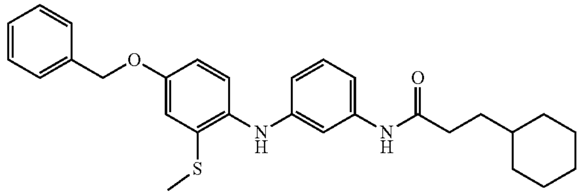

-continued
95
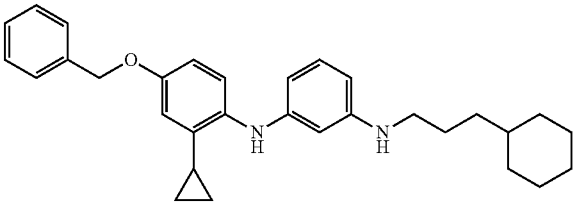
96
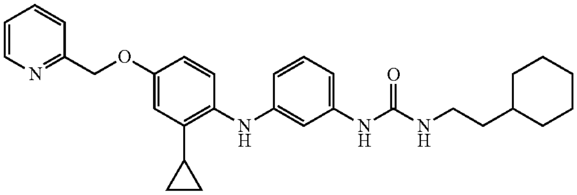
97
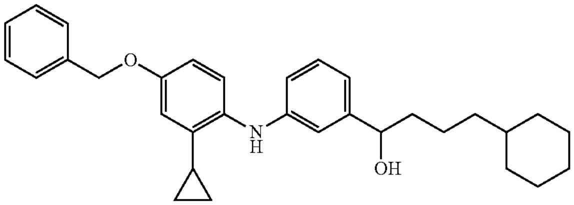
98
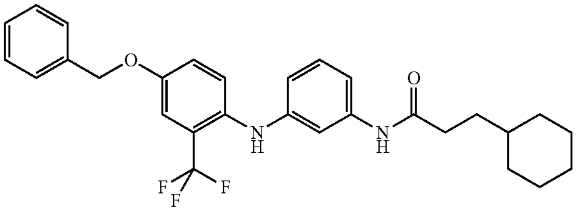
99
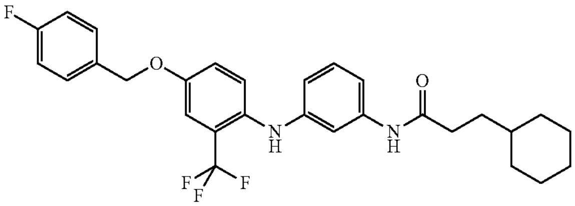
100
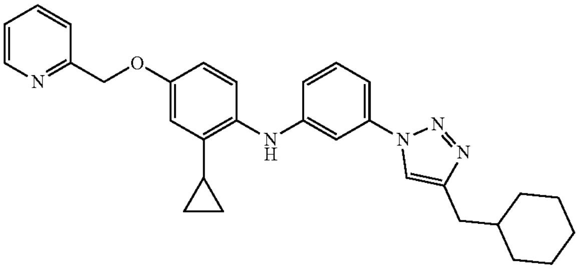
-continued
101
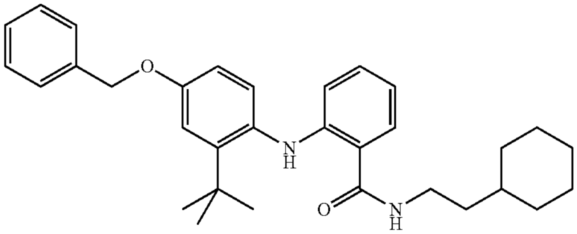
102
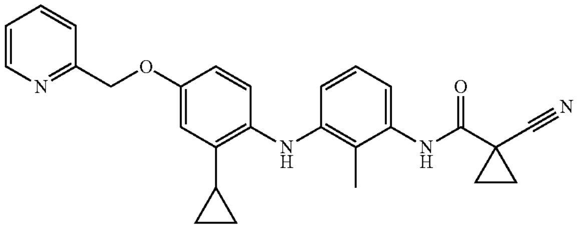
103
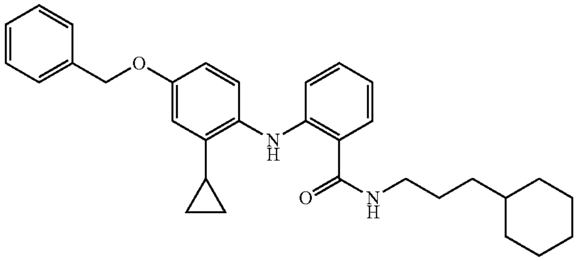
104
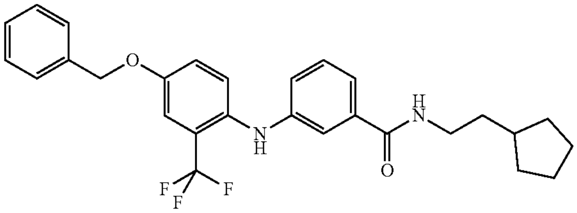
105
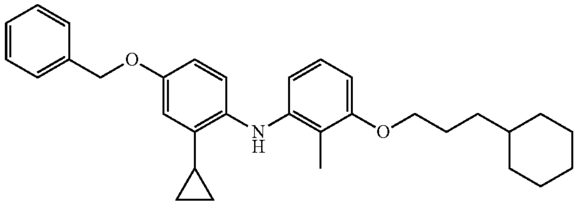
106
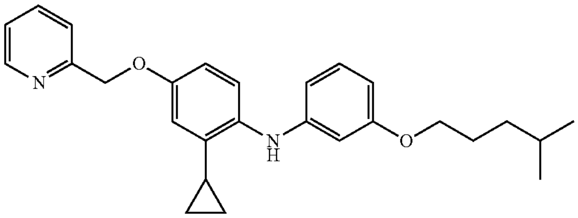

-continued
107
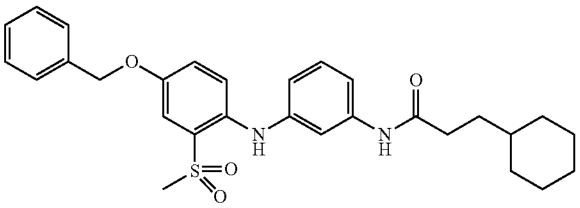
108
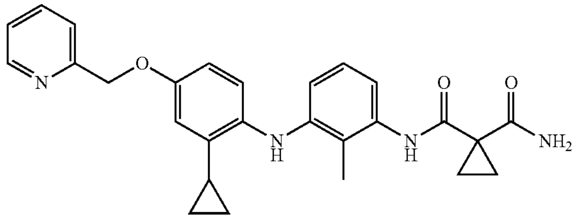
109
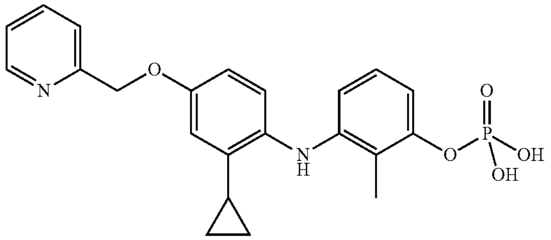
110
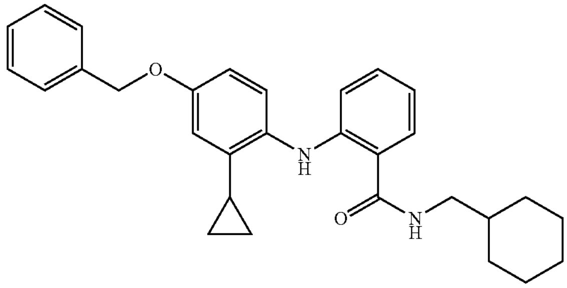
111
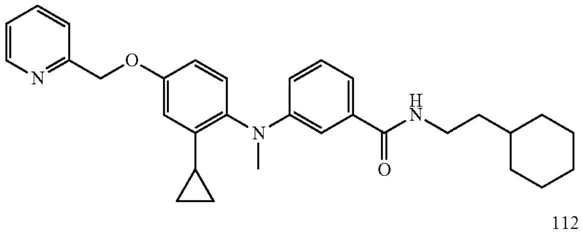
112
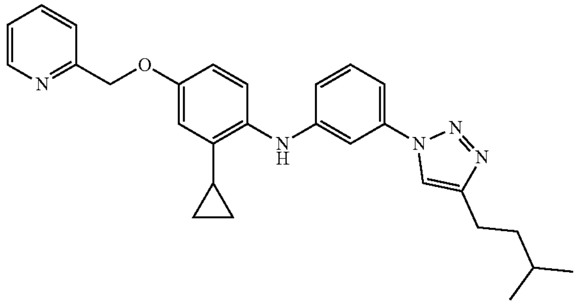
-continued
113
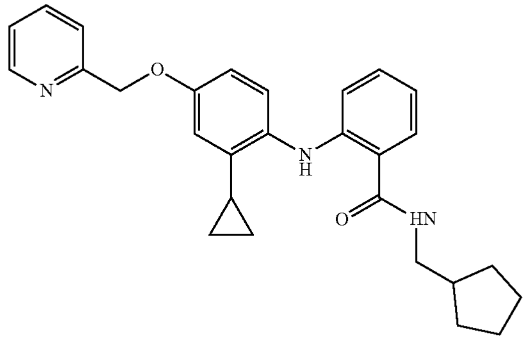
114
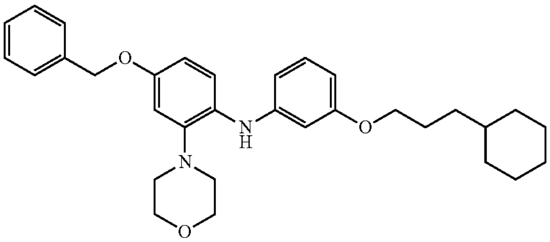
115
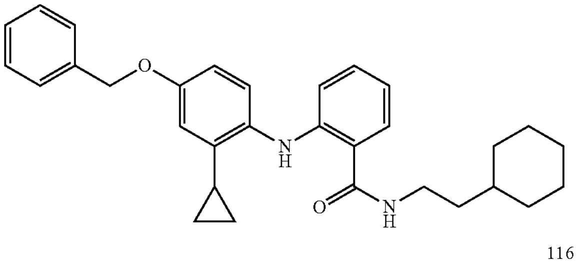
116
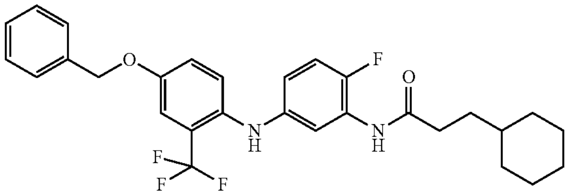
118
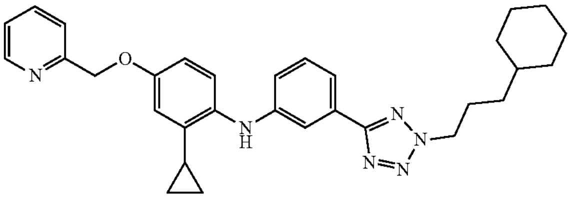
119
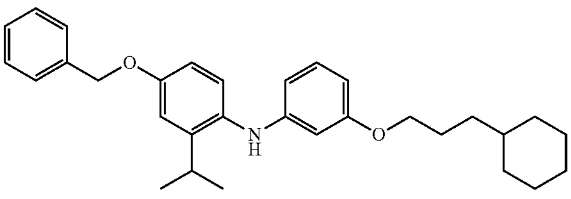

120
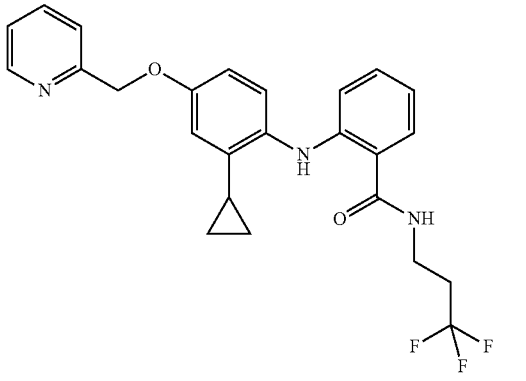
121
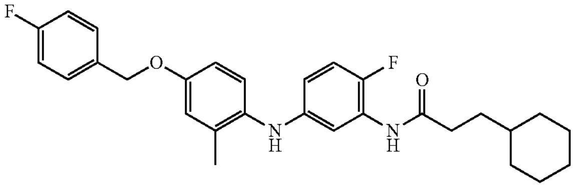
122
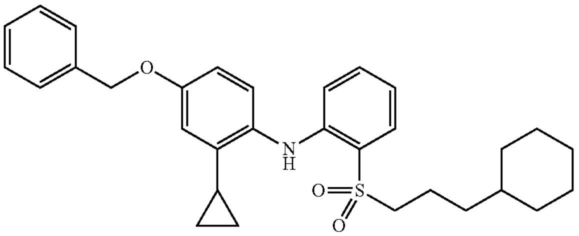
123
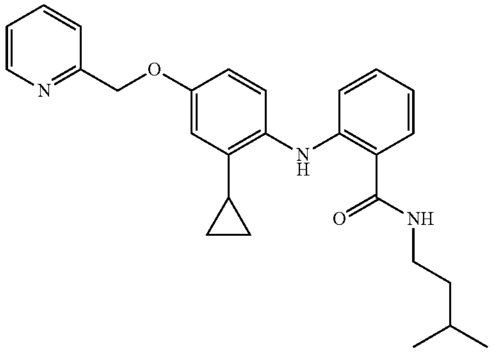
124
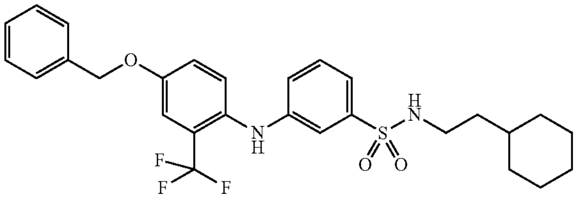
125
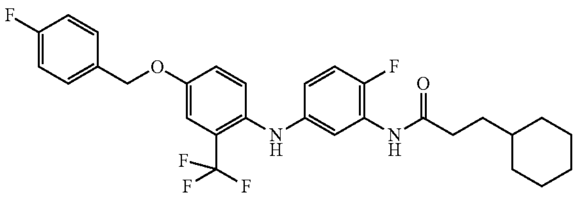
126
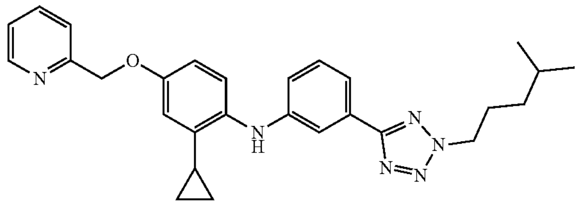
127
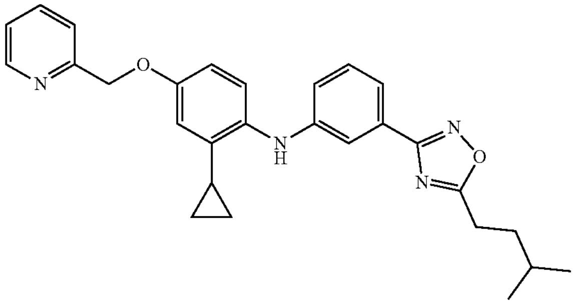
128
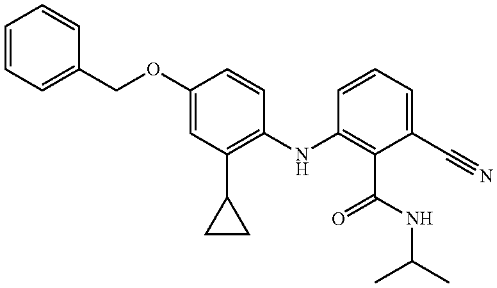
129
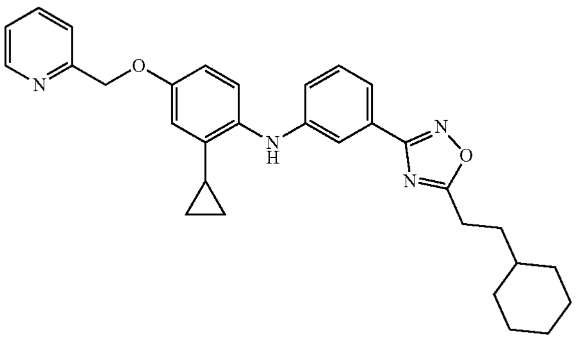

-continued
130
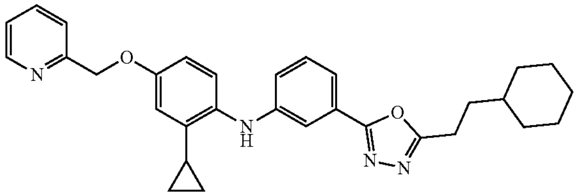
131
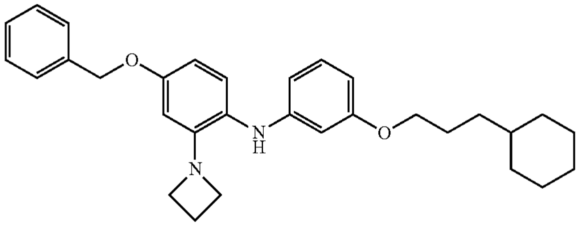
132
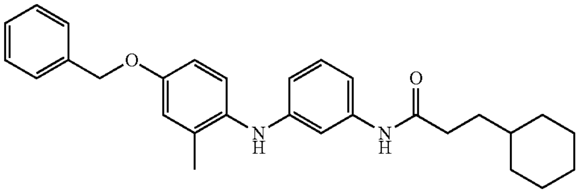
133
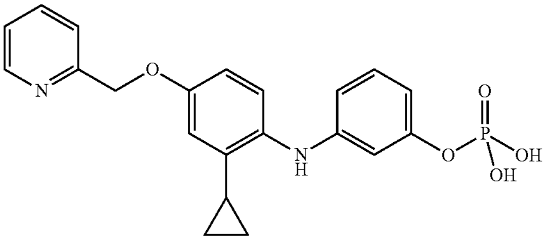
134
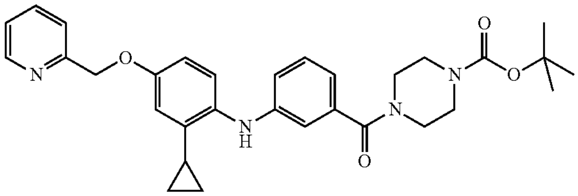
135
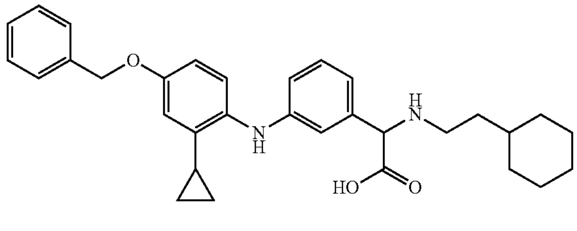
-continued
136
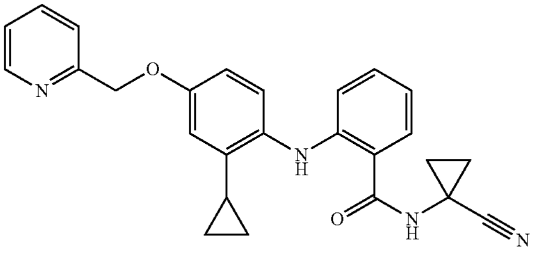
137
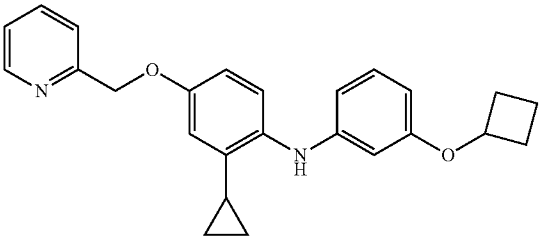
138
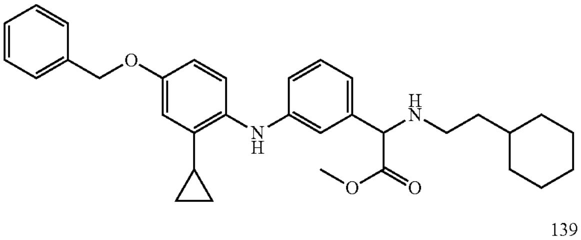
139
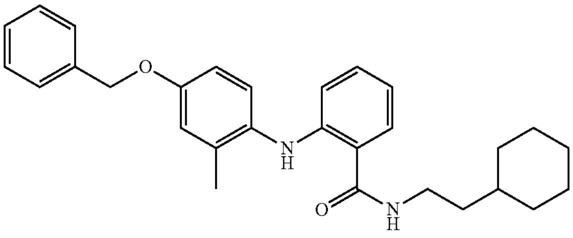
140
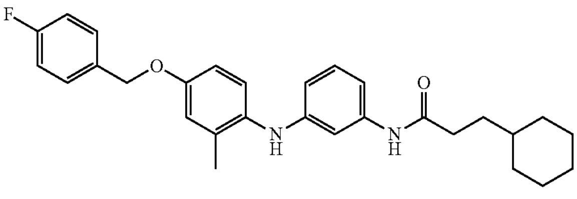
141
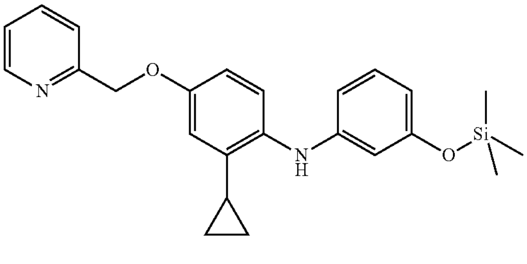

-continued
142
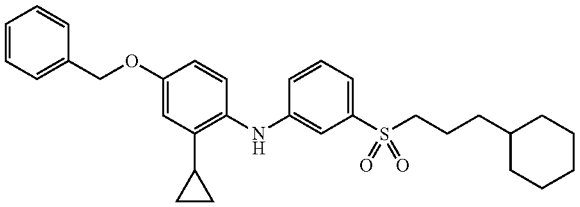
144
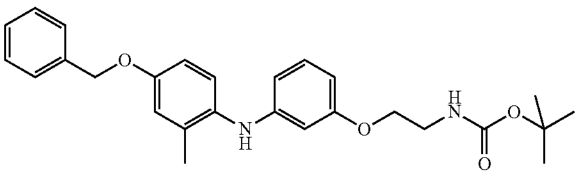
145
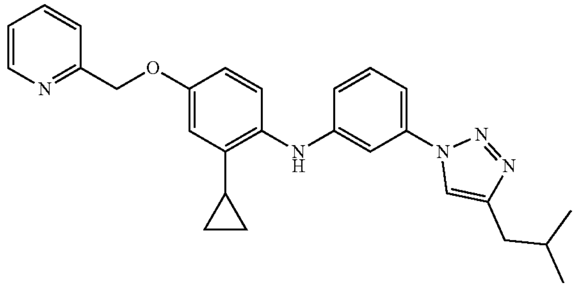
146
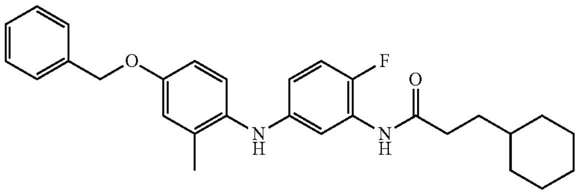
147
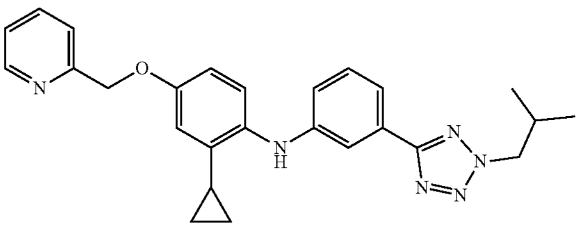
148
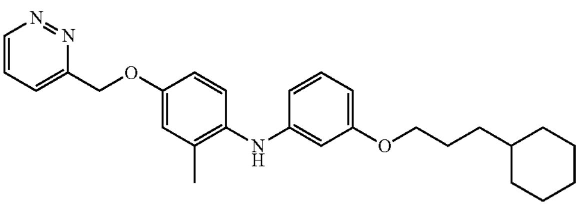
-continued
149
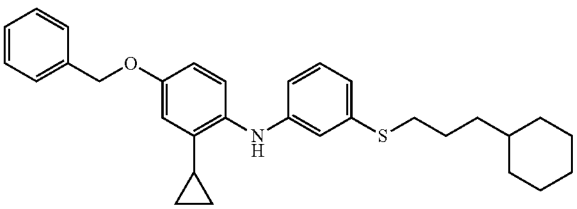
150
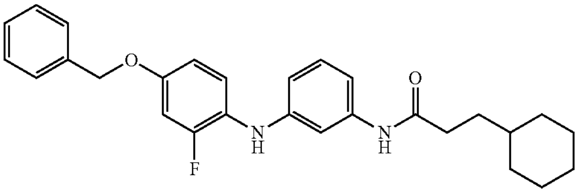
151
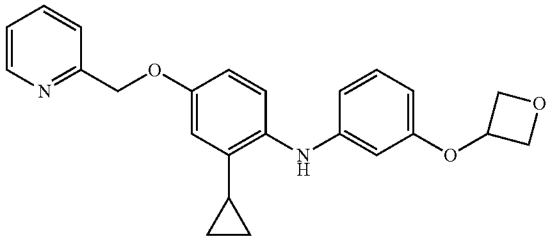
152
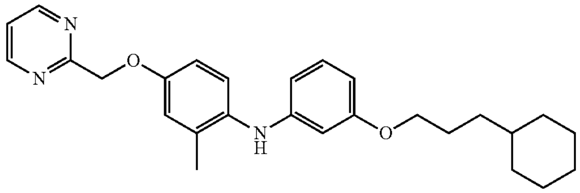
153
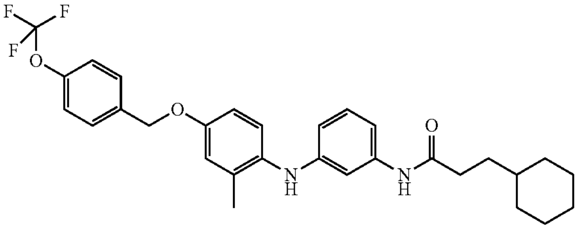
154
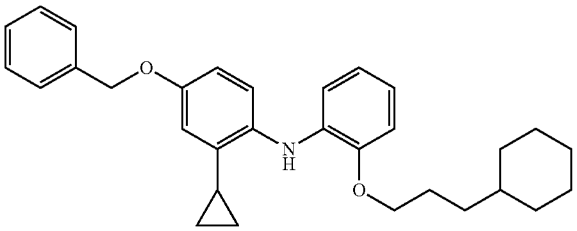

-continued
155
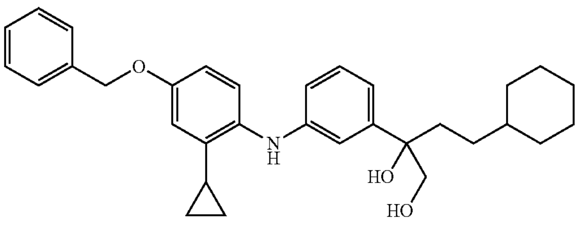
156
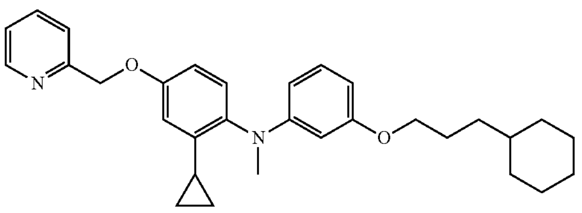
157
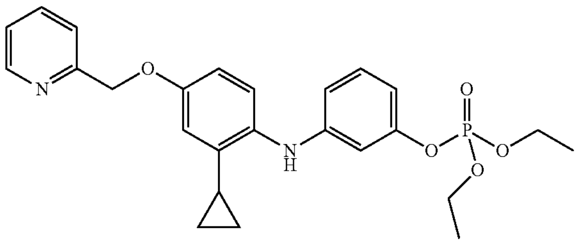
158
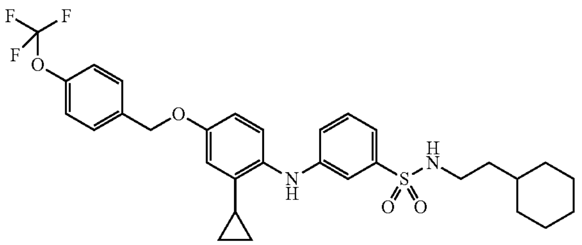
159
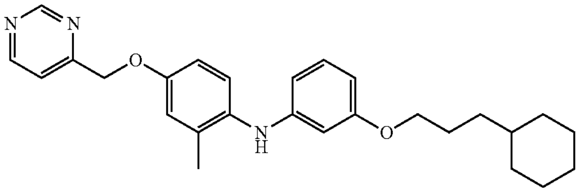
160
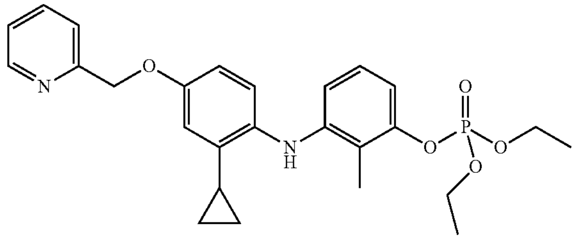
-continued
162
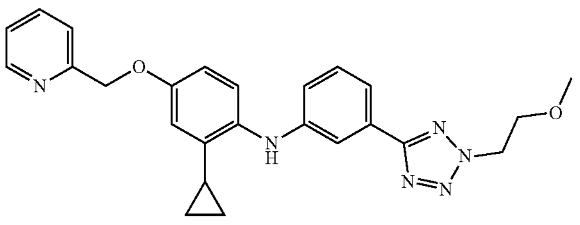
163
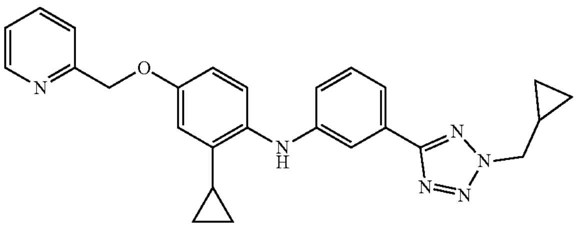
167
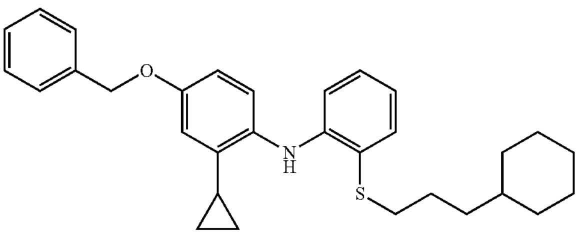
169
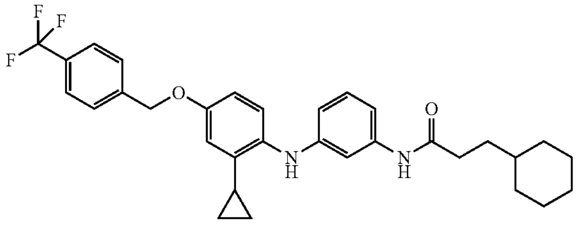
170
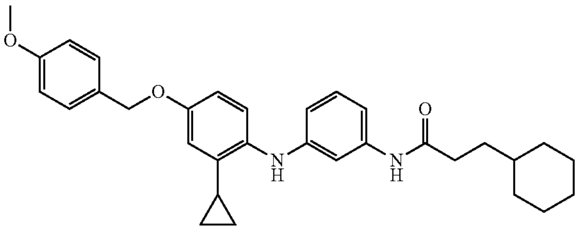
171
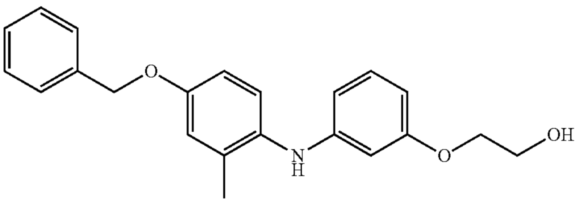

-continued
172
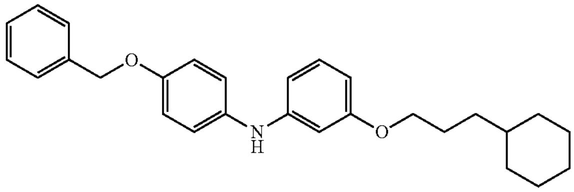
174
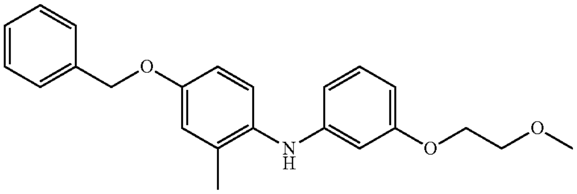
175
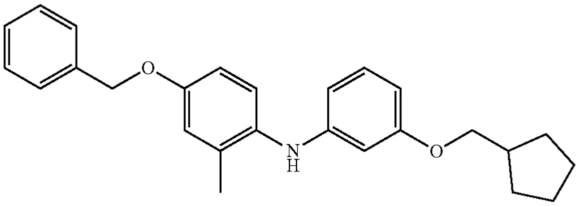
176
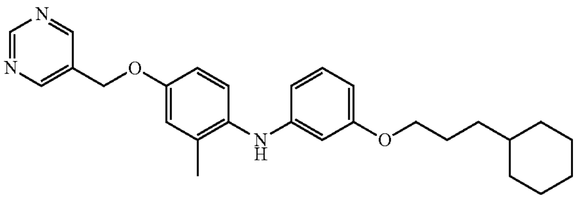
177
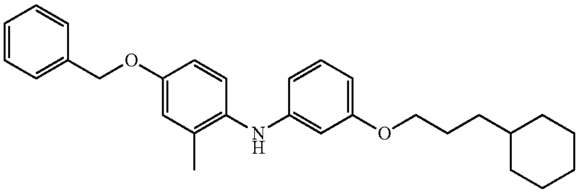
178
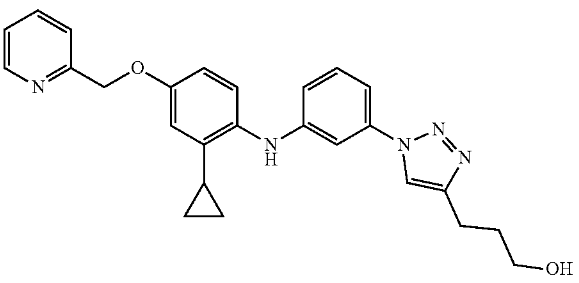
-continued
180
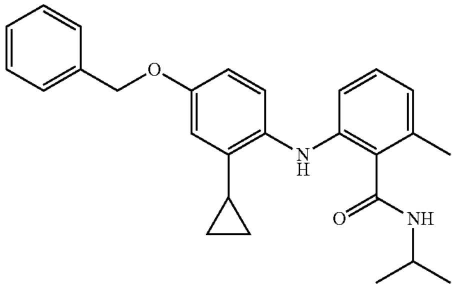
181
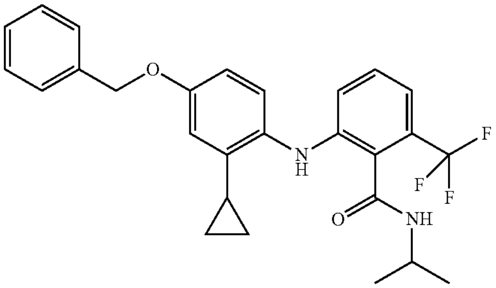
182
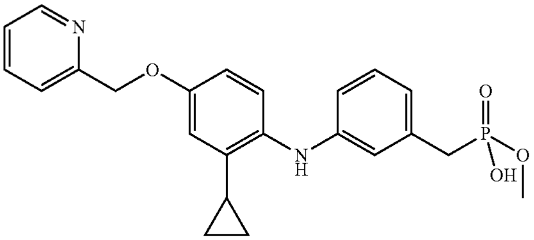
183
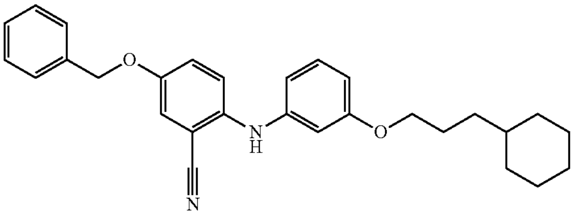
184
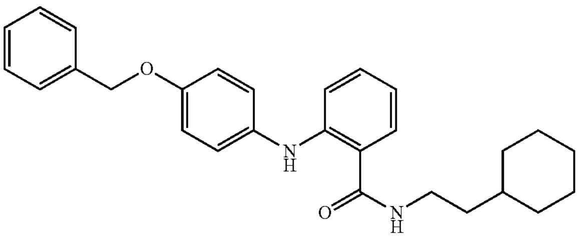
185
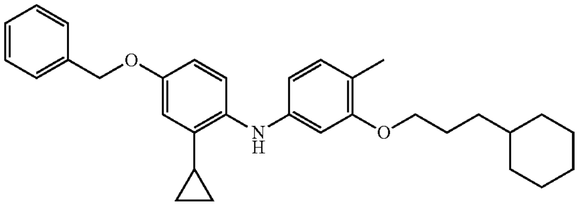

-continued
186
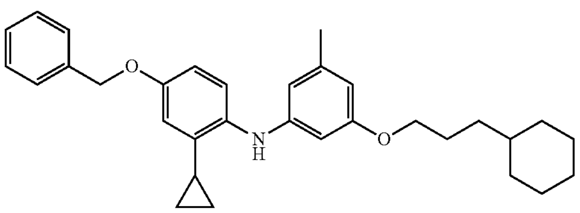
187
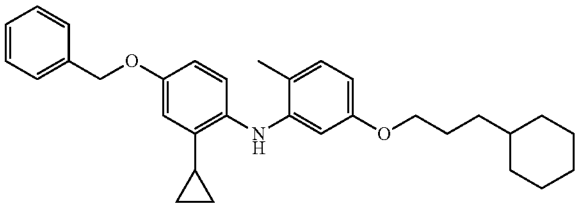
188
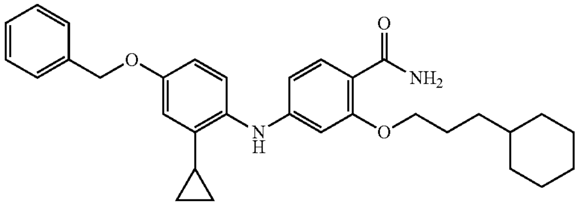
189
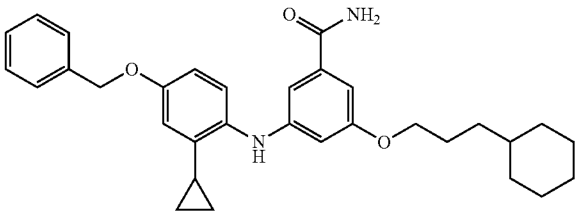
190
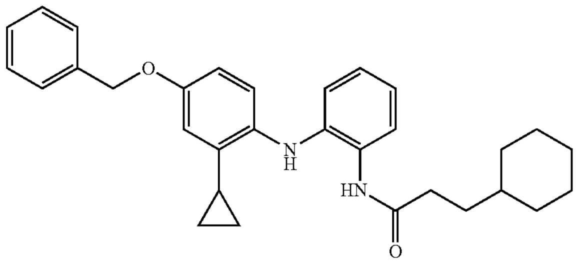
191
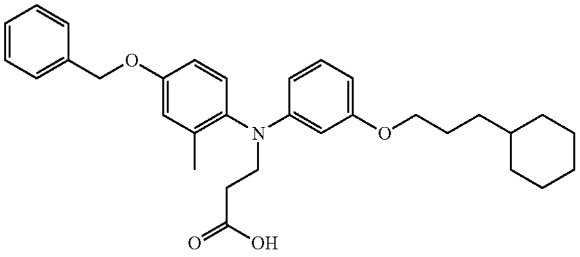
-continued
192
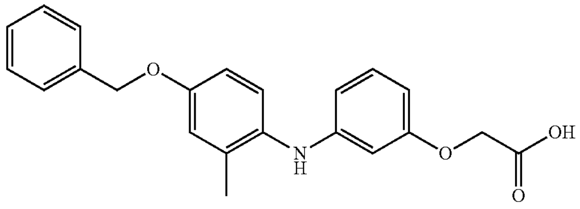
194
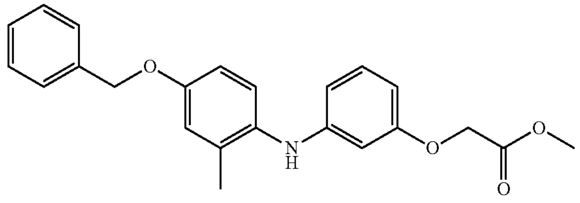
196
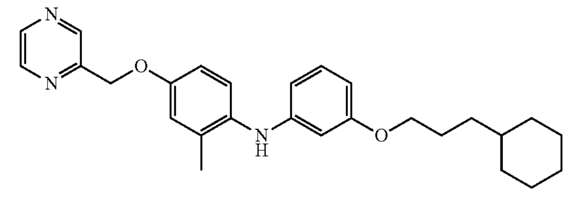
201
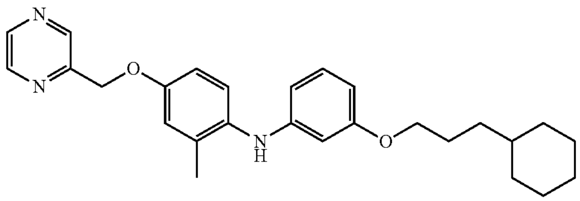
202
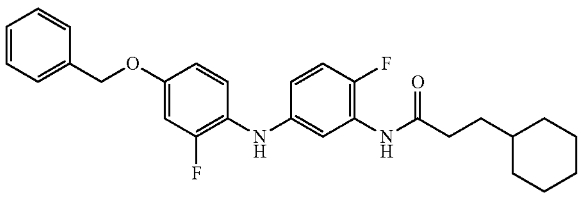
203
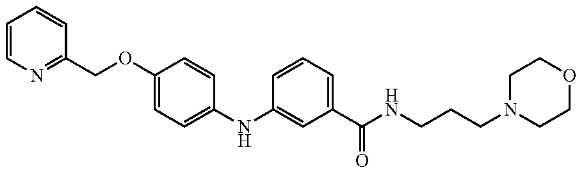
204
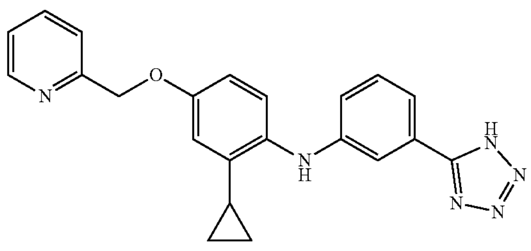

-continued

205

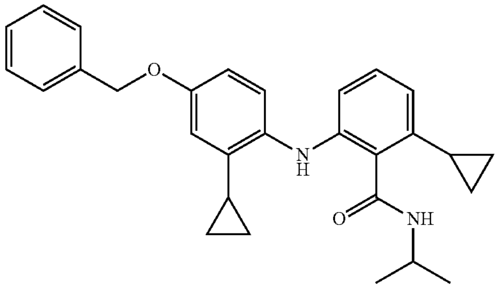

206

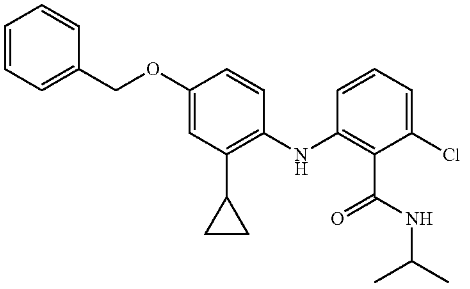

or a pharmaceutically acceptable salt thereof.

10. A method for treating a patient having a RNA virus infection caused by a virus belonging to group IV or V of the Baltimore classification comprising administering to the patient in need thereof a therapeutically effective quantity of the compound of formula (Ie) according to claim 1, a pharmaceutically acceptable salt thereof, or any of compounds (36) to (206):

36

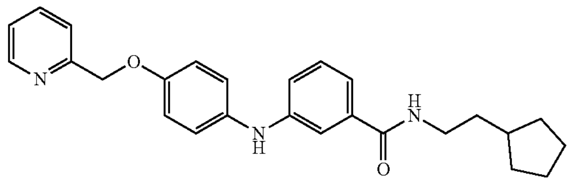

37

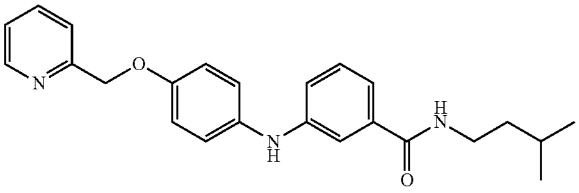

38

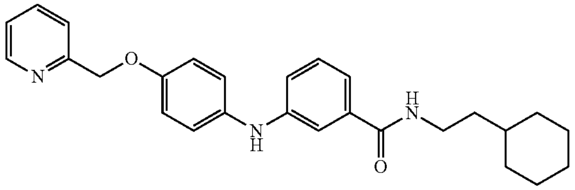

-continued

39

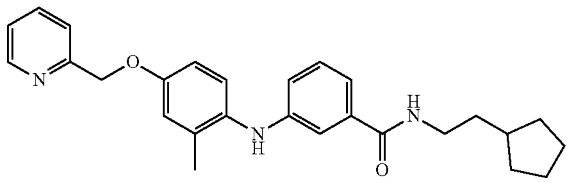

40

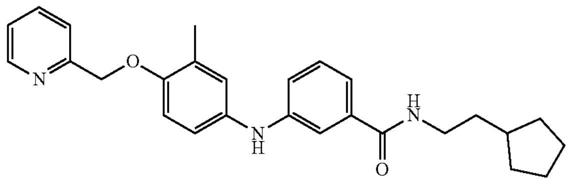

41

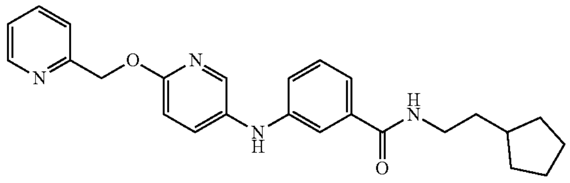

42

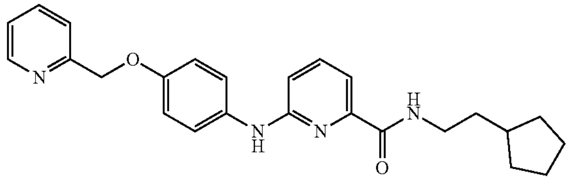

43

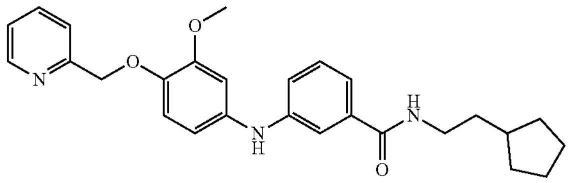

44

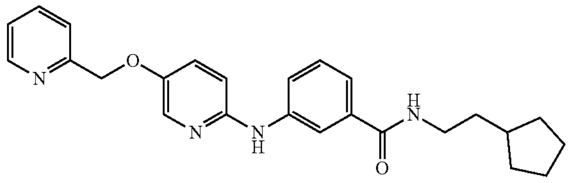

45

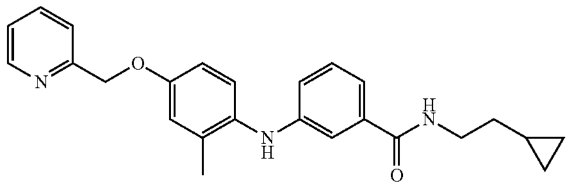

-continued
46
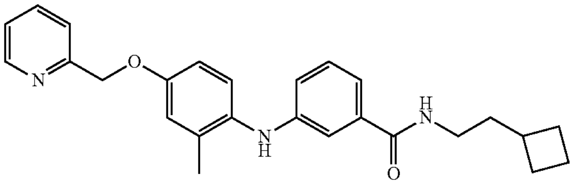
47
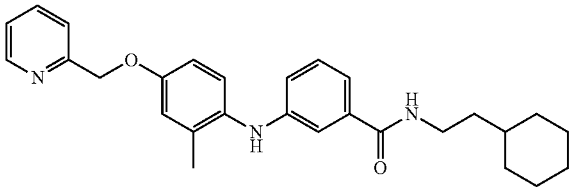
48
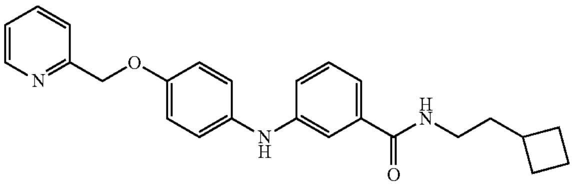
49
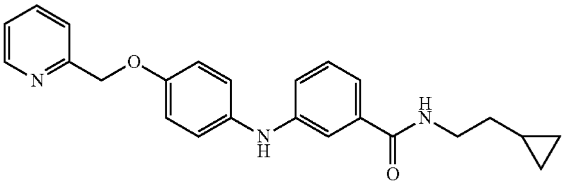
50
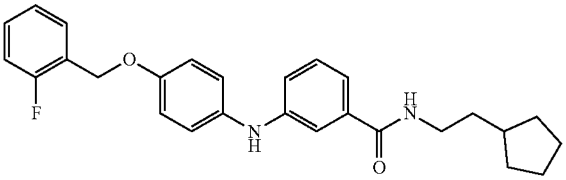
51
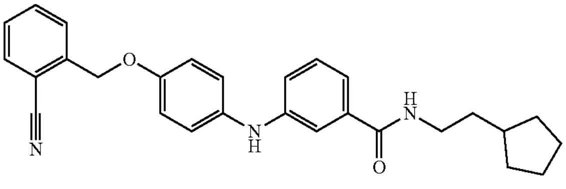
52
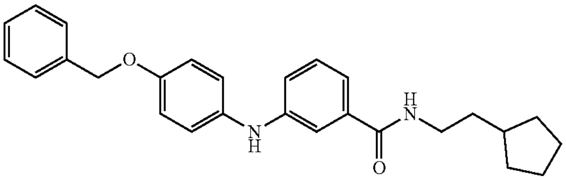
-continued
53
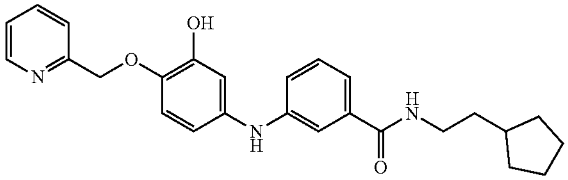
54
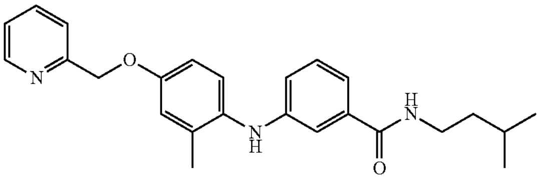
55
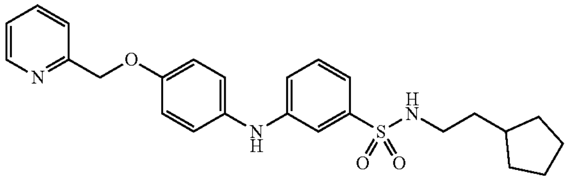
56
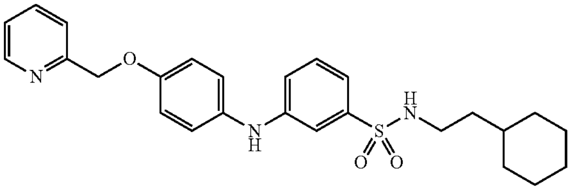
57
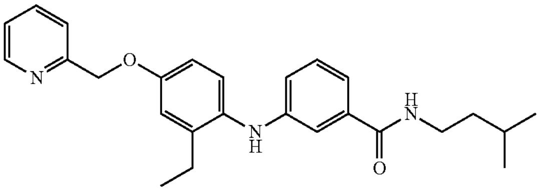
58
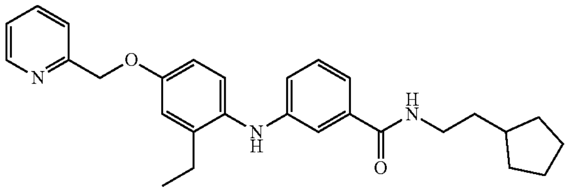
59
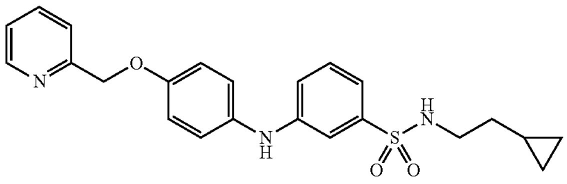

-continued
60
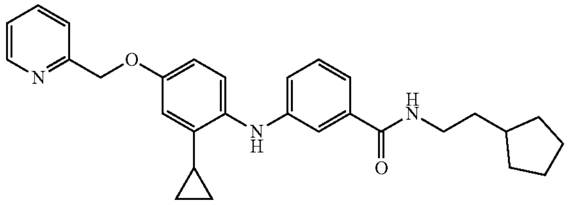
61
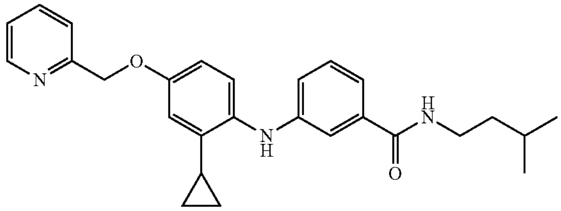
62
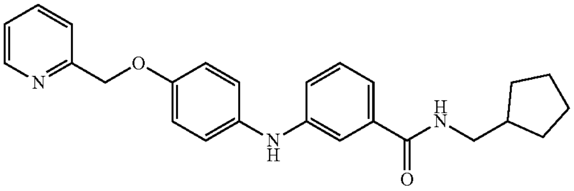
63
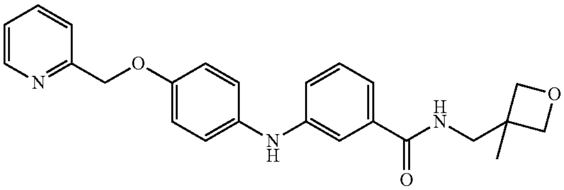
64
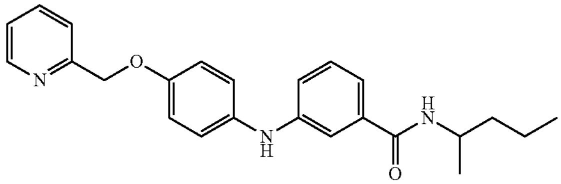
65
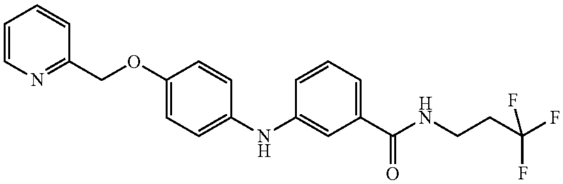
66
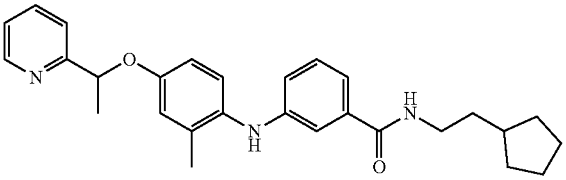
-continued
67
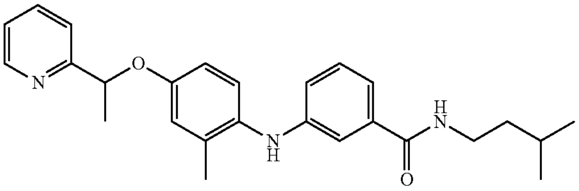
68
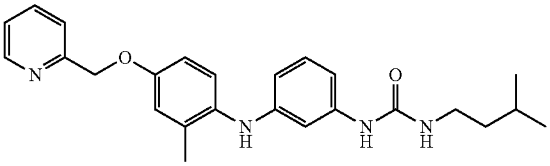
69
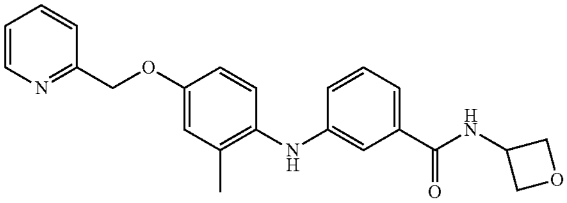
70
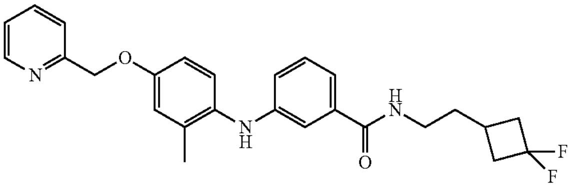
71
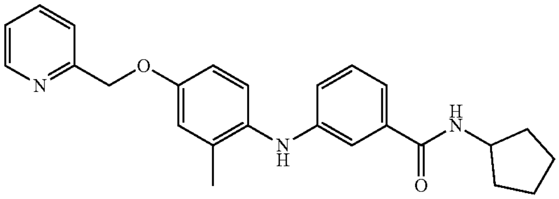
72
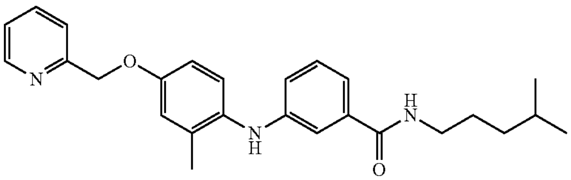
73
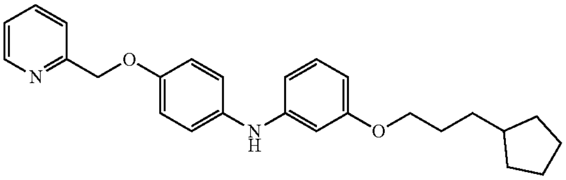

-continued
74
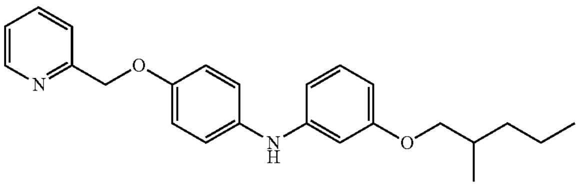
75
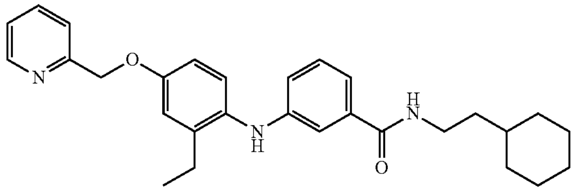
76
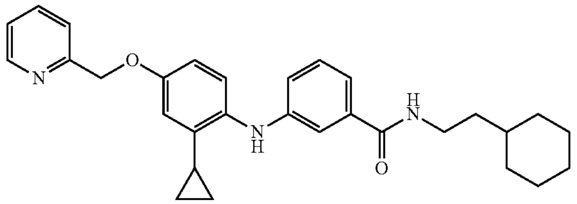
77
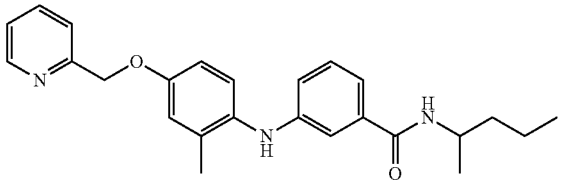
78
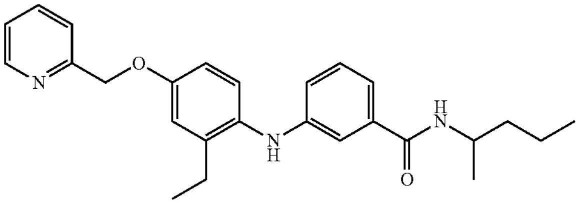
79
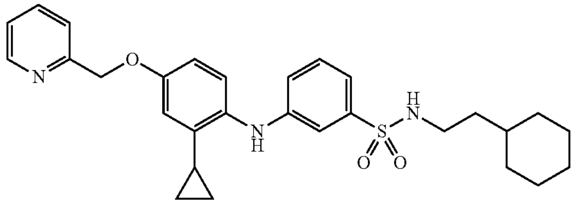
80
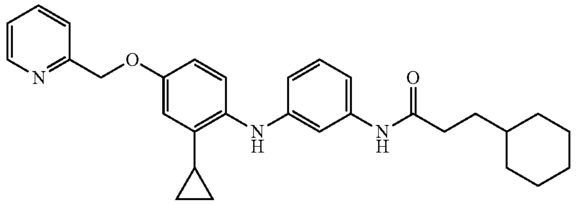
-continued
81
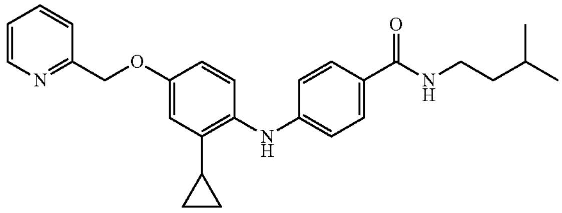
82
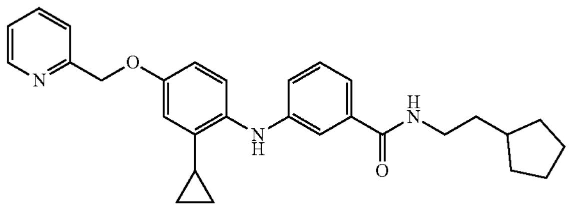
83
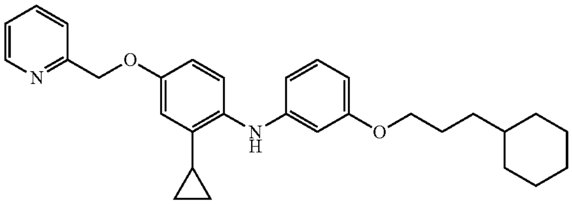
84
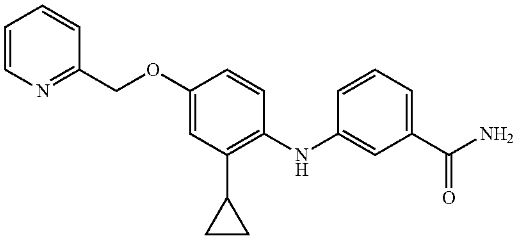
85
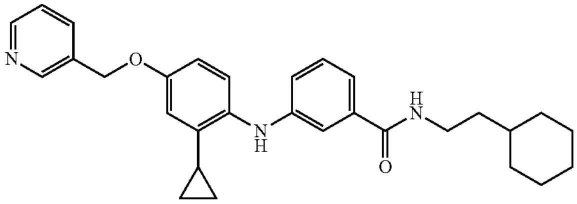
86
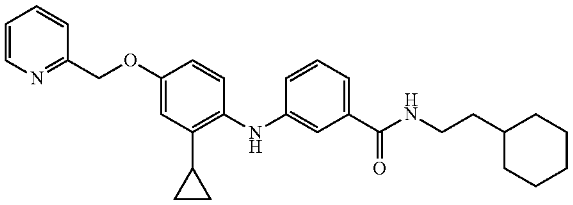

-continued
87
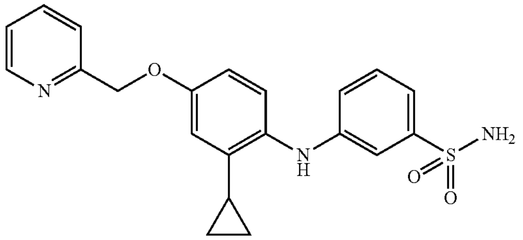
88
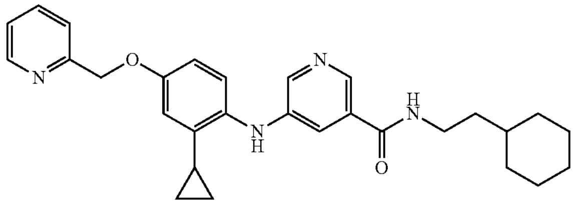
89
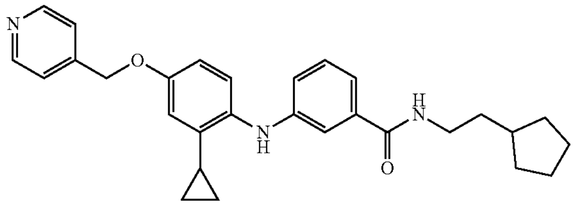
90
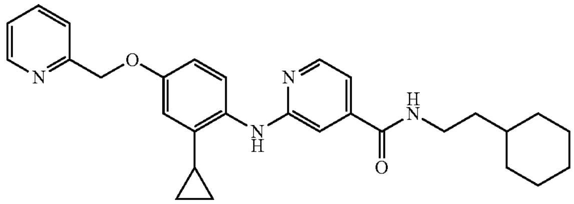
91
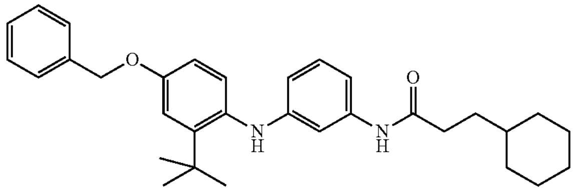
92
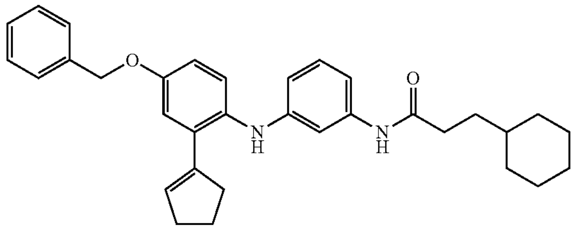
-continued
93
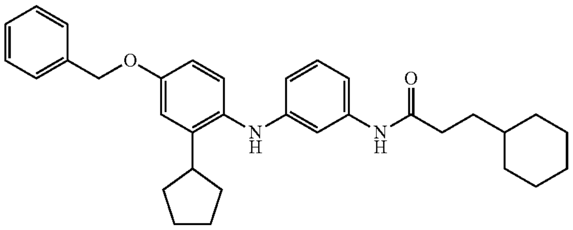
94
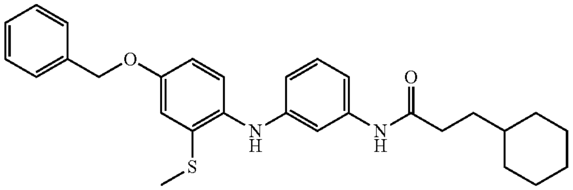
95
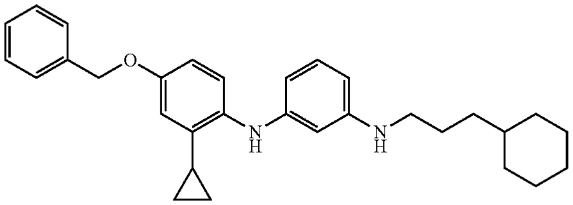
96
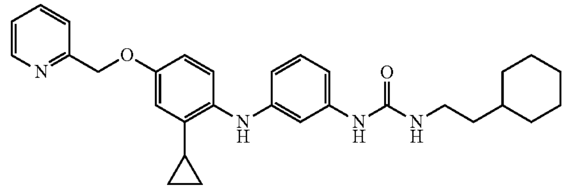
97
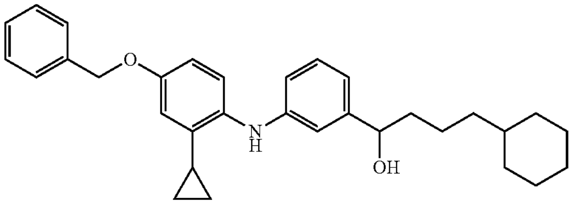
98
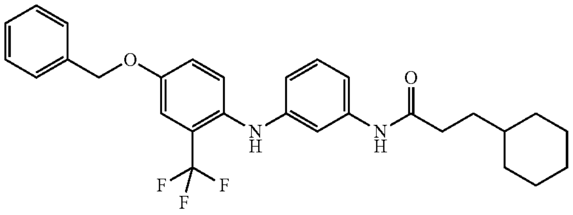
99
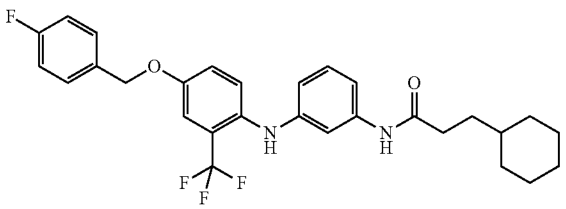

-continued
100
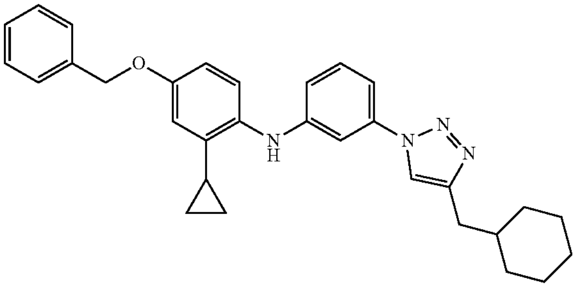
101
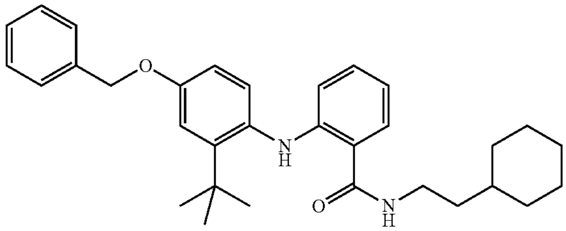
102
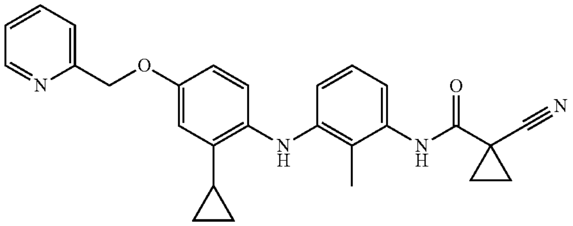
103
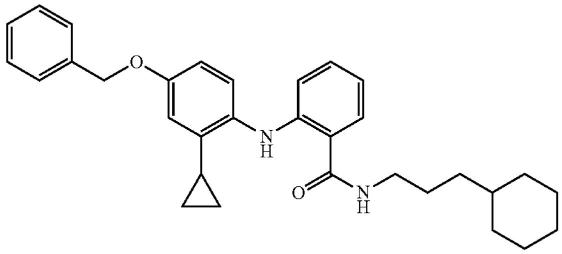
104
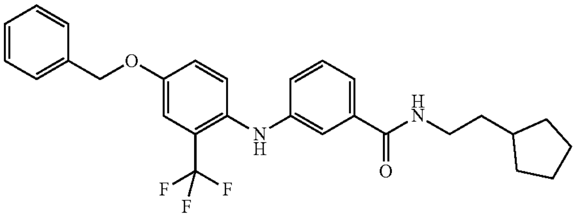
105
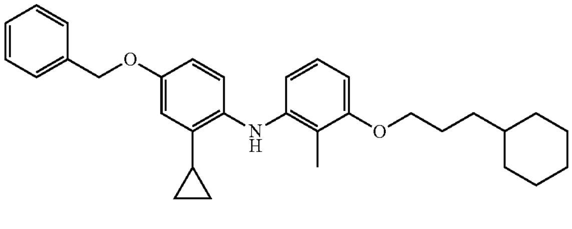
-continued
106
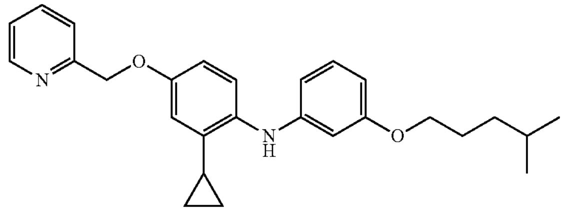
107
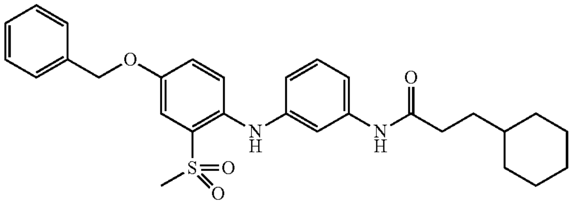
108
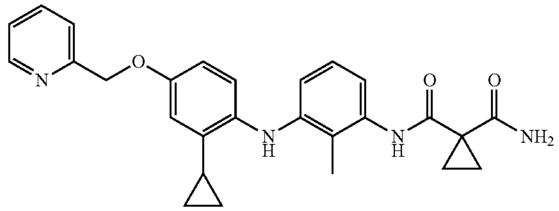
109
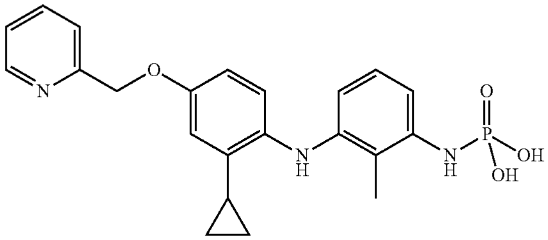
110
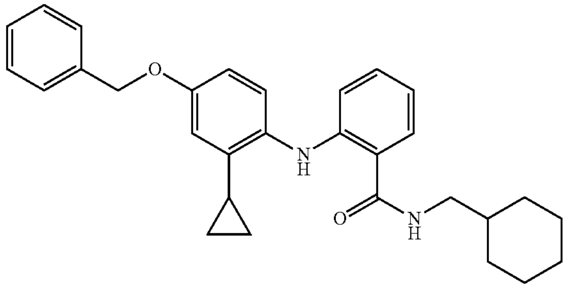
111
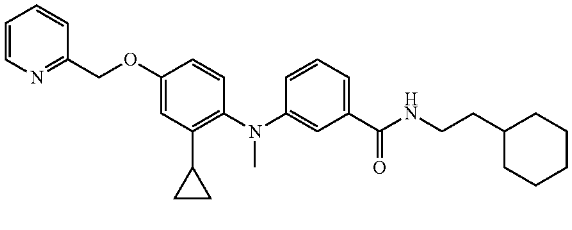

112
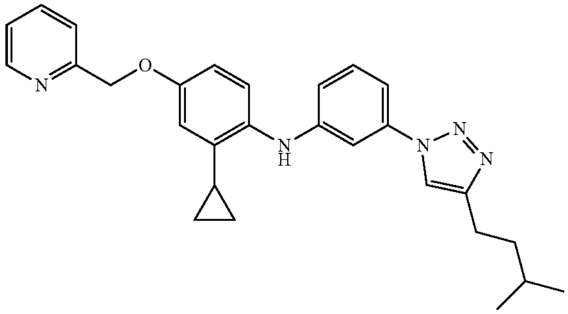
113
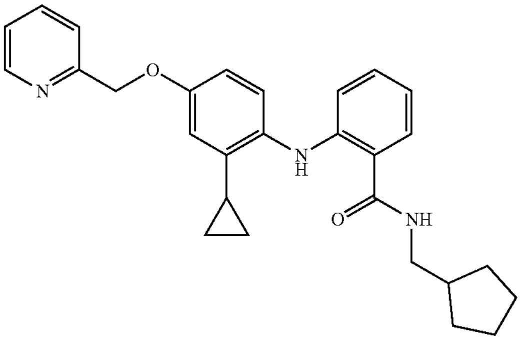
114
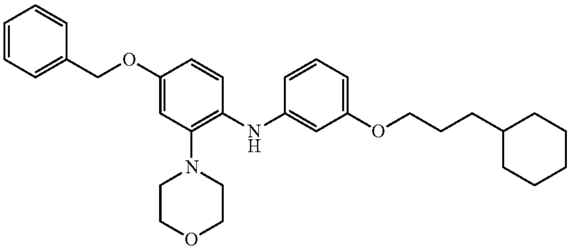
115
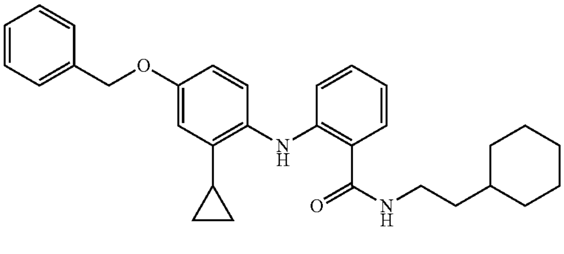
116
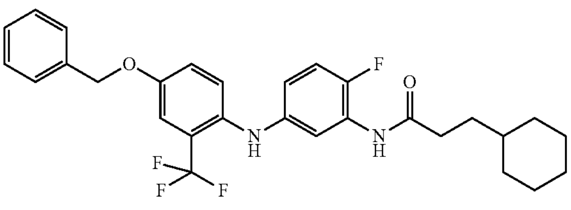
117
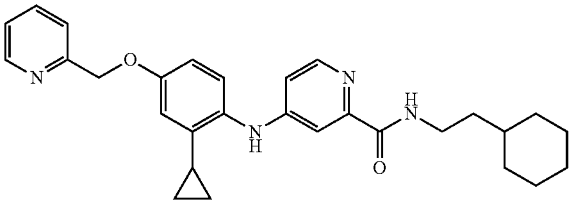
118
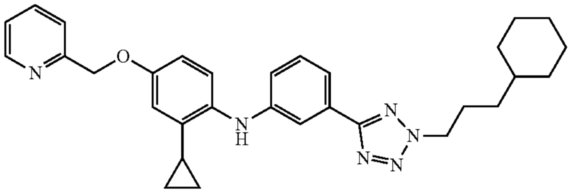
119
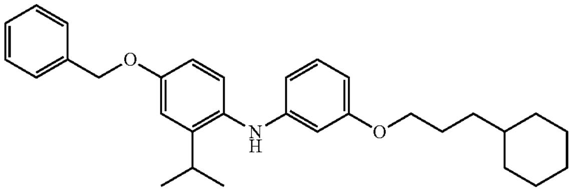
120
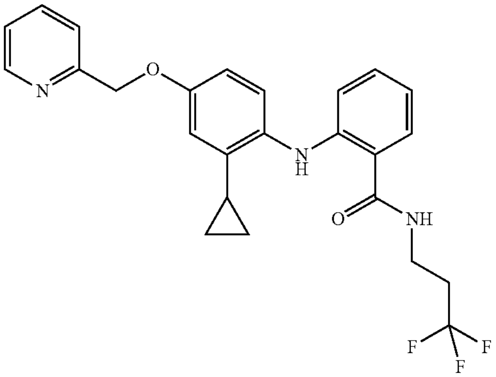
121
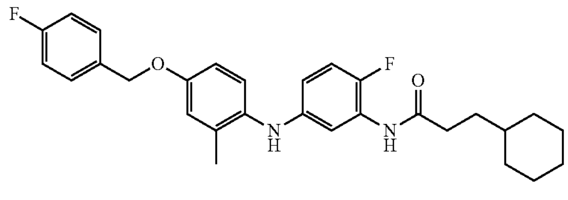
122
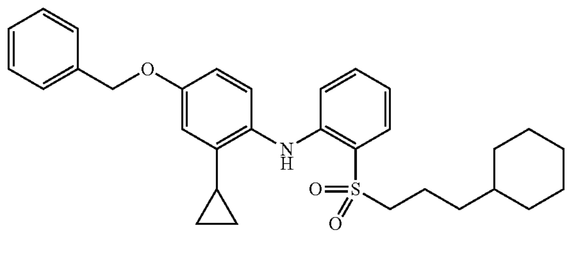

-continued
123
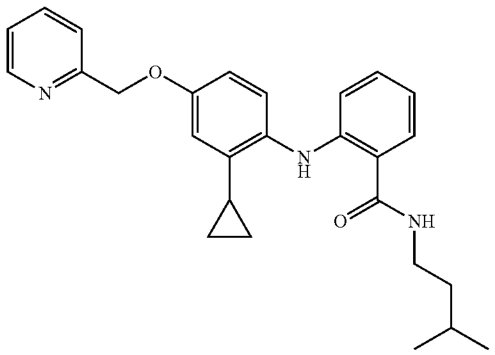
124
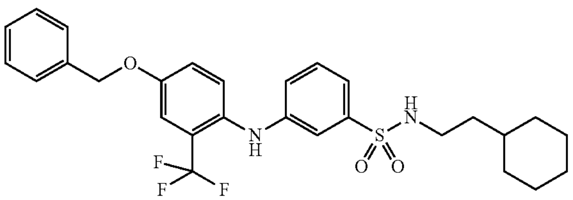
125
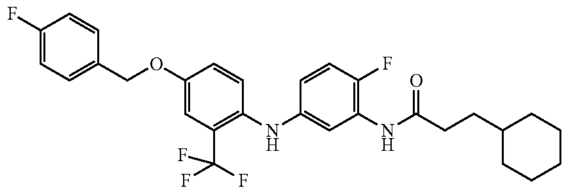
126
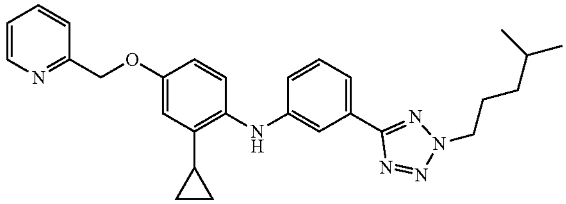
127
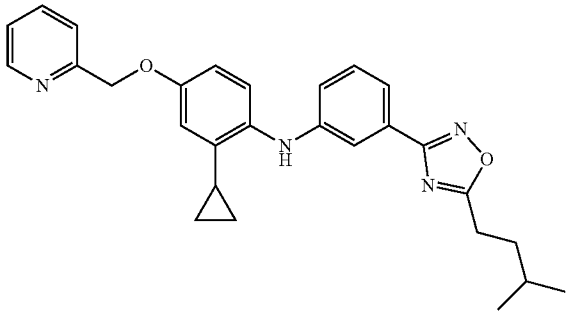
-continued
128
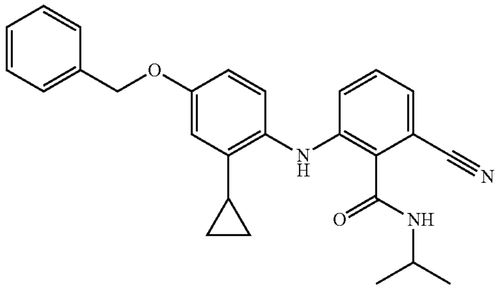
129
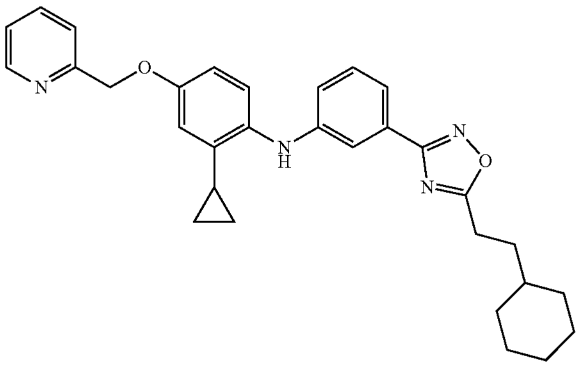
130
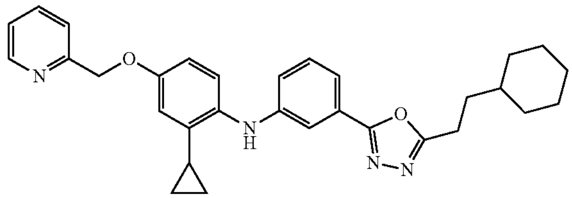
131
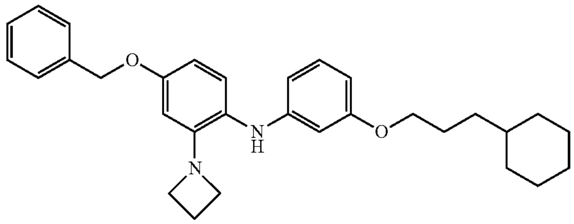
132
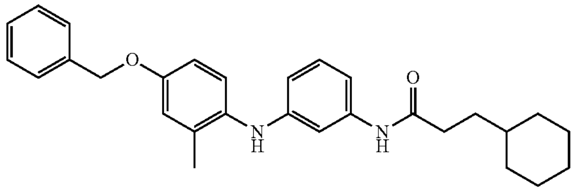
133
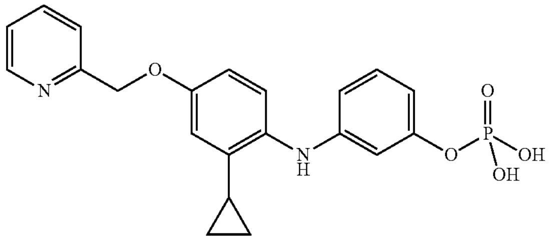

-continued
134
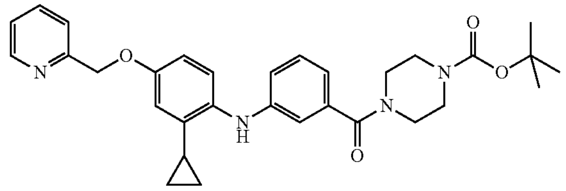
135
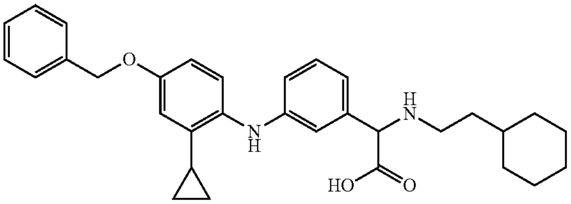
136
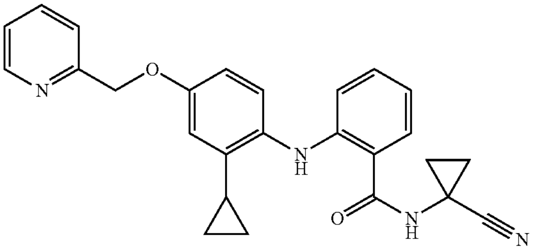
137
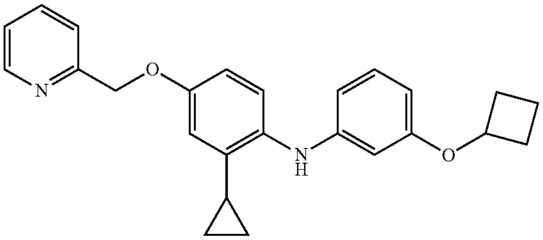
138
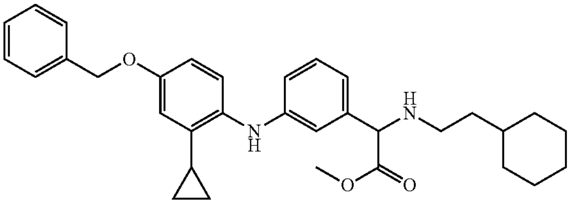
139
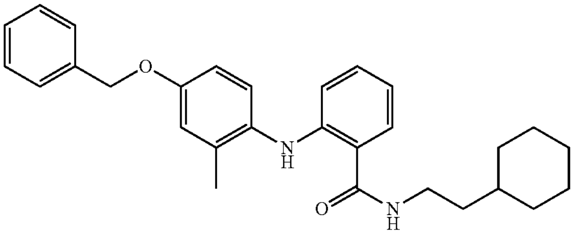
-continued
140
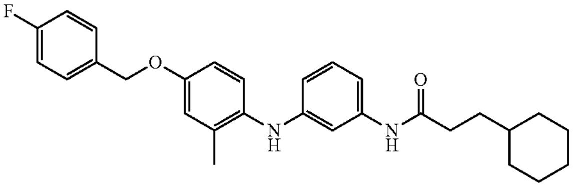
141
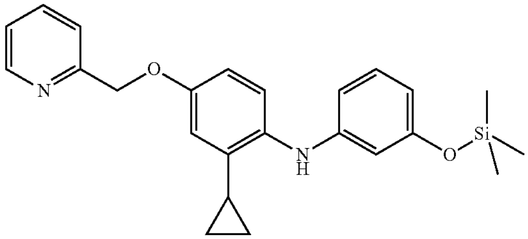
142
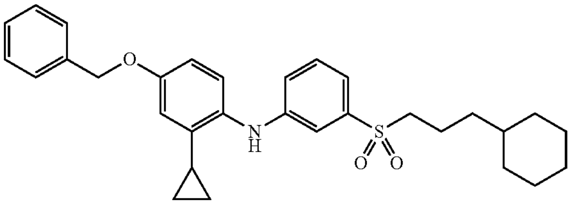
143
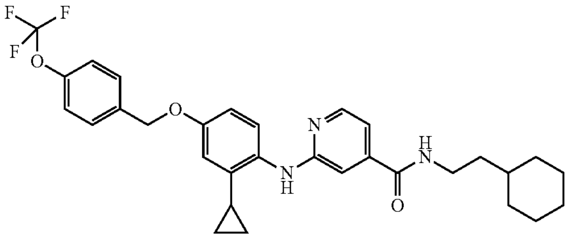
144
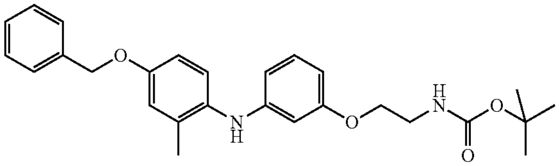
145
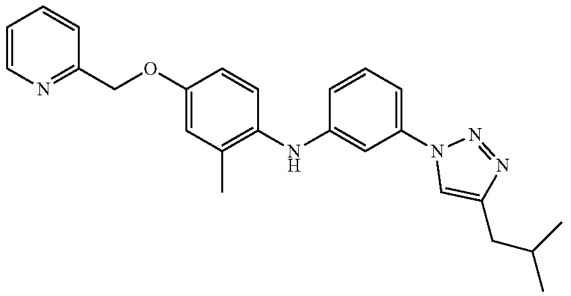

-continued
146
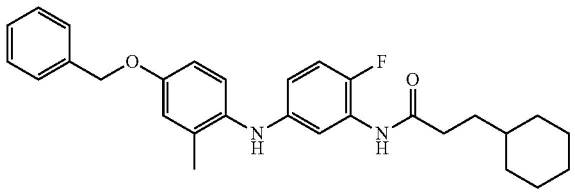
147
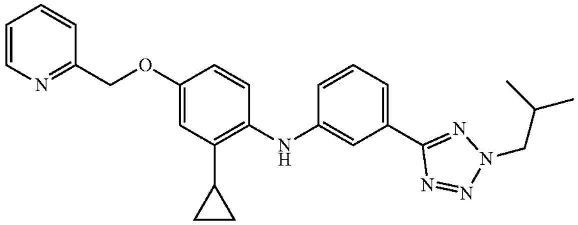
148
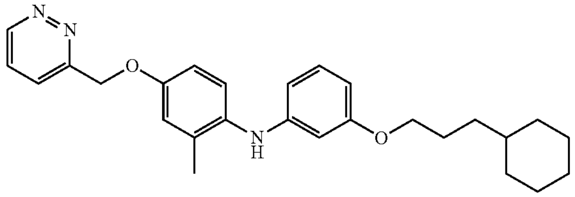
149
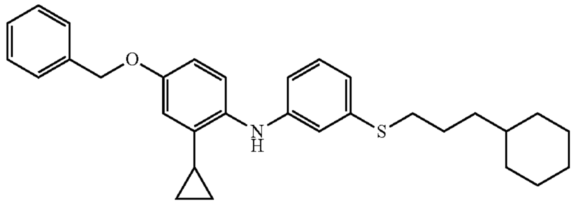
150
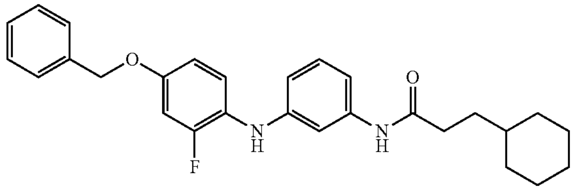
151
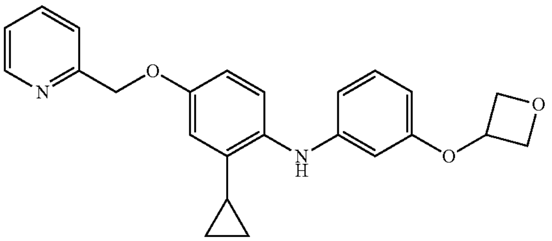
152
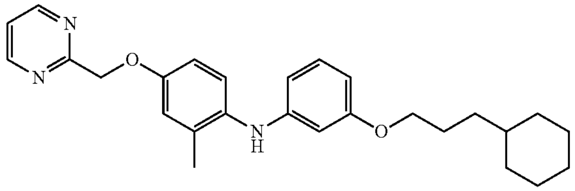
-continued
153
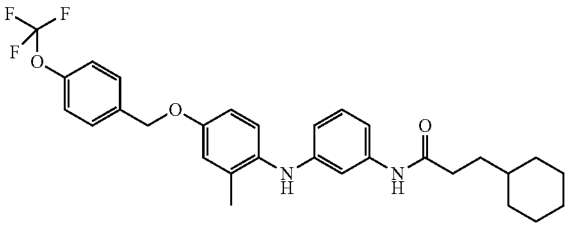
154
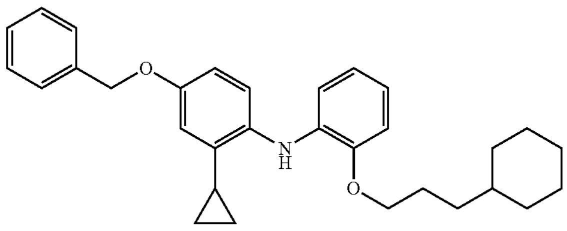
155
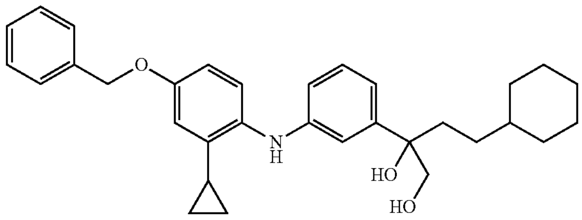
156
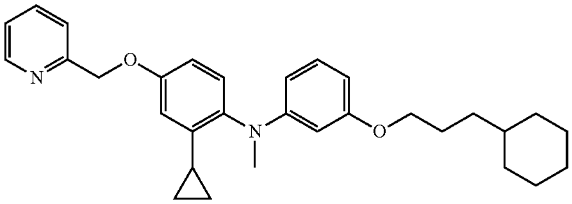
157
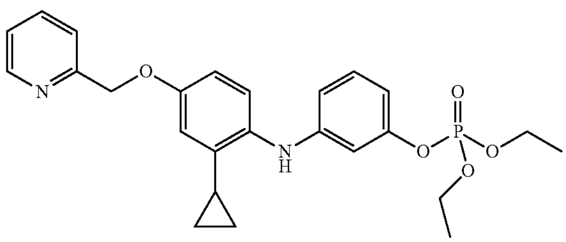
158
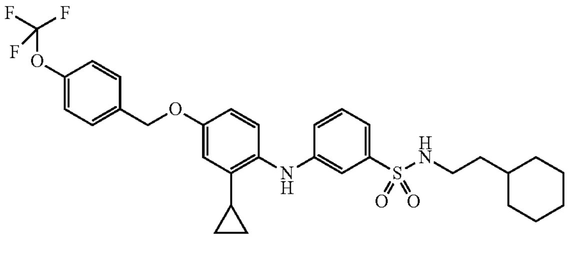

-continued
159
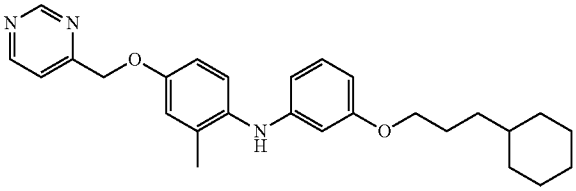
160
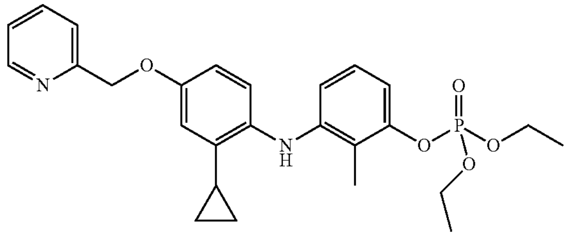
161
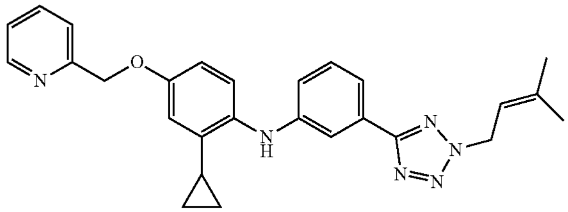
162
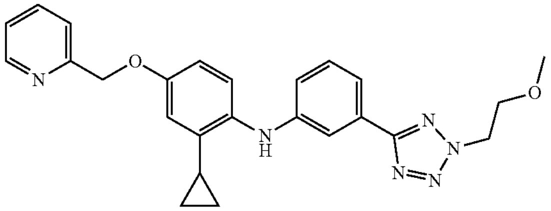
163
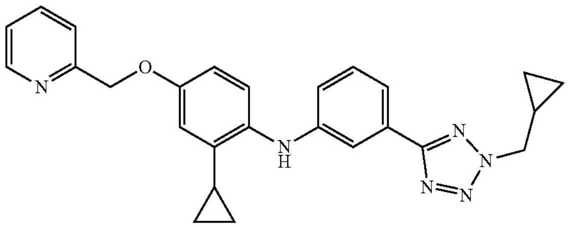
164
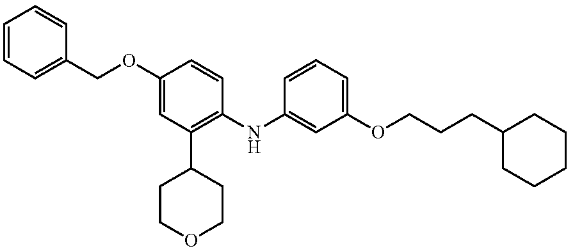
-continued
165
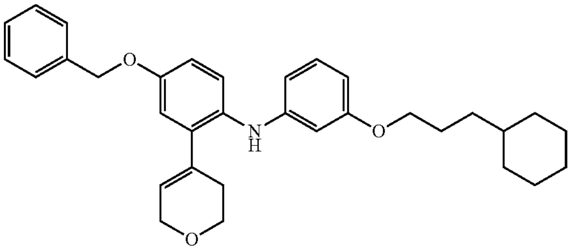
166
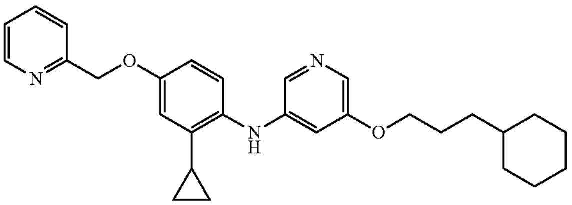
167
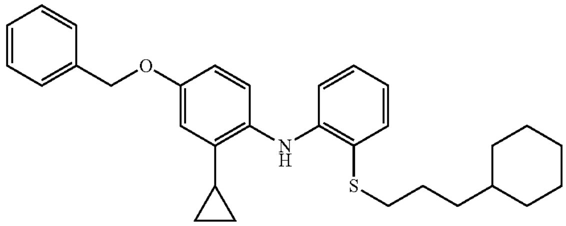
168
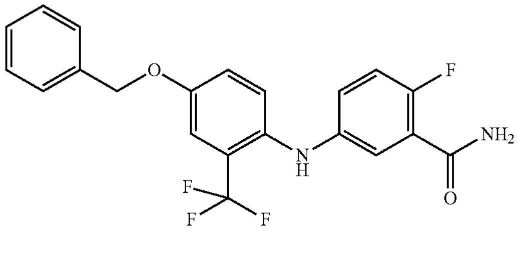
169
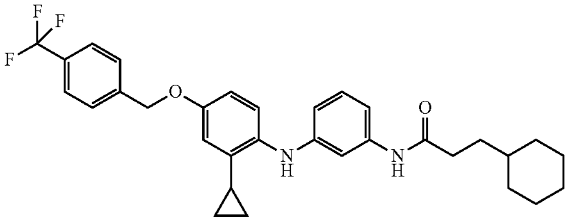
170
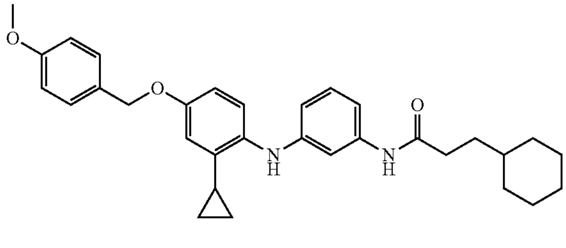

-continued
171
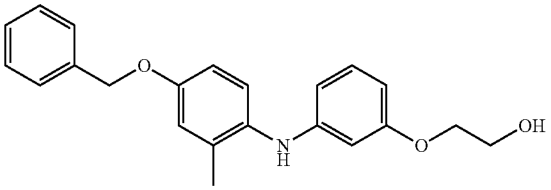
172
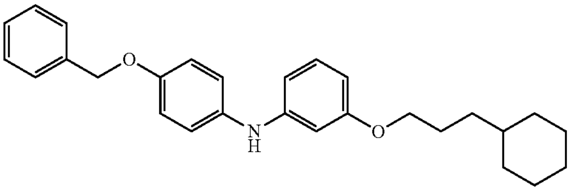
173
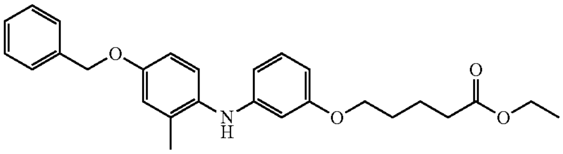
174
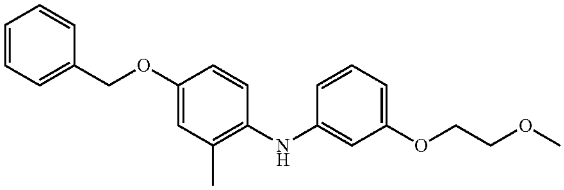
175
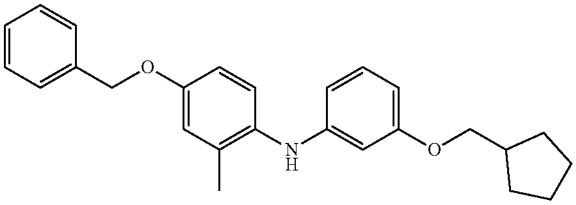
176
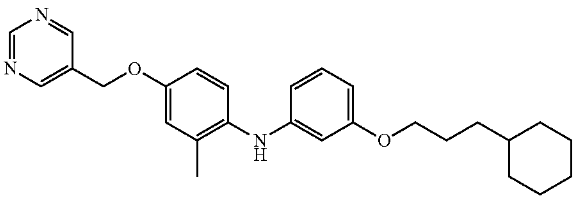
177
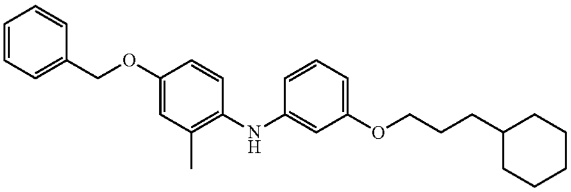
-continued
178
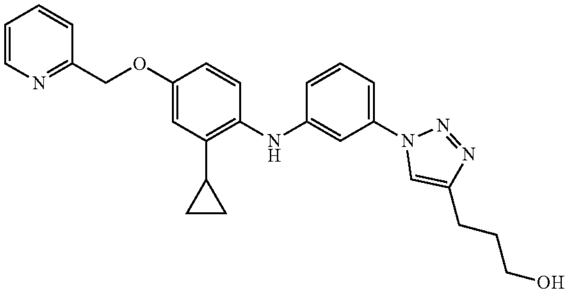
179
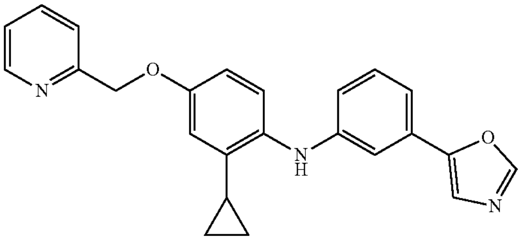
180
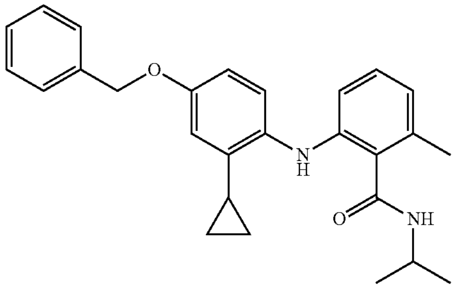
181
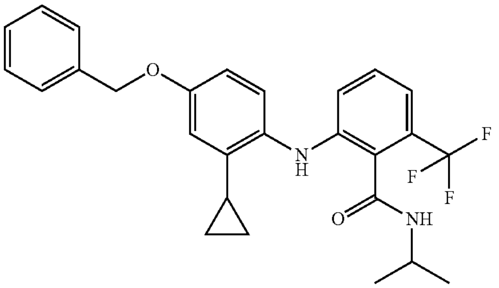
182
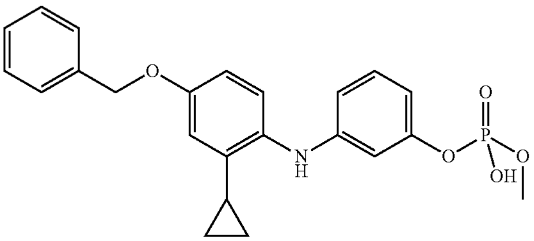

-continued
183
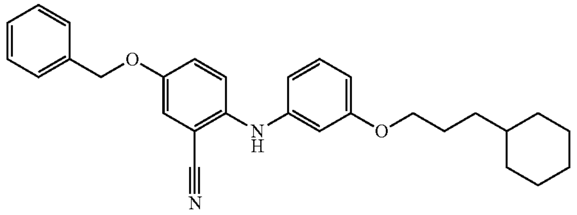
184
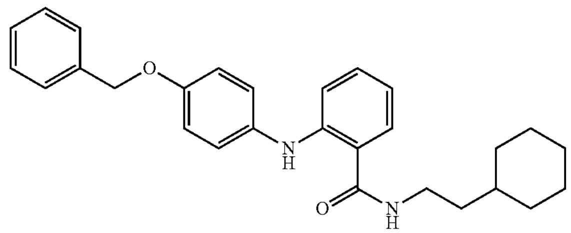
185
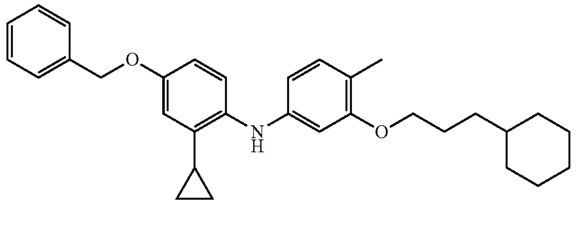
186
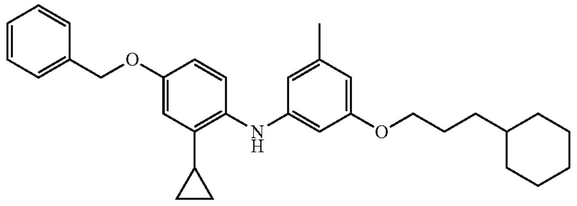
187
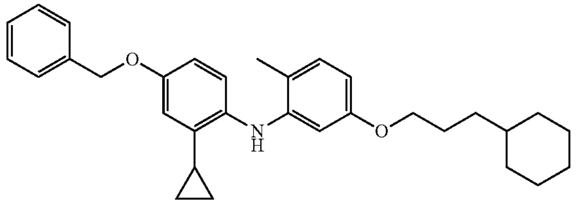
188
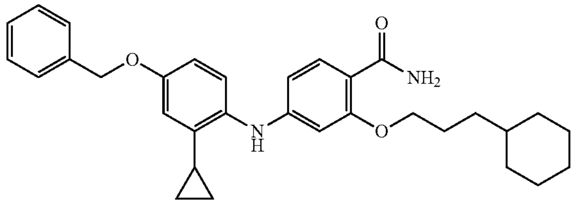
-continued
189
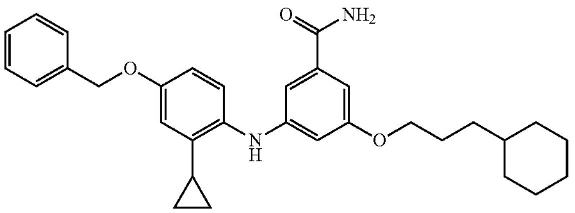
190
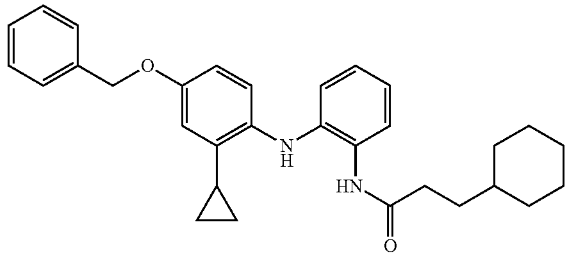
191
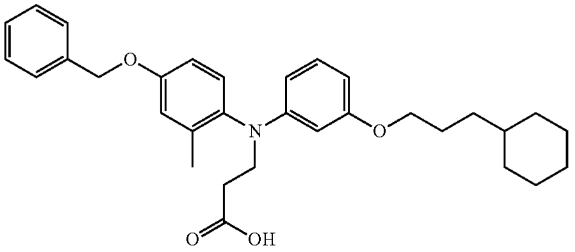
192
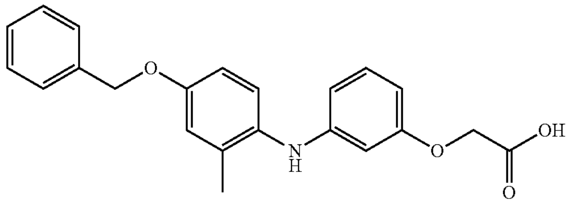
193
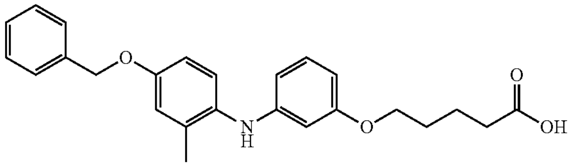
194
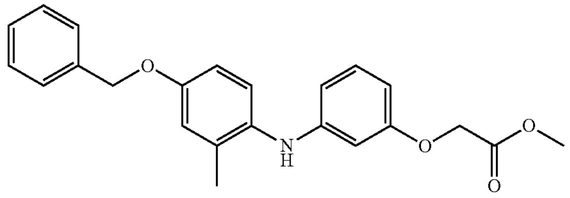

-continued

195

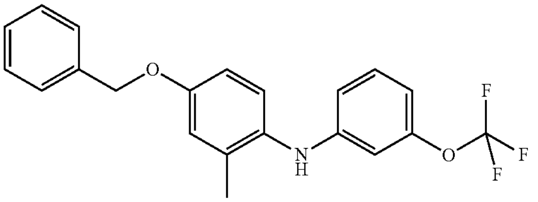

196

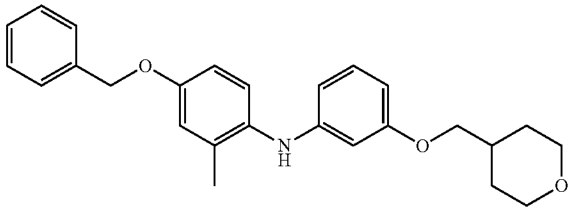

197

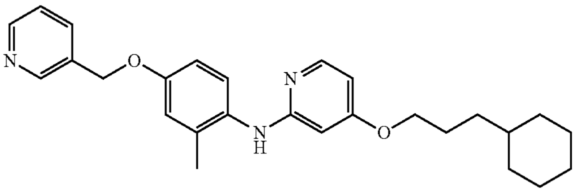

198

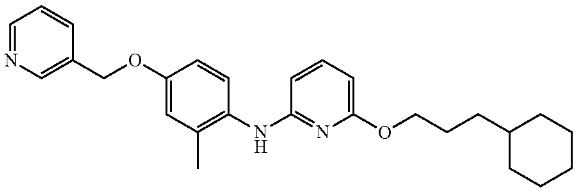

199

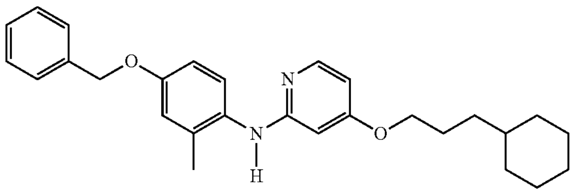

200

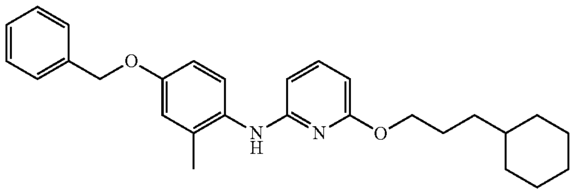

201

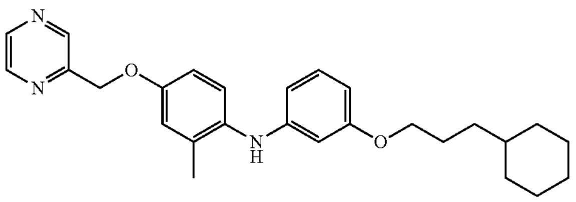

-continued

202

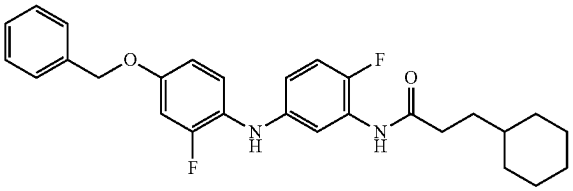

203

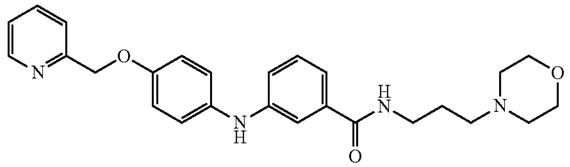

204

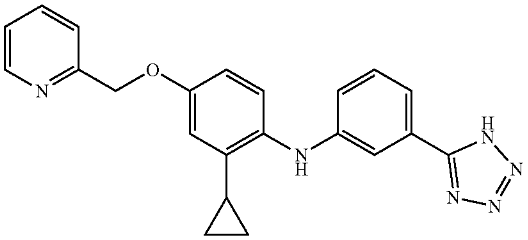

205

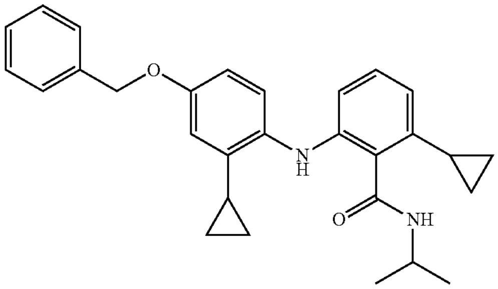

206

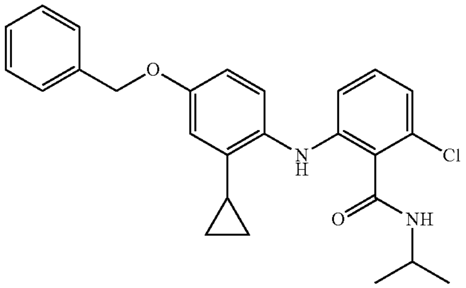

or a pharmaceutically acceptable thereof.

11. The method according to claim 10, wherein the RNA virus infection caused by a RNA virus belonging to group IV or V of the Baltimore classification is selected from RSV, Chikungunya, influenza and Dengue infection.

12. A pharmaceutical composition comprising at least one compound as defined in claim 1, a pharmaceutically acceptable salt thereof, or any of compounds (36) to (206):

-continued
36
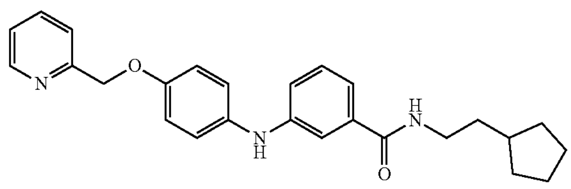
37
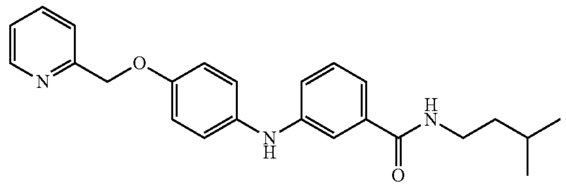
38
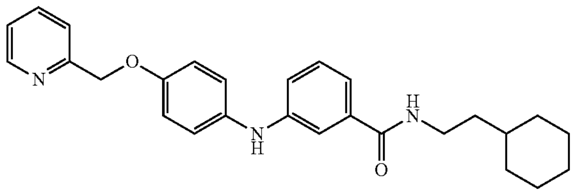
39
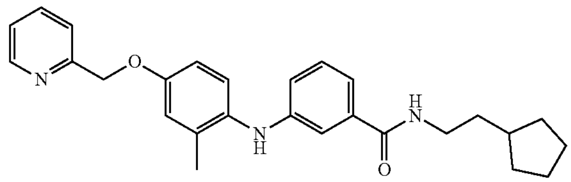
40
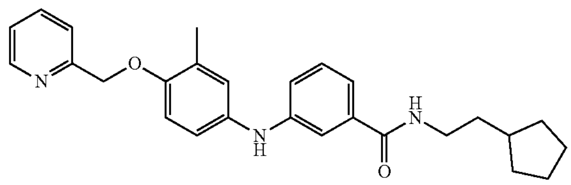
41
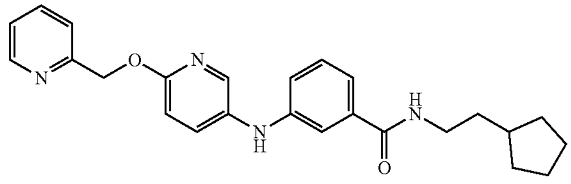
42
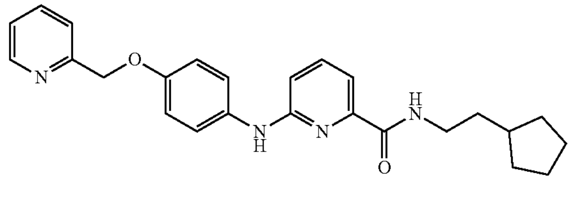
43
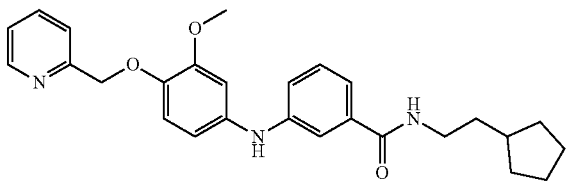
44
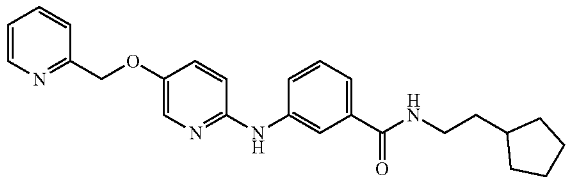
45
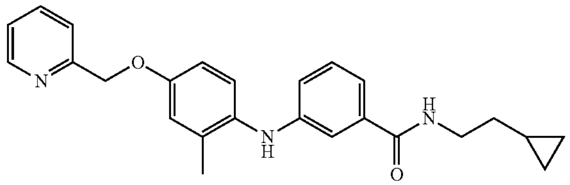
46
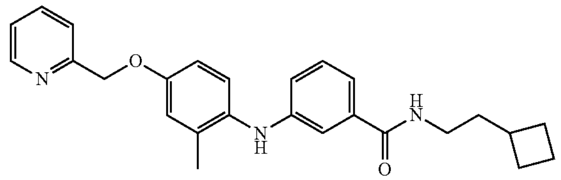
47
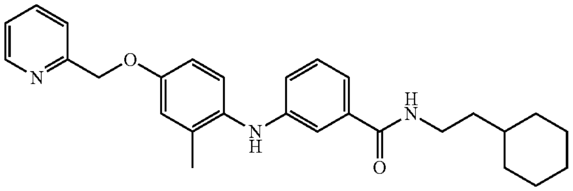
48
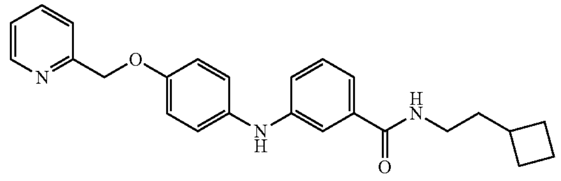
49
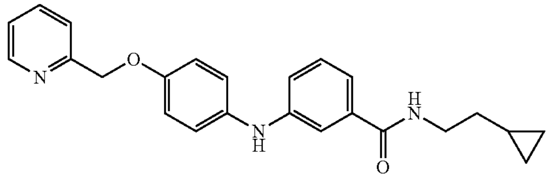

-continued
50
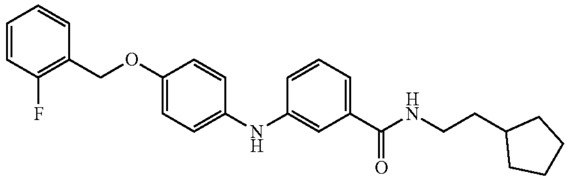
51
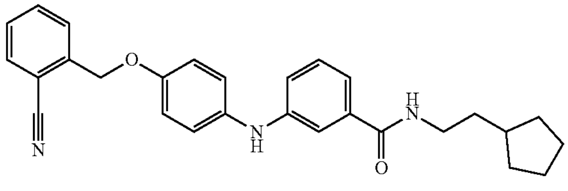
52
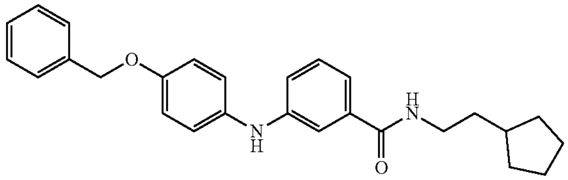
53
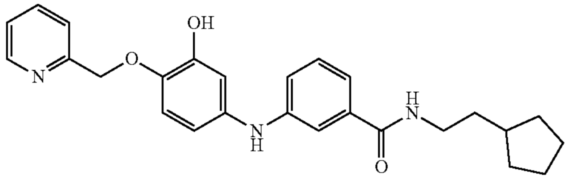
54
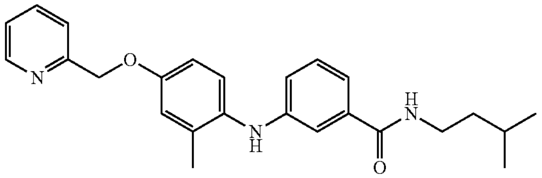
55
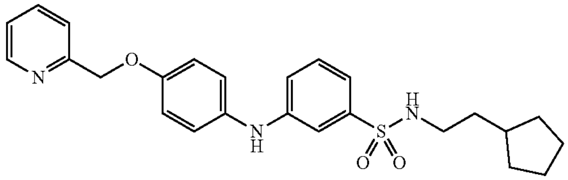
56
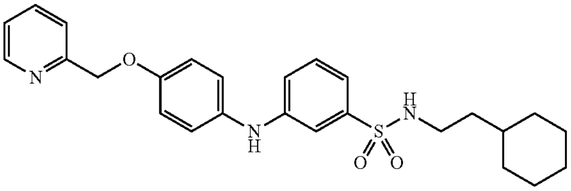
-continued
57
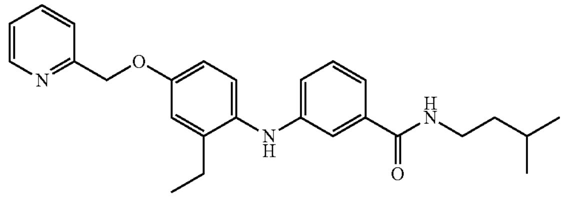
58
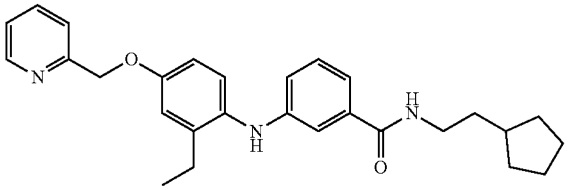
59
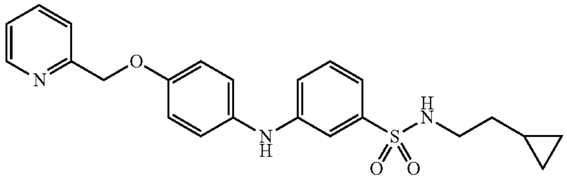
60
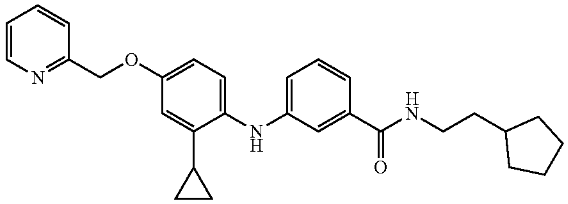
61
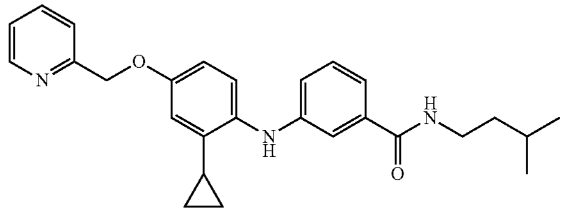
62
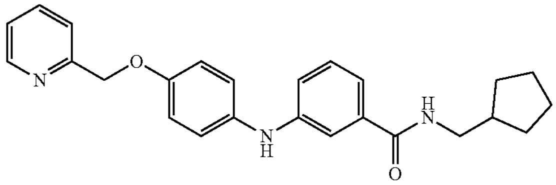
63
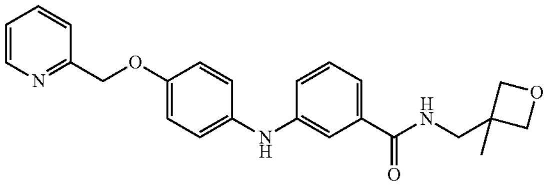

-continued
64
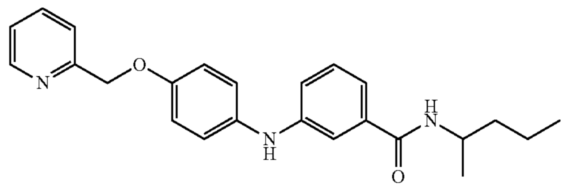
65
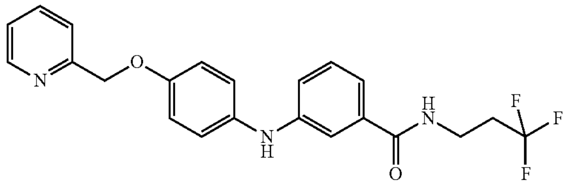
66
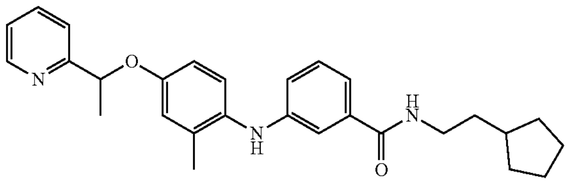
67
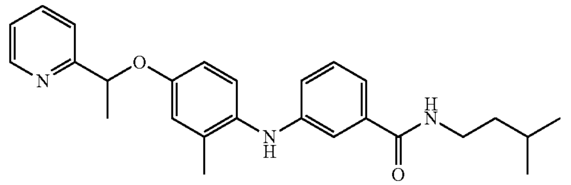
68
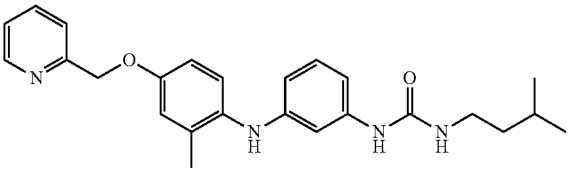
69
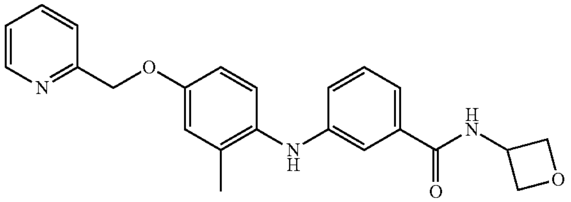
70
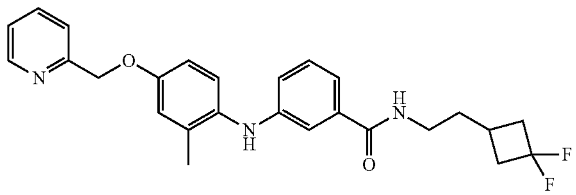
-continued
71
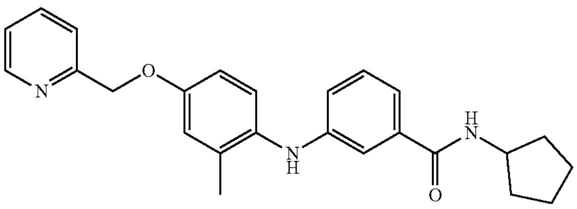
72
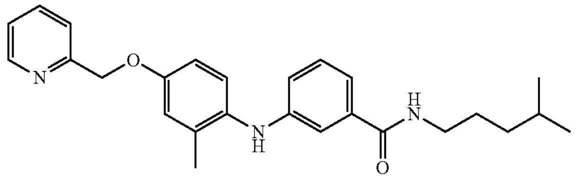
73
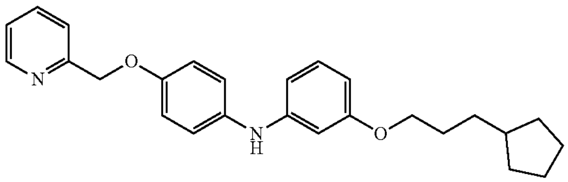
74
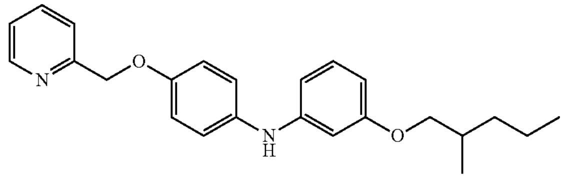
75
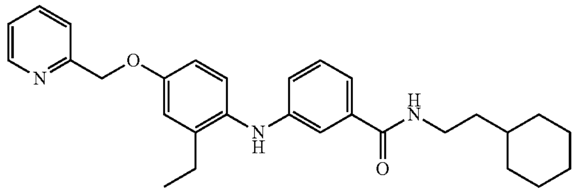
76
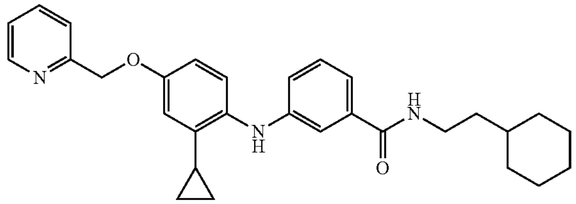
77
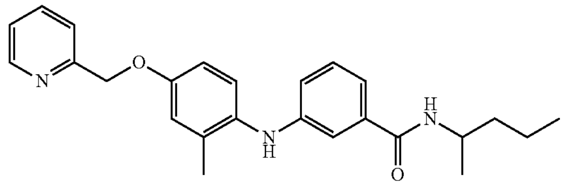

-continued
78
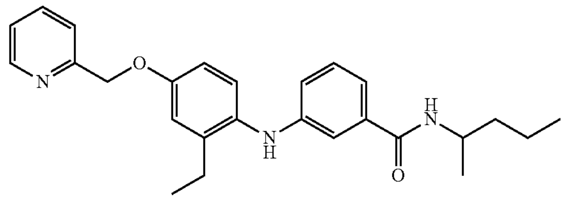
79
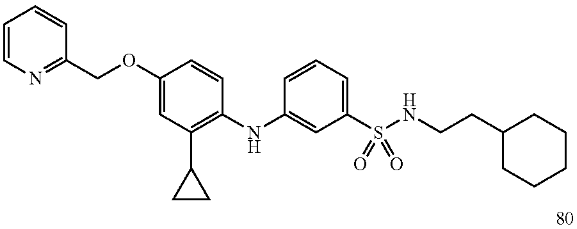
80
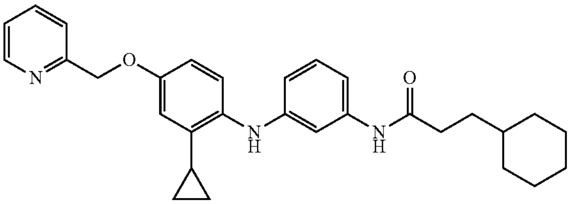
81
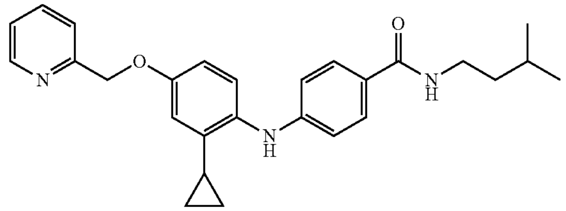
82
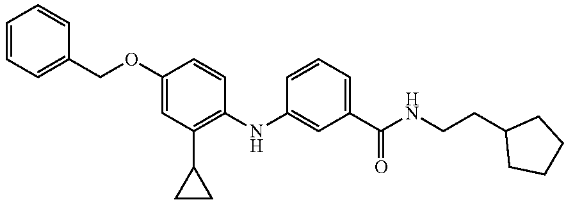
83
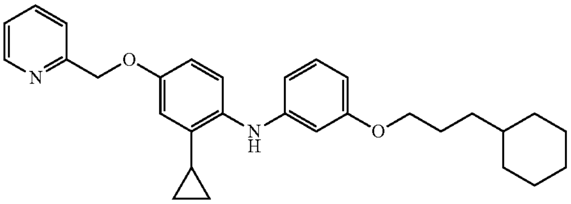
84
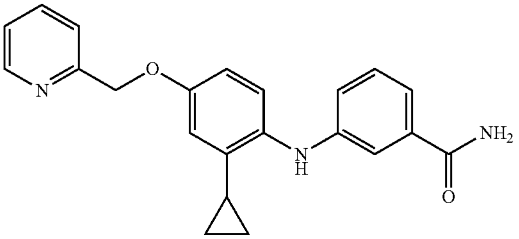
-continued
85
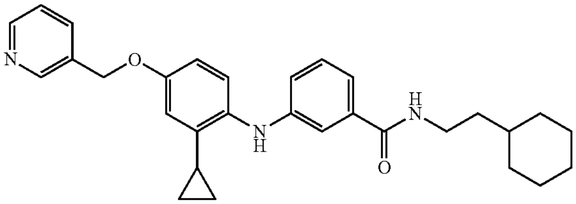
86
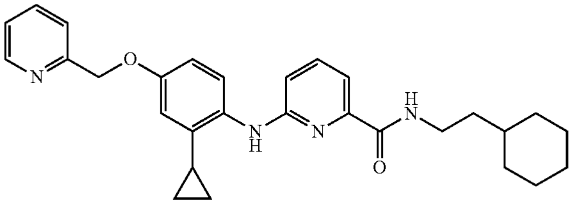
87
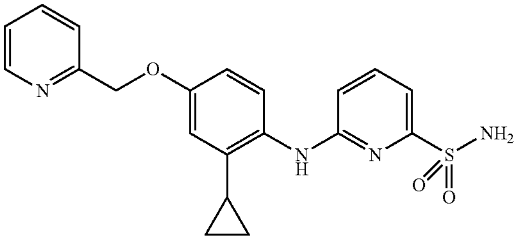
88
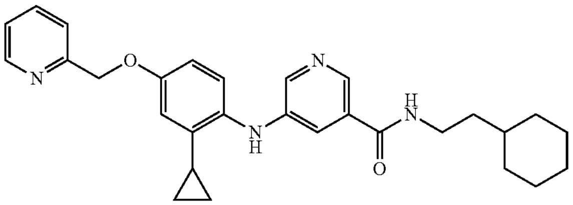
89
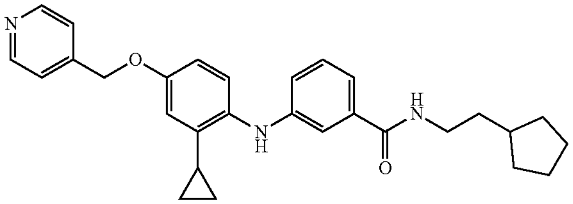
90
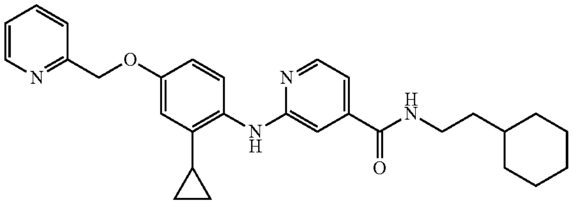
91
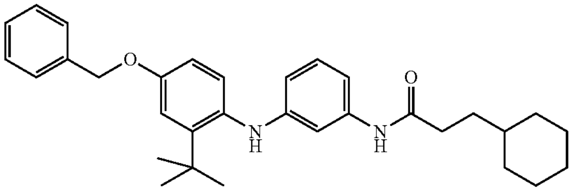

-continued
92
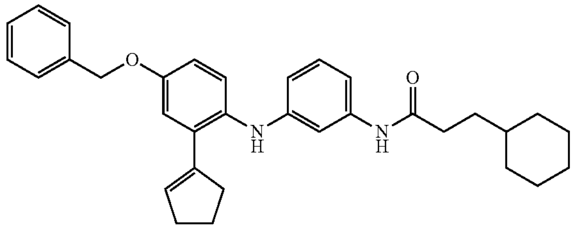
93
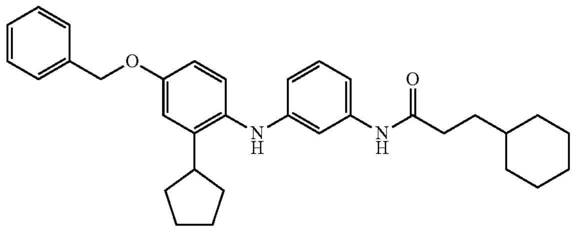
94
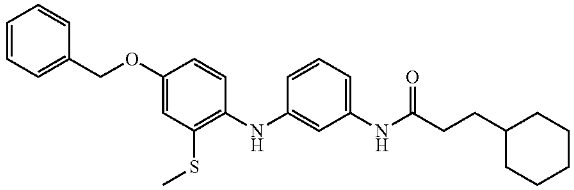
95
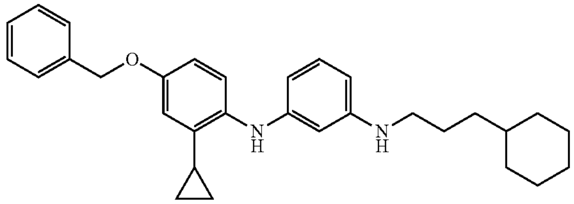
96
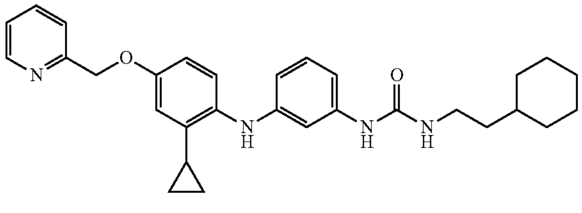
97
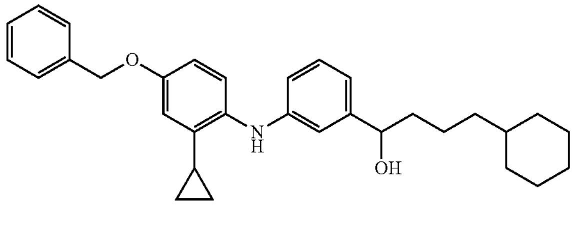
-continued
98
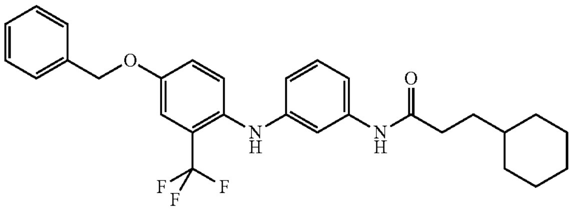
99
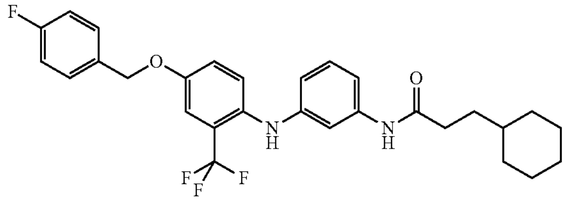
100
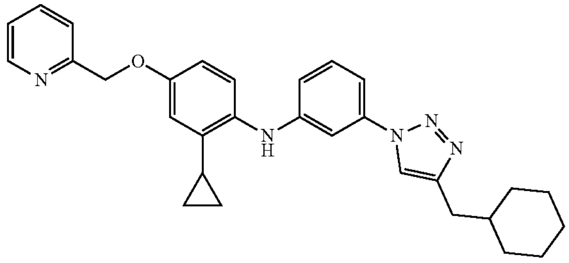
101
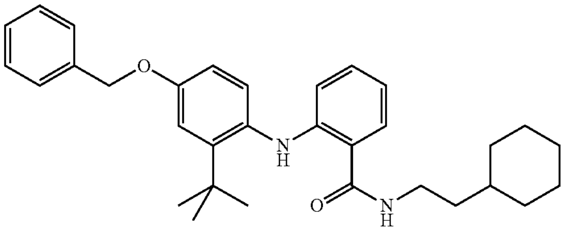
102
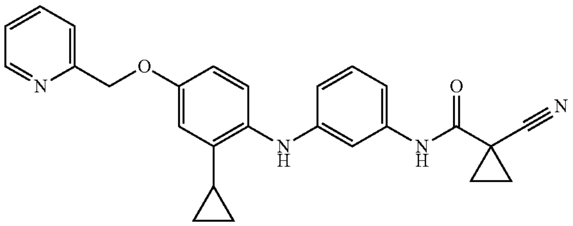
103
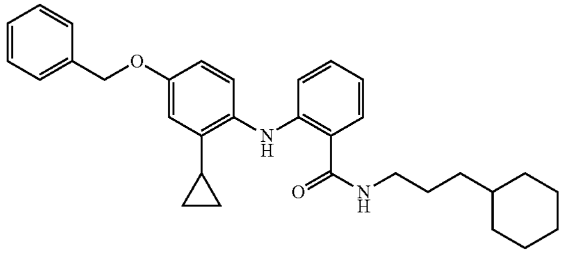

-continued
104
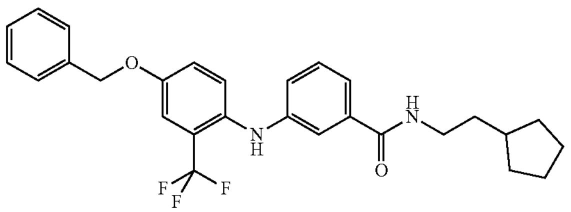
105
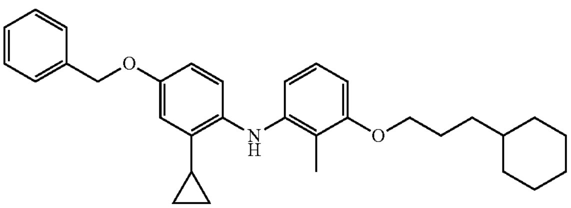
106
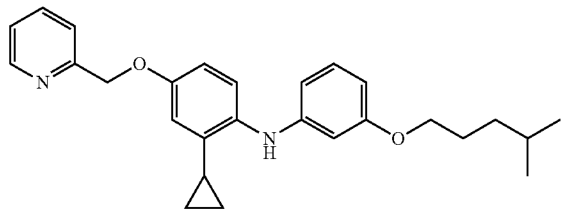
107
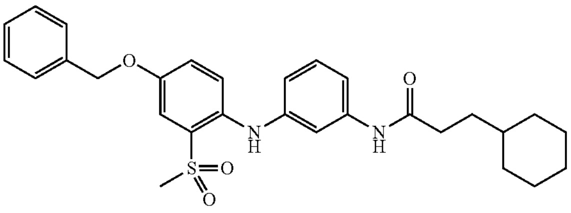
108
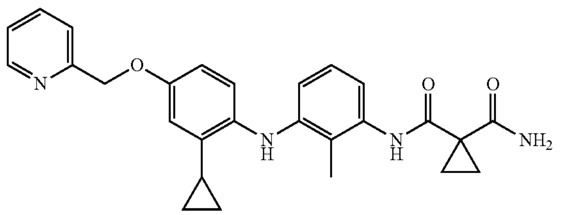
109
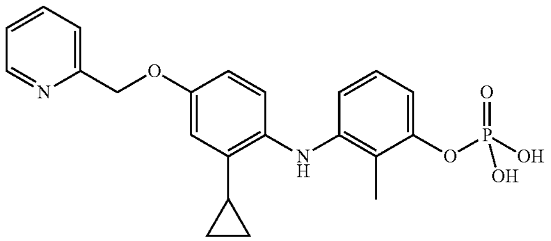
-continued
110
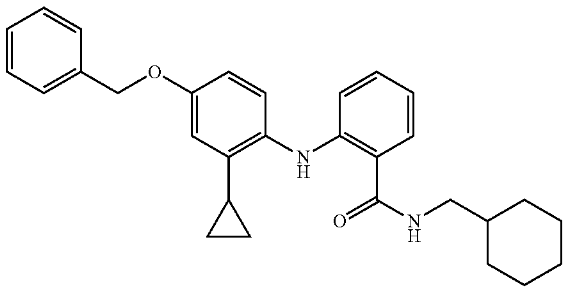
111
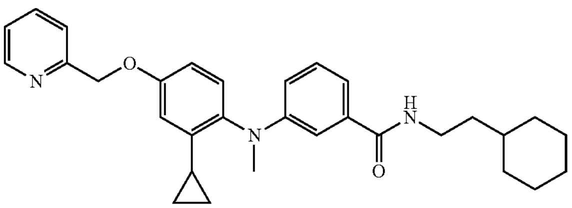
112
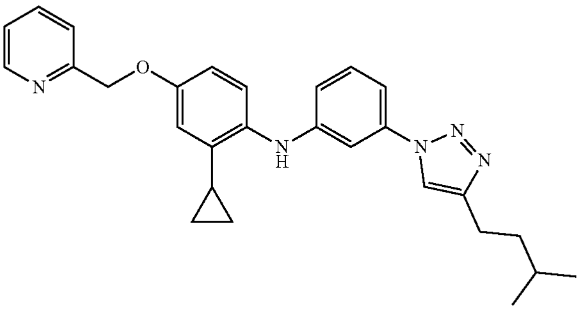
113
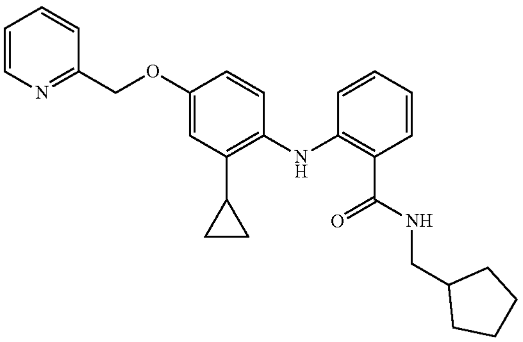
114
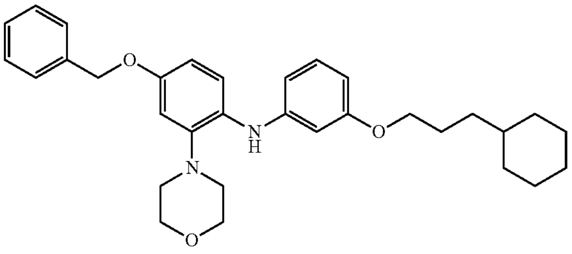

-continued
115
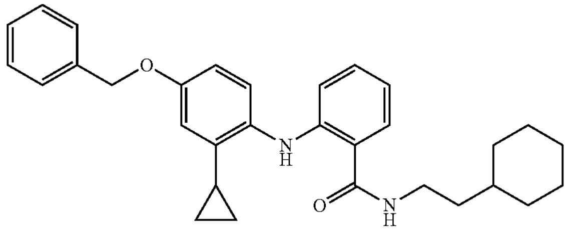
116
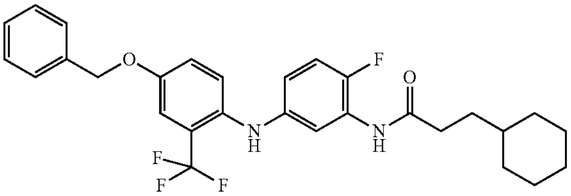
117
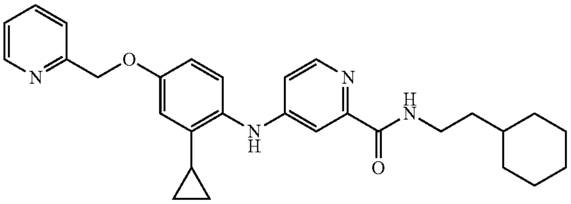
118
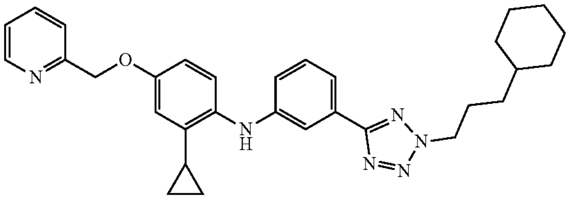
119
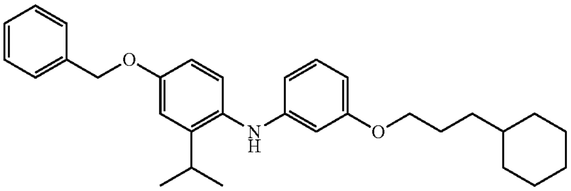
120
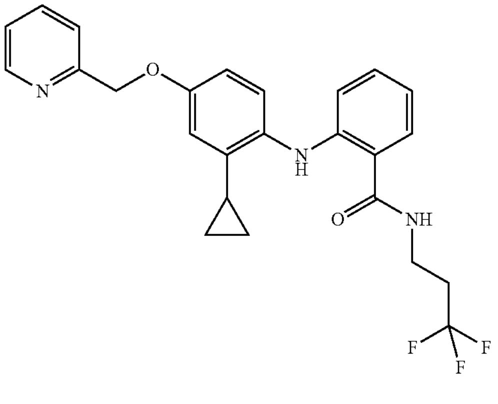
-continued
121
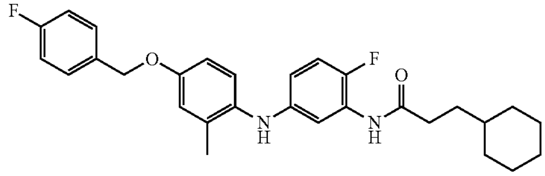
122
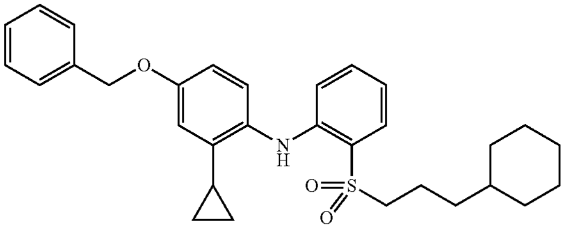
123
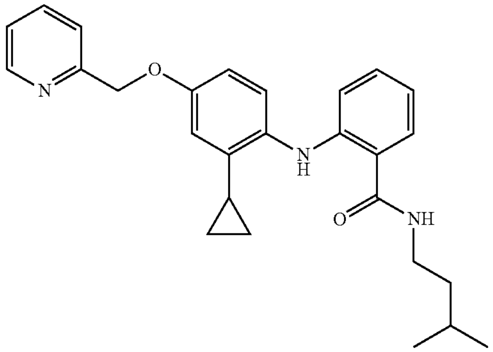
124
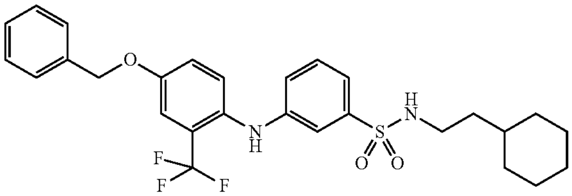
125
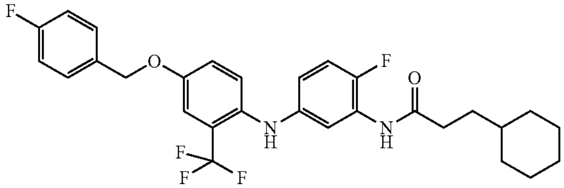
126
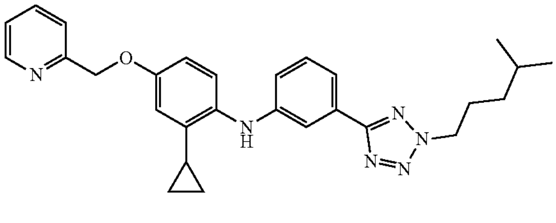

-continued
127
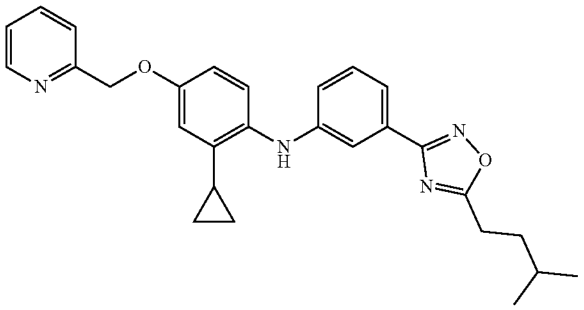
128
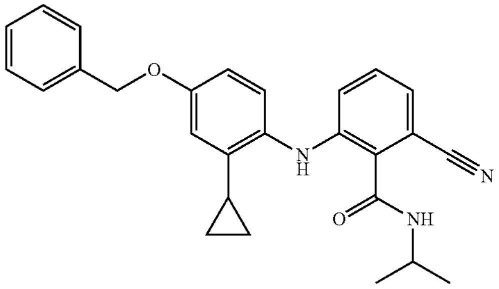
129
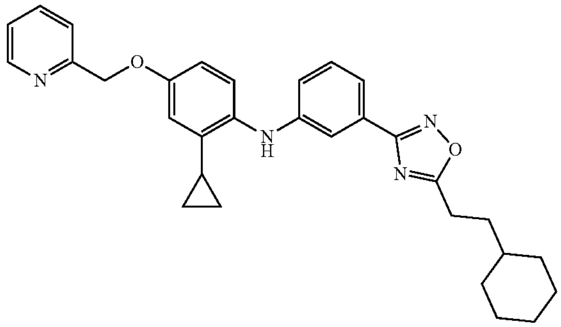
130
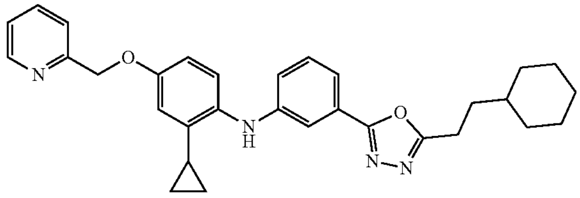
131
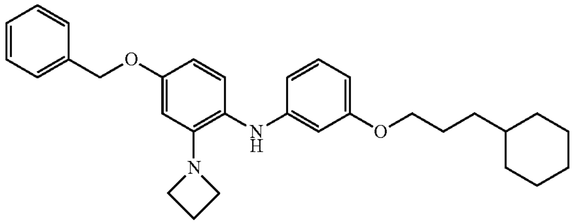
-continued
132
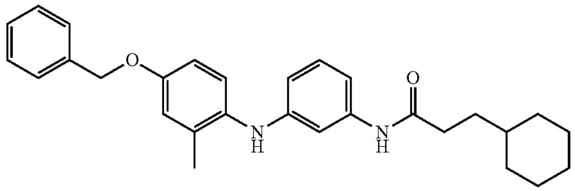
133
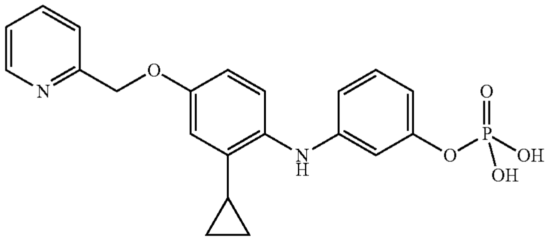
134
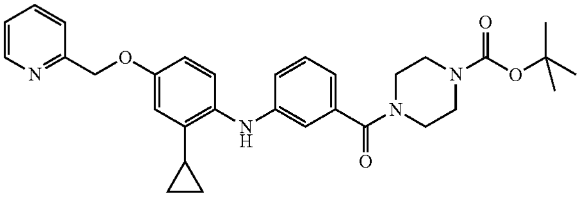
135
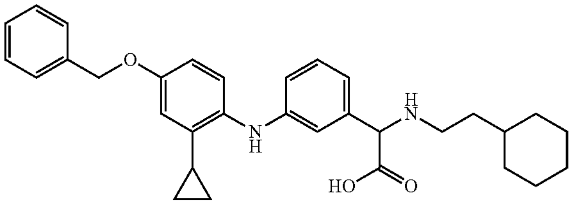
136
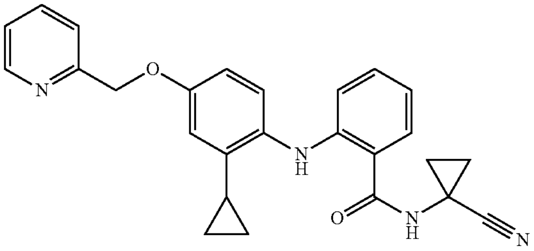
137
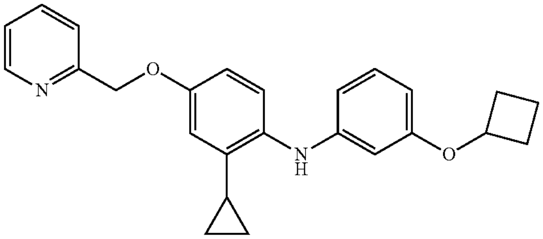

-continued
138
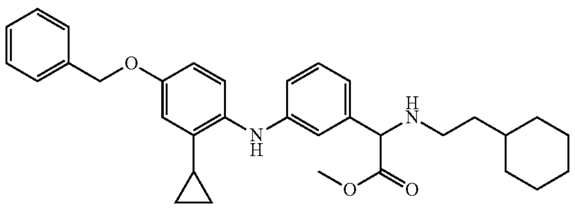
139
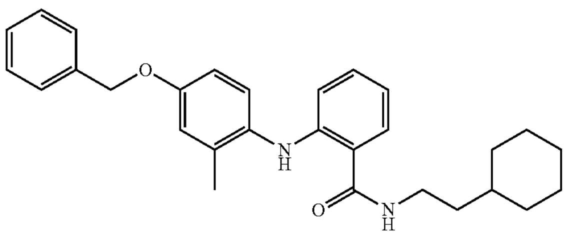
140
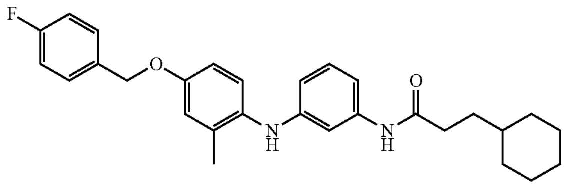
141
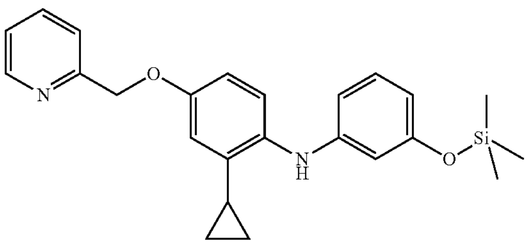
142
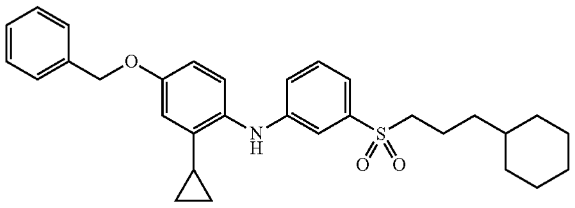
143
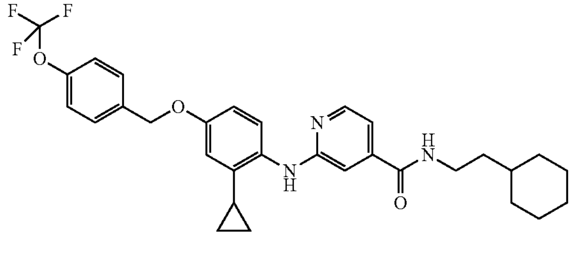
-continued
144
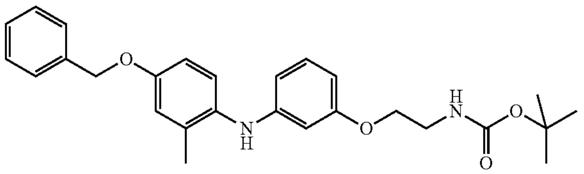
145
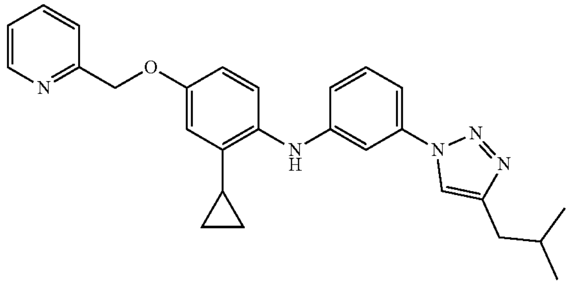
146
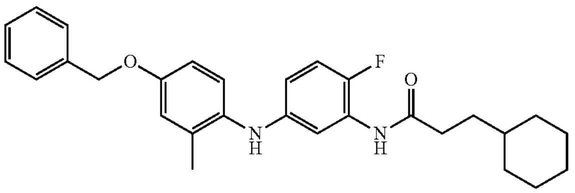
147
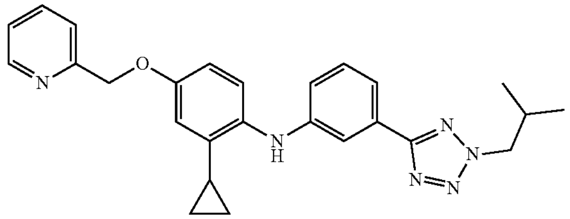
148
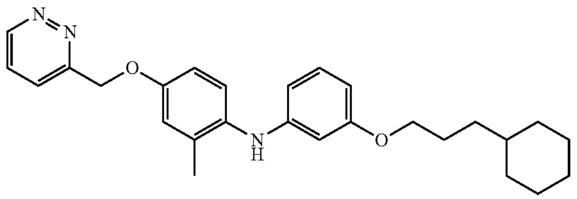
149
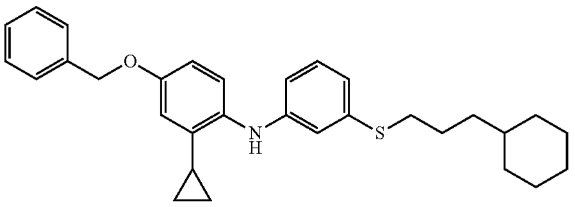

-continued
150
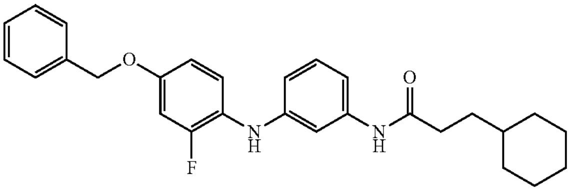
151
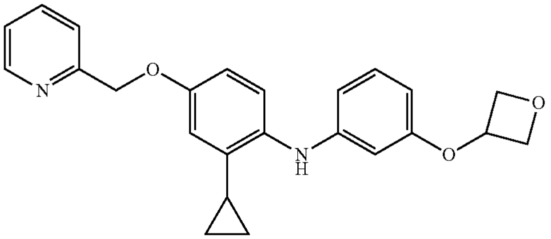
152
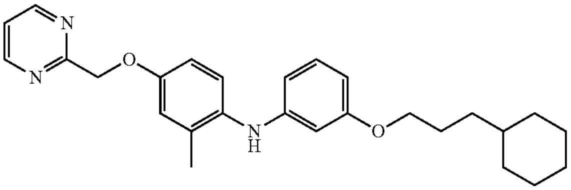
153
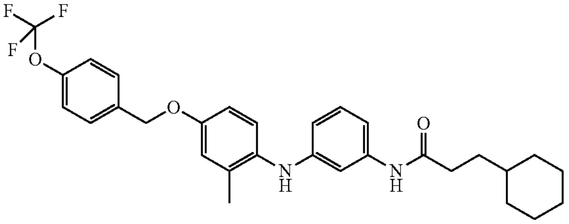
154
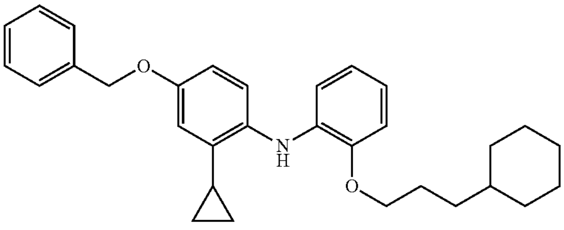
155
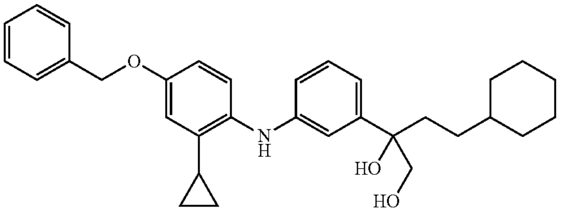
-continued
156
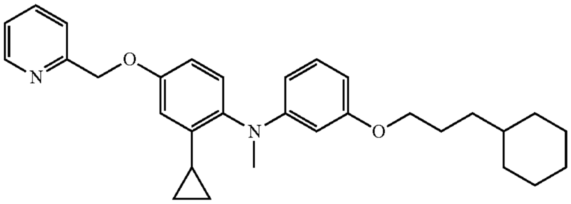
157
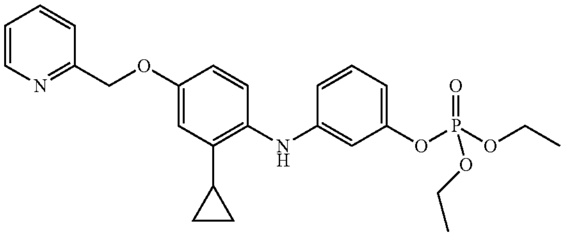
158
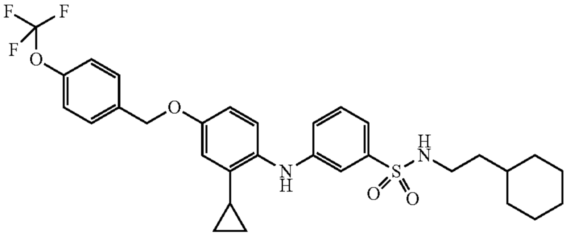
159
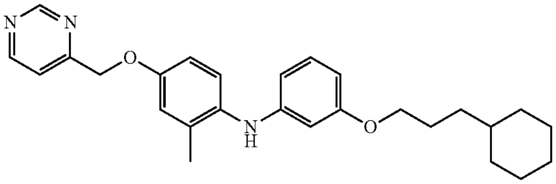
160
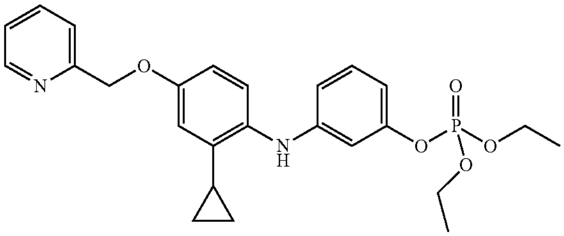
161
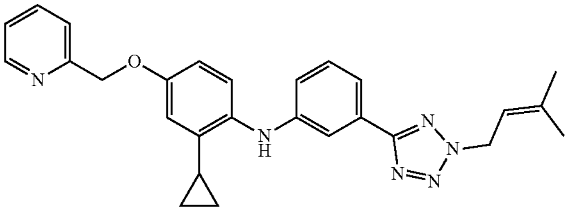

-continued
162
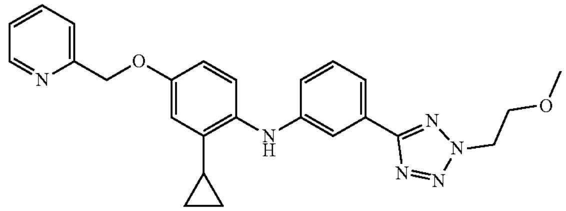
163
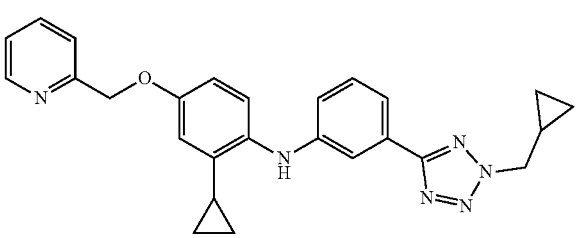
164
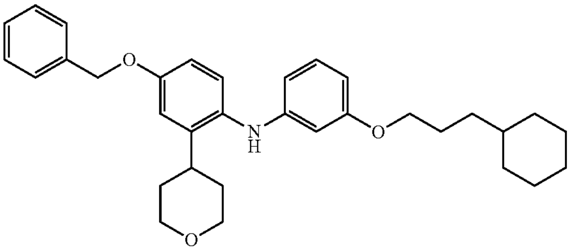
165
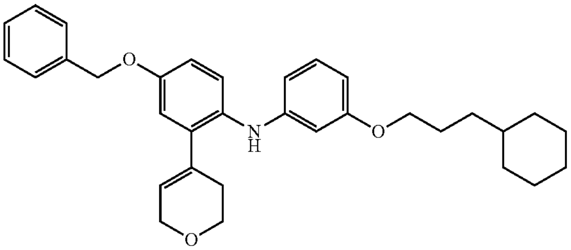
166
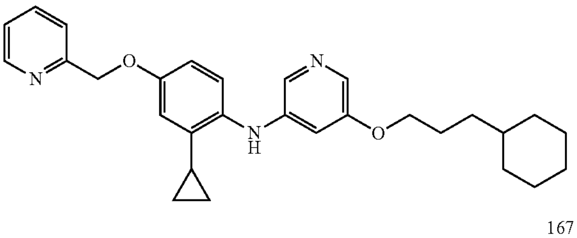
167
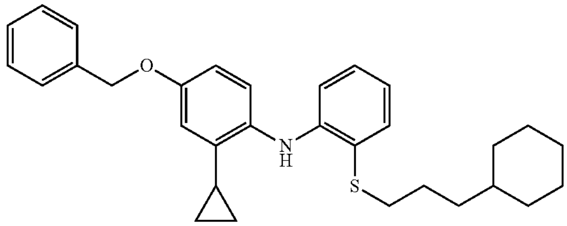
-continued
168
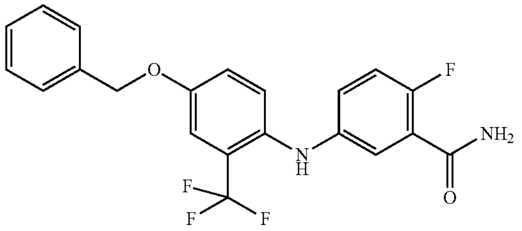
169
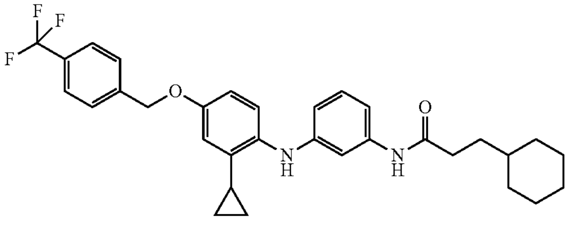
170
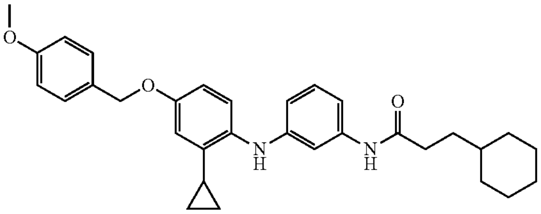
171
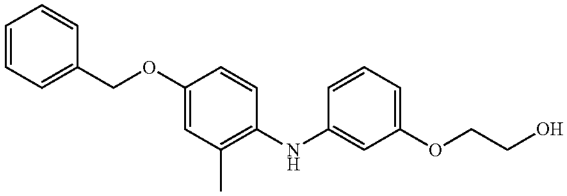
172
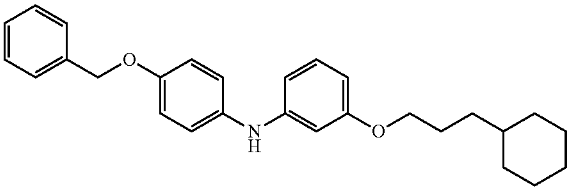
173
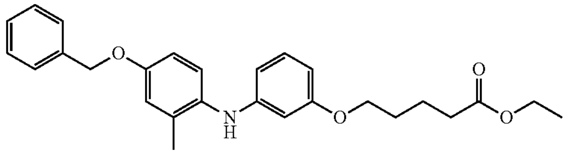
174
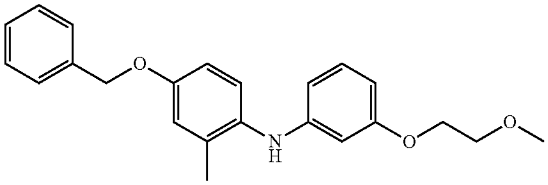

-continued
175
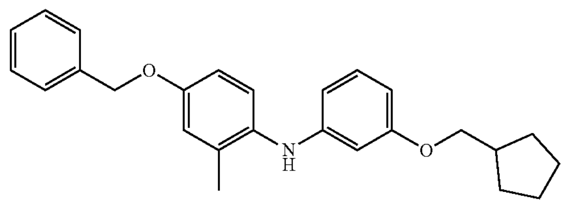
176
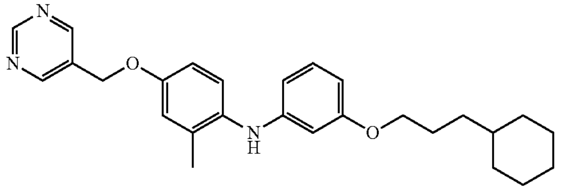
177
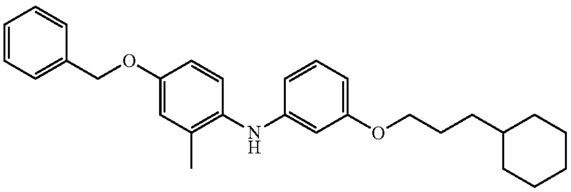
178
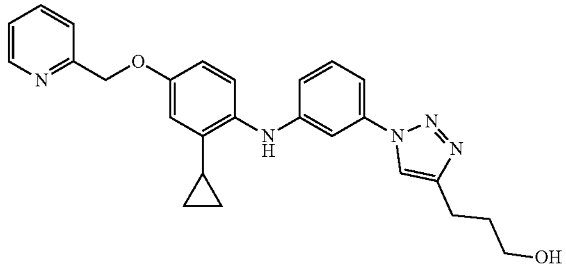
179
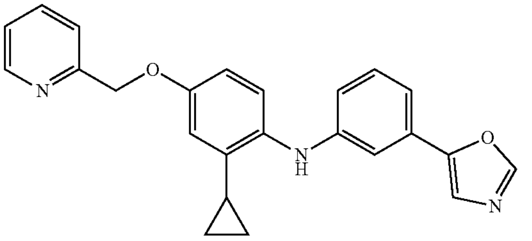
180
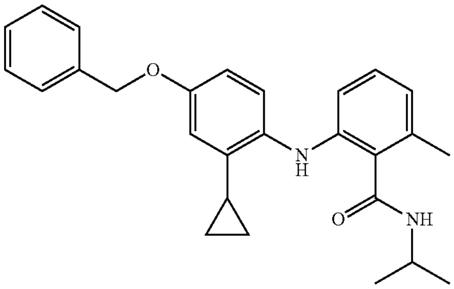
-continued
181
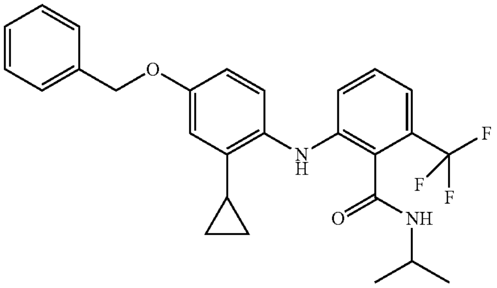
182
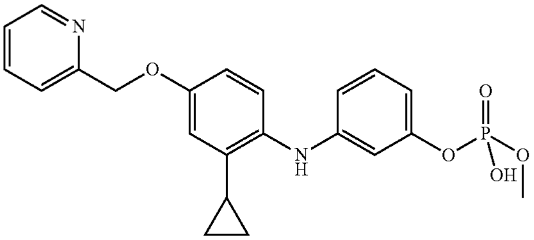
183
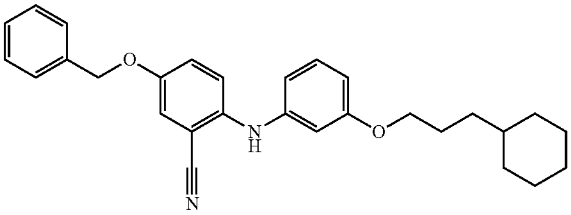
184
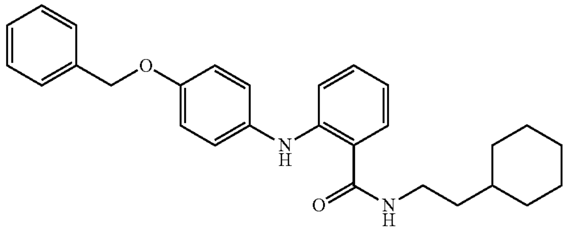
185
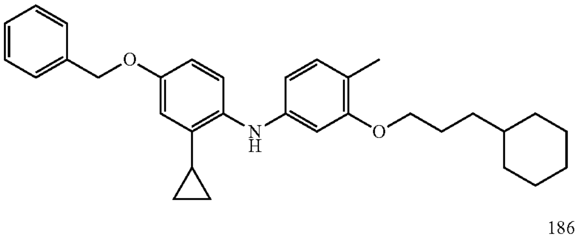
186
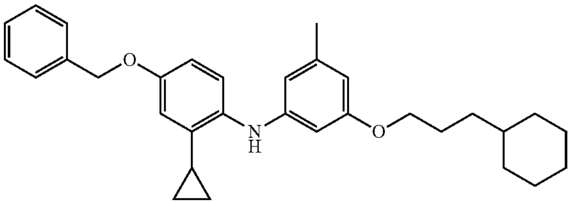

-continued
187
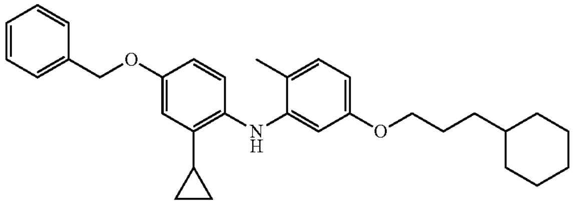
188
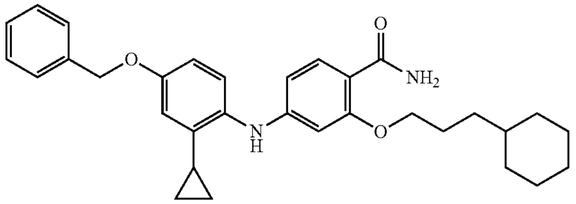
189
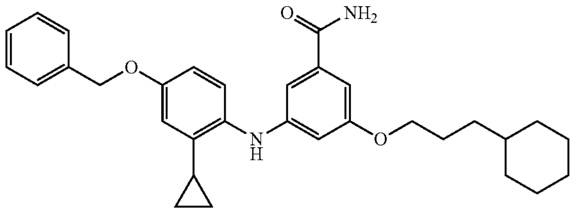
190
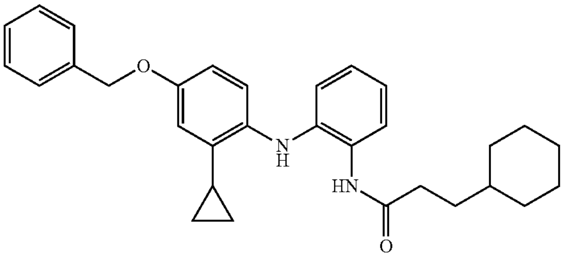
191
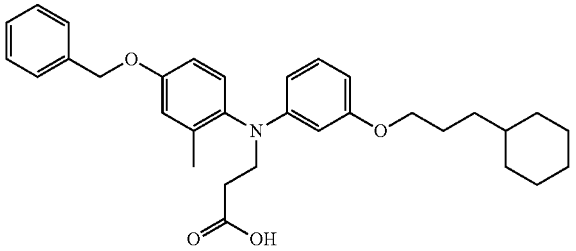
192
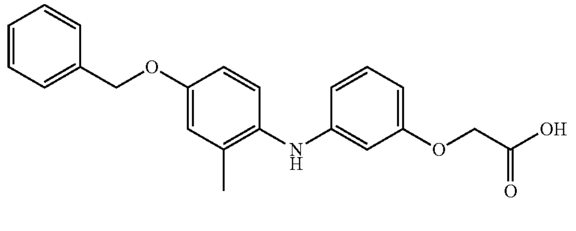
-continued
193
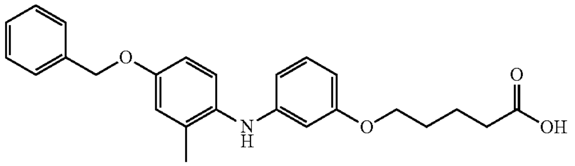
194
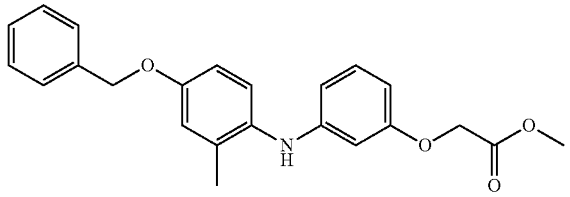
195
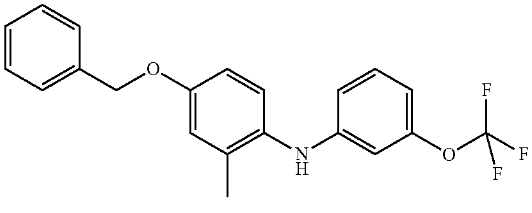
196
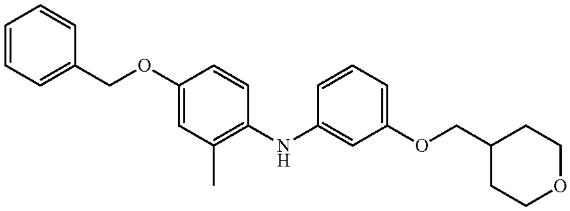
197
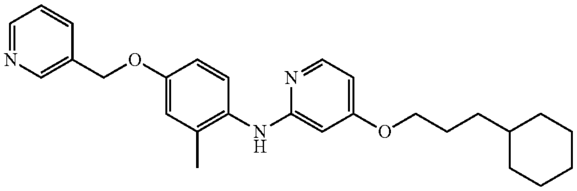
198
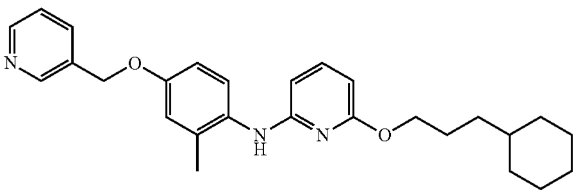
199
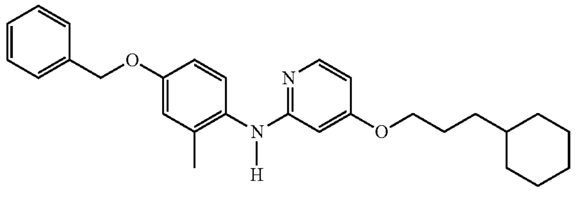

-continued
200
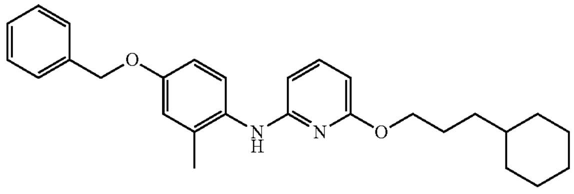
201
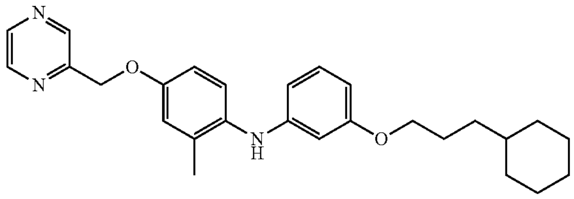
202
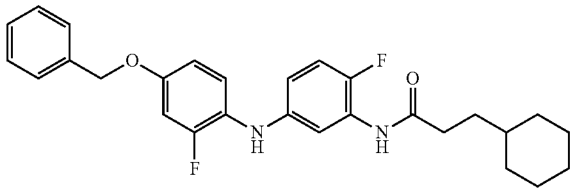
203
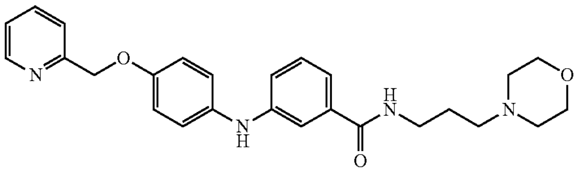
204
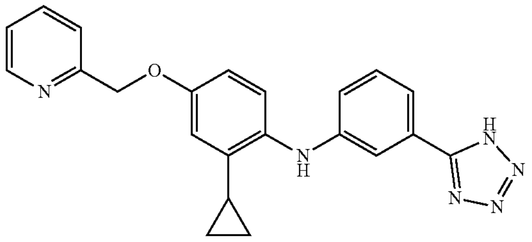
205
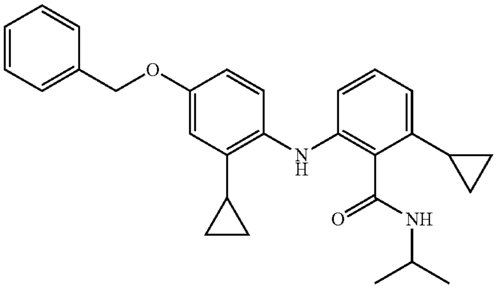
-continued
206
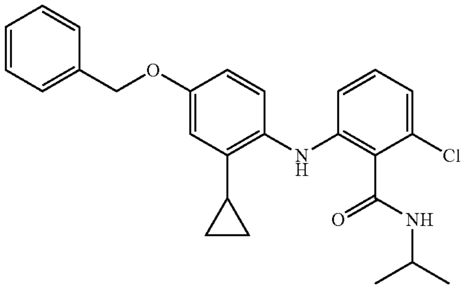
or a pharmaceutically acceptable salt thereof, and
at least one pharmaceutically acceptable excipient.
13. A synthesis process for manufacturing the compound of formula (Ie) as defined in claim 1 or a pharmaceutically acceptable salt thereof, or any of the following compounds (36) to (206) or a pharmaceutically acceptable salt thereof:
36
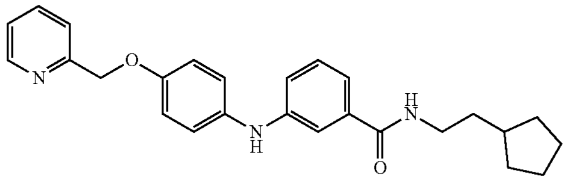
37
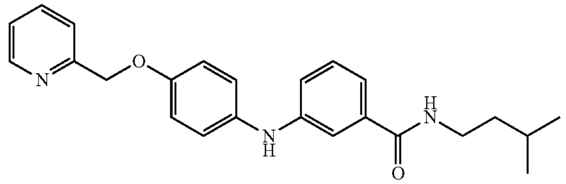
38
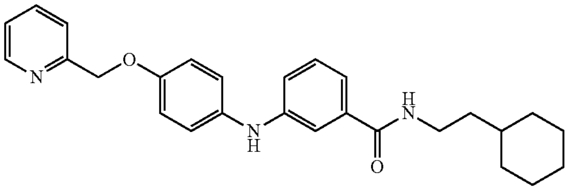
39
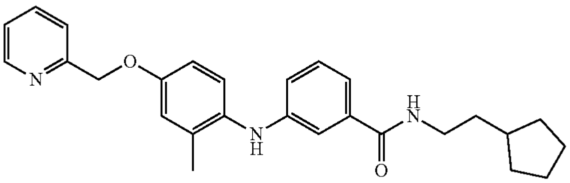
40
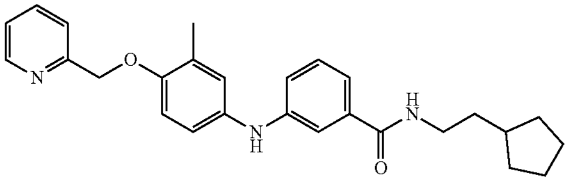

-continued
41
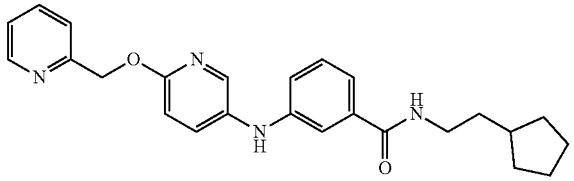
42
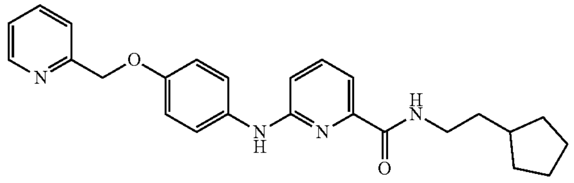
43
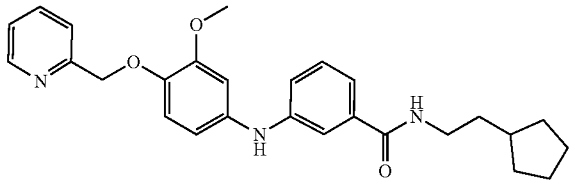
44
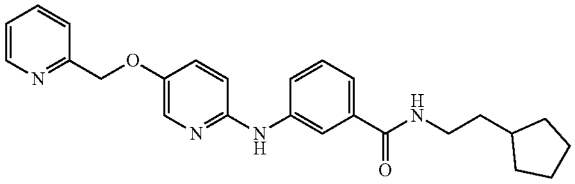
45
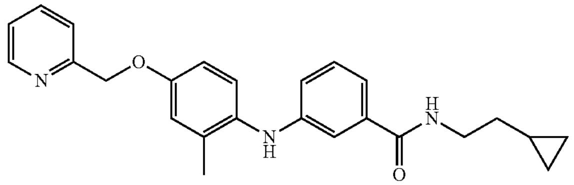
46
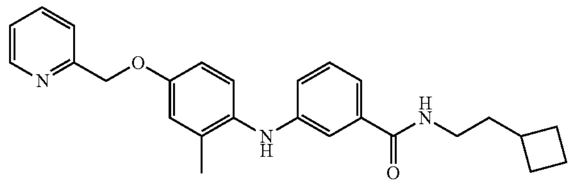
47
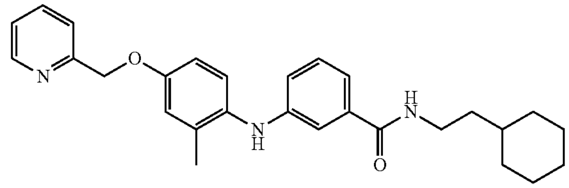
-continued
48
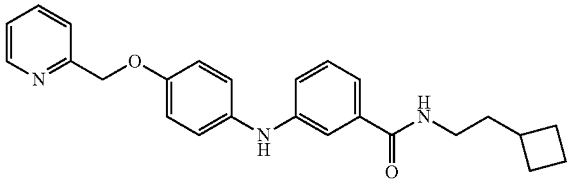
49
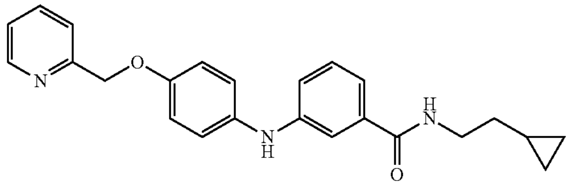
50
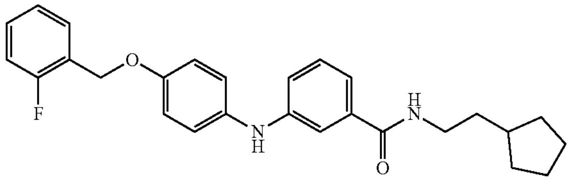
51
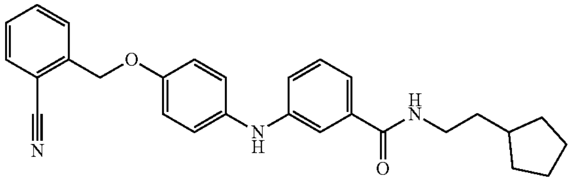
52
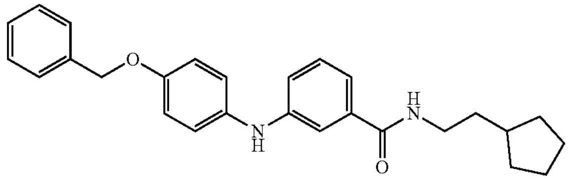
53
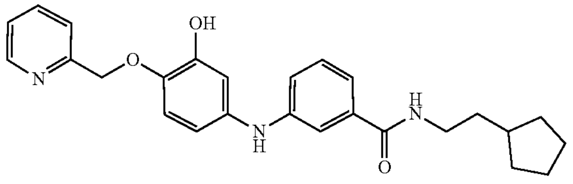
54
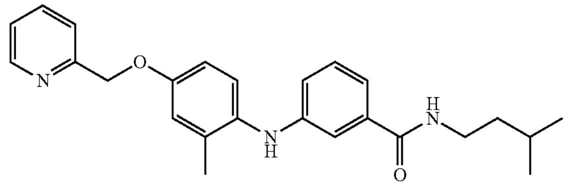

-continued
55
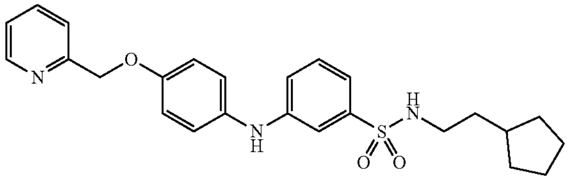
56
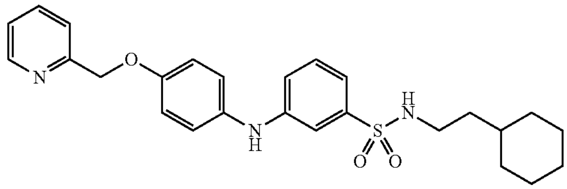
57
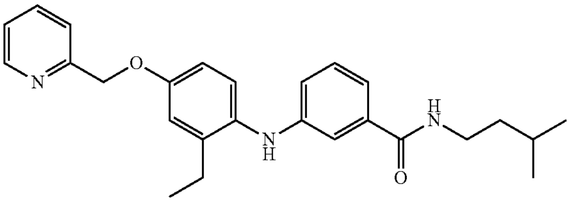
58
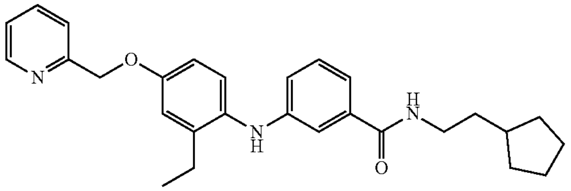
59
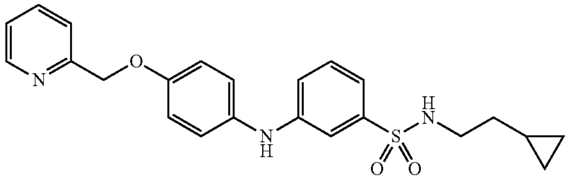
60
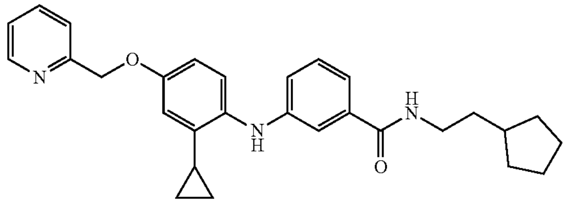
61
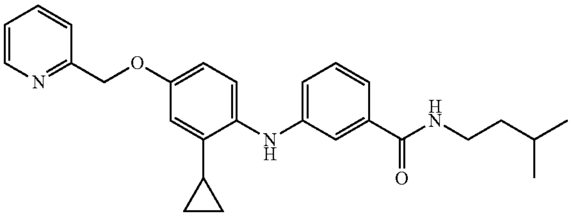
-continued
62
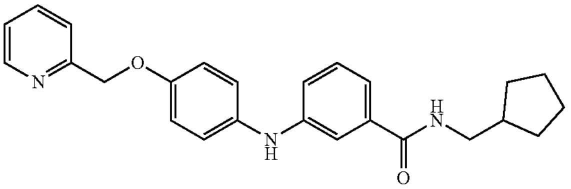
63
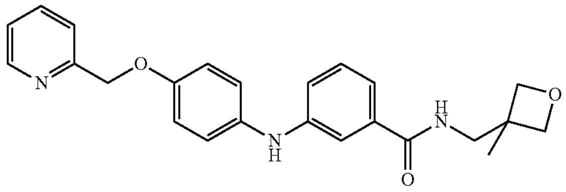
64
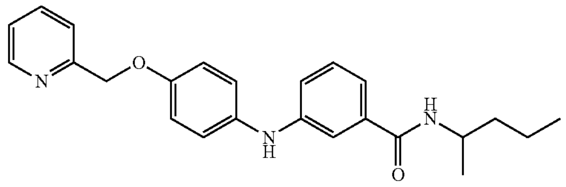
65
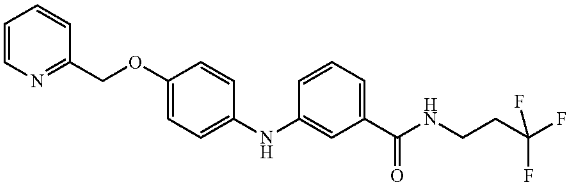
66
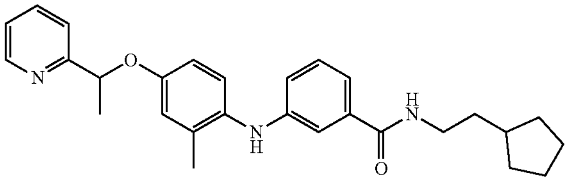
67
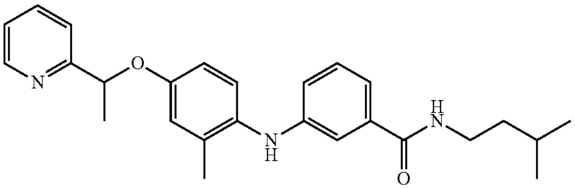
68
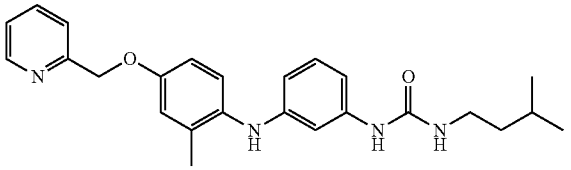

-continued
69
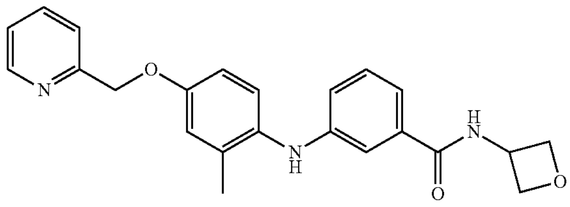
70
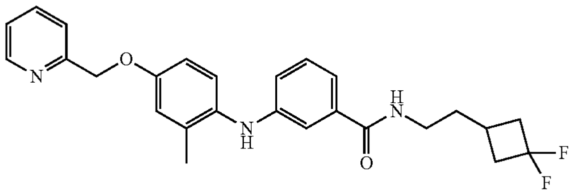
71
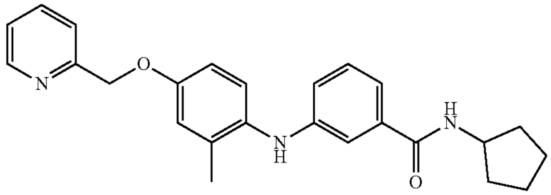
72
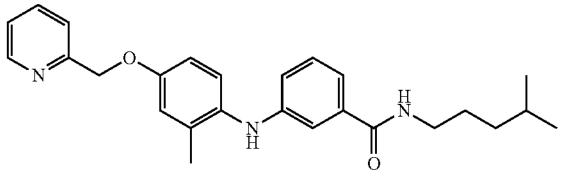
73
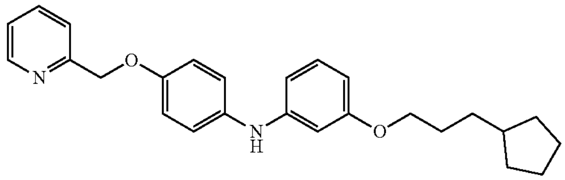
74
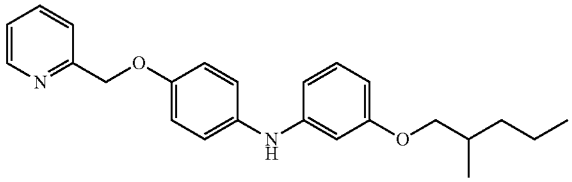
75
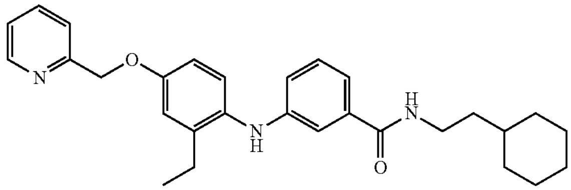
-continued
76
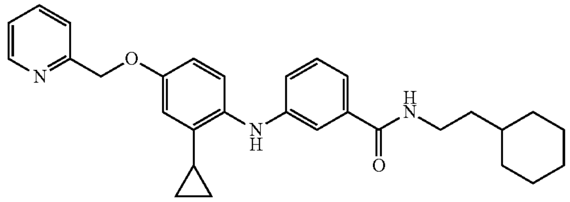
77
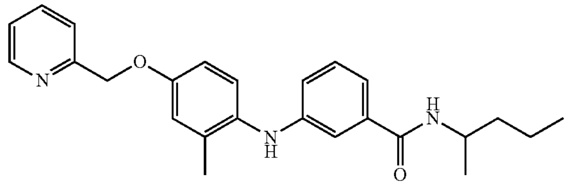
78
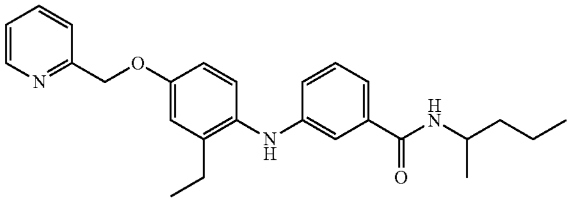
79
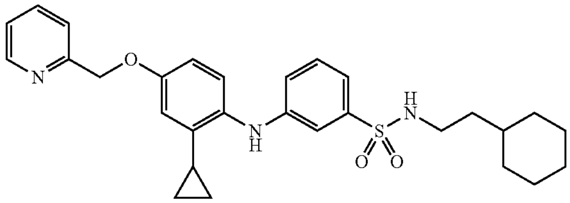
80
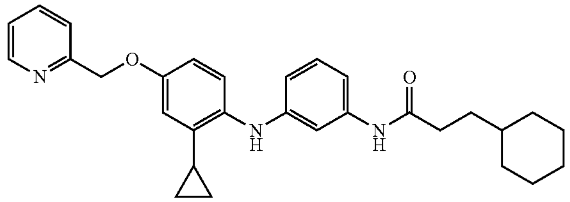
81
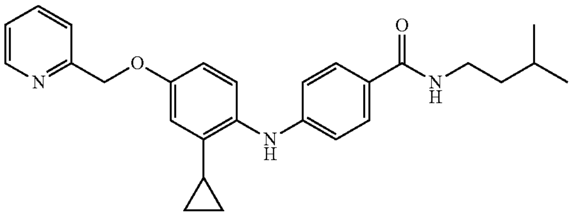
82
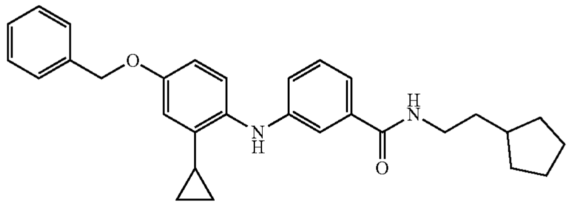

-continued
83
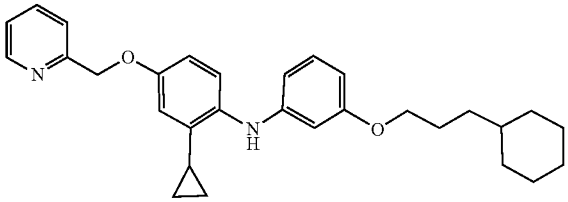
84
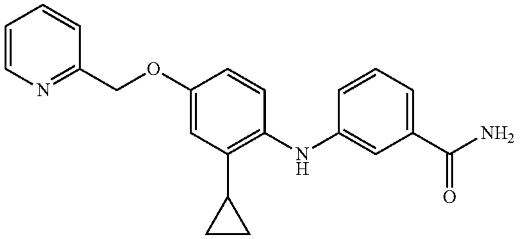
85
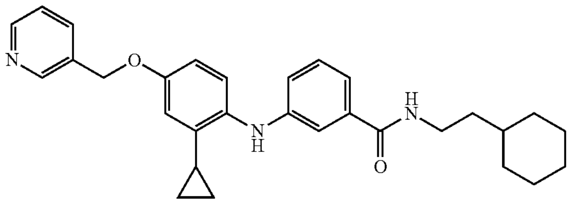
86
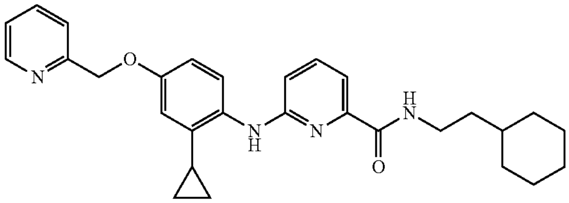
87
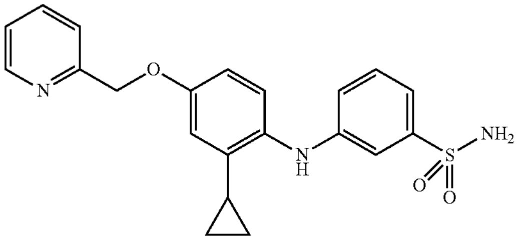
88
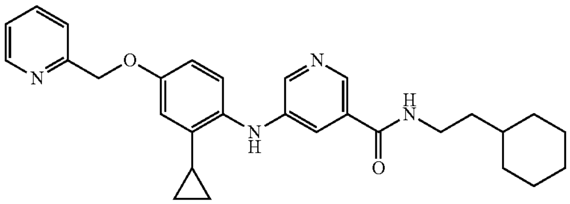
-continued
89
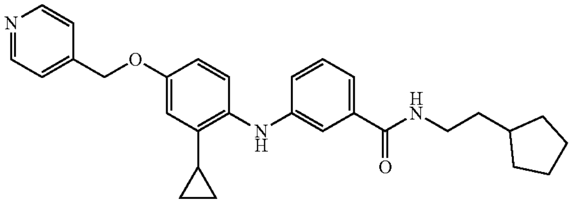
90
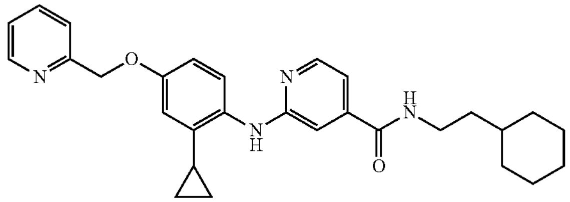
91
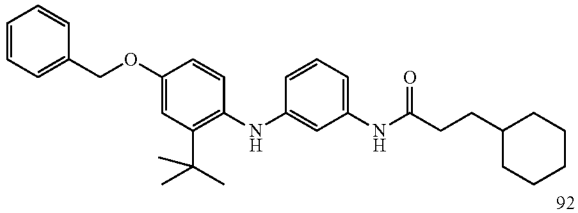
92
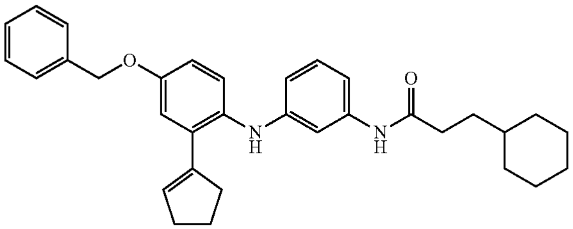
93
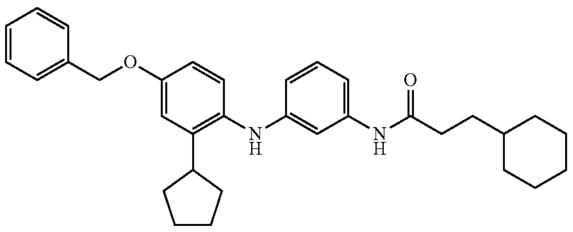
94
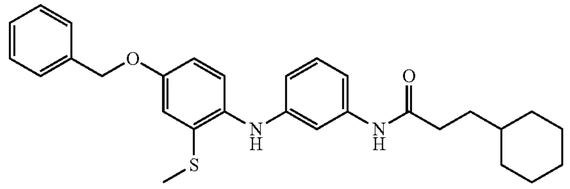
95
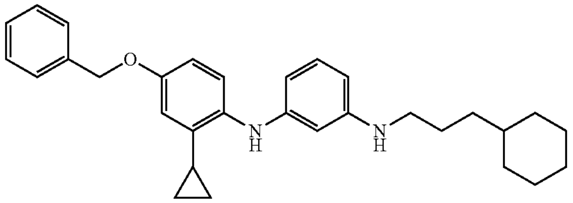

96
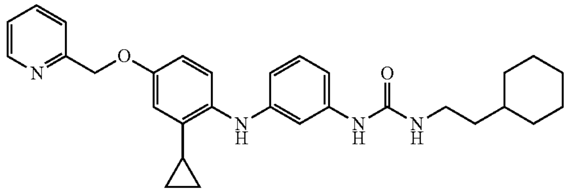
97
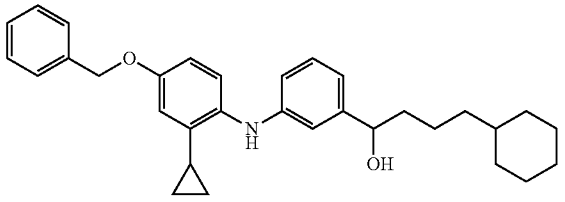
98
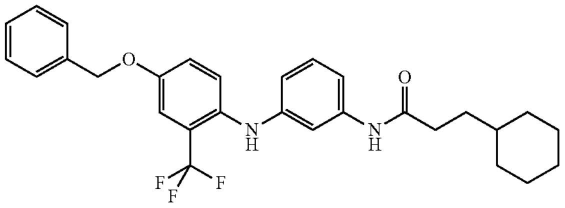
99
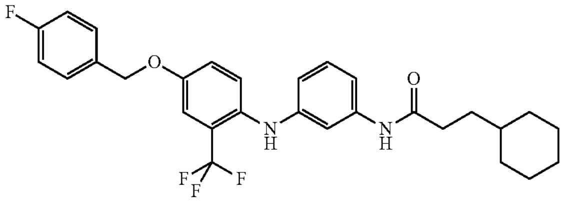
100
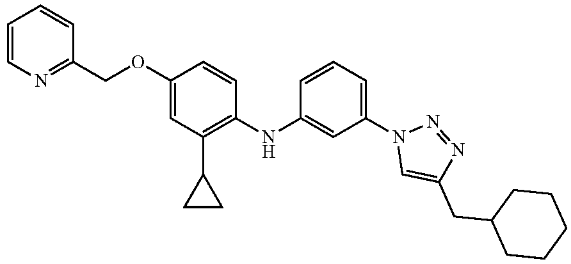
101
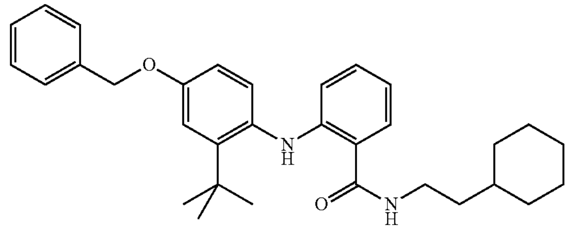
102
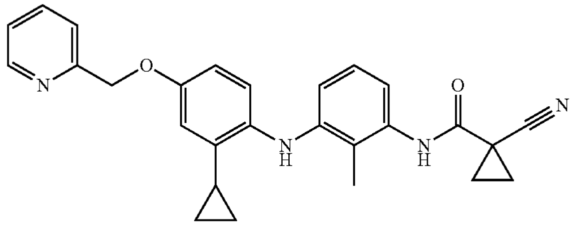
103
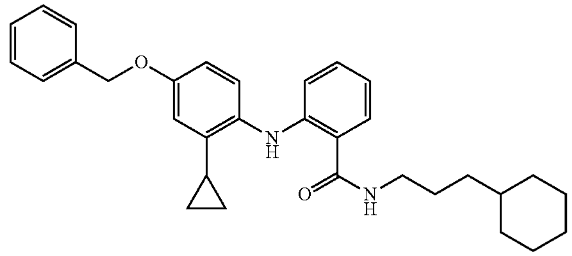
104
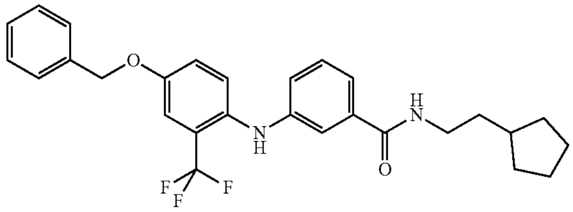
105
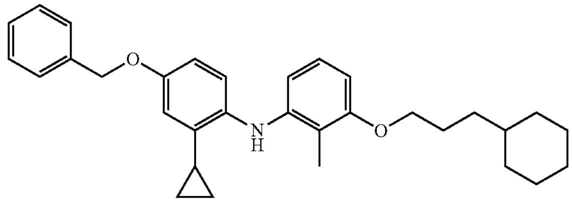
106
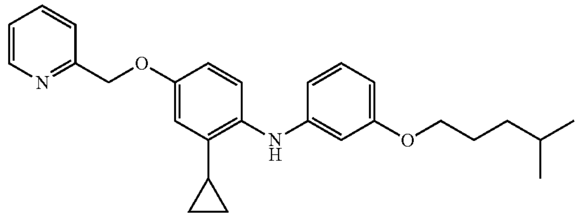
107
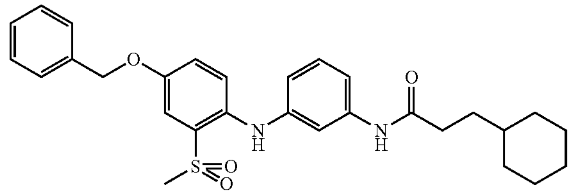

-continued
108
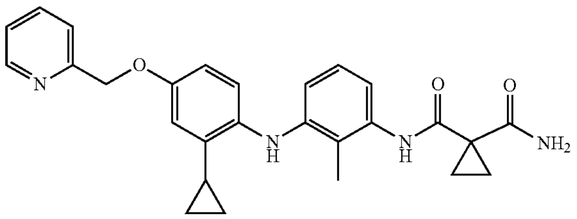
109
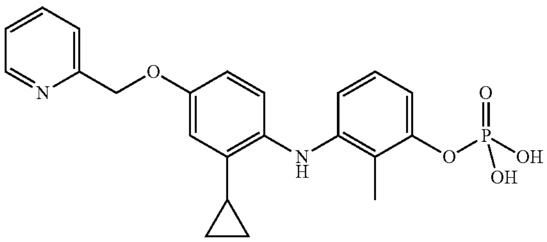
110
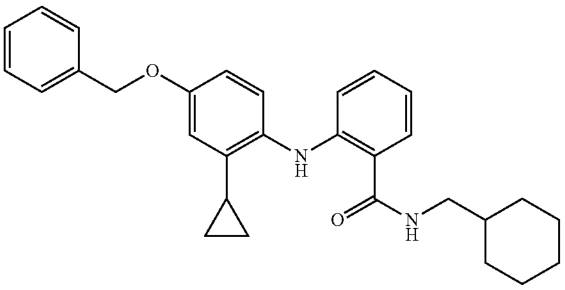
111
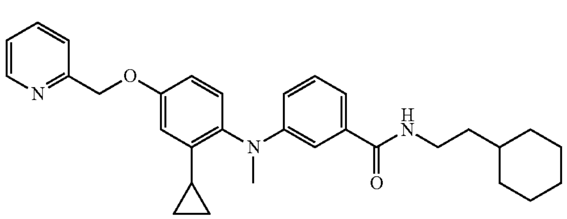
112
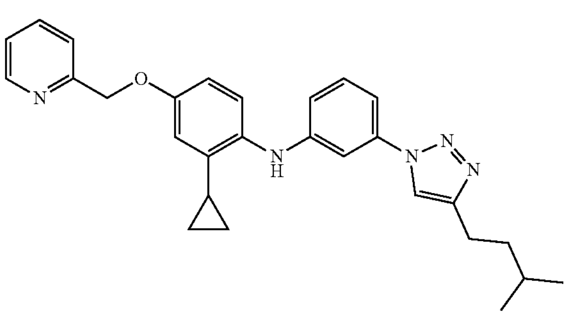
-continued
113
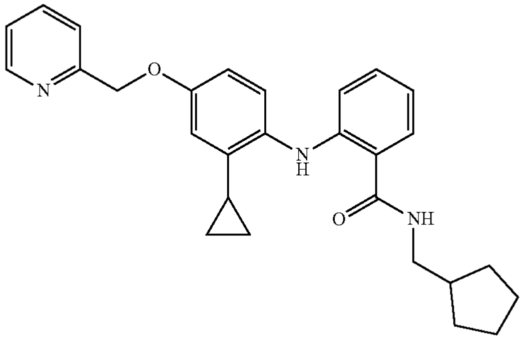
114
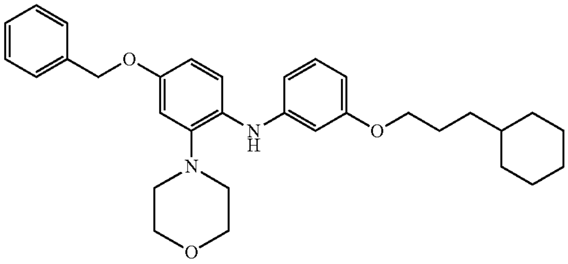
115
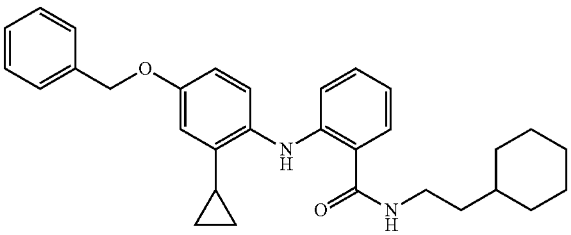
116
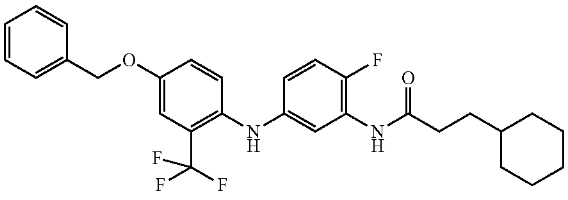
117
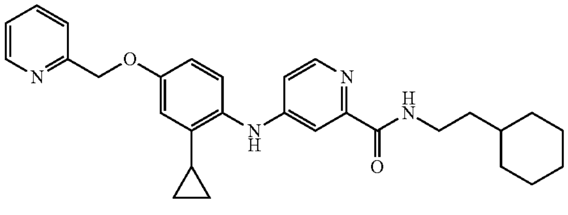
118
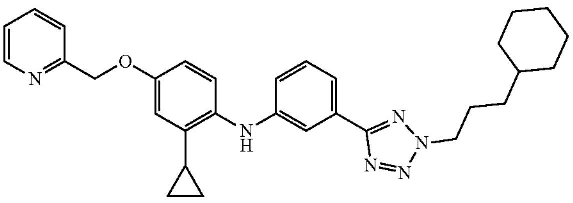

119
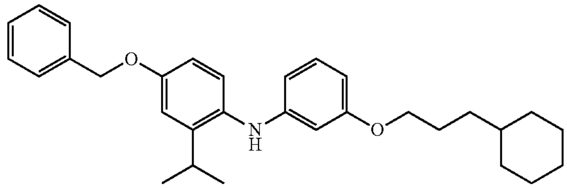
120
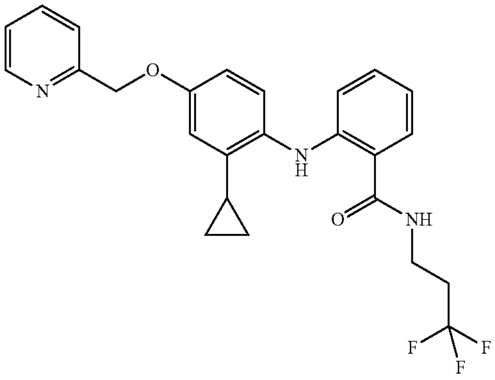
121
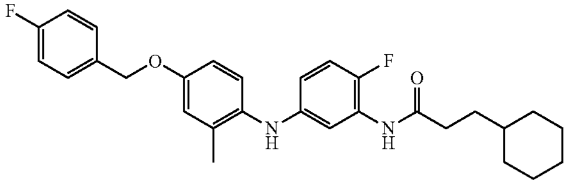
122
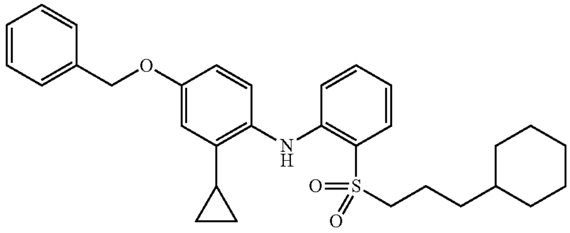
123
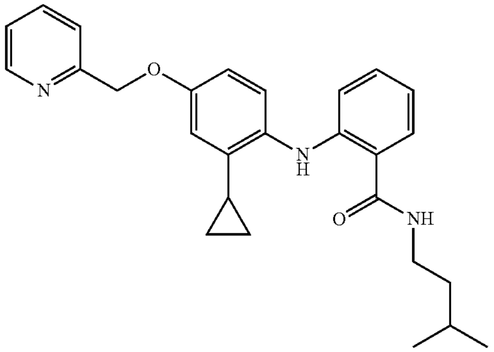
124
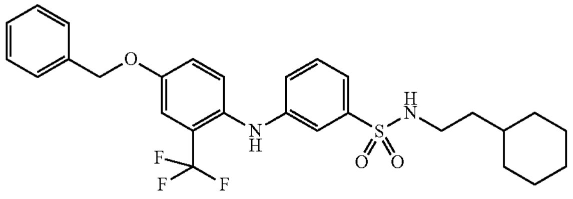
125
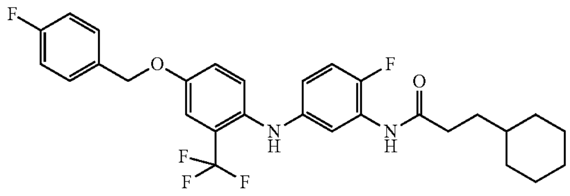
126
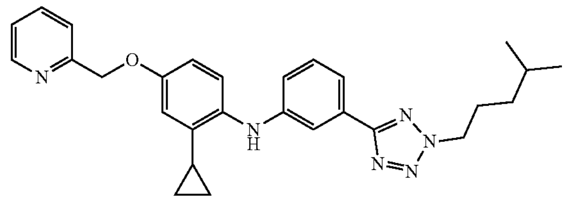
127
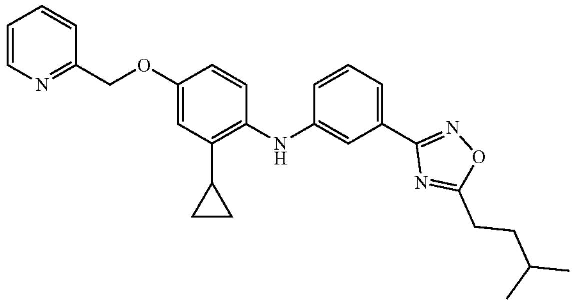
128
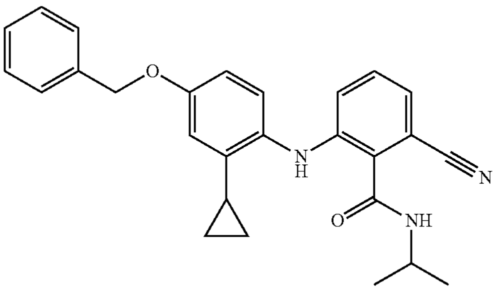
129
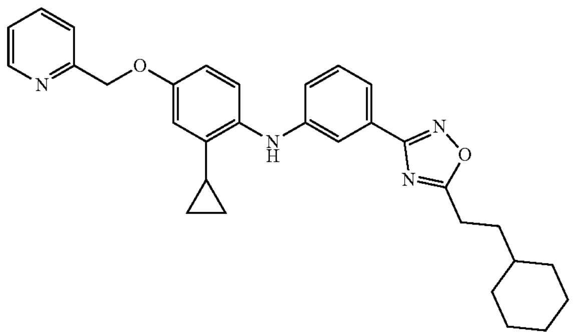

-continued
130
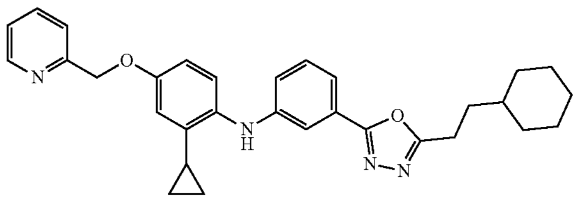
131
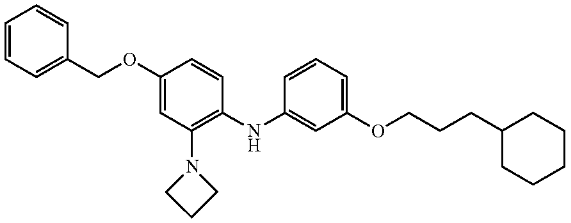
132
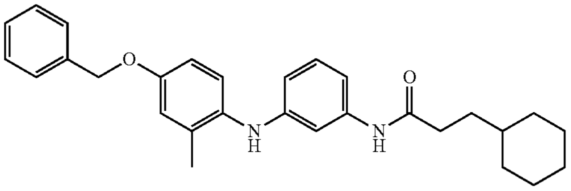
133
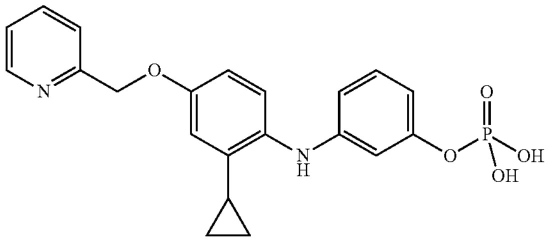
134
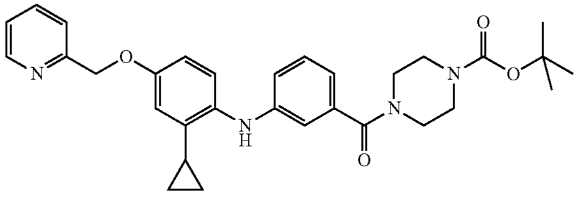
135
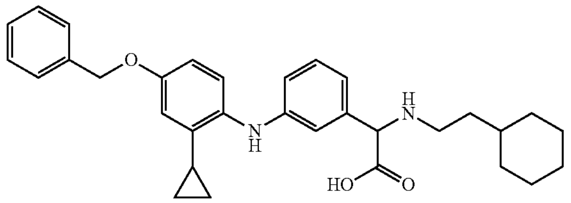
-continued
136
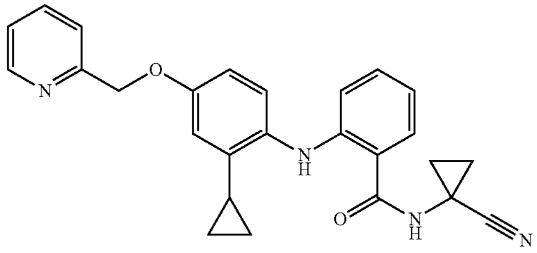
137
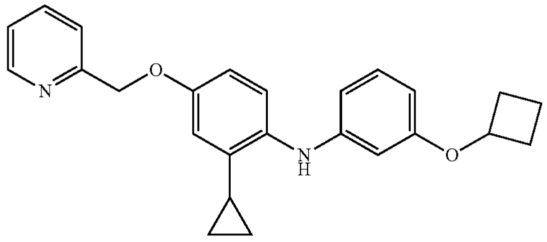
138
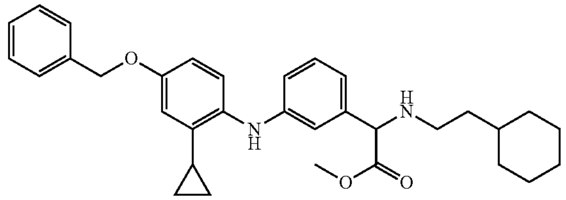
139
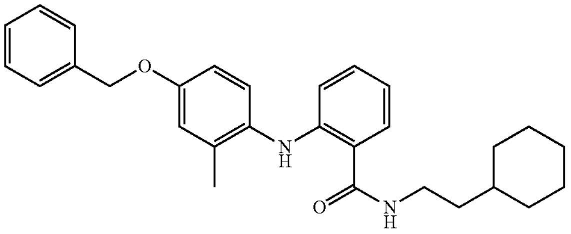
140
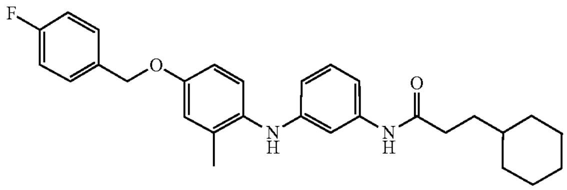
141
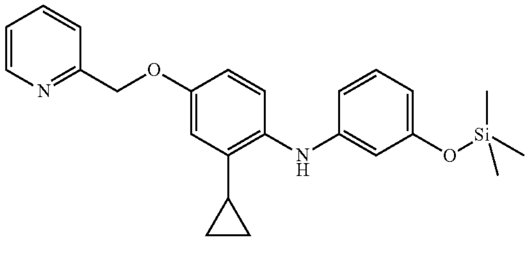

-continued
142
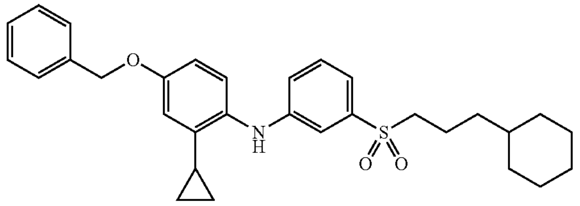
143
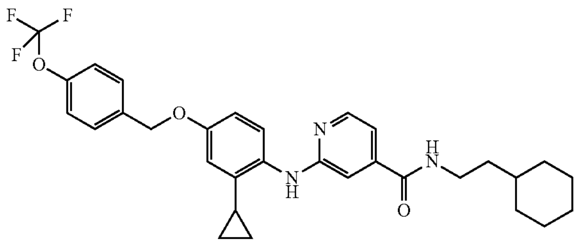
144
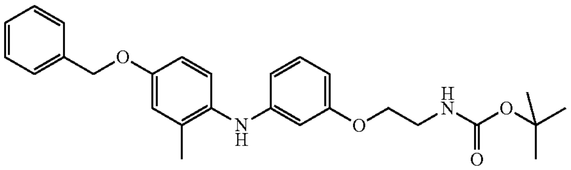
145
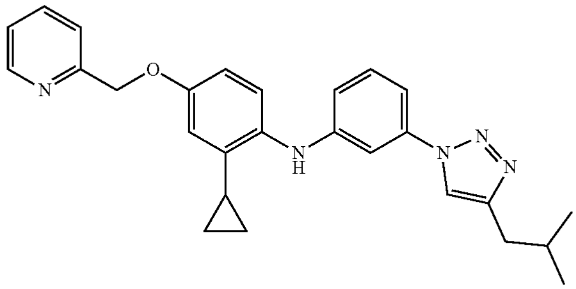
146
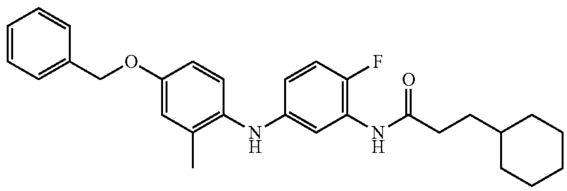
147
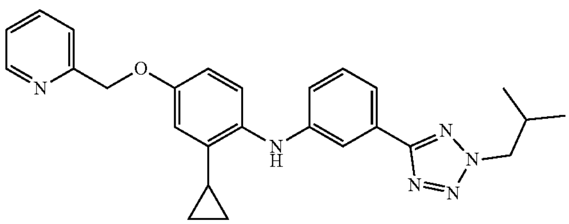
-continued
148
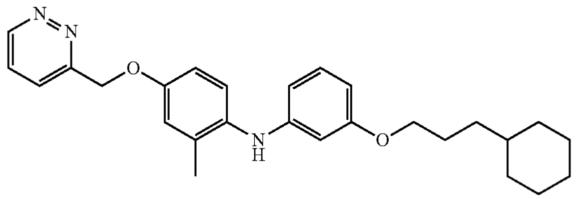
149
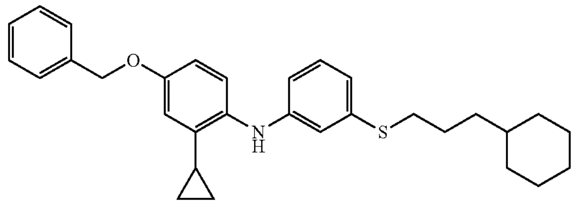
150
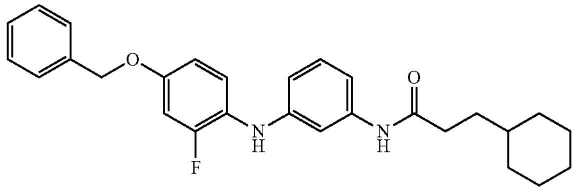
151
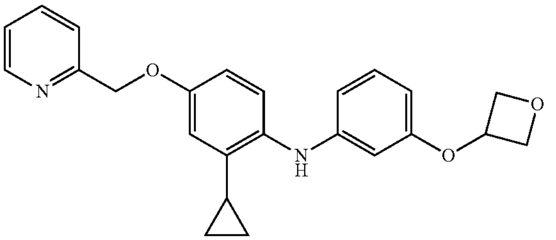
152
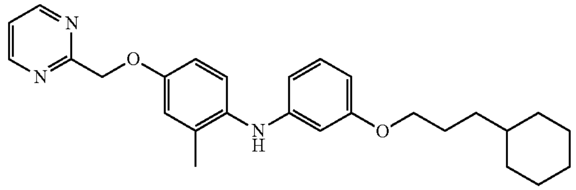
153
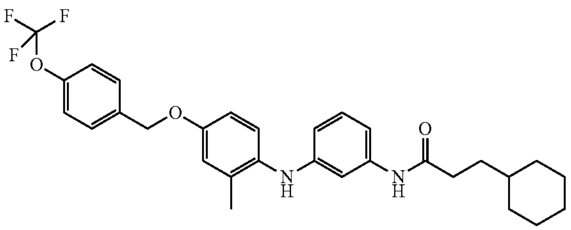

-continued
154
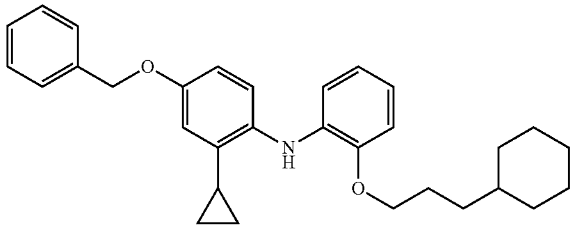
155
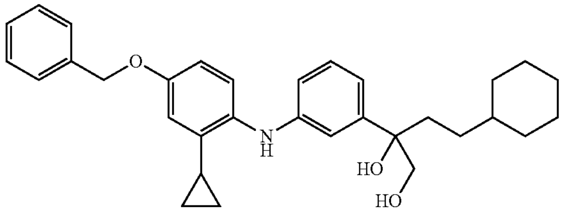
156
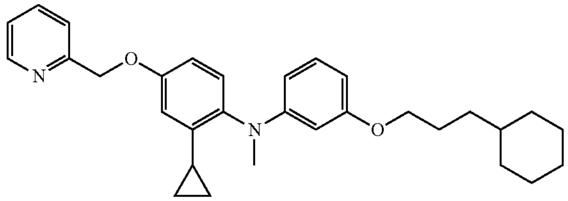
157
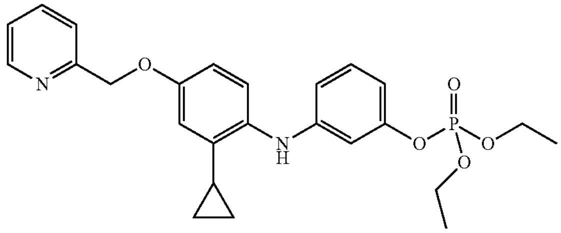
158
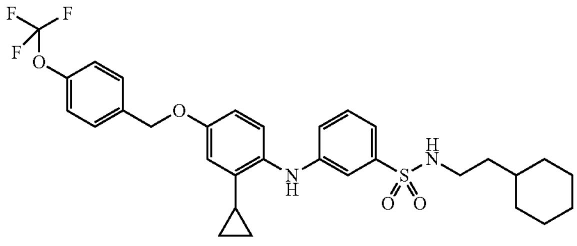
159
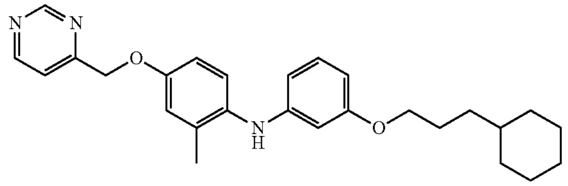
-continued
160
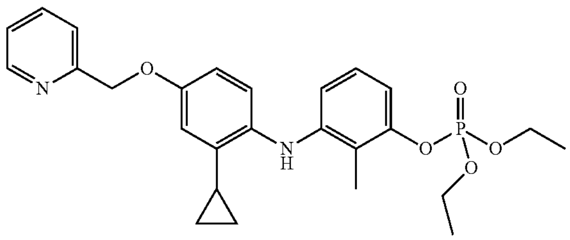
161
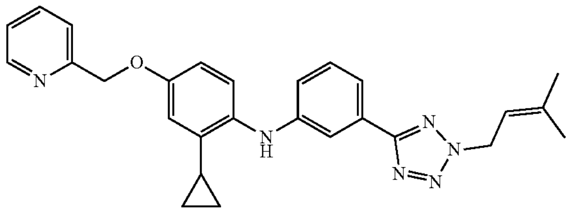
162
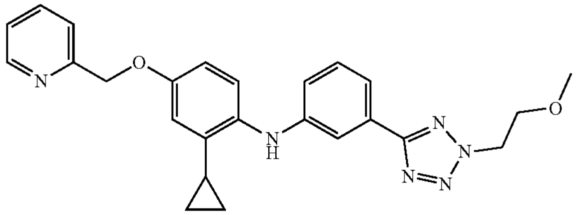
163
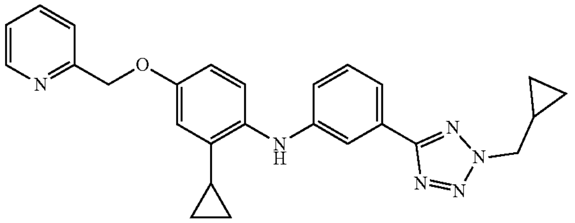
164
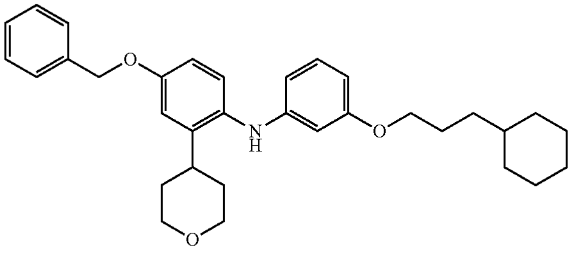
165
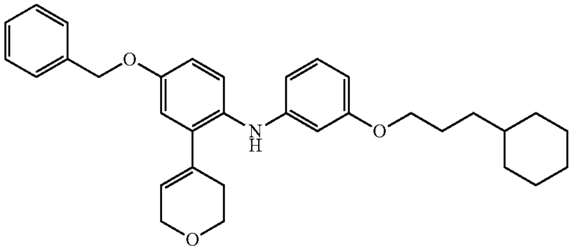

166
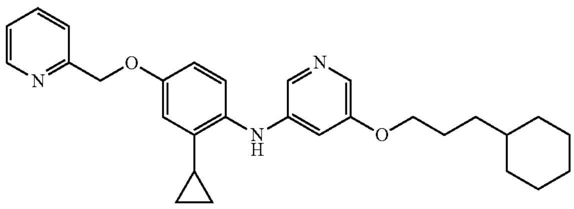
167
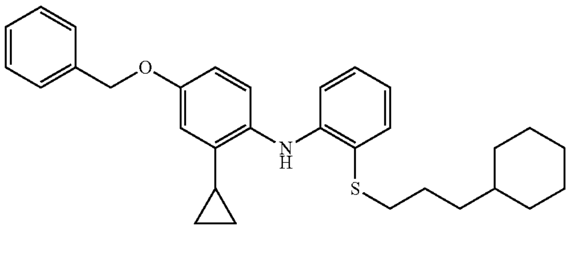
168
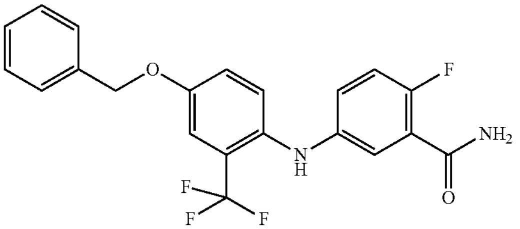
169
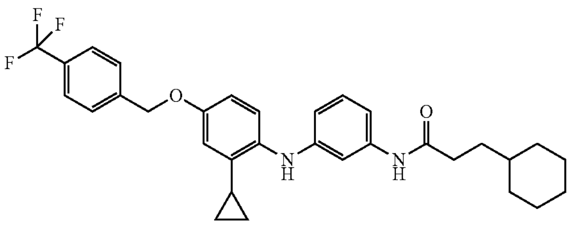
170
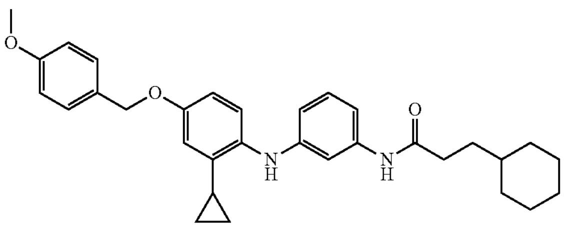
171
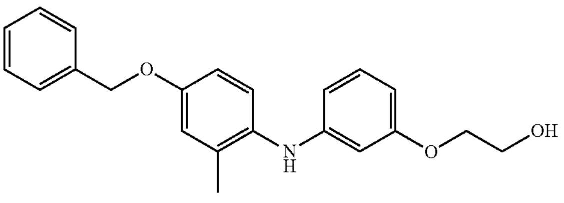
172
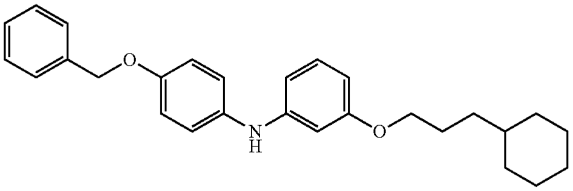
173
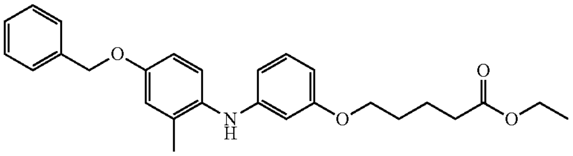
174
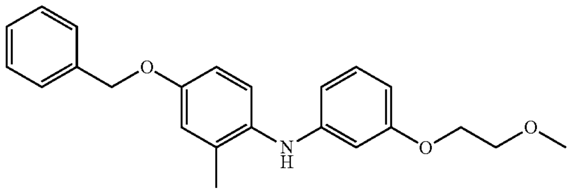
175
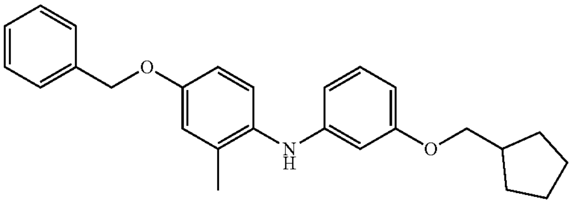
176
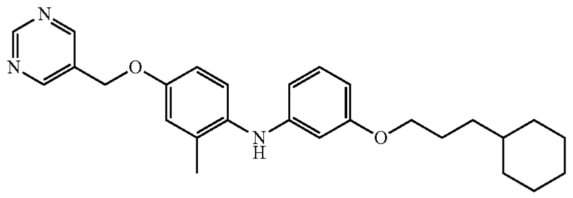
177
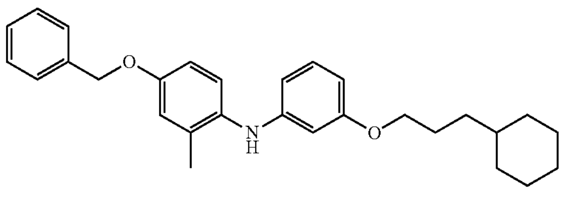
178
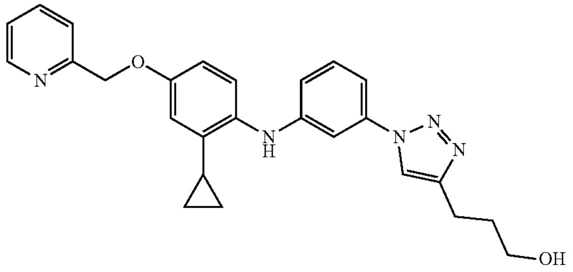

-continued
179
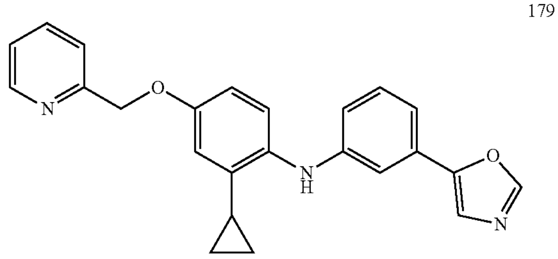
180
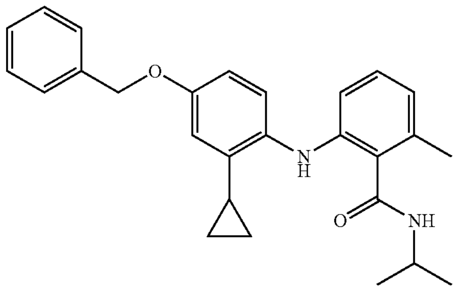
181
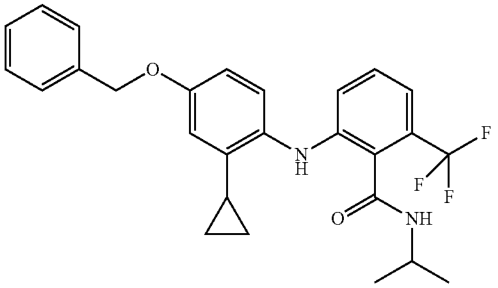
182
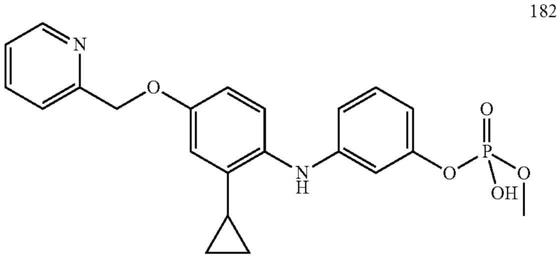
183
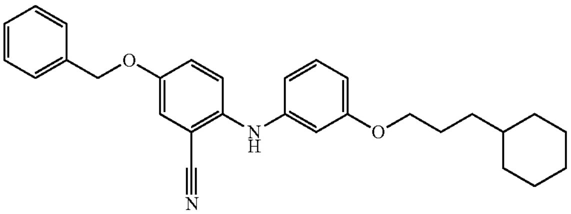
184
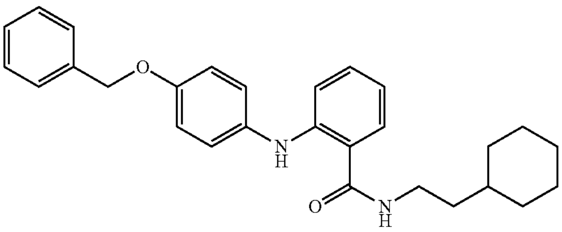
-continued
185
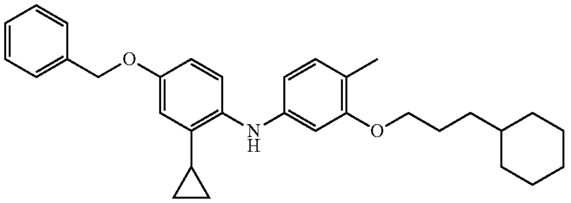
186
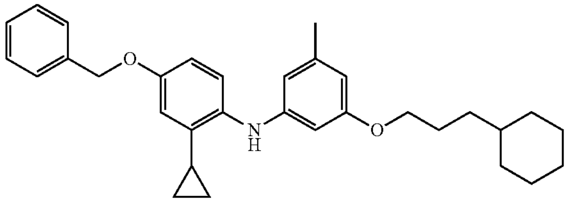
187
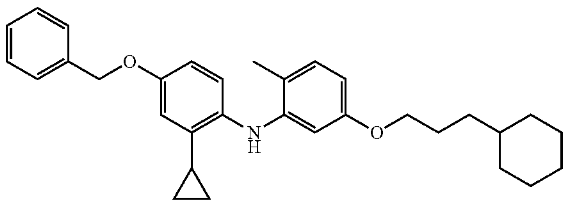
188
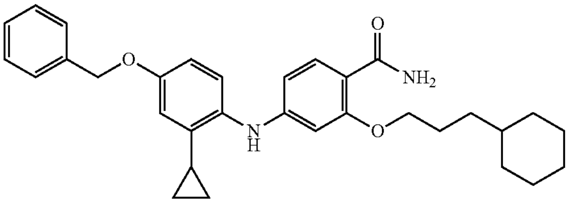
189
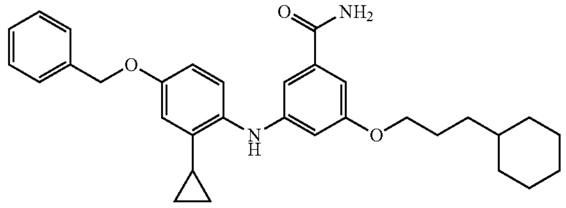
190
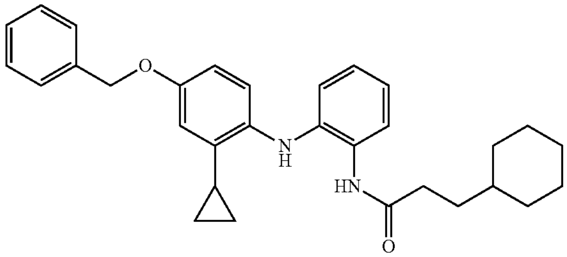

191
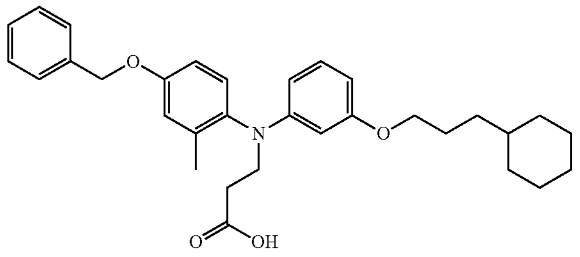
192
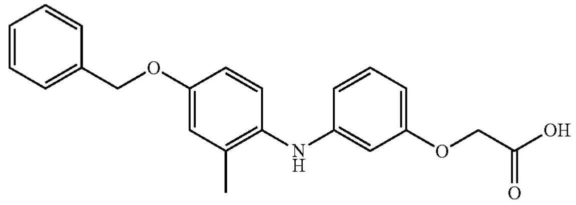
193
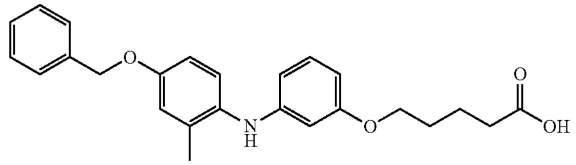
194
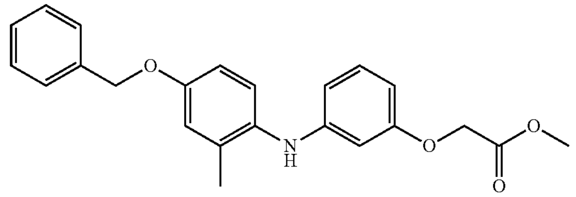
195
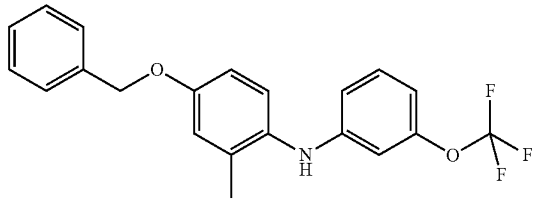
196
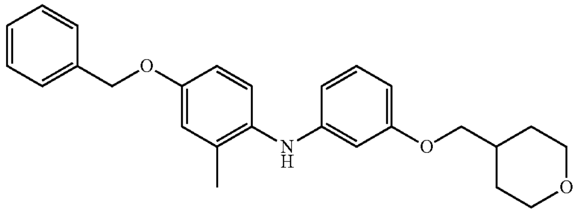
197
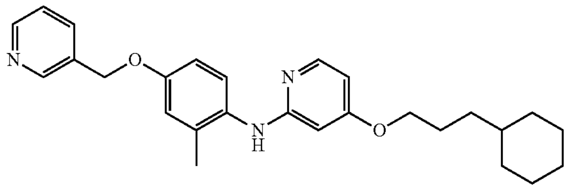
198
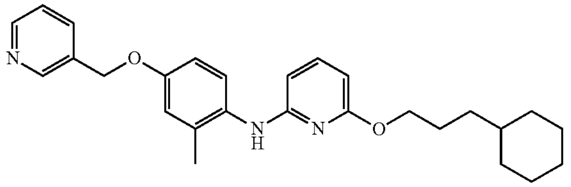
199
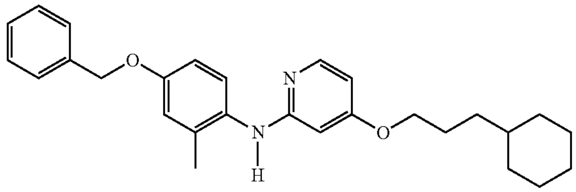
200
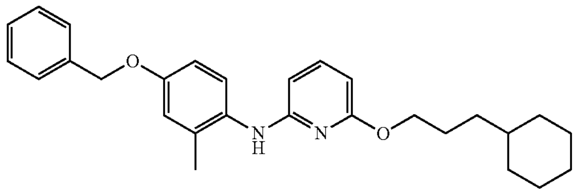
201
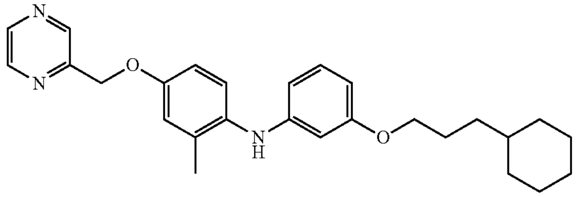
202
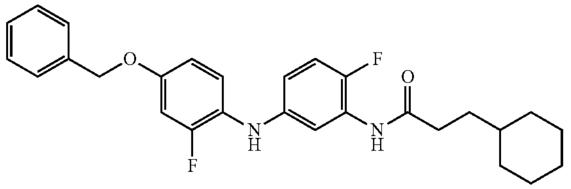
203
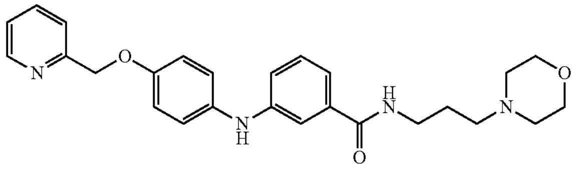
204
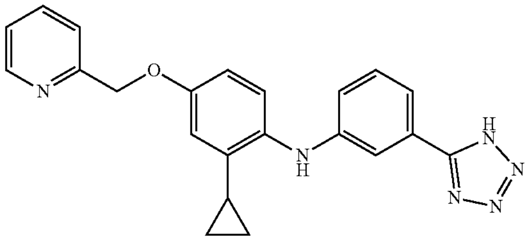

-continued

205

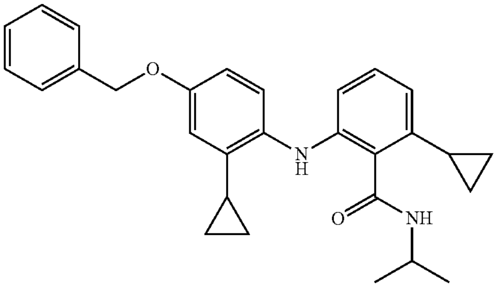

206

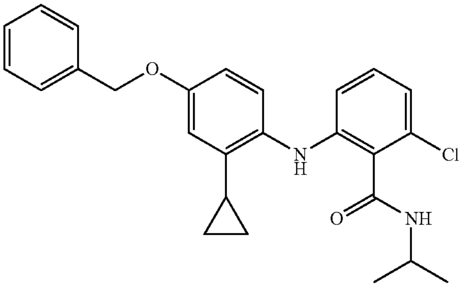

the method comprising at least a step of coupling a compound of formula (IIe)

(IIe)

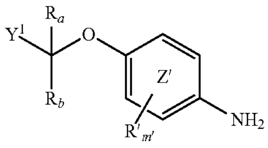

with a compound of formula (IIIe)

(IIIe)

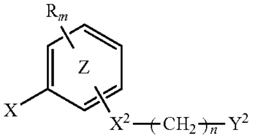

in presence of an inorganic base and a diphosphine and in the presence of an organometallic catalyst, to obtain the compound of formula (Ie) or a pharmaceutically acceptable salt thereof, or to obtain any of the compounds (36) to (206) or a pharmaceutically acceptable salt thereof, wherein R, R', m, m', n

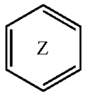

ring,

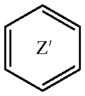

ring, $X^2$, $Y^2$, $R_a$ and $R_b$ are as defined in claim 1 or in compounds (36) to (206), X is a chlorine atom, an iodine atom or a bromine atom, and $Y^1$ is a phenyl group, a pyridine group, a pyrazine group, a pyridazine group or a pyrimidine group.

14. The compound of formula (Ie) according to claim 1, or a pharmaceutically acceptable salt thereof, wherein $X^2$ represents a triazole, a tetrazole or an oxadiazole.

15. A compound selected from:

41

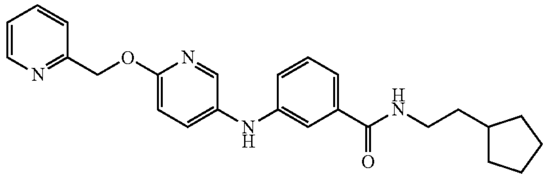

42

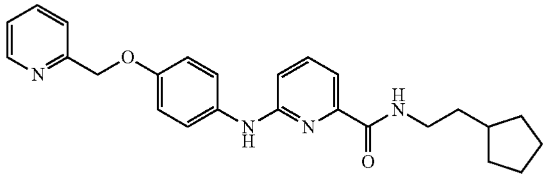

44

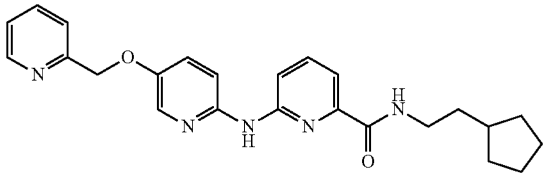

84

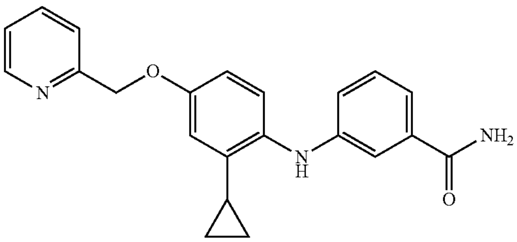

86

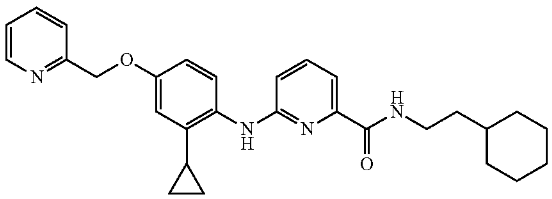

-continued
87
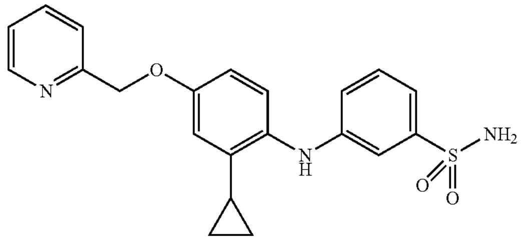
88
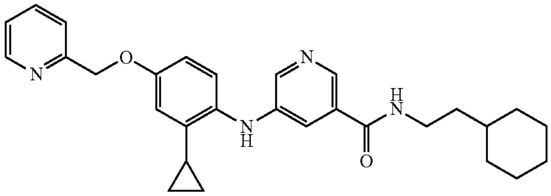
90
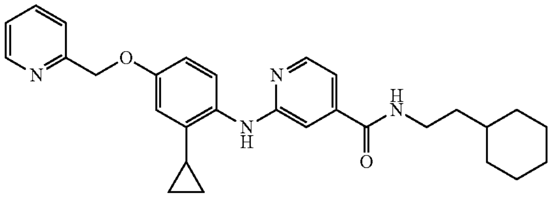
117
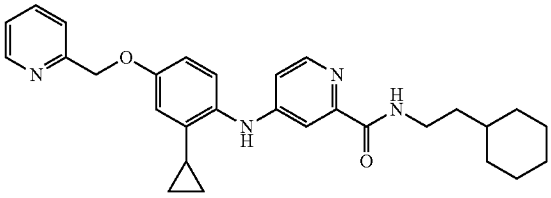
143
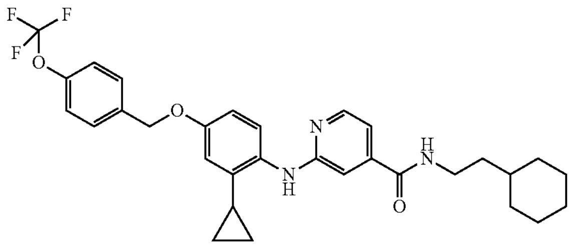
161
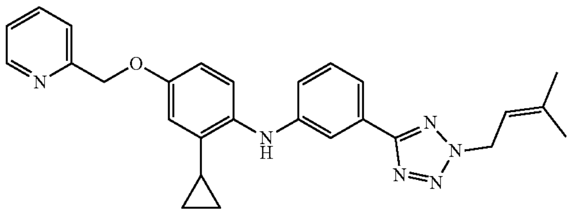
-continued
164
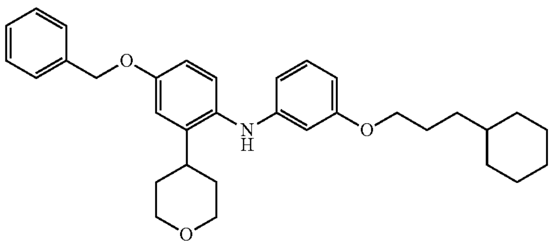
165
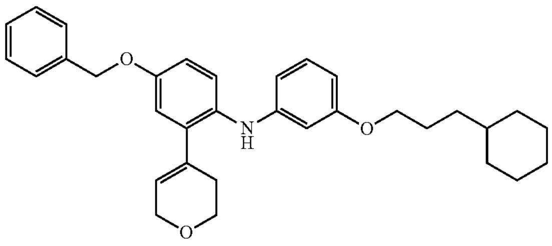
166
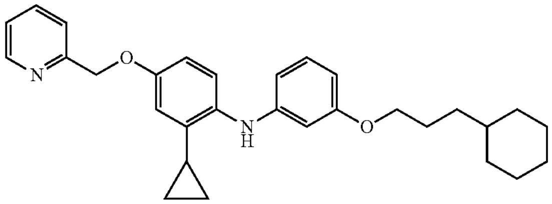
168
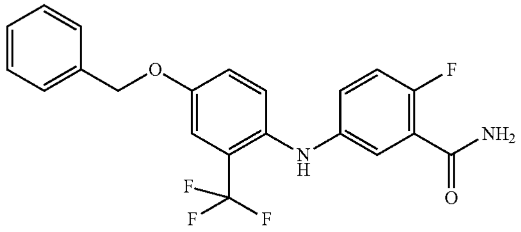
173
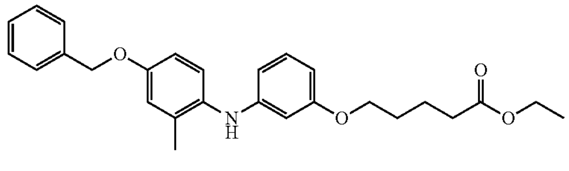
179
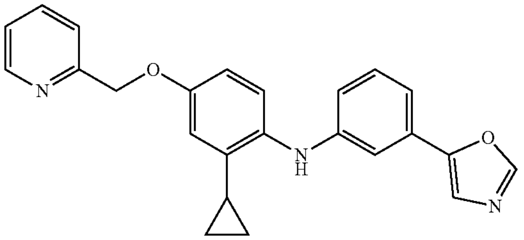

-continued

193

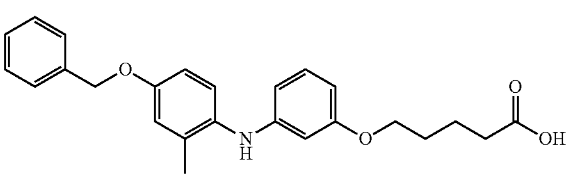

195

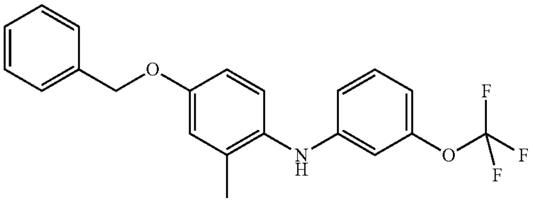

197

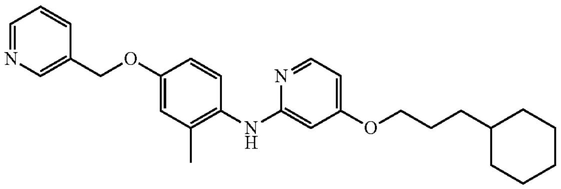

198

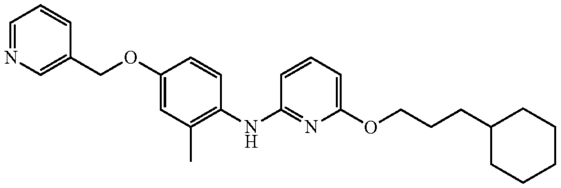

199

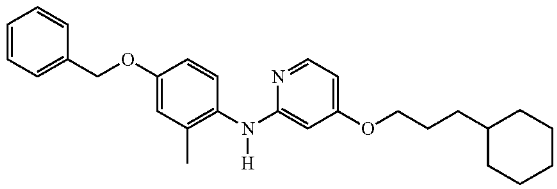

200

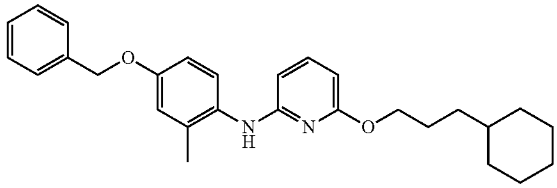

or a pharmaceutically acceptable salt thereof.

16. A method for treating a patient having a RNA virus infection caused by a virus belonging to group IV or V of the Baltimore classification comprising administering to the patient in need thereof a therapeutically effective quantity of the compound of formula (I):

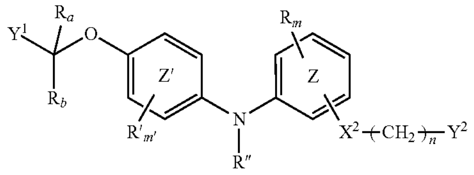

(I)

wherein:

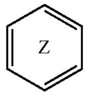

ring and

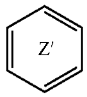

ring independently mean a phenylene or a pyridylene group, $Y^1$ represents an aryl group selected from a phenyl group, a pyridyl group, a pyrazinyl group, a pyridazinyl or a pyrimidinyl group, the aryl group being optionally substituted by one or two substituent(s) selected from a halogen atom, a $(C_1-C_4)$alkyl group, a cyano group, a $(C_1-C_5)$alkoxy group, a trifluoromethyl group, a trifluoromethoxy group, a —SO2—$NR_aR_b$ group, a —$SO_3H$ group, a —OH group, a —O—$SO_2$—$OR_c$ group or a —O—P(=O)—$(OR_c)(OR_d)$ group, $R_a$, $R_b$, $R_c$ and $R_d$ independently represent a hydrogen atom or a (C1-C4) alkyl group, $X^2$ represents a —O— group, a —NH— group, a —S— group, a —CO—NH— group, a —NH—CO—NH— group, a —NH—CO— group, a —CH(OH)— group, a —CH(COOH)NH— group, a —$CH(COOCH_3)NH$— group, a —$C(OH)(CH_2OH)$—, a

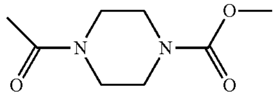

group, a divalent 5-membered heteroaromatic ring comprising 1, 2, 3, or 4 heteroatoms, a —$SO_2$— group, or a —$SO_2$—NH— group, n is 0, 1, 2 or 3, m and m' are independently 0, 1, or 2, $Y_2$ represents
a hydrogen atom,
a hydroxyl group,
a $(C_1-C_4)$alkoxy group,
a —$CHC(OH)_2$,
a $COOR_f$, wherein $R_f$ represents a hydrogen atom or a $(C_1-C_4)$alkyl group,
a morpholinyl group,
a dihydropyranyl group, a

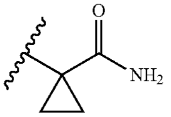 [SMILES: *C1(C(N)=O)CC1]

group,
a

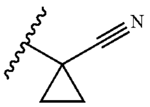 [SMILES: *C1(C#N)CC1]

group,
a —$PO(OR_f)(OR'_f)$ group, wherein $R_f$ and $R'_f$ independently represents a hydrogen atom or a $(C_1-C_4)$alkyl group,
an oxetanyl group,
a —$Si(CH_3)_3$ group,
a —NHCOO—$(C_1-C_4)$alkyl group,
or
a —$CR^1R^2R^3$ group, wherein $R^1$, $R^2$ and $R^3$ independently represent a hydrogen atom, a fluorine atom or a $(C_1-C_4)$alkyl group, being understood that no more than one of $R^1$, $R^2$ and $R^3$ is a hydrogen atom, or $R^1$ and $R^2$ form together with the carbon atom bearing them a $(C_3-C_8)$cycloalkyl group, the $(C_3-C_8)$cycloalkyl group being optionally substituted by one or two $(C_1-C_4)$alkyl group, halogen atom or $(C_1-C_4)$alkoxy group, and the $(C_3-C_8)$cycloalkyl group being optionally interrupted on the $R^1$ and/or $R^2$ by an oxygen atom,
or alternatively $X^2$-$Y^2$ represents a group —$CONR_cR_d$, wherein $R_c$ and $R_d$ form, together with the nitrogen atom a heterocyclic group, optionally substituted by a hydroxy group or a $(C_1-C_4)$alkyl group, R and R' independently represent
a $(C_1-C_4)$alkyl group,
a -S-$(C_1-C_4)$alkyl group,
a $(C_3-C_6)$cycloalkyl group,
a halogen atom,
a trifluoromethyl group,
a —$SO_2(C_1-C_4)$alkyl group,
a $(C_3-C_6)$cycloalkenyl group,
a $(C_1-C_5)$alkoxy group,
a —$SO_2$-$NR_aR_b$ group,
a —$SO_3H$ or $SO_2$—$CH_3$ group,
a —OH group,
a —$CONHR_g$, wherein $R_g$ represents a hydrogen atom or a $(C_1-C_4)$alkyl group,
a —O—$SO_2$—$OR_c$ group,
a azetidinyl group,
a morpholinyl group, or
a cyano group, R" represents a hydrogen atom, a $(C_1-C_4)$alkyl group optionally substituted by a —COOH group, or any of its pharmaceutically acceptable salts.

17. The method according to claim 16, wherein the RNA virus infection caused by a RNA virus belonging to group IV or V of the Baltimore classification is selected from RSV, Chikungunya, influenza, and Dengue infection.

* * * * *